US012807682B2

(12) United States Patent
Vázquez Gómez et al.

(10) Patent No.: US 12,807,682 B2
(45) **Date of Patent: *Nov. 24, 2026**

(54) SCAFFOLD PROTEINS AND THERAPEUTIC NANOCONJUGATES BASED ON NIDOGEN

(71) Applicants: UNIVERSITAT AUTÒNOMA DE BARCELONA, Cerdanyola del Vallès (ES); FUNDACIÓ INSTITUT DE RECERCA DE L'HOSPITAL DE LA SANTA CREU I SANT PAU, Barcelona (ES); CONSORCIO CENTRO DE INVESTIGACIÓN BIOMÉDICA EN RED, Madrid (ES); NANOLIGENT, S.L., Barcelona (ES)

(72) Inventors: Esther Vázquez Gómez, Cerdanyola del Vallès (ES); Antonio Villaverde Corrales, Cerdanyola del Vallès (ES); Naroa Serna Romero, Cerdanyola del Vallès (ES); Juan Cedano Rodríguez, Cerdanyola del Vallès (ES); Olivia Cano Garrido, Barcelona (ES); Ugutz Unzueta Elorza, Barcelona (ES); Ramón Mangues Bafalluy, Barcelona (ES); Patricia Virginia Álamo Vargas, Madrid (ES); Eloi Parladé Molist, Barcelona (ES)

(73) Assignees: UNIVERSITAT AUTÒNOMA DE BARCELONA, Barcelona (ES); NANOLIGENT, S.L., Barcelona (ES); CONSORCIO CENTRO DE INVESTIGACIÓN BIOMÉDICA EN RED, Madrid (ES); FUNDACIÓ INSTITUT DE RECERCA DE L'HOSPITAL DE LA SANTA CREU I SANT PAU

( * ) Notice: Subject to any disclaimer, the term of this patent is extended or adjusted under 35 U.S.C. 154(b) by 0 days.

This patent is subject to a terminal disclaimer.

(21) Appl. No.: 19/339,279

(22) Filed: Sep. 24, 2025

(65) Prior Publication Data

US 2026/0184764 A1 Jul. 2, 2026

Related U.S. Application Data

(62) Division of application No. 17/789,036, filed as application No. PCT/EP2021/050409 on Jan. 11, 2021, now Pat. No. 12,649,776.

(30) Foreign Application Priority Data

Dec. 26, 2019 (EP) .................................... 19383201

(51) Int. Cl.

| | |
|---|---|
| ***C07K 14/78*** | (2006.01) |
| ***A61K 9/51*** | (2006.01) |
| ***A61K 47/64*** | (2017.01) |
| ***A61K 47/69*** | (2017.01) |
| ***A61P 1/00*** | (2006.01) |
| ***A61P 35/00*** | (2006.01) |
| ***A61P 35/04*** | (2006.01) |
| ***C12N 15/10*** | (2006.01) |
| ***G01N 33/50*** | (2006.01) |
| *A61K 38/00* | (2006.01) |

(52) U.S. Cl.

CPC ............ *C07K 14/78* (2013.01); *A61K 9/5169* (2013.01); *A61K 9/5192* (2013.01); *A61K 47/642* (2017.08); *A61K 47/6435* (2017.08); *A61K 47/6455* (2017.08); *A61K 47/6931* (2017.08); *A61P 1/00* (2018.01); *A61P 35/00* (2018.01); *A61P 35/04* (2018.01); *C12N 15/1044* (2013.01); *G01N 33/5011* (2013.01); *G01N 33/5032* (2013.01); *A61K 38/00* (2013.01)

(58) Field of Classification Search

CPC .... C07K 14/78; A61K 9/5169; A61K 9/5192; A61K 47/642; A61K 47/6435; A61K 47/6455; A61K 47/6931; A61K 38/00; A61P 1/00; A61P 35/00; A61P 35/04; C12N 15/1044; G01N 33/5011; G01N 33/5032

See application file for complete search history.

*Primary Examiner* — Robert S Cabral

(74) *Attorney, Agent, or Firm* — Sterne, Kessler, Goldstein & Fox P.L.L.C.

(57) ABSTRACT

The present invention relates to proteins suitable for being used as scaffolds to which a peptide of interest is bound, or which are comprised within a conjugate to which an agent of interest is attached. It also relates to said conjugates suitable for the selective delivery of their conjugated agents of interest to specific cell and tissue types, wherein said agent 5 can be a therapeutic agent or an imaging agent. It also relates to nanoparticles comprising such conjugates and the therapeutic uses thereof.

30 Claims, 31 Drawing Sheets

Specification includes a Sequence Listing.

A

B

C

C

D

A

B

A

B

A

B

C

A

B

A

B

C

D

Human Nidogen (P14543):

MLASSSRIRAAWTRALLLPLLLAGPVGCLSRQELFPFGPGQGDLELEDGDDFVSPALELSGALRFYDRSDIDAVYVTTNGIIATSEPPAKESHPGL
FPPTFGAVAPFLADLDTTDGLGKVYYREDLSPSITQRAAECVHRGFPEISFQPSSAVVVTWESVAPYQGPSRDPDQKGKRNTFQAVLASSDSSS
YAIFLYPEDGLQFHTTFSKKENNQVPAVVAFSQGSVGFLWKSNGAYNIFANDRESVENLAKSSNSGQQGVWVFEIGSPATTNGVVPADVILG
TEDGAEYDDEDEDYDLATTRLGLEDVGTTPFSYKALRRGGADTYSVPSVLSPRRAATERPLGPPTERTRSFQLAVETFHQQHPQVIDVDEVEET
GVVFSYNTDSRQTCANNRHQCSVHAECRDYATGFCCSCVAGYTGNGRQCVAEGSPQRVNGKVKGRIFVGSSQVPIVFENTDL<u>H</u>SYVVMNH
G<u>R</u>SYTAISTIPETVGYSLLPLAPVGGIIGWMFAVEQDGFKNGFSITGGEFTRQAEVTFVGHPGNLVIKQRFSGIDEHGHLTIDTELEGRVPQIPFG
SSVHIEPYTELYHYSTSVITSSSTREYTVTEPERDGASPSRIYTYQWRQTITFQECVHDDSRPALPSTQQLSVDSV<u>F</u>VLYNQEEKIL<u>R</u>YALSNSIGPV
REGSPDALQNPCYIGTHGCDTNAACRPGPRTQFTCECSIGFRGDGRTCYDIDECSEQPSVCGSHTICNNHPGTFRCECVEGYQFSDEGTCVAV
VDQRPINYCETGLHNCDIPQRAQCIYTGGSSYTCSCLPGFSGDGQACQDVDECQPSRCHPDAFCYNTPGSFTCQCKPGYQGDGFRCVPGEVE
KTRCQHEREHILGAAGATDPQRPIPPGLFVPECDAHGHYAPTQCHGSTGYCWCVDRDGREVEGTRTRPGMTPPCLSTVAPPIHQGPAVPTA
VIPLPPGTHLLFAQTGKIERLPLEGNTMRKTEAKAFLHVPAKVIIGLAFDCVDKMVYWTDITEPSIGRASLHGGEPTTIIRQDLGSPEGIAVDHLG
RNIFWTDSNLDRIEVAKLDGTQRRVLFETDLVNPRGIVTDSVRGNLYWTDWNRDNPKIETSYMDGTNRRILVQDDLGLPNGLTFDAFSSQLC
WVDAGTNRAECLNPSQPSRRKALEGLQYPFAVTSYGKNLYFTDWKMNSVVALDLAISKETDAFQPHKQTRLYGITTALSQCPQGHNYCSVN
NGGCTHLCLATPGSRTCRCPDNTLGVDCIEQK

NIDOmut2:

SPQRVNGKVKGRIFVGSSQVPIVFENTDLASYVVMNHGNSYTAISTIPETVGYSLLPLAPVGGIIGWMFAVEQDGFKNGFSITGGEFTRQAEVT
FVGHPGNLVIKQRFSGIDEHGHLTIDTELEGRVPQIPFGSSVHIEPYTELYHYSTSVITSSSTREYTVTEPERDGASPSRIYTYQWRQTITFQECVH
DDSRPALPSTQQLSVDSVSVLYNQEEKILAYALSNSIGPVREGSPDA

T22-NIDOmut2-H6:

<u>RRWCYRKCYKGYCYRKCR</u>GGSSRSSSPQRVNGKVKGRIFVGSSQVPIVFENTDL<u>A</u>SYVVMNHG<u>N</u>SYTAISTIPETVGYSLLPLAPVGGIIGWMF
AVEQDGFKNGFSITGGEFTRQAEVTFVGHPGNLVIKQRFSGIDEHGHLTIDTELEGRVPQIPFGSSVHIEPYTELYHYSTSVITSSSTREYTVTEPE
RDGASPSRIYTYQWRQTITFQECVHDDSRPALPSTQQLSVDSV<u>S</u>VLYNQEEKIL<u>A</u>YALSNSIGPVREGSPDAK*HHHHHH*

Fig. 13B

SCAFFOLD PROTEINS AND THERAPEUTIC NANOCONJUGATES BASED ON NIDOGEN

CROSS REFERENCE TO RELATED APPLICATIONS

This application is a divisional of U.S. application Ser. No. 17/789,036 filed Jun. 24, 2022, which was a § 371 National Stage Application of PCT/EP2021/050409, filed Jan. 11, 2021, which claims priority to and the benefit of European Patent Application No. 19383201.1, filed Dec. 26, 2019, the entire disclosures of each of which are incorporated herein by reference for all purposes.

REFERENCE TO SEQUENCE LISTING SUBMITTED ELECTRONICALLY

The content of the electronically submitted replacement Sequence Listing in XML format (Name: 5489_0050002_SequenceListing_ST26.xml; Size: 162,308 bytes; and Date of Creation: Oct. 1, 2025) submitted herewith, is incorporated herein by reference in its entirety.

FIELD OF THE INVENTION

The present invention relates to the field of nanostructured protein materials, more specifically to therapeutic agent-carrying polypeptides which can be used for therapy.

BACKGROUND OF THE INVENTION

The systemic administration of drugs in form of nanoconjugates benefits from enhanced drug stability when compared to free molecules. Valuable additional properties such as cell targeting might be also merged into a given hybrid composite through the chemical incorporation of functional groups in nanoscale vehicles, taking profit from the high surface/volume ratio of nanomaterials. When administered systemically, the resulting drug loaded conjugates sizing between ~8 and 100 nm escape from renal filtration in absence of aggregation in lung or other highly vascularized organs. This fact, combined with appropriate physicochemical properties of the material might result in extended circulation time and prolonged drug exposure to target organs, thus enhancing the therapeutic impact and benefits for the patient.

Among the diversity of materials under investigation as drug carriers, that includes metals, ceramics, polymers and carbon nanotubes, proteins offer unique properties regarding biocompatibility and degradability that, in the context of rising nanotoxicological concerns, make them especially appealing. As the engineering of protein self-assembling into nanostructured materials is rapidly progressing and the control over the final geometry and physicochemical properties becomes tighter, protein materials are gaining functional and structural versatility as vehicles from chemically coupled drugs.

In fact, the attachment of a cytotoxic "payload" to an antibody to form an antibody-drug conjugate (ADC) has been shown to provide a mechanism for selective delivery of the cytotoxic agent to cancer cells via the specific binding of the antibody to cancer-selective cell surface molecules. Multiple examples of this strategy have been proved to be effective, like gemtuzumab ozogamicin, which comprises an anti-CD33 antibody conjugated to a highly potent DNA-targeting antibiotic, calicheamicin, which was used against acute myeloid leukemia. Also, maytansinoids, a highly potent microtubule-disrupting agents, have been tested as payloads for ADCs, resulting in the formulation ado-trastuzumab emtansine for treating HER2-positive breast cancer.

Nonetheless, the structural complexity of antibodies may become a cumbersome hindrance in terms of cost and synthesis. The inventors previously probed into the field of nanomedicine by applying a nanoarchitectonic principle based on the addition, to a core protein, of a cationic N-terminal domain plus a C-terminal poly-histidine. [Serna, N. et al. 2016. Nanomedicine, 12:1241-51] It has been described in the art that these end-terminal tags and the resulting charge balance in the whole fusion promote self-assembling and oligomerization of monomeric proteins as robust toroid nanoparticles, stable in plasma [Cespedes, M. V. et al. 2014. ACS Nano., 8:4166-4176] and with high cellular penetrability if empowered with cell-targeting peptides. [Xu, Z. K. et al. 2015. Materials Letters, 154:140-3] The building blocks of these protein structures might also contain functional peptides such as cell-targeting agents, endosomolytic agents or nuclear localization signals, in form of fused stretches with modular organization.

Since current therapy methods still show a margin of failure, mostly due to tumor resistance phenomena which may result from intra-tumor clonal selection of those cells most resistant to the chemotherapy, for instance, there is still in the art a need for the development of more specific therapeutic approaches which can be targeted to the concrete tumor cells responsible for therapy failure and tumor progression while reducing the side and off-target effects of the therapeutic agents.

SUMMARY OF THE INVENTION

In a first aspect, the invention relates to a polypeptide comprising:

(i) eleven beta strand domains designated A, B, C, D, E, F, G, H, I, J and K and (ii) ten loop regions designated as AB, BC, CD, DE, EF, FG, GH, HI, IJ and JK loops wherein each loop region connects each two consecutive beta strand domains;

wherein at least one of the loop regions is a variant of the cognate loop region in SEQ ID NO:62, wherein the cognate loop regions in SEQ ID NO:62 are as defined in SEQ ID NO:1 (loop region AB), SEQ ID NO:2 (loop region BC), SEQ ID NO:3 (loop region CD), SEQ ID NO:4 (loop region DE), SEQ ID NO:5 (loop region EF), SEQ ID NO:6 (loop region FG), amino acids 149 to 150 in SEQ ID NO:62 (loop region GH), SEQ ID NO:7 (loop region HI), SEQ ID NO:8 (loop region IJ) and SEQ ID NO:9 (loop region JK), and wherein at least one beta strand domain is a variant of the cognate beta strand in SEQ ID NO:62 and has at least 50% sequence identity with said cognate beta strand domain, wherein the cognate beta strand domains in SEQ ID NO:62 are as defined in SEQ ID NO:9 (beta strand domain A), SEQ ID NO:11 (beta strand domain B), SEQ ID NO:12 (beta strand domain C), SEQ ID NO:13 (beta strand domain D), SEQ ID NO:14 (beta strand domain E), SEQ ID NO:15 (beta strand domain F), SEQ ID NO:16 (beta strand domain G), SEQ ID NO:17 (beta strand domain H), SEQ ID NO:18 (beta strand domain I), SEQ ID NO:19 (beta strand domain J) and SEQ ID NO:20 (beta strand domain K).

In a second aspect, the invention relates to a polypeptide display library comprising a plurality of polypeptides according to the first aspect of the invention, wherein the plurality of polypeptides is formed by polypeptides that differ in the sequence of one or more loop regions.

In a third aspect, the invention relates to a polynucleotide encoding the polypeptide according to the first aspect of the invention, or a polypeptide of the polypeptide display library according to the second aspect of the invention.

In a fourth aspect, the invention relates to a vector comprising the polynucleotide according to the third aspect of the invention.

In a fifth aspect, the invention relates to a host cell comprising the polynucleotide according to the third aspect of the invention, or the vector according to the fourth aspect of the invention.

In a sixth aspect, the invention relates to a conjugate comprising (i) a first polypeptide region comprising the G2 domain of nidogen-1 or a functionally equivalent variant thereof and (ii) an agent of interest.

In a seventh aspect, the invention relates to a method for preparing a conjugate according to the sixth aspect of the invention, comprising (i) providing the polypeptide of the conjugate according to the sixth aspect of the invention comprising the G2 domain of nidogen-1 or a functionally equivalent variant thereof wherein the polypeptide is provided in an activated form and (ii) contacting said polypeptide with the agent of interest which is capable of reacting with the reactive group in the polypeptide, wherein said contacting is carried out under conditions adequate for the formation of a bond between the reactive group in the polypeptide and the group in the agent of interest.

In an eighth aspect, the invention relates to a polypeptide comprising (i) a first region comprising the G2 domain of nidogen-1 or a functionally equivalent variant thereof and (ii) a second region which comprises an antagonistic CXCR4 ligand.

In a ninth aspect, the invention relates to a method for preparing a conjugate according to the sixth aspect of the invention, comprising (i) providing the polypeptide of the conjugate according to the sixth aspect of the invention comprising the G2 domain of nidogen-1 or a functionally equivalent variant thereof and (ii) contacting said polypeptide with an activated form of the agent of interest of the conjugate according to the sixth aspect of the invention which is capable of reacting with at least one group in the polypeptide and wherein the contacting is carried out under conditions adequate for the formation of a bond between the reactive group in the agent of interest and the group in polypeptide.

In a tenth aspect, the invention relates to a method for preparing a conjugate according to the sixth aspect of the invention, comprising (i) providing the polypeptide of the conjugate according to the sixth aspect of the invention comprising the G2 domain of nidogen-1 or a functionally equivalent variant thereof wherein the polypeptide is provided in an activated form and (ii) contacting said polypeptide with the agent of interest which is capable of reacting with the reactive group in the polypeptide, wherein said contacting is carried out under conditions adequate for the formation of a bond between the reactive group in the polypeptide and the group in the agent of interest.

In an eleventh aspect, the invention relates to a polypeptide comprising a first region comprising (i) the G2 domain of nidogen-1 or a functionally equivalent variant thereof and (ii) a second region which comprises an antagonistic CXCR4 ligand.

In a twelfth aspect, the invention relates to a method for preparing a nanoparticle comprising multiple copies of the polypeptide according to the eleventh aspect of the invention, said method comprising placing a preparation of said polypeptide under conditions adequate for the assembly of a plurality of copies of the polypeptide into a nanoparticle.

In a thirteenth aspect, the invention relates to a method for preparing a nanoparticle comprising multiple copies of the conjugate according to the sixth aspect of the invention or multiple copies of the polypeptide according to the eleventh aspect of the invention selected from:

(i) A method which comprises placing a preparation of said conjugate or said polypeptide under conditions adequate for the assembly of a plurality of copies of the conjugate or of the polypeptide into a nanoparticle or (ii) A method which comprises i. placing a plurality of polypeptides each comprising 1. a first polypeptide region which is the G2 domain of nidogen-1 or a functionally equivalent variant thereof, 2. a second polypeptide region which is capable of specifically binding to a target of interest wherein said second polypeptide is a polycationic peptide and 3. a third polypeptide region which is a positively charged amino acid-rich region, wherein the polycationic peptide and the positively charged amino acid-rich region are located at the ends of the polypeptide and wherein the polypeptide is provided in an activated form, wherein said activated form of the polypeptide contains a reactive group, wherein said placing is carried out under conditions adequate for the formation of a nanoparticle containing a plurality of copies of the polypeptide and ii. contacting the nanoparticle obtained in step I with an activated form of the agent of interest which contains a group which is capable of reacting with the reactive group in the polypeptide, wherein said contacting is carried out under conditions adequate for the formation of a bond between the reactive group in the polypeptide and the group in the agent of interest.

In a fourteenth aspect, the invention relates to a method for preparing a biparatopic nanoparticle comprising multiple copies of a first type of conjugate and multiple copies of a second type of conjugate, wherein the first and second types of conjugates are as defined in the sixth aspect of the invention and wherein the first and the second type of conjugates differ in the sequence of the polycationic peptide, said method being selected from (i) A method which comprises contacting a preparation of said first type of conjugate with a preparation of said second type of conjugate under conditions adequate for the assembly of a plurality of copies of the two types of conjugates into a nanoparticle or (ii) A method which comprises i. contacting a preparation of a first polypeptide with a preparation of a second polypeptide wherein the first and second types of polypeptides comprise a. a first polypeptide region which is the G2 domain of nidogen-1 or a functionally equivalent variant thereof,
b. a second polypeptide region which is capable of specifically binding to a target of interest wherein said second polypeptide is a polycationic peptide, and/or comprises an additional positively charged peptide sequence located at its N- or C-terminal end and the sequence of the polycationic peptide of one polypeptide is different from the sequence of the polycationic peptide of the other polypeptide,
c. a third polypeptide region which is a positively charged amino acid-rich region,
d. optionally, a positively charged peptide sequence located at the N- or C-terminal end of the polycationic peptide, wherein the polycationic peptide and the positively charged amino acid-rich region are located at the ends of the polypeptides, wherein the first and second polypeptides differ in their polycationic peptide, wherein the first and/or second polypeptides are as the conjugates defined in the sixth aspect of the invention, wherein the first and/or the second polypeptides are provided in an activated form, wherein said activated form of the polypeptides contains a reactive group, wherein said placing is carried out under conditions adequate for the formation of a nanoparticle containing a plurality of copies of polypeptides, ii. contacting the nanoparticle obtained in step i with an activated form of the agent of interest which contains a group which is capable of reacting with the reactive group in each polypeptide, wherein said contacting is carried out under conditions adequate for the formation of a bond between the reactive group in the polypeptides and the group in the agent of interest.

In a fifteenth aspect, the invention relates to a method for preparing a biparatopic nanoparticle comprising multiple copies at least one conjugate according to the sixth aspect of the invention and multiple copies of at least one polypeptide according to the eleventh aspect of the invention wherein the polycationic peptide of the first type of conjugate is different from the sequence of the second region of the at least one polypeptide, said method being selected from (i) A method which comprises placing a preparation of multiple copies of said at least one conjugate and multiple copies of said at least one polypeptide under conditions adequate for the assembly of a plurality of copies of the two conjugates into a nanoparticle or (ii) A method which comprises i. contacting a preparation of a first polypeptide with a preparation of a second polypeptide wherein the first and second type of polypeptides comprise
a. a first polypeptide region which is the G2 domain of nidogen-1 or a functionally equivalent variant thereof,
b. a second polypeptide region which is capable of specifically binding to a target of interest wherein said second polypeptide is a polycationic peptide, and/or comprises an additional positively charged peptide sequence located at its N- or C-terminal end and the sequence of the polycationic peptide of one polypeptide is different from the sequence of the polycationic peptide of the other polypeptide,
c. a third polypeptide region which is a positively charged amino acid-rich region, wherein the polycationic peptide and the positively charged amino acid-rich region are located at the ends of the polypeptides, wherein the first polypeptide is as the conjugated defined in the sixth aspect of the invention and the second polypeptide is as defined in the eleventh aspect of the invention, wherein the polycationic peptide of the first polypeptide is different from the polycationic peptide of the second polypeptide, wherein the first and/or the second polypeptides are provided in an activated form, wherein said activated form of the polypeptides contains a reactive group, wherein said placing is carried out under conditions adequate for the formation of a nanoparticle containing a plurality of copies of polypeptides, ii. contacting the nanoparticle obtained in step i with an activated form of the agent of interest which contains a group which is capable of reacting with the reactive group in each polypeptide, wherein said contacting is carried out under conditions adequate for the formation of a bond between the reactive group in the polypeptides and the group in the agent of interest.

In a sixteenth aspect, the invention relates to a nanoparticle comprising multiple copies of the conjugate according to the sixth aspect of the invention, multiple copies of the polypeptide according to the eleventh aspect of the invention or which has been obtained by the method according to the twelfth or thirteenth aspect of the invention.

In a seventeenth aspect, the invention relates to a biparatopic nanoparticle that comprises multiple copies of a first and a second type of conjugates, wherein both said first and second types of conjugates are as defined in the sixth aspect of the invention or as the polypeptide defined in the eleventh aspect of the invention and wherein the first and second types of conjugates differ in the polycationic peptide or a biparatopic nanoparticle that has been obtained by a method according to the fourteenth or fifteenth aspect of the invention.

In an eighteenth aspect, the invention relates to a biparatopic nanoparticle that comprises multiple copies of a conjugate according to the sixth aspect of the invention and multiple copies of a polypeptide according to the eleventh aspect of the invention, wherein the polycationic region of the conjugate is different from the first region of the polypeptide, or a biparatopic nanoparticle that has been obtained by a method according to the fourteenth or fifteenth aspect of the invention.

In a nineteenth aspect, the invention relates to a conjugate according to the sixth aspect of the invention, a polypeptide according to the eleventh aspect of the invention or a nanoparticle according to the sixteenth, seventeenth or eighteenth aspect of the invention for use in medicine.

In a twentieth aspect, the invention relates to a method for the imaging of a target cell which comprises specific binding sites for one or more components of the conjugate according to the sixth aspect of the invention, of the polypeptide according to the eleventh aspect of the invention or of the nanoparticle according to the sixteenth, seventeenth or eighteenth aspect of the invention, the method comprising (i) contacting a sample containing said cell with a conjugate according to the sixth aspect of the invention, with a polypeptide according to the eleventh aspect of the invention or with a nanoparticle according to the sixteenth, seventeenth or eighteenth aspect of the invention under conditions adequate for the binding of the conjugate, of the polypeptide or of the nanoparticle to the cell and wherein the agent of interest is an imaging agent and (ii) Imaging the cell by detecting the signal provided by the imaging agent.

In a twenty-first aspect, the invention relates to a method for identifying a polypeptide that binds to a target peptide, said method comprising:

i) contacting a target peptide with the polypeptide display library according to the second aspect of the invention conditions that allow a polypeptide to interact with the target peptide, ii) recovering those members of the library that have specifically interacted with the target peptide, and iii) identifying the sequence of the polypeptide that interacts with the target peptide.

In a twenty-second aspect, the invention relates to a use of a polypeptide according to the first aspect of the invention for presenting a peptide, wherein said peptide is found in one of the loop regions.

In a twenty-third aspect, the invention relates to a method for determining the presence of a target peptide in a sample comprising:

i) contacting the proteins present in the sample with a polypeptide according to the first aspect of the invention, wherein the sequence of at least one of the loop regions in the polypeptide is a sequence that is capable of specifically binding to the target peptide, ii) determining if there is an interaction between the target peptide and the polypeptide, wherein if there is an interaction between the polypeptide and the target peptide, then the target peptide is present in the sample.

DESCRIPTION OF THE FIGURES

FIG. 13B shows the amino acid sequence of Human Nidogen 1, HSNBT scaffold and T22-HSNBT-H6 protein. In Human Nidogen, G2 β-barrel domain is highlighted in black and candidate amino acids to be mutated indicated in bold black and underlined. In NIDOmut2 sequence, incorporated mutations are indicated in bold black. In T22-NIDOmut2-H6, N-terminal T22 ligand is indicated in underlined black, short linker is indicated in bold black, incorporated mutations are indicated in bold underlined and C-terminal poly-histidine tail is highlighted in bold black italics.

DETAILED DESCRIPTION OF THE INVENTION

I—Polypeptide of the Invention

Figure 1:
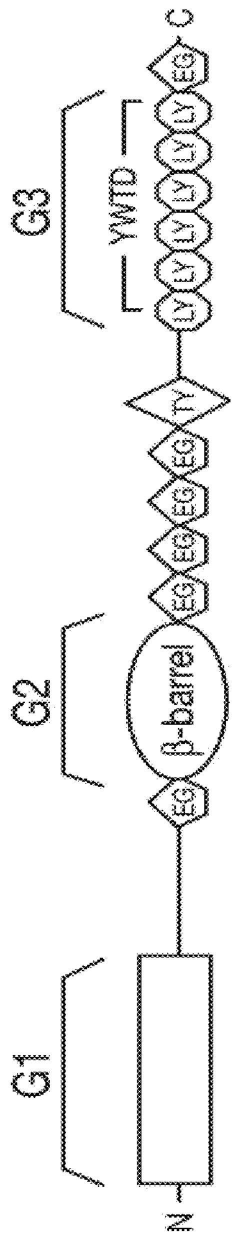
FIG. 1 shows the structure of Human Nidogen-1 protein as depicted in Takagi J. et al. (Nature 424, 969-974, 2003). G1, G2 and G3 indicate the three main globular domains. EG represent EGF modules, TY represent thyroglobulin repeat and LY represents LDL receptor YWTD repeat.

The inventors have observed that the G2 domain from the nidogen protein, optionally modified so as to show a decreased affinity for its natural ligands, is sufficiently stable to act as a scaffold and to present peptides which have been inserted into one or more of the loop regions connecting the beta strands within said G2 domain. In addition, the inventors have also found that the G2 domain of the nidogen protein can also be used to deliver agents of interest, including therapeutic as well as diagnostic/imaging agents to cells of interest when conjugated to a ligand which shows affinity towards a receptor expressed by said cells. The inventors found that a fusion protein comprising the nidogen G2 domain and the CXCR4-specific ligand T22 and which has been coupled to an anticancer agent was capable of delivering the anticancer agent to CXCR4-expressing cells resulting in an inhibition of the proliferation of the cells to an extent significantly superior to the inhibition achieved by comparable agents wherein the T22 ligand is fused to different proteins, such as GFP or Stefin A.

Accordingly, in a first aspect, the invention relates to a polypeptide comprising:

(i) eleven beta strand domains designated A, B, C, D, E, F, G, H, I, J and K and (ii) ten loop regions designated as AB, BC, CD, DE, EF, FG, GH, HI, IJ and JK loops wherein each loop region connects each two consecutive beta strand domains;

wherein at least one of the loop regions is a variant of the cognate loop region in SEQ ID NO:62, wherein the cognate loop regions in SEQ ID NO:62 are as defined in SEQ ID NO:1 (loop region AB), SEQ ID NO:2 (loop region BC), SEQ ID NO:3 (loop region CD), SEQ ID NO:4 (loop region DE), SEQ ID NO:5 (loop region EF), SEQ ID NO:6 (loop region FG), amino acids 149 to 150 in SEQ ID NO:62 (loop region GH), SEQ ID NO:7 (loop region HI), SEQ ID NO:8 (loop region IJ) and SEQ ID NO:9 (loop region JK), and wherein at least one beta strand domain is a variant of the cognate bet strand in SEQ ID NO:62 and has at least 50% sequence identity with said cognate beta strand domain, wherein the cognate beta strand domains in SEQ ID NO:62 are as defined in SEQ ID NO:9 (beta strand domain A), SEQ ID NO:11 (beta strand domain B), SEQ ID NO:12 (beta strand domain C), SEQ ID NO:13 (beta strand domain D), SEQ ID NO:14 (beta strand domain E), SEQ ID NO:15 (beta strand domain F), SEQ ID NO:16 (beta strand domain G), SEQ ID NO:17 (beta strand domain H), SEQ ID NO:18 (beta strand domain I), SEQ ID NO:19 (beta strand domain J) and SEQ ID NO:20 (beta strand domain K).

The polypeptide is referred hereinafter as the "polypeptide according to the first aspect of the invention" or the "polypeptide of the invention"

The term "polypeptide", as used herein, generally refers to a linear chain of amino acid residues of any length, joined together with peptide bonds. The term "peptide" as used herein, refers to a linear chain of amino acids as a polypeptide, although shorter than that of a polypeptide. It generally refers to amino acid chains of 2-50 amino acids. It will be understood that the terms "peptide bond", "peptide", "polypeptide" and "protein" are known to the person skilled in the art.

The polypeptide of the invention is a variant of the "nidogen G2 domain".

The term "nidogen-1" as used herein, refers to the glycoprotein formerly known as entactin. Nidogen-1 is disclosed in Uniprot Database with accession number P14543-1 (version dated Jul. 7, 2009) (SEQ ID NO:72).

The term "G2 domain of nidogen-1", as used herein, refers to the domain G2 of the protein nidogen 1 as defined above. The nidogen-1 G2 domain is as shown in SEQ ID NO:62 which corresponds to amino acid numbers 430 and 667 of the amino acid sequence of the nidogen-1 protein, with identification number P14543-1 of the Uniprot Database (version dated Jul. 7, 2009) (SEQ ID NO:72). In another embodiment, the domain G2 of nidogen 1 is as shown in SEQ ID NO:64, which lacks the first two amino acids of SEQ ID NO:62, and thus, corresponds to a region consisting on amino acid numbers 432 and 667 of the amino acid sequence of the nidogen-1 protein precursor with identification number P14543-1 of the Uniprot Database (version dated Jul. 7, 2009) (SEQ ID NO:72). In the native nidogen-1 sequence, the G2 domain is flanked by short EGF-like domains. However, for the purposes of the present invention, the nidogen-1 G2 domain lacks EGF-like domains at the N- or at the C-terminus.

In one embodiment, the polypeptide of the invention contains an N-terminal methionine residue. In another embodiment, the polypeptide of the invention does not contain a methionine at the N-terminal position.

As used herein, an "amino acid residue" refers to any naturally occurring amino acid, any amino acid derivative or any amino acid mimic known in the art. In a particular embodiment, said amino acid residue is an amino acid, i.e. a naturally occurring amino acid. In certain embodiments, the residues of the protein or peptide are sequential, without any non-amino acid interrupting the sequence of amino acid residues. In other embodiments, the sequence may comprise one or more non-amino acid moieties. In a particular embodiments, the sequence of residues of the protein or peptide may be interrupted by one or more non-amino acid moieties.

The expression "beta strand", a "beta strand domain" or "beta strand sequence", as used herein, refers to an extended polypeptide strand, or sequence, which is connected to another one through hydrogen bonding, between the NH group from one strand and the CO from the other strand. Typically, beta strands are around 3-10 amino acids long, although they can be longer, for instance they can even be 13-15 amino acids long. As a result of said strand connections between strands, beta strands form a secondary protein structure that resembles a sheet. Said secondary protein structure is referred herein as a "beta sheet". Within a beta sheet, beta strands can be arranged in a parallel, anti-parallel or mixed (parallel and anti-parallel) manner. When arranged in a parallel manner, the beta strands are aligned in the same direction from one terminus (N or C) to the other. When arranged in an anti-parallel manner, each beta strand is aligned in an opposite direction to that of the strand to which it is connected.

The expression "beta barrel", as used herein, refers to a protein secondary structure formed by a beta-sheet, wherein the first strand is bonded to the last strand by means of a hydrogen bond, leading to a closed toroidal structure.

The expression "α-helix" or "alpha helix", as used herein, refers to a protein secondary structure that consists on a right hand-helix in which the N—H group of an amino acid bonds a hydrogen to the backbone C═O group of the amino acid located three or four residues earlier in a protein sequence.

The expression "α-helical segment" or "alpha helical segment" as used herein, refers to a motif in the secondary structure of proteins that essentially comprises one or several α-helices.

As understood by a skilled person, beta strands as used herein refer to protein domains, and beta sheets as used herein, refer to protein secondary structures.

In a particular embodiment, the eleven beta strand domains of the polypeptide of the invention are comprised in, or constitute, a beta sheet secondary structure. In a preferred embodiment, the twelve beta strand domains of the polypeptide of the invention are comprised in, or constitute, a beta barrel secondary structure.

The term "loop", "loop region", "loop sequence", "omega loop", "omega loop region" or "omega loop sequence", as used herein, refers to a non-regular, non-repeating protein structural motif, consisting of a polypeptide chain of six or more amino acid residues with any amino acid sequence. The residues that make up the beginning and the end of the loop are close together in space with no intervening regular secondary structural motifs in between. They generally connect two protein domains comprised in a secondary protein structure, such as beta strands, or directly secondary protein structures, such as alpha helices. Said loops often allow a protein domain or a protein secondary structure to which they are connected by one end, to change its direction (N- to C-terminus, or C- to N-terminus) with respect to another protein domain or protein structure to which the loop is connected by its other end. They are most often located in the external surface of the protein and thus generally participate in interactions between the protein to which they belong and other molecules.

In a particular embodiment, the polypeptide of the first aspect of the invention is a variant nidogen G2 domain which contains a heterologous polypeptide within one or more of the loop regions. In one embodiment, the heterologous polypeptide is inserted within the loop region, i.e. the loop region conserves all the amino acids found in the cognate loop domain in SEQ ID NO:62 or SEQ ID NO:63 but the heterologous polypeptide is inserted between two consecutive amino acids. In another embodiment, the heterologous polypeptide within one or more of the loop regions is found as an insertion within the loop region which replaces the partially or completely the sequence of the loop region.

The length of the heterologous polypeptide is not particularly limitative. Thus, the heterologous polypeptide may comprise at least two, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100 or more amino acids.

In another embodiment, the polypeptide of the first aspect of the invention is a variant nidogen G2 domain which contains an heterologous polypeptide within one or more of the loop regions and which contains a mutation in one or more beta strands, wherein the mutation is located at position 9 in beta strand B as defined in SEQ ID NO:11 (corresponding to the amino acid at position 30 in SEQ ID NO:62 or at amino acid at position 459 in the human nidogen 1 precursor as defined in the sequence provided in the Uniprot Database with accession number P14543-1 (version dated Jul. 7, 2009) or SEQ ID NO:72), at position 1 in beta strand C as defined in SEQ ID NO:12 (corresponding to the amino acid at position 39 in SEQ ID NO:62 or at amino acid at position 468 in the human nidogen 1 precursor as defined in the sequence provided in the Uniprot Database with accession number P14543-1 (version dated Jul. 7, 2009) or SEQ ID NO:72), at position 10 in beta strand J as defined in SEQ ID NO:19 (corresponding to the amino acid position 210 in SEQ ID NO:62 or at amino acid at position 639 in the human nidogen 1 precursor as defined in the sequence provided in the Uniprot Database with accession number P14543-1 (version dated Jul. 7, 2009) or SEQ ID NO:72) or at position 3 in beta strand K as defined in SEQ ID NO:20 (corresponding to the amino acid position 221 in SEQ ID NO:62 or at amino acid at position 650 in the human nidogen 1 precursor as defined in the sequence provided in the Uniprot Database with accession number P14543-1 (version dated Jul. 7, 2009) or SEQ ID NO:72).

In one embodiment, the mutation at position 9 in beta strand B as defined in SEQ ID NO:11 is a H459A mutation, the mutation at position 1 in beta strand C as defined in SEQ ID NO:12 is a R468N mutation, the mutation at position 10 in beta strand J as defined in SEQ ID NO:19 is a F639S mutation and/or the at position 3 in beta strand K as defined in SEQ ID NO:20 is a R650A.

In one embodiment, the variant human nidogen G2 domain contains the H459A and the R468N mutations. In one embodiment, the variant human nidogen G2 domain contains the H459A and the F639S mutations. In one embodiment, the variant human nidogen G2 domain contains the H459A and the R650A mutations. In one embodiment, the variant human nidogen G2 domain contains the R468N and the F639S mutations. In one embodiment, the variant human nidogen G2 domain contains the R468N and the R650A mutations. In one embodiment, the variant human nidogen G2 domain contains the H459A, the R468N, and the F639S mutations. In one embodiment, the variant human nidogen G2 domain contains the H459A, the R468N, and the R650A mutations. In one embodiment, the variant human nidogen G2 domain contains the R468N, the F639S and the R650A mutations. In one embodiment, the variant human nidogen G2 domain contains the H459A, the R468N, the F639S and the R650A mutations. In a preferred embodiment, the nidogen G2 domain variant has a sequence as defined in SEQ ID NO:64 or 65 (hereinafter referred to as NIDOmut2).

In another embodiment, the polypeptide of the first aspect of the invention is a nidogen G2 domain variant as defined in any of the embodiments above and, in particular, the nidogen G2 domain variant having the H459A, the R468N, the F639S and the R650A mutations which, in addition, comprises a mutation at a position selected from the group consisting of 543 (corresponding to histidine at position 114 in SEQ ID NO:62) and position 545 (corresponding to histidine at position 116 in SEQ ID NO:62). In another embodiment, position H543 is mutated to Lys. In another embodiment, position H545 is mutated to Asn. In some embodiments, the polypeptide of the first aspect of the invention is a variant nidogen G2 domain that comprises the H459A, the R468N, the F639S, the R650A and the H543K mutations. In some embodiments, the polypeptide of the first aspect of the invention is a variant nidogen G2 domain that comprises the H459A, the R468N, the F639S, the R650A and the H545N mutations. In another embodiment, the nidogen G2 domain variant comprises a H543K mutation and a H545N mutation. In one embodiment, the nidogen G2 domain variant comprises or consists of SEQ ID NO:87 (hereinafter referred to NIDOmut3), which is characterized in that it contains the H459A, the R468N, the F639S, the R650A, the H543K and the H545N mutations.

In another embodiment, the polypeptide of the first aspect of the invention is a variant nidogen G2 domain as defined in any of the embodiments above and, in particular, the NIDOmut3 variant, which, in addition comprises a mutation selected from the group consisting of:

- a mutation at valine at position 449 (corresponding to position 20 in SEQ ID NO:62). Preferably, the valine at position 449 is mutated to Thr. In a preferred embodiment, the nidogen G2 domain variant has a sequence as defined in SEQ ID NO:88 (hereinafter referred to as NIDOmut3-V45T).
- a mutation at valine at position 525 (corresponding to position 96 in SEQ ID NO:62). Preferably, the valine at position 449 is mutated to Gln. In a preferred embodiment, the nidogen G2 domain variant has a sequence as defined in SEQ ID NO:89 (hereinafter referred to as NIDOmut3-V121Q).
- a mutation at the phenylalanine at position 561 (corresponding to position 142 in SEQ ID NO:62). Preferably, the phenylalanine at position 561 is mutated to Glutamic acid. In a preferred embodiment, the nidogen G2 domain variant has a sequence as defined in SEQ ID NO:90 (hereinafter referred to as NIDOmut3-F157E).
- a mutation at the valine at position 619 (corresponding to position 190 in SEQ ID NO:62). Preferably, the valine at position 619 is mutated to threonine. In a preferred embodiment, the nidogen G2 domain variant has a sequence as defined in of SEQ ID NO:91 (hereinafter referred to as NIDOmut3-V215T).

In another embodiment, the polypeptide of the first aspect of the invention is a variant nidogen G2 domain as defined in any of the embodiments above, and in addition comprises the V449T, the V525Q, the F561E and the V619T mutations. In some embodiments, the polypeptide of the first aspect of the invention is a variant nidogen G2 domain that comprises the H459A, the R468N, the F639S, the R650A, the H543K, the V449T, the V525Q, the F561E and the V619T mutations. In some embodiments, the polypeptide of the first aspect of the invention is a variant nidogen G2 domain that comprises the H459A, the R468N, the F639S, the R650A, the V449T, the H545N, the V525Q, the F561E and the V619T mutations. In some embodiments, the polypeptide of the first aspect of the invention is a variant nidogen G2 domain that comprises the H459A, the R468N, the F639S, the R650A, the H543K, the H545N, the V449T, the V525Q, the F561E and the V619T mutations. In another embodiment, the variant nidogen G2 domain comprises or consists of the sequence as defined in SEQ ID NO:92 (hereinafter referred to as NIDOmut4).

In another embodiment, the polypeptide of the first aspect of the invention is a variant nidogen G2 domain as defined in any of the embodiments above and, in particular the NIDOmut4), which in addition comprises a mutation at the threonine at position 619 (corresponding to position 190 in SEQ ID NO:62). Preferably, the threonine at position 619 is mutated to valine. In another embodiment, the polypeptide of the first aspect of the invention is a variant nidogen G2 domain as defined in any of the embodiments above in which the amino acid at position 619 (corresponding to position 190 in SEQ ID NO:62) is the same residue that appear in the human nidogen G2 domain as defined in the UniProt database under accession number P14534), i.e. a Valine. Accordingly, in one embodiment, the polypeptide of the first aspect of the invention is a nidogen G2 domain variant having the H459A, the R468N, the F639S, the R650A, the H543K, the H545N, the V449T, the V525Q and the F561E mutations. In one embodiment, the polypeptide of the first aspect of the invention is a nidogen G2 domain variant having the sequence of SEQ ID NO:93 (hereinafter referred to as NIDOmut4_T215V).

In another embodiment, the polypeptide of the first aspect of the invention is a variant nidogen G2 domain as defined in any of the embodiments above and, in particular, the NIDOMut4, which, in addition comprises a mutation at the cysteine at position 618 (corresponding to position 189 in SEQ ID NO:62). Preferably, the cysteine at position 618 is mutated to serine. Accordingly, in one embodiment, the polypeptide of the first aspect of the invention is a nidogen G2 domain variant having the H459A, the R468N, the F639S, the R650A, the H543K, the H545N, the V449T, the V525Q, the V619T, the F561E and the C618S mutations. In one embodiment, the polypeptide of the first aspect of the invention is a nidogen G2 domain variant having the sequence of SEQ ID NO:94 (hereinafter referred to as NIDOmut5).

In another embodiment, the polypeptide of the first aspect of the invention is a variant nidogen G2 domain as defined in any of the embodiments above and, in particular the NIDOMut3 variant, which in addition comprises a mutation selected from the group consisting of:

- a mutation at valine at position 580 (corresponding to position 151 in SEQ ID NO:62). Preferably, the valine at position 580 is mutated to Thr. In one embodiment, the polypeptide of the first aspect of the invention is a nidogen G2 domain variant having the sequence of SEQ ID NO:95 (hereinafter referred to as NIDOmut3-V176T).
- a mutation at isoleucine at position 604 (corresponding to position 175 in SEQ ID NO:62). Preferably, the isoleucine at position 604 is mutated to Thr. In one embodiment, the polypeptide of the first aspect of the invention is a nidogen G2 domain variant having the sequence of SEQ ID NO:96 (hereinafter referred to as NIDOmut3-1200T).
- a mutation at the valine at position 638 (corresponding to position 209 in SEQ ID NO:62). Preferably, the valine at position 638 is mutated to tyrosine. In one embodiment, the polypeptide of the first aspect of the invention is a nidogen G2 domain variant having the sequence of SEQ ID NO:97 (hereinafter referred to as NIDOmut3-V236Y).
- a mutation at the leucine at position 641 (corresponding to position 212 in SEQ ID NO:62). Preferably, the leucine at position 641 is mutated to threonine. In one embodiment, the polypeptide of the first aspect of the invention is a nidogen G2 domain variant having the sequence of SEQ ID NO:98 (hereinafter referred to as NIDOmut3-L237T).
- a mutation at serine at position 469 (corresponding to position 40 in SEQ ID NO:62). Preferably, the serine at position 469 is mutated to Ile. In one embodiment, the polypeptide of the first aspect of the invention is a nidogen G2 domain variant having the sequence of SEQ ID NO:99 (hereinafter referred to as NIDOmut3-S65I).
- a mutation at arginine at position 518 (corresponding to position 89 in SEQ ID NO:62). Preferably, the arginine at position 518 is mutated to Ile. In one embodiment, the polypeptide of the first aspect of the invention is a nidogen G2 domain variant having the sequence of SEQ ID NO:100 (hereinafter referred to as NIDOmut3-R114I.

a mutation at the cysteine at position 618 (corresponding to position 189 in SEQ ID NO:62). Preferably, the cysteine at position 618 is mutated to serine. Accordingly, in one embodiment, the polypeptide of the first aspect of the invention is a nidogen G2 domain variant having the sequence of SEQ ID NO:101 (hereinafter referred to as NIDOmut3-C214S).

In some embodiments, the polypeptide of the first aspect of the invention is a variant nidogen G2 domain as defined in any of the embodiments above and, in particular the NIDOmut3 variant, which, in addition, contains mutations at the 469 (preferably a S469I mutation) and at the 518 position (preferably a R518I mutation). Accordingly, in one embodiment, the polypeptide of the first aspect of the invention is a nidogen G2 domain variant having the H459A, the R468N, the F639S, the R650A, the H543K, the H545N, the S469I and the R518I mutations and corresponds to the sequence of SEQ ID NO:102 (hereinafter referred to as NIDOmut3-S65I_R114I).

In some embodiments, the polypeptide of the first aspect of the invention is a variant nidogen G2 domain as defined in any of the embodiments above and, in particular the NIDOmut5 variant, which, in addition, contains mutations at the 469 (preferably a S469I mutation) and at the 518 position (preferably a R518I mutation). Accordingly, in one embodiment, the polypeptide of the first aspect of the invention is a nidogen G2 domain variant having the H459A, the R468N, the F639S, the R650A, the H543K, the H545N, the V449T, the V525Q, the V619T, the F561E, the S469I and the R518I mutations, as defined in SEQ ID NO:103 (hereinafter referred to as NIDOmut5-S65I_R114I).

In some embodiments, the polypeptide of the first aspect of the invention is a variant nidogen G2 domain as defined in any of the embodiments above and, in particular the NIDOmut5 variant, which, in addition, contains a mutation at serine at position 469 (corresponding to position 40 in SEQ ID NO:62). Preferably, the serine at position 469 is mutated to Ile. Accordingly, in one embodiment, the polypeptide of the first aspect of the invention is a nidogen G2 domain variant having the H459A, the R468N, the F639S, the R650A, the H543K, the H545N, the V449T, the V525Q, the V619T, the F561E and the S469I mutations. In one embodiment, the polypeptide of the first aspect of the invention is a nidogen G2 domain variant having the sequence of SEQ ID NO:104 (hereinafter referred to as NIDOmut5-S65I).

In some embodiments, the polypeptide of the first aspect of the invention is a variant nidogen G2 domain as defined in any of the embodiments above and, in particular the NIDOmut5 variant, which, in addition, contains a mutation at arginine at position 518 (corresponding to position 89 in SEQ ID NO:62). Preferably, the arginine at position 518 is mutated to Ile Accordingly, in one embodiment, the polypeptide of the first aspect of the invention is a nidogen G2 domain variant having the H459A, the R468N, the F639S, the R650A, the H543K, the H545N, the V449T, the V525Q, the V619T, the F561E and the R518I mutations. In one embodiment, the polypeptide of the first aspect of the invention is a nidogen G2 domain variant having the sequence of SEQ ID NO:104 (hereinafter referred to as NIDOmut5-R114I).

The nidogen G2 domain variants suitable for use in the present invention are summarized in the Table below.

TABLE 1

Summary table of nidogen G2 domain variants suitable for use in the present invention. Numbering of positions in the G2 domain as in the sequence with accession number P14543-1 in the Uniprot Database version dated Jul. 7, 2009.

| Nidogen G2 domain variant | Mutations with respect to the native human nidogen (numbering of positions as in the sequence with accession number P14543-1 in the Uniprot Database version dated Jul. 7, 2009 |
|---|---|
| NIDOmut2 | H459A, R468N, F639S, R650A |
| NIDOmut3 | H459A, R468N, F639S, R650A, H543K, H545N |
| NIDOmut3_V45T | H459A, R468N, F639S, R650A, H543K, H545N, V449T |
| NIDOmut3_V121Q | H459A, R468N, F639S, R650A, H543K, H545N, V525Q |
| NIDOmut3-F157E | H459A, R468N, F639S, R650A, H543K, H545N, F561E |
| NIDOmut3-V215T | H459A, R468N, F639S, R650A, H543K, H545N, V619T |
| NIDOmut4 | H459A, R468N, F639S, R650A, H543K, H545N, V449T, V525Q, F561E, V619T |
| NIDOmut4_T215V | H459A, R468N, F639S, R650A, H543K, H545N, V449T, V525Q, F561E |
| NIDOmut5 | H459A, R468N, F639S, R650A, H543K, H545N, V449T, V525Q, V619T, F561E, C618S |
| NIDOmut3-V176T | H459A, R468N, F639S, R650A, H543K, H545N, V580T |
| NIDOmut3-I200T | H459A, R468N, F639S, R650A, H543K, H545N, I604T |
| NIDOmut3-V236Y | H459A, R468N, F639S, R650A, H543K, H545N, V640Y |
| NIDOmut3-L237T | H459A, R468N, F639S, R650A, H543K, H545N, L641T |
| NIDOmut3-S65I | H459A, R468N, F639S, R650A, H543K, H545N, S469I |
| NIDOmut3-R114I | H459A, R468N, F639S, R650A, H543K, H545N, R518I |
| NIDOmut3-C214S | H459A, R468N, F639S, R650A, H543K, H545N, C618S |
| NIDOmut3-S65I_R114I | H459A, R468N, F639S, R650A, H543K, H545N, S469I R518I |
| NIDOmut5-S65I_R114I | H459A, R468N, F639S, R650A, H543K, H545N, V449T, V525Q, V619T, F561E, C618S, S469I, R518I |
| NIDOmut5-S65I | H459A, R468N, F639S, R650A, H543K, H545N, V449T, V525Q, V619T, F561E, C618S, S469I |
| NIDOmut5_R114I | H459A, R468N, F639S, R650A, H543K, H545N, V449T, V525Q, V619T, F561E, C618S, R518I |

The heterologous polypeptide may be inserted within the loop region, i.e. the loop region conserves all the amino acids found in the cognate loop domain in SEQ ID NO:62 or SEQ ID NO:63 but the heterologous polypeptide is inserted between two consecutive amino acids. The length of the heterologous polypeptide is not particularly limitative. Thus, the heterologous polypeptide may comprise at least two, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100 or more amino acids.

In another embodiment, the heterologous polypeptide may be replacing part of the loop region, i.e. the loop region contains a deletion with respect to the sequence of the cognate loop domain in SEQ ID NO:62 or SEQ ID NO:63 and the deleted sequence is replaced by the heterologous polypeptide is inserted between two consecutive amino acids. It will be understood that the length of the deletion need not be the same as the length of the heterologous peptide. Accordingly, the loop region may contain a deletion which is of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or of 100% of the total length of the region. The length of the heterologous polypeptide is not particularly limitative. Thus, the heterologous polypeptide may comprise at least two, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100 or more amino acids.

Wherein the variant G2 nidogen domain contains more than one heterologous polypeptide, the heterologous polypeptides may be found within the same loop region or, preferably, in different loop regions. Moreover, wherein the variant G2 nidogen domain contains more than one heterologous polypeptide, the heterologous polypeptides may be the same or different.

The heterologous polypeptide forming part of the variant G2 nidogen domain according to the invention specifically binds to a target peptide. More preferably, the heterologous polypeptide specifically binds to a target peptide which does not show any specific binding for any other region of the variant G2 nidogen domain of the invention or of the first polypeptide of the invention.

The term “binding”, “bond”, “binds”, according to the invention refers to the interaction of affinity binding molecules, or specific binding pairs, between them, as a result of non-covalent bonds, such as, but not limited to, hydrogen bonds, hydrophobic interactions, van der Waals bonds, ionic bonds or a combination of the above.

The expression “specifically binds”, “specifically binding”, “specifically recognizes”, or “specifically interacts”, when used in the present invention to refer to the binding of a polypeptide to a specific or target molecule, is understood as the capacity of said polypeptide to bind specifically to said molecule by means of complementarity between the three-dimensional structures of the two polypeptide and the target molecule, with a substantially high affinity such that the binding between said polypeptide and the target molecule preferably takes place before the binding of said polypeptide with other molecules present in proximity, such as in a reaction mixture. The capacity of a polypeptide to specifically bind to a target molecule in a reaction mixture may be tested, for example, by assessing binding of said polypeptide under conventional conditions to the target molecule of interest as well as to a number of more or less (structurally and/or functionally) closely related molecules. Only if the polypeptide binds to the target molecule but does not or does not essentially bind to any other closely related molecules, said binding is considered specific for the target molecule. A binding between a polypeptide and a target molecule can be considered specific if the binding affinity between both has a dissociation constant (KD) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M or less than $10^{-15}$ M. Methods to determine the binding between a polypeptide and a target molecule, and the KD of said binding, include methods well-known by an expert in the field. Non-limiting examples of such methods include gel-shift assays, such as electrophoretic mobility shift assay (EMSA), co-immunoprecipitation assays followed by: mass spectrometry, gas chromatography associated to mass spectrometry, liquid chromatography associated to mass spectrometry, or western blot analysis. An additional method is the oil-cushion method [see Hesselgesset et al, 1998, J. Immunol., 160:877-883].

In a particular embodiment, the binding of the polypeptide to a target molecule is considered specific, if the binding between said polypeptide and the target molecule has a dissociation constant (KD) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M or less than $10^{-15}$ M. Similarly, the binding between a loop region and a specific target molecule is considered specific, if the binding between said loop region and the target molecule has a dissociation constant (KD) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M or less than $10^{-15}$ M.

In the polypeptide of the invention, loop region AB connects beta strands A and B, loop region BC connects beta strands B and C, loop region CD connects beta strands C and D, loop region DE connects beta strands D and E, loop region EF connects beta strands E and F, loop region FG' connects beta strands F and G, loop region GH connects beta strands G and H, loop region HI connects beta strands H and I, loop region IJ connects beta strands I and J and loop region JK connects beta strands J and K In a particular embodiment, beta strand A is connected to beta strand B by loop region AB in the polypeptide of the first aspect of the invention. In another particular embodiment, beta strand B is connected to beta strand C by loop region BC in the polypeptide of the first aspect of the invention. In another particular embodiment, beta strand C is connected to beta strand D by loop region CD in the polypeptide of the first aspect of the invention. In another particular embodiment, beta strand D is connected to beta strand E by loop region DE in the polypeptide of the first aspect of the invention. In another particular embodiment, beta strand E is connected to beta strand F by loop region EF in the polypeptide of the first aspect of the invention. In another particular embodiment, beta strand F is connected to beta strand G by loop region FG in the polypeptide of the first aspect of the invention. In another particular embodiment, beta strand G is connected to beta strand H by loop region GH in the polypeptide of the first aspect of the invention. In another particular embodiment, beta strand H is connected to beta strand I by loop region HI in the polypeptide of the first aspect of the invention. In another particular embodiment, beta strand I is connected to beta strand J by loop region IJ in the polypeptide of the first aspect of the invention. In another particular embodiment, beta strand J is connected to beta strand K by loop region JK in the polypeptide of the first aspect of the invention.

The expression “cognate loop region in SEQ ID NO:62” as used herein, refers to a loop region as it appears in SEQ ID NO:62, which is the wild-type nidogen G2 domain of human origin. As it will be understood by a skilled person, each loop region in the polypeptide of the first aspect of the invention has its cognate loop region in SEQ ID NO:62.

As it will be understood by a skilled person, two amino acid sequences are considered to encode the same protein domains or secondary protein structures, if they show a certain degree of sequence identity and they encode the same type of protein domain or of protein secondary structure, i.e. they both form a beta strand, a loop region, an alpha helix, an α-helical segment, a beta sheet, or beta barrel. In a particular embodiment, the amino acid sequence encoding two protein domains or secondary protein structures that are considered to be the same, show a degree of sequence identity of at least 50%, at least 60%, at least 70%, at least 75%, at least 80%, at least 85%, at least 90%, at least 95%, at least 98%, at least 99%, at least 99.5% at least 99.75%, at least 99.8%, at least 99.9%, at least 99.95%, at least 99.975%, at least 99.99%. The degree of identity between two amino acid sequences can be determined by conventional methods, for example, by means of standard sequence alignment algorithms known in the state of the art, such as, for example BLAST [Altschul S. F. et al., J. Mol. Biol, 1990 Oct. 5; 215 (3): 403-10]. Methods to determine whether an amino acid sequence within a protein forms, or maintains, a specific domain or protein secondary structure are well known by a skilled person, and include methods to determine the secondary structure of a protein such as the bioinformatics tool DSSPcont (Carter, Andersen, & Rost, 2003) and STRIDE (Heinig & Frishman, 2004), once the atomic coordinates of the protein has been obtained following methods well-known by a skilled person, such as X-ray crystallography or protein NMR.

The cognate loop region in SEQ ID NO:62 of loop regions AB comprises, essentially comprises or consists of SEQ ID NO:1. In another particular embodiment, the cognate loop region in SEQ ID NO:62 of loop region BC comprises, essentially comprises or consists of SEQ ID NO:2. In another particular embodiment, the cognate loop region in SEQ ID NO:62 of loop region CD comprises, essentially comprises or consists of SEQ ID NO. 3. In another particular embodiment, the cognate loop region in SEQ ID NO. 62 of loop region DE comprises, essentially comprises or consists of SEQ ID NO:4. In another particular embodiment, the cognate loop region in SEQ ID NO:62 of loop region EF comprises, essentially comprises or consists of SEQ ID NO:5. In another particular embodiment, the cognate loop region in SEQ ID NO:62 of loop region FG comprises, essentially comprises or consists of SEQ ID NO:6. In another particular embodiment, the cognate loop region in SEQ ID NO:62 of loop region GH comprises, essentially comprises or consists of amino acids 149 to 150 in SEQ ID NO:62. In another particular embodiment, the cognate loop region in SEQ ID NO:62 of loop region HI comprises, essentially comprises or consists of SEQ ID NO:7. In another particular embodiment, the cognate loop region in SEQ ID NO:62 of loop region IJ comprises, essentially comprises or consists of SEQ ID NO:8. In another particular embodiment, the cognate loop region in SEQ ID NO:62 of loop region JK comprises, essentially comprises or consists of SEQ ID NO:9.

In particular embodiment, a loop region of the polypeptide of the first aspect of the invention is a variant of its cognate loop region in SEQ ID NO:62.

The expression "a loop region variant", as used herein, refers to a loop region of the polypeptide of the first aspect that comprises in its sequence a modification, insertion and/or deletion of one or more amino acids with respect to the sequence of its cognate loop region in SEQ ID NO:62. In a particular embodiment said loop region from the polypeptide of the first aspect is elected from the group of loop regions consisting of AB, BC, CD, DE, EF, FG, GH, HI, IJ and JK.

Thus, in a particular embodiment, the variant of at least one of the loop regions of the polypeptide of the first aspect of the invention results from the mutation by deletion, substitution or addition of at least one amino acid in the sequence of its cognate loop region in SEQ ID: 62.

In a certain embodiment, the loop region variant of the polypeptide of the first aspect has a degree of sequence identity with the sequence of its cognate loop region in SEQ ID NO:62 of at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%. Methods to determine the degree of sequence identity between two sequences have been provided above.

In a particular embodiment, loop region AB is a loop region variant of its cognate loop region in SEQ ID NO:62. In another particular embodiment, loop region BC is a loop region variant of its cognate loop region in SEQ ID NO:62. In another particular embodiment, loop region CD is a loop region variant of its cognate loop region in SEQ ID NO:62. In another particular embodiment, loop region DE is a loop region variant of its cognate loop region in SEQ ID NO:62. In another particular embodiment, loop region EF is a loop region variant of its cognate loop region in SEQ ID NO:62. In another particular embodiment, loop region FG is a loop region variant of its cognate loop region in SEQ ID NO:62. In another particular embodiment, loop region GH is a loop region variant of its cognate loop region in SEQ ID NO:62. In another particular embodiment, loop region HI is a loop region variant of its cognate loop region in SEQ ID NO:62. In another particular embodiment, loop region IJ is a loop region variant of its cognate loop region in SEQ ID NO:62. In another particular embodiment, loop region JK is a loop region variant of its cognate loop region in SEQ ID NO:62.

In a particular embodiment, the sequence of the AB loop region in the variant nidogen G2 domain according to the invention is a variant of SEQ ID NO:1, whereas the sequence of at least 1, at least 2, at least 3, at least 4, at least 5, at least 6, at least 7, at least 8 or all of the BC, CD, DE, EF, FG', GH, HI, IJ and JK loop regions of the polypeptide of the first aspect of the invention are identical to the sequences of their cognate loop region in SEQ ID NO:62. In another particular embodiment, the sequence of loop region AB is a variant of SEQ ID NO:1, and the sequence of at least 1, at least 2, at least 3, at least 4, at least 5, at least 6, at least 7, at least 8, at least 9, or all of the loop regions of the polypeptide of the first aspect of the invention is the sequence of their cognate loop region in SEQ ID NO:62. In another particular embodiment, the sequence of loop region AB is a variant of SEQ ID NO:1, and the rest of the sequence of the polypeptide of the first aspect of the invention is identical to the remaining of the sequence in SEQ ID NO:62.

In a certain embodiment, the loop region AB variant of SEQ ID NO:1 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:1.

In another particular embodiment, the sequence of loop region AB of the polypeptide of the first aspect of the invention is SEQ ID NO:1.

In a particular embodiment, the sequence of loop region BC is a variant of SEQ ID NO:2. In another particular embodiment, the sequence of loop region BC is a variant of SEQ ID NO:2, and the sequence of at least 1, at least 2, at least 3, at least 4, at least 5, at least 6, at least 7, at least 8 or all of the AB, CD, DE, EF, FG, GH, HI, IJ and JK loop regions of the polypeptide of the first aspect of the invention is the sequence of their cognate loop region in SEQ ID NO:62 indicated above. In another particular embodiment, the sequence of loop region BC is a variant of SEQ ID NO:2, and the sequence of at least 1, at least 2, at least 3, at least 4, at least 5, at least 6, at least 7, at least 8 or all of the loop regions of the polypeptide of the first aspect of the invention is the sequence of their cognate loop region in SEQ ID NO:62. In another particular embodiment, the sequence of loop region BC is a variant of SEQ ID NO:2, and the rest of the sequence of the polypeptide of the first aspect of the invention is as the rest of the sequence in SEQ ID NO:62.

In a certain embodiment, the loop region BC variant of SEQ ID NO:2 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:2.

In another particular embodiment, the sequence of loop region BC of the polypeptide of the first aspect of the invention is SEQ ID NO:2.

In a particular embodiment, the sequence of loop region CD is a variant of SEQ ID NO:3. In another particular embodiment, the sequence of loop region CD is a variant of SEQ ID NO:3, and sequence of at least 1, at least 2, at least 3, at least 4, at least 5, at least 6, at least 7, at least 8, at least 9, or all of the AB, BC, DE, EF, FG, GH, HI, IJ and JK, loop regions of the first aspect of the invention is the sequence of their cognate loop region in SEQ ID NO:62 indicated above. In another particular embodiment, the sequence of loop region CD is a variant of SEQ ID NO:3, and sequence of at least 1, at least 2, at least 3, at least 4, at least 5, at least 6, at least 7, at least 8, at least 9, or all of the loop regions of the polypeptide of the first aspect of the invention have the sequence of their cognate loop region in SEQ ID NO:62. In another particular embodiment, the sequence of loop region CD is a variant of SEQ ID NO:3, and the rest of the sequence of the polypeptide of the first aspect of the invention is as the rest of the sequence in SEQ ID NO:62.

In a certain embodiment, the loop region CD variant of SEQ ID NO:3 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:3.

In another particular embodiment, the sequence of loop region CD of the polypeptide of the first aspect of the invention is SEQ ID NO:3.

In a particular embodiment, the sequence of the loop region CD is a variant of the cognate domain in SEQ ID NO:62 in which sequence is modified with respect to the cognate region in those regions of the loop which do not show alpha-helical structure. As shown by Hopf et al. (supra.), the CD loop region in the native G2 domain contains three regions with alpha helical structures, which are known as α1, α2 and α3. These regions are defined as SEQ ID NO:21, 22 and 23, respectively. These regions separate the CD loop region into 4 loop regions which correspond, respectively, to the region between the end of the beta strand C and α1 (hereinafter Cα region) between α1 and α2, between α2 and α3 and between α3 and the beginning of beta strand D (hereinafter αD region). In one embodiment, the Cα region comprises, essentially comprises or consists of SEQ ID NO:24. In one embodiment, the αD region comprises, essentially comprises or consists of amino acids GG.

In one embodiment, the sequence of the loop region is a variant of the cognate region SEQ ID NO:3 in which the sequences of SEQ ID NO:21, 22 and 23 are preserved with respect to the cognate region. In another embodiment, the sequence of the loop region is a variant of the cognate region SEQ ID NO:3 contains one or more mutations in the Cα region. In another embodiment, the sequence of the loop region is a variant of the cognate region SEQ ID NO:3 contains one or more mutations in the αD region. In another embodiment, the sequence of the loop region is a variant of the cognate region SEQ ID NO:3 contains one or more mutations in the Cα region and in the αD region.

In a certain embodiment, the Cα region in the polypeptide of the invention has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:24.

In another particular embodiment, the sequence of loop region Ca of the polypeptide of the first aspect of the invention is SEQ ID NO:24.

In a certain embodiment, the loop region αD variant has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with the sequence consisting of amino acids GG.

In a particular embodiment, the sequence of loop region DE is a variant of SEQ ID NO:4. In another particular embodiment, the sequence of loop region DE is a variant of SEQ ID NO:4, and sequence of at least 1, at least 2, at least 3, at least 4, at least 5, at least 6, at least 7, at least 8, at least 9, or all of the AB, BC, CD, EF, FG, GH, HI, IJ and JK loop regions of the polypeptide of first aspect of the invention contains the sequence of their cognate loop region in SEQ ID NO:62 indicated above. In another particular embodiment, the sequence of loop region DE is a variant of SEQ ID NO:4, and sequence of at least 1, at least 2, at least 3, at least 4, at least 5, at least 6, at least 7, at least 8, at least 9, or all of the loop regions of the polypeptide of the first aspect of the invention is the sequence of their cognate loop region in SEQ ID NO:62. In another particular embodiment, the sequence of loop region DE is a variant of SEQ ID NO:4, and the rest of the sequence of the polypeptide of the first aspect of the invention is as the rest of the sequence in SEQ ID NO:62.

In a certain embodiment, the loop region DE variant of SEQ ID NO:4 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:4.

In another particular embodiment, the sequence of loop region DE of the polypeptide of the first aspect of the invention is SEQ ID NO:4.

In a particular embodiment, the sequence of loop region EF is a variant of SEQ ID NO:5. In another particular embodiment, the sequence of loop region EF is a variant of SEQ ID NO:5, and sequence of at least 1, at least 2, at least 3, at least 4, at least 5, at least 6, at least 7, at least 8, at least 9, or all of the AB, BC, CD, DE, FG, GH, HI, IJ and JK loop regions of the first aspect of the invention is the sequence of their cognate loop region in SEQ ID NO:62 indicated above. In another particular embodiment, the sequence of loop region EF is a variant of SEQ ID NO:5, and sequence of at least 1, at least 2, at least 3, at least 4, at least 5, at least 6, at least 7, at least 8, at least 9, or all of the loop regions of the polypeptide of the first aspect of the invention is the sequence of their cognate loop region in SEQ ID NO:62. In another particular embodiment, the sequence of loop region EF is a variant of SEQ ID NO:5, and the rest of the sequence of the polypeptide of the first aspect of the invention is as the rest of the sequence in SEQ ID NO:62.

In a certain embodiment, the loop region EF variant of SEQ ID NO:5 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:5.

In another particular embodiment, the sequence of loop region EF of the polypeptide of the first aspect of the invention is SEQ ID NO:5.

In a particular embodiment, the sequence of loop region FG is a variant of SEQ ID NO:6. In another particular embodiment, the sequence of loop region FG is a variant of SEQ ID NO:6, and sequence of at least 1, at least 2, at least 3, at least 4, at least 5, at least 6, at least 7, at least 8, at least 9, or all of the AB, BC, CD, DE, EF, GH, HI, IJ and JK is the sequence of their cognate loop region in SEQ ID NO:62 indicated above. In another particular embodiment, sequence of loop region FG is a variant of SEQ ID NO:6, and sequence of at least 1, at least 2, at least 3, at least 4, at least 5, at least 6, at least 7, at least 8, at least 9, or all of the loop regions of the polypeptide of the first aspect of the invention is the sequence of their cognate loop region in SEQ ID NO:62. In another particular embodiment, the sequence of loop region FG is a variant of SEQ ID NO:6, and the rest of the sequence of the polypeptide of the first aspect of the invention is as the rest of the sequence in SEQ ID NO:62.

In a certain embodiment, the loop region FG variant of SEQ ID NO:6 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:6.

In another particular embodiment, the sequence of loop region FG of the polypeptide of the first aspect of the invention is SEQ ID NO:6.

In a particular embodiment, the sequence of loop region GH is a variant of the sequence TS, corresponding to amino acids 149 to 150 in SEQ ID NO:62 (or amino acids 147 to 148 in SEQ ID NO:63). In another particular embodiment, the sequence of loop region GH is a variant of the sequence corresponding to amino acids 149 to 150 in SEQ ID NO:62, and sequence of at least 1, at least 2, at least 3, at least 4, at least 5, at least 6, at least 7, at least 8, at least 9, or all of the AB, BC, CD, DE, EF, FG, HI, IJ and JK of the polypeptide of the first aspect of the invention is the sequence of their cognate loop region in SEQ ID NO:62 indicated above. In another particular embodiment, the sequence of loop region GH is a variant of the sequence corresponding to amino acids 149 to 150 in SEQ ID NO:62, and sequence of at least 1, at least 2, at least 3, at least 4, at least 5, at least 6, at least 7, at least 8, at least 9, or all of the loop regions of the polypeptide of the first aspect of the invention is the sequence of their cognate loop region in SEQ ID NO:62. In another particular embodiment, the sequence of loop region GH is a variant of the sequence corresponding to amino acids 149 to 150 in SEQ ID NO:62, and the rest of the sequence of the polypeptide of the first aspect of the invention is as the rest of the sequence in SEQ ID NO:62.

In a certain embodiment, the loop region GH variant of the sequence corresponding to amino acids 149 to 150 in SEQ ID NO:62 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with the sequence corresponding to amino acids 149 to 150 in SEQ ID NO:62.

In another particular embodiment, the sequence of loop region GH of the polypeptide of the first aspect of the invention is the sequence corresponding to amino acids 149 to 150 in SEQ ID NO:62.

In a particular embodiment, the sequence of loop region HI is a variant of SEQ ID NO:7. In another particular embodiment, the sequence of loop region HI is a variant of SEQ ID NO:7, and sequence of at least 1, at least 2, at least 3, at least 4, at least 5, at least 6, at least 7, at least 8, at least 9, or all of the AB, BC, CD, DE, EF, FG, GH, IJ and JK of the polypeptide of the first aspect of the invention is the sequence of their cognate loop region in SEQ ID NO:62 indicated above. In another particular embodiment, the sequence of loop region HI is a variant of SEQ ID NO:7, and sequence of at least 1, at least 2, at least 3, at least 4, at least 5, at least 6, at least 7, at least 8, at least 9, or all of the loop regions of the polypeptide of the first aspect of the invention is the sequence of their cognate loop region in SEQ ID NO:62. In another particular embodiment, the sequence of loop region HI is a variant of SEQ ID NO:7, and the rest of the sequence of the polypeptide of the first aspect of the invention is as the rest of the sequence in SEQ ID NO:62.

In a certain embodiment, the loop region HI variant of SEQ ID NO:7 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:7.

In another particular embodiment, the sequence of loop region HI of the polypeptide of the first aspect of the invention is SEQ ID NO:7.

In a particular embodiment, the sequence of loop region IJ is a variant of SEQ ID NO:8. In another particular embodiment, the sequence of loop region IJ is a variant of SEQ ID NO:8, and sequence of at least 1, at least 2, at least 3, at least 4, at least 5, at least 6, at least 7, at least 8, at least 9, or all of the AB, BC, CD, DE, EF, FG, GH, HI, and JK loop regions of polypeptide of the first aspect of the invention is the sequence of their cognate loop region in SEQ ID NO:62 indicated above. In another particular embodiment, the sequence of loop region IJ is a variant of SEQ ID NO:8, and sequence of at least 1, at least 2, at least 3, at least 4, at least 5, at least 6, at least 7, at least 8, at least 9, or all of the loop regions of the polypeptide of the first aspect of the invention is the sequence of their cognate loop region in SEQ ID NO:62. In another particular embodiment, the sequence of loop region IJ is a variant of SEQ ID NO:8, and the rest of the sequence of the polypeptide of the first aspect of the invention is as the rest of the sequence in SEQ ID NO:62.

In a certain embodiment, the loop region IJ variant of SEQ ID NO:8 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:8.

In another particular embodiment, the sequence of loop region IJ of the polypeptide of the first aspect of the invention is SEQ ID NO:8.

In a particular embodiment, the sequence of loop region JK is a variant of SEQ ID NO:9. In another particular embodiment, the sequence of loop region JK is a variant of SEQ ID NO:9, and sequence of at least 1, at least 2, at least 3, at least 4, at least 5, at least 6, at least 7, at least 8, at least 9, or all of the AB, BC, CD, DE, EF, FG, GH, HI, and IJ of the polypeptide of the first aspect of the invention is the sequence of their cognate loop region in SEQ ID NO:62 indicated above. In another particular embodiment, the sequence of loop region JK is a variant of SEQ ID NO:9, and sequence of at least 1, at least 2, at least 3, at least 4, at least 5, at least 6, at least 7, at least 8, at least 9, or all of the loop regions of the polypeptide of the first aspect of the invention is the sequence of their cognate loop region in SEQ ID NO:62. In another particular embodiment, the sequence of loop region JK is a variant of SEQ ID NO:9, and the rest of the sequence of the polypeptide of the first aspect of the invention is as the rest of the sequence in SEQ ID NO:62.

In a certain embodiment, the loop region JK variant of SEQ ID NO:9 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:10.

In another particular embodiment, the sequence of loop region JK of the polypeptide of the first aspect of the invention is SEQ ID NO:9.

In a particular embodiment, at least one of the sequences located upstream, immediately upstream, downstream or immediately downstream a variant loop region in the polypeptide of the first aspect of the invention comprises a modification, insertion and/or deletion of one or more amino acids with respect to the sequence (referred to as its reference sequence) in SEQ ID NO:62, placed in the same location with respect to the cognate loop region of said loop region variant. However, said at least one sequence encode the same protein domain or secondary structures, as defined above, in the polypeptide of the first aspect of the invention as its reference sequence in the polypeptide with SEQ ID NO:62. Methods to determine if two amino acid sequences form the same protein domain or secondary structure, such as a loop region, an α-helical segment or an α-helix, are those provided above to determine if two amino acid sequences form the same protein structure.

In a particular embodiment, the at least one sequence comprising a modification, insertion and/or deletion of one or more amino acids with respect to its reference sequence, has at least at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, with its reference sequence in SEQ ID NO:62. Methods to determine the degree of sequence identity between two amino acid sequences have been provided above.

The expression "cognate beta strand domain in SEQ ID NO:62" as used herein, refers to a beta strand domain in SEQ ID NO:62 located between amino acid sequences in the protein with SEQ ID NO:62 encoding the same loop regions or protein secondary structures as the sequences between which said beta strand domain variant is located in the polypeptide of the first aspect of the invention. As it will be understood by a skilled person, each beta strand domain in the first polypeptide of the invention has its cognate beta strand domain in SEQ ID NO:62.

Each of the beta strands domains in the variant nidogen G2 domain may be identical to the cognate beta strand in SEQ ID NO:62 or may differ in one or more amino acids so that the overall sequence identity between the beta strand in the variant nidogen G2 domain and the cognate beta strand domain in SEQ ID NO:62 may be of at least 50%. In preferred embodiments, the sequence identity between the beta strand in the variant nidogen G2 domain and the cognate beta strand domain in SEQ ID NO:62 is of at least 55%, at least 60%, at least 65%, at least 70%, at least 75%, at least 80%, at least 85%, at least 90%, at least 95%, at least 96%, at least 97%, at least 98% or at least 99%.

In a particular embodiment, the beta strand domain A is a beta strand domain variant of its cognate beta strand domain in SEQ ID NO:62. In a particular embodiment, beta strand domain B is a beta strand domain variant of its cognate beta strand domain in SEQ ID NO:62. In a particular embodiment, beta strand domain C is a beta strand domain variant of its cognate beta strand domain in SEQ ID NO:62. In a particular embodiment, beta strand domain D is a beta strand domain variant of its cognate beta strand domain in SEQ ID NO:62. In a particular embodiment, beta strand domain E is a beta strand domain variant of its cognate beta strand domain in SEQ ID NO:62. In a particular embodiment, beta strand domain F is a beta strand domain variant of its cognate beta strand domain in SEQ ID NO:62. In a particular embodiment, beta strand domain G is a beta strand domain variant of its cognate beta strand domain in SEQ ID NO:62. In a particular embodiment, beta strand domain H is a beta strand domain variant of its cognate beta strand domain in SEQ ID NO:62. In a particular embodiment, beta strand domain I is a beta strand domain variant of its cognate beta strand domain in SEQ ID NO:62. In a particular embodiment, beta strand domain J is a beta strand domain variant of its cognate beta strand domain in SEQ ID NO:62. In a particular embodiment, beta strand domain K is a beta strand domain variant of its cognate beta strand domain in SEQ ID NO:62.

In a particular embodiment, a beta strand domain of the polypeptide of the first aspect of the invention is a variant of its cognate beta strand in SEQ ID NO:62.

The expression "beta strand domain variant", as used herein, refers to a beta strand domain from the polypeptide of the first aspect of the invention that comprises in its sequence a modification, insertion and/or deletion of one or more amino acids with respect to the sequence of its cognate beta strand domain in SEQ ID NO:62. In a particular embodiment, said beta strand domain from the polypeptide of the first aspect is selected from the group consisting of A, B, C, D, E, F, G, H, I, J or K, In a certain embodiment, the beta strand domain variant of the polypeptide of the first aspect has a degree of sequence identity with the sequence of its cognate beta strand domain in SEQ ID NO:62 of at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%. Methods to determine the degree of sequence identity have been provided above.

In a particular embodiment, the cognate beta strand domain in SEQ ID NO:62 for beta strand domain A has SEQ ID NO:10. In another particular embodiment, the cognate beta strand domain in SEQ ID NO:62 for beta strand domain B has SEQ ID NO:11. In another particular embodiment, the cognate beta strand domain in SEQ ID NO:62 for beta strand domain C has SEQ ID NO:12. In another particular embodiment, the cognate beta strand domain in SEQ ID NO:62 for beta strand domain D has SEQ ID NO:13. In another particular embodiment, the cognate beta strand domain in SEQ ID NO:62 for beta strand domain E has SEQ ID NO:14. In another particular embodiment, the cognate beta strand domain in SEQ ID NO:62 for beta strand domain F has SEQ ID NO:15. In another particular embodiment, the cognate beta strand domain in SEQ ID NO:62 for beta strand domain G has SEQ ID NO:16. In another particular embodiment, the cognate beta strand domain in SEQ ID NO:62 for beta strand domain H has SEQ ID NO:17. In another particular embodiment, the cognate beta strand domain in SEQ ID NO:62 for beta strand domain I has SEQ ID NO:18. In another particular embodiment, the cognate beta strand domain in SEQ ID NO:62 for beta strand domain J has SEQ ID NO:19. In another particular embodiment, the cognate beta strand domain in SEQ ID NO:62 for beta strand domain K has SEQ ID NO:20.

Accordingly, in a particular embodiment, the sequence of the beta strand A is a variant of SEQ ID NO:10. In another particular embodiment, the sequence of beta strand domain A is a variant of SEQ ID NO:10, and at least 1, at least 2, at least 3, at least 4, at least 5, at least 6, at least 7, at least 8, at least 9, or all of the B-K beta strand domains of the polypeptide of the first aspect of the invention have the sequence of their cognate beta strand domain in SEQ ID NO:62 indicated above. In another particular embodiment, the sequence of beta strand A is a variant of SEQ ID NO:10, and at least 1, at least 2, at least 3, at least 4, at least 5, at least 6, at least 7, at least 8, at least 9, or all of the beta strand domains of the polypeptide of the first aspect of the invention have the sequence of their cognate beta strand domain in SEQ ID NO:62. In another particular embodiment, the sequence of beta strand A is a variant of SEQ ID NO:10, and the rest of the sequence of the polypeptide of the first aspect of the invention is as the rest of the sequence in SEQ ID NO:62.

In a certain embodiment, the beta strand domain A variant of SEQ ID NO:10 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:11.

In another particular embodiment, the sequence of beta strand domain A of the polypeptide of the first aspect of the invention is SEQ ID NO:10.

In a particular embodiment, the sequence of the beta strand B is a variant of SEQ ID NO:11. In another particular embodiment, the sequence of beta strand domain B is a variant of SEQ ID NO:11, and at least 1, at least 2, at least 3, at least 4, at least 5, at least 6, at least 7, at least 8, at least 9, or all of the A, C-K beta strand domains of the polypeptide of the first aspect of the invention have the sequence of their cognate beta strand domain in SEQ ID NO:62 indicated above. In another particular embodiment, the sequence of beta strand B is a variant of SEQ ID NO:11, and at least 1, at least 2, at least 3, at least 4, at least 5, at least 6, at least 7, at least 8, at least 9, or all of the beta strand domains of the polypeptide of the first aspect of the invention have the sequence of their cognate beta strand domain in SEQ ID NO:62. In another particular embodiment, the sequence of beta strand B is a variant of SEQ ID NO:11, and the rest of the sequence of the polypeptide of the first aspect of the invention is as the rest of the sequence in SEQ ID NO:62.

In a certain embodiment, the beta strand domain B variant of SEQ ID NO:11 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:12.

In another particular embodiment, the sequence of beta strand domain B of the polypeptide of the first aspect of the invention is SEQ ID NO:11.

In a particular embodiment, the sequence of the beta strand C is a variant of SEQ ID NO:12. In another particular embodiment, the sequence of beta strand domain C is a variant of SEQ ID NO:12, and at least 1, at least 2, at least 3, at least 4, at least 5, at least 6, at least 7, at least 8, at least 9, or all of the A, B, D-K beta strand domains of the polypeptide of the first aspect of the invention have the sequence of their cognate beta strand domain in SEQ ID NO:62 indicated above. In another particular embodiment, the sequence of beta strand C is a variant of SEQ ID NO:12, and at least 1, at least 2, at least 3, at least 4, at least 5, at least 6, at least 7, at least 8, at least 9, or all of the beta strand domains of the polypeptide of the first aspect of the invention have the sequence of their cognate beta strand domain in SEQ ID NO:62. In another particular embodiment, the sequence of beta strand C is a variant of SEQ ID NO:12, and the rest of the sequence of the polypeptide of the first aspect of the invention is as the rest of the sequence in SEQ ID NO:62.

In a certain embodiment, the beta strand domain C variant of SEQ ID NO:12 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:12.

In another particular embodiment, the sequence of beta strand domain C of the polypeptide of the first aspect of the invention is SEQ ID NO:12.

In a particular embodiment, the sequence of the beta strand D is a variant of SEQ ID NO:13. In another particular embodiment, the sequence of beta strand domain D is a variant of SEQ ID NO:13, and at least 1, at least 2, at least 3, at least 4, at least 5, at least 6, at least 7, at least 8, at least 9, or all of the A-C, E-K beta strand domains of the polypeptide of the first aspect of the invention have the sequence of their cognate beta strand domain in SEQ ID NO:62 indicated above. In another particular embodiment, the sequence of beta strand D is a variant of SEQ ID NO:13, and at least 1, at least 2, at least 3, at least 4, at least 5, at least 6, at least 7, at least 8, at least 9, or all of the beta strand domains of the polypeptide of the first aspect of the invention have the sequence of their cognate beta strand domain in SEQ ID NO:62. In another particular embodiment, the sequence of beta strand D is a variant of SEQ ID NO:13, and the rest of the sequence of the polypeptide of the first aspect of the invention is as the rest of the sequence in SEQ ID NO:62.

In a certain embodiment, the beta strand domain D variant of SEQ ID NO:13 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:13.

In another particular embodiment, the sequence of beta strand domain D of the polypeptide of the first aspect of the invention is SEQ ID NO:13.

In a particular embodiment, the sequence of the beta strand E is a variant of SEQ ID NO:14. In another particular embodiment, the sequence of beta strand domain E is a variant of SEQ ID NO:14, and at least 1, at least 2, at least 3, at least 4, at least 5, at least 6, at least 7, at least 8, at least 9, or all of the A-D, F-K beta strand domains of the polypeptide of the first aspect of the invention have the sequence of their cognate beta strand domain in SEQ ID NO:62 indicated above. In another particular embodiment, the sequence of beta strand E is a variant of SEQ ID NO:14, and at least 1, at least 2, at least 3, at least 4, at least 5, at least 6, at least 7, at least 8, at least 9, or all of the beta strand domains of the polypeptide of the first aspect of the invention have the sequence of their cognate beta strand domain in SEQ ID NO:62. In another particular embodiment, the sequence of beta strand E is a variant of SEQ ID NO:14, and the rest of the sequence of the polypeptide of the first aspect of the invention is as the rest of the sequence in SEQ ID NO:62.

In a certain embodiment, the beta strand domain E variant of SEQ ID NO:14 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:14.

In another particular embodiment, the sequence of beta strand domain E of the polypeptide of the first aspect of the invention is SEQ ID NO:14.

In a particular embodiment, the sequence of the beta strand F is a variant of SEQ ID NO:15. In another particular embodiment, the sequence of beta strand domain F is a variant of SEQ ID NO:15, and at least 1, at least 2, at least 3, at least 4, at least 5, at least 6, at least 7, at least 8, at least 9, or all of the A-E, G-K beta strand domains of the polypeptide of the first aspect of the invention have the sequence of their cognate beta strand domain in SEQ ID NO:62 indicated above. In another particular embodiment, the sequence of beta strand F is a variant of SEQ ID NO:15, and at least 1, at least 2, at least 3, at least 4, at least 5, at least 6, at least 7, at least 8, at least 9, or all of the beta strand domains of the polypeptide of the first aspect of the invention have the sequence of their cognate beta strand domain in SEQ ID NO:62. In another particular embodiment, the sequence of beta strand F is a variant of SEQ ID NO:15, and the rest of the sequence of the polypeptide of the first aspect of the invention is as the rest of the sequence in SEQ ID NO:62.

In a certain embodiment, the beta strand domain F variant of SEQ ID NO:15 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:15.

In another particular embodiment, the sequence of beta strand domain F of the polypeptide of the first aspect of the invention is SEQ ID NO:15.

In a particular embodiment, the sequence of the beta strand G is a variant of SEQ ID NO:16. In another particular embodiment, the sequence of beta strand domain G is a variant of SEQ ID NO:16, and at least 1, at least 2, at least 3, at least 4, at least 5, at least 6, at least 7, at least 8, at least 9, or all of the A-F and H-K beta strand domains of the polypeptide of the first aspect of the invention have the sequence of their cognate beta strand domain in SEQ ID NO:62 indicated above. In another particular embodiment, the sequence of beta strand G is a variant of SEQ ID NO:16, and at least 1, at least 2, at least 3, at least 4, at least 5, at least 6, at least 7, at least 8, at least 9, or all of the beta strand domains of the polypeptide of the first aspect of the invention have the sequence of their cognate beta strand domain in SEQ ID NO:62. In another particular embodiment, the sequence of beta strand G is a variant of SEQ ID NO:16, and the rest of the sequence of the polypeptide of the first aspect of the invention is as the rest of the sequence in SEQ ID NO:62.

In a certain embodiment, the beta strand domain G variant of SEQ ID NO:16 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:16.

In another particular embodiment, the sequence of beta strand domain G of the polypeptide of the first aspect of the invention is SEQ ID NO:16.

In a particular embodiment, the sequence of the beta strand H is a variant of SEQ ID NO:17. In another particular embodiment, the sequence of beta strand domain H is a variant of SEQ ID NO:18, and at least 1, at least 2, at least 3, at least 4, at least 5, at least 6, at least 7, at least 8, at least 9, or all of the A-G, I-K beta strand domains of the polypeptide of the first aspect of the invention have the sequence of their cognate beta strand domain in SEQ ID NO:62 indicated above. In another particular embodiment, the sequence of beta strand H is a variant of SEQ ID NO:17, and at least 1, at least 2, at least 3, at least 4, at least 5, at least 6, at least 7, at least 8, at least 9, or all of the beta strand domains of the polypeptide of the first aspect of the invention have the sequence of their cognate beta strand domain in SEQ ID NO:62. In another particular embodiment, the sequence of beta strand H is a variant of SEQ ID NO:17, and the rest of the sequence of the polypeptide of the first aspect of the invention is as the rest of the sequence in SEQ ID NO:62.

In a certain embodiment, the beta strand domain H variant of SEQ ID NO:17 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:17.

In another particular embodiment, the sequence of beta strand domain H of the polypeptide of the first aspect of the invention is SEQ ID NO:17

In a particular embodiment, the sequence of the beta strand I is a variant of SEQ ID NO:18. In another particular embodiment, the sequence of beta strand domain I is a variant of SEQ ID NO:18, and at least 1, at least 2, at least 3, at least 4, at least 5, at least 6, at least 7, at least 8, at least 9, or all of the A-H, J, K beta strand domains of the polypeptide of the first aspect of the invention have the sequence of their cognate beta strand domain in SEQ ID NO:62 indicated above. In another particular embodiment, the sequence of beta strand I is a variant of SEQ ID NO:18, and at least 1, at least 2, at least 3, at least 4, at least 5, at least 6, at least 7, at least 8, at least 9, or all of the beta strand domains of the polypeptide of the first aspect of the invention have the sequence of their cognate beta strand domain in SEQ ID NO:62. In another particular embodiment, the sequence of beta strand I is a variant of SEQ ID NO:18, and the rest of the sequence of the polypeptide of the first aspect of the invention is as the rest of the sequence in SEQ ID NO:62.

In a certain embodiment, the beta strand domain I variant of SEQ ID NO:18 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:19.

In another particular embodiment, the sequence of beta strand domain I of the polypeptide of the first aspect of the invention is SEQ ID NO:18.

In a particular embodiment, the sequence of the beta strand J is a variant of SEQ ID NO:19. In another particular embodiment, the sequence of beta strand domain J is a variant of SEQ ID NO:19, and at least 1, at least 2, at least 3, at least 4, at least 5, at least 6, at least 7, at least 8, at least 9, or all of the A-I, K beta strand domains of the polypeptide of the first aspect of the invention have the sequence of their cognate beta strand domain in SEQ ID NO:62 indicated above. In another particular embodiment, the sequence of beta strand J is a variant of SEQ ID NO:19, and at least 1, at least 2, at least 3, at least 4, at least 5, at least 6, at least 7, at least 8, at least 9, or all of the beta strand domains of the polypeptide of the first aspect of the invention have the sequence of their cognate beta strand domain in SEQ ID NO:62. In another particular embodiment, the sequence of beta strand J is a variant of SEQ ID NO:19, and the rest of the sequence of the polypeptide of the first aspect of the invention is as the rest of the sequence in SEQ ID NO:62.

In a certain embodiment, the beta strand domain J variant of SEQ ID NO:19 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:19.

In another particular embodiment, the sequence of beta strand domain J of the polypeptide of the first aspect of the invention is SEQ ID NO:19.

In a particular embodiment, the sequence of the beta strand K is a variant of SEQ ID NO:20. In another particular embodiment, the sequence of beta strand domain K is a variant of SEQ ID NO:20, and at least 1, at least 2, at least 3, at least 4, at least 5, at least 6, at least 7, at least 8, at least 9, or all of the A-J beta strand domains of the polypeptide of the first aspect of the invention have the sequence of their cognate beta strand domain in SEQ ID NO:62 indicated above. In another particular embodiment, the sequence of beta strand K is a variant of SEQ ID NO:20, and at least 1, at least 2, at least 3, at least 4, at least 5, at least 6, at least 7, at least 8, at least 9, or all of the beta strand domains of the polypeptide of the first aspect of the invention have the sequence of their cognate beta strand domain in SEQ ID NO:62. In another particular embodiment, the sequence of beta strand K is a variant of SEQ ID NO:20, and the rest of the sequence of the polypeptide of the first aspect of the invention is as the rest of the sequence in SEQ ID NO:62.

In a certain embodiment, the beta strand domain K variant of SEQ ID NO:20 has at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% sequence identity with SEQ ID NO:20.

In another particular embodiment, the sequence of beta strand domain K of the polypeptide of the first aspect of the invention is SEQ ID NO:20.

In one embodiment, the polypeptide according to first aspect of the present invention contains a variant of at least one of the loop regions with respect with the cognate loop region in SEQ ID NO:62 which results from the mutation by deletion, substitution or addition of at least one amino acid with respect to the sequence of the cognate loop region. In one embodiment, the variant nidogen G2 domain contains a mutation in the loop region AB with respect to the cognate AB loop region SEQ ID NO:1. In one embodiment, the variant nidogen G2 domain contains a mutation in the loop region BC with respect to the cognate BC loop region SEQ ID NO:2. In one embodiment, the variant nidogen G2 domain contains a mutation in the loop region CD with respect to the cognate CD loop region SEQ ID NO:3. In one embodiment, the variant nidogen G2 domain contains a mutation in the loop region DE with respect to the cognate DE loop region SEQ ID NO:4. In one embodiment, the variant nidogen G2 domain contains a mutation in the loop region EF with respect to the cognate EF loop region SEQ ID NO:5. In one embodiment, the variant nidogen G2 domain contains a mutation in the loop region FG with respect to the cognate FG loop region SEQ ID NO:6. In one embodiment, the variant nidogen G2 domain contains a mutation in the loop region GH with respect to the cognate GH loop region corresponding to amino acids 149 to 150 in SEQ ID NO:62. In one embodiment, the variant nidogen G2 domain contains a mutation in the loop region HI with respect to the cognate HI loop region SEQ ID NO:7. In one embodiment, the variant nidogen G2 domain contains a mutation in the loop region IJ with respect to the cognate IJ loop region SEQ ID NO:8. In one embodiment, the variant nidogen G2 domain contains a mutation in the loop region JK with respect to the cognate JK loop region SEQ ID NO:9.

The α-helical segment CαD of the variant nidogen G2 domain may be identical to the cognate α-helical segment in SEQ ID NO:62 or may differ in one or more amino acids so that the overall sequence identity between the α-helical segment CαD in the variant nidogen G2 domain and the cognate α-helical segment in SEQ ID NO:62 with SEQ ID NO:26 may be of at least 50%.

In preferred embodiment, the sequence identity between the α-helical segment CαD in the variant nidogen G2 domain and the cognate α-helical segment in SEQ ID NO:62 with SEQ ID NO:24 is of at least 55%, at least 60%, at least 65%, at least 70%, at least 75%, at least 80%, at least 85%, at least 90%, at least 95%, at least 96%, at least 97%, at least 98% or at least 99%.

Methods to determine the degree of sequence identity have been provided above. In a particular embodiment, said α-helical segment CαD that differs in one or more amino acids as indicated just above is referred to as an α-helical segment variant of the cognate α-helical segment in SEQ ID NO:62.

In a particular embodiment, the polypeptide of the first aspect has a beta barrel structure. In a preferred embodiment, it has the beta barrel structure of the beta barrel domain of the G2 domain of nidogen-1. In a particular embodiment, it has the beta barrel structure of the sequence with SEQ ID NO:62.

The beta barrel domain of G2 domain of nidogen-1, and the beta barrel structure of the sequence with SEQ ID NO:62, consists of an 11-stranded beta-barrel. The beta strands of said beta barrel are herein referred to as I, II, III, IV, V, VI, VII, VIII, IX, X, XI. They correspond to the cognate beta strands in SEQ ID NO:62 of the beta strands A-K of the polypeptide of the first aspect. The interior of the beta barrel is traversed by the hydrophobic, predominantly alpha helical segment connecting strands III and IV. The N-terminal half of the barrel comprises two beta-meanders (strands I-III and IV-VI) linked by the buried alpha-helical segment. The polypeptide chain then crosses the bottom of the barrel and forms a five-stranded Greek key motif in the C-terminal half of the domain.

The expression "beta-meander", as used herein, refers to 2 or more consecutive antiparallel β-strands linked together by hairpin loops. The term "hairpin loop" as used herein, refers to two antiparallel strands linked by a short loop of two to five residues, of which one is frequently a glycine or a proline, both of which can assume the dihedral-angle conformations required for a tight turn or a β-bulge loop.

The expression "Greek key", as used herein, refers to a secondary protein structure consisting of four adjacent antiparallel strands and their linking loops. In this structure, three antiparallel strands are connected by hairpins, while the fourth is adjacent to the first and linked to the third by a longer loop.

Thus, in a particular embodiment, beta strands A-C as well as beta strands D-F of the variant of domain G2 form a beta meander. In another particular embodiment, said beta meanders are connected by the α-helical segment CαD of the variant of domain G2. In another particular embodiment, beta strands G-K of the variant of domain G2 form a five-stranded Greek key motif. In another particular embodiment, the beta strands of the variant of domain G2 are arranged in an antiparallel fashion, except beta strands A and F.

Methods to determine the secondary structure of a polypeptide, or whether two amino acid sequences encode the same domain or secondary protein structure have been provided above.

II—Polypeptide Display Library

In a second aspect, the invention relates to a polypeptide display library comprising a plurality of polypeptides according to the first aspect of the invention, wherein the plurality of polypeptides is formed by polypeptides that differ in the sequence of one or more loop regions.

The expression "polypeptide display library" as used herein, refers to a library, or pool, of polypeptides, comprising a plurality of polypeptides with different amino acid sequences. Each polypeptide of the library is as defined in the first aspect of the invention and differs from at least another polypeptide of the library in the sequence of one or more loop regions.

The expression "polypeptides that differ in the sequence of one or more loop regions", as used herein, refers to the fact that each polypeptide of the library shows at least one difference in its amino acid sequence with respect to the amino acid sequence of at least another polypeptide of the library, wherein said at least one difference is comprised in the amino acid sequence of a loop region of the polypeptides. Thus, in a particular embodiment, the polypeptides of the library are polypeptides of the first aspect comprising at least one loop region variant, as defined in the first aspect, which is different to the corresponding loop region in another polypeptide of the library. In a particular embodiment, said loop region variant is selected from the group consisting of A, B, C, D, E, F, G, H, I, J or K and is as described in the definition and embodiments of "loop region variant" of the first aspect of the invention.

The expression "show at least one difference in its amino acid sequence with respect to the amino acid sequence of at least another polypeptide of the library, wherein said sequence is comprised in the amino acid sequence of a loop region of the polypeptides", as used herein, refers to the fact that a loop region variant, as defined above, of a first polypeptide of the library comprises at least one insertion, deletion, or modification of at least one amino acid in its sequence with respect to the amino acid sequence of the corresponding loop region in a second polypeptide of the library. As understood by a skilled person, when the loop region variant in the first polypeptide is loop region AB, the corresponding loop region in the second polypeptide is also loop region AB in the second polypeptide. When the loop region variant in the first polypeptide is loop region BC, the corresponding loop region in the second polypeptide is also loop region BC in the second polypeptide. When the loop region variant in the first polypeptide is loop region CD, the corresponding loop region in the second polypeptide is also loop region CD in the second polypeptide. When the loop region variant in the first polypeptide is loop region DE, the corresponding loop region in the second polypeptide is also loop region DE in the second polypeptide. When the loop region variant in the first polypeptide is loop region EF, the corresponding loop region in the second polypeptide is also loop region EF in the second polypeptide. When the loop region variant in the first polypeptide is loop region FG, the corresponding loop region in the second polypeptide is also loop region FG in the second polypeptide. When the loop region variant in the first polypeptide is loop region GH, the corresponding loop region in the second polypeptide is also loop region GH in the second polypeptide. When the loop region variant in the first polypeptide is loop region HI, the corresponding loop region in the second polypeptide is also loop region HI in the second polypeptide. When the loop region variant in the first polypeptide is loop region IJ, the corresponding loop region in the second polypeptide is also loop region IJ in the second polypeptide. When the loop region variant in the first polypeptide is loop region JK, the corresponding loop region in the second polypeptide is also loop region JK in the second polypeptide In a particular embodiment, said loop region variant of the first polypeptide of the library shows a degree of sequence identity with the corresponding loop region of the said second polypeptide of the library of at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%. In another particular embodiment, the whole sequence of said first polypeptide shows a degree of sequence identity with the whole sequence of the second polypeptide of at least 50%, at least 55%, at least 60%, at least 65%, at least 70%, at least 75%, at least 80%, at least 85%, at least 90%, at least 95%, at least 96%, at least 97%, at least 98%, at least 99%, at least 99.5%, at least 99.75%, at least 99.9%, at least 99.95%, at least 99.975%, at least 99.98%, at least 99.99%, at least 99.999%. Methods to determine the percentage of sequence identity have been provided in the first aspect of the invention.

In a particular embodiment, the first polypeptide of the library shows a difference in the amino acid sequence of at least 2 loop regions, at least 3 loop regions, at least 4 loop regions, at least 5 loop regions, at least 6 loop region, at least 7 loop regions, at least 8 loop regions, at least 9 loop regions, at least 10 loop regions, at least 11 loop regions with respect to the corresponding loop region in at least another polypeptide of the library, referred to as the second polypeptide of the library. The term corresponding loop region in the second polypeptide is as indicated above for each loop region of the first polypeptide. The difference in the amino acid sequence is as defined above as well. Additionally, each of said amino acid sequences show the degree of sequence identity with that of the corresponding loop region in the second polypeptide indicated above as well.

In a particular embodiment, the polypeptides of the library are capable of specifically binding other molecules, preferably peptides or proteins, present in their proximity, for instance within a sample, by means of at least one of their loop regions. In a preferred embodiment, the polypeptide of the library showing a difference in the amino acid sequence in one or more of their corresponding loop regions, specifically bind different molecules, preferably peptides or proteins, present in their proximity, for instance within a sample. As understood by a skilled person, said difference in their binding capacity can simply consist in that one polypeptide is capable to specifically bind one molecule, preferably a peptide or protein of a sample, and another polypeptide of the library with a difference in one or more loop regions is not. Alternatively, it can consist in that one polypeptide is capable of specifically binding one or more molecules, preferably peptides or proteins, while another polypeptide of the library with a difference in one or more loop regions is not capable of specifically binding said one or more molecules, but is capable of binding other one or more molecules, preferably peptides present in a sample. In a particular embodiment, the first polypeptide of the library is capable of specifically binding a target molecule of interest, preferably a peptide or protein of interest, by means of at least one loop region variant showing a difference in its sequence with respect to the corresponding loop region in the second polypeptide of the library, while the second polypeptide of the library is not capable to specifically bind to said target molecule.

In another particular embodiment, a loop region variant of a first polypeptide of the library specifically binds a target peptide, whereas its cognate loop region in SEQ ID NO:62 is not capable of specifically binding to said target peptide.

In another particular embodiment, the polypeptides of the polypeptide library having the same loop region variant in one of the loop regions selected from AB, BC, CD, DE, EF, FG, GH, HI, IJ, JK, specifically bind a specific target peptide through said loop region variant, whereas the polypeptides of the library not having said specific loop region variant do not.

The terms "bind", "binding", "specifically binds", "specifically binding", "specifically interacts", have been defined in the first aspect of the invention. Methods to determine the binding between a polypeptide and a target molecule, as well as the K of such binding have also been provided in said definition.

In a particular embodiment, the binding of a polypeptide of the library to a target molecule is considered specific, if the binding between said polypeptide and the target molecule has a dissociation constant ($K_d$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M or less than $10^{-15}$ M. Similarly, the binding between a loop region, preferably a loop region variant, and a specific target molecule is considered specific, if the binding between said loop region and the target molecule has a dissociation constant (KD) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M or less than $10^{-15}$ M.

In a particular embodiment, each polypeptide of the library of the second aspect of the invention, as a phenotype, is linked directly or indirectly to a nucleic acid as a genotype corresponding to said phenotype.

The term "genotype", when used in the present invention, refers to the nucleic acid molecules encoding, or comprising a sequence encoding, one or several peptides, polypeptides or proteins. Said group of peptides, polypeptides or proteins conform the phenotype corresponding to said genotype. As understood by a skilled person, the genotype can be formed by a single nucleic acid molecule, encoding a single peptide, polypeptide or protein. In this case, the phenotype is conformed by said peptide, polypeptide or protein. Said nucleic acid can be any of the nucleic acids specified in the definition of nucleic acid below.

In a particular embodiment, the genotype is formed by a single nucleic acid molecule encoding a single polypeptide of the polypeptide display library. In another particular embodiment, the genotype is formed by several nucleic acid molecules encoding the same polypeptide of the polypeptide display library. In another particular embodiment, said nucleic acid molecules have the same nucleic acid sequence.

The definition of the terms peptide, polypeptide and protein has been provided in the first aspect of the invention.

The term "nucleic acid", "nucleotide sequence", or "polynucleotide" is used interchangeably in the present invention to refer to the polymeric form of the ribonucleoside phosphate ester (adenosine, guanosine, uridine or cytidine; "RNA molecules") or deoxy ribonucleosides (deoxyadenosine, deoxyguanosine, deoxythymidine or deoxycytidine; "DNA molecules") or any phosphoester analog thereof such as phosphorothioates and thioesters, in a single stranded or double stranded form. Thus, the term includes single stranded DNA or RNA molecules. It also includes double stranded molecules formed by DNA-DNA, DNA-RNA and RNA-RNA strands. The term "nucleic acid sequence" and, in particular, the DNA or RNA molecule, refers only to the primary or secondary structure of the molecule and does not limit any particular type of tertiary structure. Thus, this term encompasses double stranded DNA, as comprised in linear or circular DNA molecules, supercoiled DNA plasmids and chromosomes. IN a particular embodiment, the nucleic acid is a DNA molecule. In another particular embodiment, it is an RNA molecule.

The term "phenotype", when used in the present invention, refers to a peptide, polypeptide, or protein, or group of peptide, polypeptides or proteins. The nucleic acid/s encoding, or comprising the sequence encoding it/them is the genotype corresponding to said phenotype. As understood by a skilled person, in the context of the present invention, a phenotype can consist on a single peptide, polypeptide or protein. The genotype associated to said phenotype is the nucleic acid molecule, or a group of nucleic acid molecules, encoding it.

In a particular embodiment, the phenotype is a polypeptide of the polypeptide library as defined in the first aspect of the invention and above in this aspect of the invention. In a particular embodiment, it is the first polypeptide of the library as defined above.

The expression "a phenotype linked directly or indirectly to a nucleic acid as a genotype corresponding to said phenotype" when used in the present invention, is understood as a polypeptide of the polypeptide display library (i.e. the phenotype as defined above), that is linked to the nucleic acid encoding it (i.e. the genotype as defined above). Said linkage leads to a complex formed by the polypeptide of the library and nucleic acid/s encoding it. In a particular embodiment, the polypeptide is exposed in the outer surface of said complex. Therefore, in a particular embodiment, the polypeptide display library is formed by complexes comprising a polypeptide of the first aspect of the invention, directly or indirectly linked to a nucleic acid encoding it. Said polypeptide is considered a phenotype, and said nucleic acid is considered the genotype corresponding to the phenotype.

In a particular embodiment, the polypeptides of the library are not inked to any nucleic acid encoding them.

Each polypeptide of the library, whether being part of a complex as described above or not, is referred to as a "member of the library". Therefore, said term, as used herein, refers to any polypeptide of the library, wherein said polypeptide can be directly or indirectly linked to a nucleic acid, wherein the nucleic acid encodes or comprises a sequence encoding said polypeptide, or be simply a polypeptide of the library that is not linked by any means to a nucleic acid comprising a sequence encoding it. Thus, in a particular embodiment, the member of the library is the polypeptide of the library as defined above. In another particular embodiment, it is a complex comprising a polypeptide of the first aspect of the invention, directly or indirectly linked to a nucleic acid encoding it.

A direct link consists on a direct interaction between the polypeptide of the library and the nucleic acid encoding it, resulting on a polypeptide-nucleic acid complex wherein the polypeptide binds or is covalently attached to the nucleic acid/s encoding it, wherein the polypeptide is comprised in the outer surface of said polypeptide-nucleic acid complex. As understood by a skilled person, said complex can also comprise additional proteins and/or nucleic acids.

In a particular embodiment, the binding of the polypeptide of the complex to the nucleic acid is direct. In another particular embodiment, it is indirect, so that the polypeptide binds or is covalently to the nucleic acid encoding it by means of another peptide, protein, protein complex, or molecule, binding to said nucleic acid.

The terms "covalently attached", "covalent attachment", or "covalently coupled", as used herein, refers to the interaction between two molecules, either directly covalently joined through a chemical covalent bond to one another, or indirectly covalently joined to one another through an intervening moiety or moieties, such as a linker, a bridge, or a spacer.

In another particular embodiment, the covalent attachment between the polypeptide of the library and the nucleic acid encoding it is direct, so that the polypeptide is covalently joined to the nucleic acid/s encoding it. In another particular embodiment, it is indirect, so that the polypeptide is joined to the nucleic acid/s encoding it through an intervening moiety or moieties, such as a linker, a bridge, or a spacer. In preferred embodiment, it is joined through a linker.

The term "linker moiety", or "linker", as used herein, refers to a molecule connecting two molecules, or compounds. It is also intended that the linking moiety is not limited in its chemical nature and/or structure; therefore, the linking moiety may be a polysaccharide, a polypeptide, a fatty acid, a phospholipid, or a chemical derivative thereof, among others. It is further intended that the at least one of the molecules covalently attached to another one through a linker, or even both of said molecules, is/are bound to said linker through any chemical bond, such as peptide bond, isopeptide bond, amide bond, imine bond, and etcetera.

In a particular embodiment, the polypeptide display library is formed by complexes comprising a polypeptide of the first aspect of the invention directly linked to a nucleic acid encoding said polypeptide, wherein the polypeptide-nucleic acid complex is selected from the group consisting of:

- a complex consisting on the polypeptide of the library binding to the nucleic acid encoding it
- a complex consisting on the polypeptide of the library binding to the nucleic acid encoding it and on additional proteins, peptides and/or nucleic acids,
- a polypeptide-nucleic acid conjugate,
- a ribosome, or a portion of a ribosome, The term "conjugate", as used herein, refers to any compound resulting from the covalent attachment of two or more individual compounds, or molecules, being said covalent attachment as define above. The conjugate, per definition, is never found in nature as such.

The individual compounds covalently attached in the conjugate of the second aspect of the invention are a polypeptide of the library and the nucleic acid encoding it. Thus, in a particular embodiment, the conjugate of the second aspect of the invention comprises the polypeptide of the library directly attached to the nucleic acid encoding it through a chemical covalent bond. In another particular embodiment, the conjugate of the second aspect of the invention comprises the polypeptide of the library attached to the nucleic acid encoding it through an intervening moiety or moieties, such as a linker, a bridge, a spacer, a moiety or moieties. In a particular embodiment they are attached through a linker.

The term "ribosome", as used herein refers to a highly complex cellular machine, essential for protein synthesis. Ribosomes link amino acids together in the order specified by messenger RNA (mRNA) molecules. It is made up of specialized RNA known as ribosomal RNA (rRNA) as well as dozens of distinct proteins (the exact number varies between species). The ribosomal proteins and rRNAs are arranged into two distinct ribosomal pieces of different size, known generally as the large and small subunit of the ribosome.

The expression "ribosome portion", as used herein, refers to an isolated part of a ribosome, which can consist for instance on the isolated large or small subunit of a ribosome. It also refers to a ribosome that only comprises a part of its ribosomal proteins, or a part of its rRNAs.

In another particular embodiment, the polypeptide-nucleic acid complex of the second aspect of the invention, comprises in its outer surface only one polypeptide of the library. In another particular embodiment, it comprises at least 1, at least 2, at least 3, at least 4, at least 5, a least 6, at least 7, at least 8, at least 9, at least 10, at least 15, at least 20, at least 25, at least 30, at least 35, at least 40, at least 45, at least 50, at least 60, at least 70, at least 80, at least 90, at least 100, at least 150, at least 250, at least 500, at least 1*103 copies of a polypeptide of the library. In a particular embodiment, said copies have the same amino acid sequence. In another particular embodiment, said complex does not comprise any other polypeptide of the library.

In another particular embodiment, the polypeptide-nucleic acid complex of the second aspect of the invention comprises only one nucleic acid encoding the amino acid sequence of the polypeptide of the library comprised in the complex. Said polypeptide and said polypeptide sequence is that specified in the embodiment above.

In a particular embodiment, the complex of the second aspect of the invention comprises at least 1, at least 2, at least 3, at least 4, at least 5, a least 6, at least 7, at least 8, at least 9, at least 10, at least 15, at least 20, at least 25, at least 30, at least 35, at least 40, at least 45, at least 50, at least 60, at least 70, at least 80, at least 90, at least 100 copies of a nucleic acid encoding the amino acid sequence of the polypeptide of the library comprised in the complex. Said polypeptide and said polypeptide sequence is that specified in the embodiment above. In a particular embodiment, said nucleic acids have the same nucleotide sequence.

An indirect link consists on a genetic fusion between the polypeptide of the library and the nucleic acid by a microorganism that comprises both the polypeptide and the nucleic acid. The polypeptide of the library is comprised in the outer surface of the microorganism. The nucleic acid is preferably comprised in the interior part of the microorganism.

In a particular embodiment, said microorganism comprises in its outer surface, only one polypeptide of the library. In a particular embodiment, it comprises in its outer surface at least 1, at least 2, at least 3, at least 4, at least 5, a least 6, at least 7, at least 8, at least 9, at least 10, at least 15, at least 20, at least 25, at least 30, at least 35, at least 40, at least 45, at least 50, at least 60, at least 70, at least 80, at least 90, at least 100, at least 150, at least 250, at least 500, at least 1*103 copies of a polypeptide of the library. In a particular embodiment, said copies have the same amino acid sequence. In another particular embodiment, said microorganism does not comprise any other polypeptide of the library.

In another particular embodiment, the microorganism comprises only one nucleic acid encoding the amino acid sequence of the polypeptide of the library comprised in the microorganism. Said polypeptide and said polypeptide sequence is that specified in the embodiment above.

In another particular embodiment, the microorganism comprises at least 1, at least 2, at least 3, at least 4, at least 5, a least 6, at least 7, at least 8, at least 9, at least 10, at least 15, at least 20, at least 25, at least 30, at least 35, at least 40, at least 45, at least 50, at least 60, at least 70, at least 80, at least 90, at least 100 copies of a nucleic acid encoding the amino acid sequence of the polypeptide of the library comprised in the microorganism. Said polypeptide and said polypeptide sequence is that specified in the embodiment above. In a particular embodiment, said nucleic acids have the same nucleotide sequence.

In a particular embodiment, the microorganism is capable to replicate. In a particular embodiment, the replicated microorganism is an exact copy of the microorganism from which it derives. In another particular embodiment, replication of said microorganism leads to a microorganism with the same polypeptide of the library and the same nucleic acid encoding it comprised in the microorganism from which it derives. Thus, as it will be understood by a skilled person, the replication of the microorganism allows the amplification of the polypeptide of the library, as well as of the nucleic acid encoding it.

In a particular embodiment, the microorganism is selected from the group consisting of a phage, a bacteriophage, a virus, a bacterium, and a yeast. In a preferred embodiment, it is a phage. In another preferred embodiment, it is a bacteriophage.

In a particular embodiment, the bacteriophage is selected from the group consisting of an Enterobacteria phage M13, T4 bacteriophage, T7 bacteriophage, or an *Escherichia* Lambda virus.

In a certain embodiment, all the terms and embodiments described in the first aspect of the invention are equally applicable to this aspect of the invention.

III—Polynucleotides, Vectors and Host Cells

In a third aspect, the invention relates to a polynucleotide encoding the polypeptide according to the first aspect of the invention, or encoding a polypeptide of the polypeptide display library according to the second aspect of the invention.

The term polynucleotide has been defined in the second aspect of the invention.

In a certain embodiment, all the terms and embodiments described in any of the previous aspects of the invention are equally applicable to the third aspect of the invention.

In a fourth aspect, the invention relates to a vector comprising the polynucleotide according to the third aspect of the invention.

The term "vector", as used herein, refers to a vehicle through which a polynucleotide or a DNA molecule can be manipulated or introduced into a cell. The vector can be a linear or circular polynucleotide or it can be a larger polynucleotide or any other type of construction such as the DNA or RNA of a viral genome, a virion or any other biological construct that allows the manipulation of DNA or its introduction in a cell. It is understood that the terms "recombinant vector", "recombinant system" can be used interchangeably with the term vector. A person skilled in the art will understand that there is no limitation as regards the type of vector which can be used because said vector can be a cloning vector suitable for propagation and for obtaining the polynucleotides or suitable gene constructs or expression vectors in different heterologous organisms suitable for purifying the polynucleotides of the invention. Thus, suitable vectors according to the present invention include expression vectors in prokaryotes such as pET (such as pET14b), pUC18, pUC19, Bluescript and their derivatives, mp18, mp19, pBR322, pMB9, ColEl, pCRl, RP4, phages and shuttle vectors such as pSA3 and pAT28, expression vectors in yeasts such as vectors of the type of 2 micron plasmids, integration plasmids, YEP vectors, centromeric plasmids and the like, expression vectors in insect cells such as the pAC series and pVL series vectors, expression vectors in plants such as vectors of expression in plants such as pIBI, pEarleyGate, pAVA, pCAMBIA, pGSA, pGWB, pMDC, pMY, pORE series vectors and the like and expression vectors in superior eukaryotic cells based on viral vectors (adenoviruses, viruses associated to adenoviruses as well as retroviruses and lentiviruses) as well as non-viral vectors such as pSilencer 4.1-CMV (Ambion), pcDNA3, pcDNA3.1/hyg pHCMV/Zeo, pCR3.1, pEFl/His, pIND/GS, pRc/HCMV2, pSV40/Zeo2, pTRACER-HCMV, pUB6/V5-His, pVAXI, pZeoSV2, pCI, pSVL and pKSV-10, pBPV-1, pML2d and pTDT1.

The vector of the invention can be used to transform, transfect, or infect cells which can be transformed, transfected or infected by said vector. Said cells can be prokaryotic or eukaryotic. By way of example, the vector wherein said DNA sequence is introduced can be a plasmid or a vector which, when it is introduced in a host cell, is integrated in the genome of said cell and replicates together with the chromosome (or chromosomes) in which it has been integrated. Said vector can be obtained by conventional methods known by the persons skilled in the art (Sambrook et al., 2001, "Molecular cloning, to Laboratory Manual", 2nd ed., Cold Spring Harbor Laboratory Press, N.Y. Vol 1-3 a).

Therefore, in a fifth aspect, the invention relates to a host cell comprising the polynucleotide according to the third aspect of the invention, or the vector according to the fourth aspect of the invention.

The transformed, transfected or infected cells can be obtained by conventional methods known by persons skilled in the art (Sambrook et al., 2001, mentioned above). In a particular embodiment, said host cell is a animal cell transfected or infected with a suitable vector.

Host cells suitable for the comprising the polynucleotide of the third aspect of the invention, or the vector of the fourth aspect of the invention include, without being limited to, mammal, plant, insect, fungal and bacterial cells. Bacterial cells include, without being limited to, Gram-positive bacterial cells such as species of the *Bacillus, Streptomyces, Listeria* and *Staphylococcus* genus and Gram-negative bacterial cells such as cells of the *Escherichia, Salmonella* and *Pseudomonas* genera. Fungal cells preferably include cells of yeasts such as *Saccharomyces cerevisiae, Pichia pastoris* and *Hansenula polymorpha*. Insect cells include, without being limited to, *Drosophila* and Sf9 cells. Plant cells include, among others, cells of crop plants such as cereals, medicinal, ornamental or bulbous plants. Suitable mammal cells in the present invention include epithelial cell lines (human, ovine, porcine, etc.), osteosarcoma cell lines (human, etc.), neuroblastoma cell lines (human, etc.), epithelial carcinomas (human, etc.), glial cells (murine, etc.), hepatic cell lines (from monkey, etc.), CHO (Chinese Hamster Ovary) cells, COS cells, BHK cells, HeLa cells, 911, AT1080, A549, 293 or PER. C6, NTERA-2 human ECC cells, D3 cells of the mESC line, human embryonic stem cells such as HS293, BGV01, SHEF1, SHEF2, HS181, NIH3T3 cells, 293T, REH and MCF-7 and hMSC cells.

In a certain embodiment, all the terms and embodiments described in the first and second aspects of the invention are equally applicable to the third aspect of the invention. In another embodiment, all the terms and embodiments described in the first, second and third aspects of the invention are equally applicable to the fourth aspect of the invention. In another particular embodiment, all the terms and embodiments of the first, second, third and fourth aspects of the invention are equally applicable to the fifth aspect of the invention.

IV—Conjugates of the Invention

In a further aspect, the invention relates to a conjugate comprising (i) a polypeptide comprising the G2 domain of nidogen-1 or a functionally equivalent variant thereof and (ii) an agent of interest.

The polypeptide forming part of the conjugate and which comprises the G2 domain of nidogen-1 or a functionally equivalent variant thereof (as specified in point (i) above) is also referred to as the "polypeptide of the conjugate of the sixth aspect of the invention", "the polypeptide of the conjugate of the invention", or "the polypeptide of the conjugate".

The G2 domain of nidogen-1 or a functionally equivalent variant thereof comprised in the polypeptide of the conjugate of the sixth aspect of the invention is also referred to as the "first polypeptide of the conjugate", "first polypeptide region of the conjugate", "first polypeptide region", or "first polypeptide region comprised in the polypeptide of the conjugate".

The term "conjugate" has been defined in the second aspect of the invention. The two components covalently attached in the conjugate of the sixth aspect of the invention are the polypeptide of the conjugate and an agent of interest. From now on, the conjugate of the sixth aspect of the invention is also referred to as "the conjugate of the invention".

The term "polypeptide" has been defined in the first aspect of the invention. The definition and embodiments indicated in the first aspect of the invention for the term "amino acid residue" also apply to the present aspect of the invention.

The expression "agent of interest", as used herein, refers to any compound, without chemical structure limitations, provided it can be covalently attached to the polypeptide of the conjugate. In a particular embodiment, said agent is a therapeutic agent. In another particular embodiment, it is an imaging agent. The term "therapeutic agent" and "imaging agent" are defined below in sections IV-E.1 and IV-E.2.

IV.A—the First Polypeptide of the Conjugate

The conjugate of the invention contains a polypeptide comprising the G2 domain of nidogen-1 or a functionally equivalent variant thereof.

The term "nidogen-1" as used herein has been defined above in the context of the variant nidogen G2 domain and applies equally to the conjugate of the invention.

The term "G2 domain of nidogen-1", as used herein, refers to the domain G2 of the protein nidogen 1 as defined above. In the native nidogen-1 sequence, the G2 domain is flanked by short EGF-like domains. However, for the purposes of the present invention, the nidogen-1 G2 domain is formed by amino acid numbers 430 and 667 of the amino acid sequence of the nidogen-1 protein, with identification number P14543-1 of the Uniprot Database (version dated Jul. 7, 2009) (SEQ ID NO:62) and lacks EGF-like domains at the N- or at the C-terminus. In another embodiment, the domain G2 of nidogen 1 lacks the first two amino acids of SEQ ID NO:62 (SEQ ID NO:63), and thus, corresponds to a region consisting on amino acid numbers 432 and 667 of the amino acid sequence of the nidogen-1 protein, with identification number P14543-1 of the Uniprot Database (version dated Jul. 7, 2009) (SEQ ID NO:72).

The expression "functionally equivalent variant", as used herein, refers to all those peptides showing a certain degree of sequence identity with the sequence of nidogen-1 G2 domain, preferably with SEQ ID NO:63, more preferably with SEQ ID NO:62, and that substantially maintain the function of the G2 domain of nidogen-1. The function of domain G2 to be maintained in the conjugate of the sixth aspect of the invention is considered to be the tertiary structure of the domain, preferably when it is not part of the conjugate. Accordingly, said functionally equivalent variant of domain G2 substantially maintains the tertiary structure of domain G2 of nidogen-1, preferably when it is not part of the conjugate. As understood by a skilled person, the tertiary structure of the G2 domain to be maintained is preferably the tertiary structure of the beta barrel domain of the G2 domain of nidogen-1. Said structure has been defined in the first aspect of the invention.

The expression "substantially maintained", as used herein, is understood as that the structure of domain G2 of nidogen-1, preferably the structure of the beta barrel domain of G2 of nidogen-1 is maintained at least 45%, at least 50%, at least 55%, at least 60%, at least 65%, at least 70%, at least 75%, at least 80%, at least 85%, at least 90%, at least 95%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, preferably 95%, more preferably 99%, even more preferably 100%.

When expressed as a percentage, the maintenance of the tertiary structure of a protein domain is understood as the percentage of amino acids from the domain that maintain their relative position with respect to the rest of amino acids of the domain within the tertiary structure of the domain. Methods to determine the tertiary structure of a protein allowing determining the atomic coordinates of a protein are well-known by an expert on the field and include circular dichroism, X-ray crystallography or protein NMR.

In a particular embodiment, the functionally equivalent variant of domain G2 substantially maintains the percentage of the structure of domain G2 of nidogen-1 indicated above, once it is incorporated in the conjugate of the sixth aspect of the invention. In a preferred embodiment, it is substantially maintained when it is not part of the conjugate. In a preferred embodiment, the structure of domain G2 substantially maintained is the structure of the beta barrel domain of domain G2 of nidogen-1 described in the first aspect of the invention. In a particular embodiment, it is the structure of the beta barrel domain of nidogen-1 domain G2 when it is the first polypeptide of the conjugate.

In a particular embodiment, the degree of sequence identity between the G2 domain of nidogen 1 with SEQ ID NO:62 and the functionally equivalent variant is of at least 40%, at least 50%, at least 60%, at least 70%, at least 80%, at least 85%, at least 90%, at least 95%, at least 96%, at least 97%, at least 98%, at least 99%, at least 99.1%, at least 99.2%, at least 99.3%, at least 99.4% at least 99.5%, at least 99.6%, at least 99.7%, at least 99.8%, or at least 99.9%. In another particular embodiment, the degree of sequence identity between the G2 domain of nidogen 1 with SEQ ID NO:63 and the functionally equivalent variant is of at least 40%, at least 50%, at least 60%, at least 70%, at least 80%, at least 85%, at least 90%, at least 95%, at least 96%, at least 97%, at least 98%, at least 99%, at least 99.1%, at least 99.2%, at least 99.3%, at least 99.4% at least 99.5%, at least 99.6%, at least 99.7%, at least 99.8%, or at least 99.9%. Methods to determine the degree of sequence identity between two amino acid sequences have been provided in the first aspect of the invention.

Although once incorporated into the conjugate, the first polypeptide region of the conjugate need not maintain the cellular or physiological function of domain G2 of nidogen. Thus, in a particular embodiment the first polypeptide region is the G2 domain of nidogen-1 or a functionally equivalent variant thereof, with a reduced physiological function once it is incorporated into the fusion protein of the invention. In another embodiment, the first polypeptide region is the G2 domain of nidogen-1 or a functionally equivalent variant thereof, which does not have any physiological function of the G2 nidogen-1 domain, or of the beta barrel domain of the G2 nidogen-1 domain outside the conjugate. In a preferred embodiment, the first polypeptide region is a functionally equivalent variant of the G2 domain of nidogen with an already reduced physiological function, as compared to the wild-type G2 domain of nidogen-1, or to the wild-type beta barrel domain of the G2 domain of nidogen-1, already before being incorporated into the conjugate of the invention. More preferably, the first polypeptide region is a protein which does not have any of the physiological function of the G2 domain of nidogen-1, or of the wild type beta barrel domain of the G2 domain of nidogen-1, already before being incorporated into the conjugate of the invention, due to the presence of inactivating mutations.

The expression "physiological function" or "cellular function", as used herein, refers to the function of a peptide within a cell or an organism. Thus, when referred to physiological function of domain G2 of nidogen-1, or of the beta barrel domain of the G2 domain of nidogen-1 it is understood as the function of said domain when part of nidogen-1 protein. Thus, it refers to the role of the domain in the biochemical pathways, or molecular mechanisms, in which the protein nidogen-1 participates in a cell. Therefore, it is directly related with the capacity of the domain to interact with specific peptides or proteins of the cell, outside the cell, or in the outer surface of another cell. Thus, in a particular embodiment, it refers to the capacity of G2 domain, or of the beta barrel domain of the G2 domain, to interact with its usual protein binding partners. Non limiting examples of such binding partners include collagen IV and perlecan. Thus, in a particular embodiment, the first polypeptide of the conjugate is a functionally equivalent variant of domain G2 of nidogen-1 comprising mutations that inhibit the interaction of the G2 domain of nidogen-1, or of the beta barrel domain of the G2 domain of nidogen-1, with the usual binding partners of the G2 domain of nidogen-1, or of the beta barrel domain of the G2 domain of nidogen-1, preferably with collagen IV and/or Perlecan.

In another embodiment of the invention, the first polypeptide of the conjugate is a functionally equivalent variant of the G2 domain of nidogen-1 that is inert. In a particular embodiment, it is inert once incorporated in the conjugate. In another particular, it is inert already before being incorporated in the conjugate.

As used herein, the term "inert" when referred to a polypeptide, protein, fragment or domain of proteins, it is understood as a polypeptide, protein, fragment or domain of proteins without physiological or biological activity, or without the ability to specifically interact with other macromolecules for a biological function, and fragments or domains of proteins devoid of known therapeutic activity (e.g. antitumor activity). The inert polypeptide part of the conjugate is non-reactive and functions as a physical structure for the binding of the agents of interest. It is intended that the inert polypeptides do not comprise any motifs that have intrinsic enzymatic, physiological, or biological activity on their own, nor do they present immune reactivity, meaning that they stimulate neither the adaptive, nor the innate immune responses.

In general, it is intended that any intrinsic activity of the first polypeptide of the conjugate is irrelevant for the purposes of the invention and does neither contribute, nor hinder the biological activity of the agent of interest.

In a particular embodiment, the first polypeptide of the conjugate is a functionally equivalent variant of the G2 domain of nidogen-1 as any of the polypeptides described in the first aspect of the invention. Thus, in a particular embodiment, the polypeptide of the conjugate is a functionally equivalent variant of the G2 domain of nidogen-1 as any of the polypeptides described in the first aspect of the invention.

In another particular embodiment, the first polypeptide region has a sequence corresponding to amino acids 430 to 667 with respect to the sequence of human nidogen-1 defined in the Uniprot Database with accession number P14543-1 (version dated Jul. 7, 2009), i.e. it has SEQ ID NO:62. In another particular embodiment, the first polypeptide region has a sequence corresponding to amino acids 432 to 667 with respect to the sequence of human nidogen-1 defined in the Uniprot Database with accession number P14543-1 (version dated Jul. 7, 2009), i.e. it has SEQ ID NO:63.

In another particular embodiment, the first polypeptide of the conjugate is a functionally equivalent variant of the domain G2 of nidogen-1 comprising a mutation in one or more amino acid residues at positions 459, 468, 639, 650, 543, 545, 449, 525, 561, 618, 619, 151, 604, 638, 641, 469 and 518 with respect to the numbering of the sequence of human nidogen-1 defined under the UniProt database with accession number P14543-1 (version dated Jul. 7, 2009). Thus, in another particular embodiment, the polypeptide of the conjugate of the sixth aspect of the invention is a functionally equivalent variant of the domain G2 of nidogen-1 comprising a mutation in one or more amino acid residues at positions 459, 468, 639, 650, 543, 545, 449, 525, 561, 618, 619, 151, 604, 638, 641, 469 and 518 with respect to the numbering of the sequence of human nidogen-1 defined under the UniProt database with accession number P14543-1 (version dated Jul. 7, 2009).

The term "mutation", as used herein refers to any modification, or deletion of an amino acid in an amino acid sequence, or the insertion of at least one amino acid before or after an amino acid in an amino acid sequence. As understood by a skilled person, the location of a modification or deletion of an amino acid is referred by the location of the modified or deleted amino acid in the amino acid sequence before said mutation. In a particular embodiment, when the mutation is an insertion, the location of said mutation is defined by reference to the amino acid at the N-terminus of the inserted amino acid/s. In another particular embodiment, when the mutation is an insertion, the location of said mutation is defined by reference to the amino acid at the C-terminus of the inserted amino acid/s. Thus, as understood by a skilled person, a mutation in one or more amino acid residues at positions 459, 468, 639, 650, 543, 545, 449, 525, 561, 618, 619, 151, 604, 638, 641, 469 and 518 of the protein sequence indicated above, refers to a modification or deletion of the amino acids at said positions in the amino acid sequence of human nidogen-1 defined under the UniProt database with accession number P14543-1 (version dated Jul. 7, 2009). In a particular embodiment, it refers to an insertion of at least one amino acid at the C-terminus of one or more of said amino acids. In another particular embodiment, it refers to an insertion of at least one amino acid at the N-terminus of one or more of said amino acids.

In a preferred embodiment, the mutation is an amino acid modification. In a particular embodiment, the mutation at position 459 indicated above is a H459A mutation. In another preferred embodiment, the mutation at position 468 indicated above is a R468N mutation. In another preferred embodiment, the mutation at position 639 indicated above is a F639S mutation. In another particular embodiment, the mutation at position 650 indicated above is a R650A mutation.

Therefore, in a particular embodiment, the one or more mutations at positions 459, 468, 639 or 650 indicated above in the first polypeptide of the conjugate are a H459A mutation, a R468N mutation, a F639S mutation or a R650A mutation. In another particular embodiment, the one or more mutations at positions 459, 468, 639 or 650 indicated above in the polypeptide of the conjugate are a H459A mutation, a R468N mutation, a F639S mutation or a R650A mutation.

Suitable nidogen G2 domain variants that can be included in the first polypeptide region of the conjugate include, without limitation, any of the nidogen G2 domain variants defined above in the context of the first aspect of the invention including the variant carrying the NIDOmut2, NIDOmut3, the NIDOmut3-V45T, the NIDOmut3_V121Q, the NIDOmut3-F157E, the NIDOmut3-V215T, the NIDOmut4, the NIDOmut4_T215V, the NIDOmut5, NIDOmut3-V176T, the NIDOmut3-1200T, the NIDOmut3-V236Y, the NIDOmut3-L237T, the NIDOmut3-S65I, the NIDOmut3-R114I, the NIDOmut3-C214S, the NIDOmut3-S65I_R114I, the NIDOmut5-S65I_R114I, the NIDOmut3-S65I_R114I and the NIDOmut5-S65I_R114I as defined, respectively, as SEQ ID NO:64, 65 and 87 to 104.

IV-B. The Second Polypeptide Region of the Conjugate

The polypeptide of the conjugate of the sixth aspect of the invention optionally comprises a second polypeptide region which is capable of specifically binding to a target of interest.

The second polypeptide region which is capable of specifically binding to a target of interest is also referred to as the "second polypeptide of the conjugate", "second polypeptide region of the conjugate", "the second polypeptide region", or "second polypeptide region comprised in the polypeptide of the conjugate"

The expression "specifically binding" has been defined in the second aspect of the invention. In a particular embodiment, the second polypeptide of the conjugate is considered to specifically bind to a target of interest if it binds to said target with a dissociation constant (KD) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M or less than $10^{-15}$ M. Methods to determine if a polypeptide is capable of binding to a target molecule, as well as to determine the dissociation constant of said binding are provided in the definition of "specifically binding" in the second aspect of the invention.

In a particular embodiment, the second polypeptide region within the conjugate of the invention is a ligand for a cell receptor. The term "cell receptor", or "receptor on the surface of a cell" denotes a cell-associated protein that binds to "ligand". Non-limiting examples of agents of interest which are specific ligands for cell receptors and the specific receptors or cell types to which they bind are those shown in table 2 below:

TABLE 2

Ligands suitable for use in the present invention and receptors, cells or microorganisms, to which said ligands bind. On the left column, a specific ligand binding to a certain receptor is provided. The receptor to which each ligand provided in a certain row in the left column binds is indicated on the same row on the right column. Alternatively, the cell comprising said receptor, or the microorganism comprising said receptor, are indicated.

| Ligand | Cell receptor/cell type or micoorganism |
|---|---|
| Folic acid or folic acid targeting ligand, including methotrexate or aminopterin. | Folate receptor in leucocyte |
| Hyalurinic acid (HA) | CD44 |
| Xanthine scaffold, including lingaliptin | fibroblast activation protein (FAP) on wound fibroblast cells |

TABLE 2-continued

Ligands suitable for use in the present invention and receptors, cells or microorganisms, to which said ligands bind. On the left column, a specific ligand binding to a certain receptor is provided. The receptor to which each ligand provided in a certain row in the left column binds is indicated on the same row on the right column. Alternatively, the cell comprising said receptor, or the microorganism comprising said receptor, are indicated.

| Ligand | Cell receptor/cell type or micoorganism |
|---|---|
| IgG Fc | Protein A in *S. aureus* |
| Ligands of Her 2 are well-known in the art and can be any of those described in Wikman M et al., Protein Eng Des Sel 17: 455-62 (2004); Orlova A et al. Cancer Res 66: 4339-8 (2006); Ahlgren S et al., Bioconjug Chem 19: 235-43 (2008); Feldwisch J et al., JMol Biol 398: 232-47 (2010); US patents with patent number: 5,578,482; 5,856,110; 5,869,445; 5,985,553; 6,333,169; 6,987,088; 7,019,017; 7,282,365; 7,306,801; 7,435,797; 7,446,185; 7,449,480; 7,560,111; 7,674,460; 7,815,906; 7,879,325; 7,884,194; 7,993,650; 8,241,630; 8,349,585; 8,389,227; 8,501,909; 8,512,967; 8,652,474; and U.S. patent application US20110059090A1) | HER2 |
| CRPPR peptide | Cardiac endothelial cell |
| Angiotensin | angiotensin II type 1 (AT1) receptor |
| Ligand for interleukin-6 (IL-6), such as: the S7 peptide described in Su JL et al. (Cancer Res. 2019 Jul. 15; 79(14): 3791) having SEQ ID NO: 74 (LSLITRL), The IL6 ligand described in Weiergräber O et al. (FEBS Lett. 1996 Jan. 29; 379(2): 122-6 and with SEQ ID NO: 75 (WQDPHSWNSSFYRLRFELRYRAERSKTFTTW), interleukin-6 receptor (IL-6R); PDGF; angiopoietin; angiopoietin 2; Tie2; S1P; integrins av beta 3, av beta 5, and a5 beta 1; betacellulin; apelin/APJ; erythropoietin; complement factor D; TNFa; HtrA1; a VEGF receptor; ST-2 receptor; and proteins genetically linked to age-related macular degeneration (AMD) risk such as complement pathway components C2, factor B, factor H, CFHR3, C3b, C5, C5a, C3a, HtrA1, ARMS2, TIMP3, HLA, interleukin-8 (IL-8), CX3CR1, TLR3, TLR4, CETP, LIPC, COL10A1, and TNFRSF10A | Cells from the eye, such as cells from the retinal pigment epithelium. |
| Opsonins, including vitronectin, fibronectin, complement components such as C1q (including any of its component polypeptide chains A, B and C), complement fragments such as C3d, C3b and C4b, mannose-binding protein, conglutinin, surfactant proteins A and D, C-reactive protein (CRP), alpha2-macroglobulin, and immunoglobulins, for example, the Fc portion of an immunoglobulin | Microbe (virus, bacterial cell, fungal cell, protozoa) |
| Mannose-binding lectin (MBL) | Microbe (virus, bacterial cell, fungal cell, protozoa) |

In a particular embodiment, the second polypeptide of the conjugate is selected from the group of ligands provided in table 2.

In a particular embodiment, the target of interest is a receptor in the surface of a cell and the second polypeptide of the conjugate is capable of promoting internalization of the conjugate in said cell. The expression "promoting internalization of the conjugated in said cell", when referred to the second polypeptide of the conjugate, refers to a polypeptide binding to a receptor in a cell surface that undergoes endocytosis in response to the binding of said polypeptide. This binding specificity allows the delivery of the second polypeptide of the conjugate, as well as the rest of the conjugate comprising it, to the cell, tissue or organ which expresses said receptor. In this way, a conjugate comprising said polypeptide region will be directed specifically to said cells when administered to an animal or contacted in vitro with a population of cells of different types.

As used herein, "internalization" refers to a process by which a molecule or a construct comprising a molecule binds to a target element on the outer surface of the cell membrane and so that the resulting complex is internalized by the cell. Internalization may be followed up by dissociation of the resulting complex within the cytoplasm. The target element, along with the molecule or the construct, may then localize to a specific cellular compartment. Preferably, the second polypeptide of the conjugate of the invention, besides promoting internalization, will facilitate endosomal escape of the conjugate.

The expression "facilitate endosomal escape", as used herein, refers to the ability of the second polypeptide of the conjugate to induce the release of the conjugate from the endosomal compartment after internalization by receptor-mediated endocytosis.

The ability of the conjugate of the invention to be internalized by cells expressing the receptor to which the second polypeptide of the conjugate binds may be conveniently determined by fluorescence methods in the case that the polypeptide of the conjugate comprises a fluorescent protein, such as GFP. Such fusion proteins can be obtained by preparing a recombinant nucleic acid wherein the nucleic acids encoding the polypeptide of the conjugate and the fluorescent protein are fused in frame and expressed in an adequate host cell or organism. The fusion protein is then contacted with a culture of cells expressing the aforementioned receptor or in vivo with a tissue which expresses said receptor for an appropriate amount of time, after which fluorescence microscopy may be used to determine whether the construct penetrated the cell. Presence of fluorescence in the cytoplasm may be further investigated by comparing the fluorescence microscopy image resulting from the fluorescent protein to that obtained with a known cytoplasmic stain.

A wide array of uptake receptors and carriers, with an even wider number of receptor-specific ligands, are known in the art.

Non-limiting examples of receptors which may be targeted by the second polypeptide have been provided above.

In a particular embodiment, the second polypeptide of the conjugate is a polycationic peptide.

The term "polycationic peptide". or "polycationic region" as used herein, corresponds to a polypeptide sequence containing multiple positively charged amino acids. The polycationic peptide may be formed exclusively by positively charged amino acids or may contain other amino acids provided that the overall net charge of the region at pH 7 is positive.

It is well known in the art that amino acids and their corresponding amino acid residues possess different properties depending on their side chains and they may be grouped depending on those properties. Thus, at physiological pH, five amino acids show an electrical charge: arginine, histidine, and lysine are positively charged while aspartic acid and glutamic acid are negatively charged. The person skilled in the art will acknowledge then that the polycationic peptide of the invention corresponds to a polypeptide with a net electrical charge of more than one positive charge in physiological pH conditions. Accordingly, the polycationic peptide of the invention is not limited by the presence of one or more negatively charge amino acid residues as long as there are always enough positively charged amino acid residues to result in a net positive electrical charge of two or more.

Thus, in one embodiment of the invention, the polycationic peptide of the invention is selected from the group consisting of (i) a sequence which is capable of specifically interacting with a receptor on a cell surface and promoting internalization of the conjugate on said cell,
(ii) an arginine-rich sequence,
(iii) the GW-H1 peptide,
(iv) a CD44 ligand,
(v) a peptide capable of crossing the blood-brain barrier,
(vi) a cell penetrating peptide and
(vii) a nucleolin-binding peptide.

(i) Sequence which is Capable of Specifically Binding to a Receptor on a Cell Surface and Promoting Internalization of the Conjugate on Said Cell The terms "sequence which is capable of specifically binding to a receptor on a cell surface and promoting internalization of the conjugate on said cell", as used herein, refers to any sequence encoding a polypeptide capable of specifically binding to a target of interest, as defined above, wherein said target is a receptor on the surface of a cell, as defined above, and wherein the polypeptide encoded by said sequence promotes internalization of the conjugate on said cell, as defined above.

The embodiments provided above for the second polypeptide of the conjugate also apply to said polycationic peptide.

Non-limiting examples of receptors which may be targeted by the polycationic peptide of the invention, preferably the sequence which is capable of specifically binding to a receptor on a cell surface referred above, include any of the cell receptors provided above. In a particular embodiment, said receptors are selected from the group consisting of a CXCR4 receptor, an angiotensin receptor, a bombesin receptor, a bradykinin receptor, a calcitonin receptor, a chemokine receptor, a cholecystokinin receptor, a corticotropin-releasing factor receptor, an endothelin receptor, an ephrin receptor, a formylpeptide receptor, a Frizzled receptor, a galanin receptor, a the growth hormone secretagogue receptor (Ghrelin) receptor, a Kisspeptin receptor, a melanocortin receptor, Neuropeptide FF/neuropeptide AF receptor, a neuropeptide S receptor, a neuropeptide W/neuropeptide B receptor, a neuropeptide Y receptor, a neurotensin receptor, an orexin receptors, a peptide P518 receptor, a somatostatin receptor, a tachykinin receptor, a Toll-like receptor, a vasopressin and oxytocin receptor and a VEGF receptor.

In a preferred embodiment of the invention, the polycationic peptide comprising a sequence which is capable of specifically binding to a receptor on a cell surface and promoting internalization of the conjugate on said cell is a CXCR4 ligand.

The term "CXCR4", as used herein, refers to a G protein-coupled, seven-transmembrane chemokine receptor. Like other chemokine receptors, CXCR4 plays an important role in immune and inflammatory responses by mediating the directional migration and activation of leukocytes CXCR4 is expressed or overexpressed in a variety of cancer cell lines and tissues including breast, prostate, lung, ovarian, colon, colorectal, pancreatic, kidney, and brain, as well as non-Hodgkin's lymphoma and chronic lymphocytic leukemia. The only known ligand to CXCR4 is stromal cell-derived factor-1 (SDF-1, or CXCL12). The interaction between CXCR4 and SDF-1 plays an important role in multiple phases of tumorigenesis, including tumor growth, invasion, angiogenesis, and metastasis.

The expression "specifically binding" has been defined in the second aspect of the invention. As understood by a skilled person, the expression "specifically binding to CXCR4", as used herein refers to the ability of the conjugates of the invention to bind more frequently, more rapidly, with greater duration and/or with greater affinity to CXCR4 or cell expressing same than it does with alternative receptors or cells without substantially binding to other molecules.

Binding affinity is measured, for instance, by any of the methods provided in the definition of "specifically binding" in the second aspect of the invention, preferably, as described by Tamamura et al. by the oil-cushion method [see Hesselgesset et al, 1998, J. Immunol., 160:877-883]. Said method comprises contacting the peptide with CXCR4-transfected cell line (e.g. CHO cells) and a labeled CXCR4 ligand (e.g. $^{125}$I-SDF-1$\alpha$) and measuring the inhibition percentage of the targeting peptide against the binding of the labeled CXCR4 ligand.

Specific binding can be exhibited, e.g., by a low affinity targeting agent having a Kd of at least about $10^{-4}$ M. e.g., if CXCR4 has more than one binding site for a ligand, a ligand having low affinity can be useful for targeting. Specific binding also can be exhibited by a high affinity ligands, e.g. a ligand having a Kd of at least about of $10^{-7}$ M, at least about $10^{-8}$ M, at least about $10^{-9}$ M, at least about $10^{-10}$ M, or can have a Kd of at least about $10^{-11}$ M or $10^{-12}$ M or greater. Both low and high affinity-targeting ligands are useful for incorporation in the conjugates of the present invention The ability of the conjugate of the invention to be internalized by cells expressing CXCR4 may be determined by fluorescence methods where the conjugate comprises a fluorescent protein, such as GFP, as indicated above for any second polypeptide of the conjugate binding to any cell receptor. More specifically, conjugates to be internalized by cells expressing CXCR4 can be obtained by preparing a recombinant nucleic acid wherein the nucleic acids encoding the polycationic peptide and the fluorescent protein are fused in frame and expressed in an adequate host cell or organism. The fusion protein is then contacted with a culture of cells expressing CXCR4 or in vivo with a tissue which expresses CXCR4 for an appropriate amount of time, after which fluorescence microscopy may be used to determine whether the construct penetrated the cell. Presence of fluorescence in the cytoplasm may be further investigated by comparing the fluorescence microscopy image resulting from the fluorescent protein to that obtained with a known cytoplasmic stain.

In an even more preferred embodiment of the invention, the CXCR4 ligand is selected from the group comprising the RRWCYRKCYKGYCYRKCR (SEQ ID NO:25), the V1 peptide (SEQ ID NO:26), the CXCL12 peptide (SEQ ID NO:27), the vCCL2 peptide (SEQ ID NO:28), the EPI-X4 sequence (SEQ ID NO:29) or a functionally equivalent variant thereof, such as the peptide of SEQ ID NO:132.

The sequence RRWCYRKCYKGYCYRKCR (SEQ ID NO:25) is the amino acid sequence of the T22 peptide. Said peptide corresponds to a peptide derived from the protein polyphemusin II (extracted from hemocyte debris from *Lymulus polyphemus*). The vCCL2 corresponds to the viral macrophage inflammatory protein-II, an homologue of human chemokine CCL2 encoded by human herpesvirus 8. The V1 peptide corresponds to residues 1-21 of the N-terminus of vCCL2. CXCL12, C-X-C motif chemokine 12, also known as stromal cell-derived factor 1 (SDF1), is a member of the chemokine family that acts as a pro-inflammatory mediator. All four peptides are known to have interactions with the CXCR4 receptor, as shown in Liang, X. 2008. Chem. Biol. Drug. Des. 72:91-110.

EPI-X4 corresponds to residues 408-423 of human serum albumin (HSA). It has also been described to bind to the CXCR4 receptor (Zirafi et al., 2015, Cell reports, 11:1-11). In one embodiment, an optimized EPI-X4 tandem version with higher receptor affinity and serum stability (SEQ ID NO:132) is used.

In one embodiment, the polycationic peptide is the one selected from the group consisting of:

- the T140 peptide having the sequence $RRX_1CYRKX_2PYRX_3CR$ (SEQ ID NO:41) wherein $X_1$ is L-3-(2-naphtyl) alanine, X2 is D-Lys and X3 is L-Citrulline.
- the TN14003 peptide having the sequence $RRX_1CYX_2KX_3PYRX_4CR$ (SEQ ID NO:42) wherein $X_1$ is L-3-(2-naphtyl) alanine, $X_2$ is L-Citrulline, $X_3$ is dLys and $X_4$ is L-Citrulline,
- the TC14012 peptide having the sequence $RRX_1CYEKX_2PYRX_3CR$ (SEQ ID NO:43) wherein $X_1$ is L-3-(2-naphtyl) alanine, $X_2$ is D-Citrulline and $X_3$ is L-Citrulline,
- the TE14011 peptide having the sequence $RRX_1CYX_2KX_3PYRX_4CR$ (SEQ ID NO:44) wherein $X_1$ is L-3-(2-naphtyl) alanine, $X_2$ is L-Citrulline, $X_3$ is D-Glu and $X_4$ is L-Citrulline and
- the TZ14011 peptide having the sequence $RRX_1CYX_2KX_3PYRX_4CR$ (SEQ ID NO:45) wherein $X_1$ is L-3-(2-naphtyl) alanine, $X_2$ is L-Citrulline, $X_3$ is D-Lys and $X_4$ is L-Citrulline or the variant thereof wherein the N-terminal Arginine residue is acetylated (known Ac-TZ14011), The terms "functional variant" and "functionally equivalent variant" are interchangeable and are herein understood as all those peptides derived from the T22, the V1, the CXCL12, the vCCL2, and/or the EPI-X4 peptides by means of modification, insertion and/or deletion of one or more amino acids, provided that the function of binding to CXCR4 and internalizing the conjugate is substantially maintained.

In one embodiment, functionally equivalent variants of the cationic polypeptides are those showing a degree of identity with respect to the human T22, V1, CXCL12 vCCL2, and/or the EPI-X4 peptides, according to their respective SEQ ID NOs, greater than at least 40%, at least 50%, at least 60%, at least 70%, at least 80%, at least 85%, at least 90%, at least 95%, at least 96%, at least 97%, at least 98% or at least 99%. Methods to determine the degree of identity between two amino acid sequences have been provided in the first aspect of the invention. The cationic polypeptides of the invention may include post-translational modifications, such as glycosylation, acetylation, isoprenylation, myristoylation, proteolytic processing, etc.

Alternatively, suitable functional variants of the cationic polypeptide are those wherein one or more positions contain an amino acid which is a conservative substitution of the amino acid present in the T22, V1, CXCL12, vCCL2 and/or EPI-X4 peptides mentioned above. "Conservative amino acid substitutions" result from replacing one amino acid with another having similar structural and/or chemical properties For example, the following six groups each contain amino acids that are conservative substitutions for one another: 1) Alanine (A), Serine(S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). Selection of such conservative amino acid substitutions is within the skill of one of ordinary skill in the art and is described, for example by Dordo et al. et al., [J. Mol. Biol, 1999, 217; 721-739] and Taylor et al., [J. Theor. Biol., 1986, 119:205-218].

A suitable assay for determining whether a given peptide can be seen as a functionally equivalent variant thereof is, for instance, the following assay: a putative T22, V1, CXCL12, vCCL2, or EPI-X4 peptide variant is fused in frame with a marker polypeptide (e.g. a fluorescent protein). Such fusion proteins can be obtained by preparing a recombinant nucleic acid wherein the nucleic acids encoding the peptide and the fluorescent protein are fused in frame and expressed in an adequate host cell or organism. The fusion protein is then contacted with a culture of cells CXCR4 (e.g. HeLa cells) for an appropriate amount of time after which fluorescence microscopy may be used to determine whether the construct penetrated the cell. If the peptide is a functionally equivalent variant of the corresponding peptide, the marker protein will be internalized and presence of fluorescence in the cytoplasm of the cell will be visible. Furthermore, the performance of the functionally equivalent variant can be assayed by comparing the fluorescence microscopy image resulting from the fluorescent protein to that obtained with a known cytoplasmic stain (e.g. DAPI).

(ii) Arginine-Rich Sequence

As aforementioned, the arginine amino acid and its residue present positive charge at physiological pH. It will be understood that an "arginine-rich sequence" refers to a polypeptide sequence containing multiple arginine residues. Thus, the polypeptide sequence may comprise 33%, preferably 40%, preferably 45%, preferably 50%, preferably 55%, preferably 60%, preferably 65%, preferably 70%, preferably 75%, preferably 80%, preferably 85%, more preferably 90%, more preferably 95%, even more preferably 99%, yet even more preferably 100% of the amino acid residues of its complete sequence as arginine residues. It will be understood that whenever the sequence of the arginine-rich sequence comprises less than the 100% of the sequence as arginine residues, these residues do not need to be all adjacent or contiguous with respect to each other.

The person skilled in the art will recognize that a polypeptide with one or more arginine residues will be a polycationic peptide as long as the total positive electrical charge of the polypeptide at physiological pH is 2 or more, resulting not only from the positive electrical charges of the arginine residues but also from any other positively charged amino acids.

In an embodiment of the invention, the polycationic peptide of the invention is an arginine-rich sequence.

In a preferred embodiment of the invention, the arginine-rich sequence of the polycationic peptide of the invention is selected from the group consisting of SEQ ID NO:30, SEQ ID NO:31, SEQ ID NO:32 and SEQ ID NO:33.

(iii) The GW-H1 Peptide

The GW-H1 peptide was previously described by Chen and colleagues [Chen, Y-L. S. et al. 2012. Peptides, 36:257-265]. The GW-H1 peptide was first selected as an antimicrobial peptide but it is also characterized by its capability to bind to cell membranes, internalize itself to the cytoplasm, and migrate to the nuclei in eukaryotic cells. Once inside the cell, GW-H1 is capable to induce apoptosis. It has been proposed that GW-H1 exerts its cytolytic activity by folding into an amphipathic helix [Chen and colleagues, supra]. Therefore, this peptide is supposed to exert its cell lytic effects by two sequential events consisting on binding to cell membranes followed by permeabilization.

In a preferred embodiment of the invention, the polycationic peptide of the invention is the GW-H1 peptide, which has the SEQ ID NO:46.

(iv) A CD44 Ligand

CD44 is a cell-surface transmembrane glycoprotein involved in cell-cell and cell-matrix interactions, cell adhesion and migration. CD44 has been implicated in inflammation and in diseases such as cancer [Bajorath, J. 2000. Proteins. 39:103-111]. Many isoforms are known, which are expressed in a cell-specific manner and also differentially glycosylated.

Accordingly, a "CD44 ligand" will be a molecule capable of binding to CD44. CD44 is the major surface receptor for Hyaluronan, a component of the extracellular matrix, but it has other ligands, such as chondroitin sulfate, the heparin-biding domain of fibronectin, osteopontin, serglycin, collagen and laminin. Besides, CD44 can also interact with metalloproteinases and selectins.

In an embodiment of the invention, the polycationic peptide of the invention is a CD44 ligand. In a preferred embodiment of the invention, the CD44 ligand is selected from the group consisting of A5G27 (SEQ ID NO:34) and FNI/II/V (SEQ ID NO:35).

The peptide FNI/II/V corresponds to the HBFN-fragment V of Fibronectin. The peptide A5G27 corresponds to a peptide of the a5 chain of Laminin [Pesarrodona, M. et al. 2014. Int. J. of Pharmaceutics. 473:286-295].

(v) Peptide Capable of Crossing the Blood-Brain Barrier

It is well known in the art that one major obstacle for the development of therapeutic approaches for brain pathologies is the blood-brain barrier (BBB). The brain is shielded against potentially toxic substances by the presence of two barrier systems: the blood-brain barrier (BBB) and the blood-cerebrospinal fluid barrier (BCSFB). The BBB is considered to be the major route for the uptake of serum ligands since its surface area is approximately 5000-fold greater than that of BCSFB. The brain endothelium, which constitutes the BBB, represents the major obstacle for the use of potential drugs against many disorders of the CNS. As a general rule, only small lipophilic molecules may pass across the BBB, i.e., from circulating systemic blood to brain. Many drugs that have a larger size or higher hydrophobicity show promising results in animal studies for treating CNS disorders.

Therefore, a "peptide capable of crossing the blood-brain barrier" will be a peptide capable of transporting itself as well as any molecule it is bound to, preferably a protein, from the blood torrent to the CNS.

In 1983 it was reported that a peptide, β-Casomorphin-5 could overcome the BBB [Ermisch, A. et al. 1983. J. of Neurochemistry. 41:1229-1233]. Since then, many other peptides with BBB-permeating properties have been identified, characterized and catalogued, and in 2012 a comprehensive database was established, as reported by Van Dorpe et al. [Van Dorpe, S. et al. 2012. Brain Struct. Funct. 217:687-718]. Most of the peptides listed in the aforementioned database are suitable for the conjugate of the invention.

In an embodiment of the invention, the polycationic peptide of the invention is a peptide capable of crossing the blood-brain barrier. In a preferred embodiment of the invention, the peptide capable of crossing the blood-brain barrier is a selected from the group consisting of Seq-1-7 (SEQ ID NO:36), Seq-1-8 (SEQ ID NO:37), and Angiopep-2-7 (SEQ ID NO:38).

(vi) Cell Penetrating Peptide (CPP)

The terms "cell-penetrating peptide" (CPP) refers to a peptide, typically of about 5-60 amino acid residues in length, that can facilitate cellular uptake of molecular cargo, particularly proteins they are a part of. Proteins can present one or more CPPs. CPPs can also be characterized as being able to facilitate the movement or traversal of molecular cargo across/through one or more of a lipid bilayer, cell membrane, organelle membrane, vesicle membrane, or cell wall. A CPP herein will be polycationic.

Examples of CPPs useful herein, and further description of CPPs in general, are disclosed in Schmidt et al. [2010. FEBS Lett. 584:1806-1813], Holm et al. [2006. Nature Protocols 1:1001-1005], Yandek et al, [2007. Biophys. J. 92:2434-2444], Morris et al. [2001. Nat. Biotechnol. 19:1173-1176]. and U.S. Patent Application Publication No. 2014/0068797. CPPs do not depend on transporters or receptors, facilitating the traffic of the proteins they are part of directly through the lipid bilayer without the need of participation by any other cell components.

(vii) Nucleolin-Binding Peptide

Accordingly, a "nucleolin-binding peptide" is a peptide capable of binding to the nucleolin protein in a cell, preferably to the cell-surface expressed fraction of nucleolin.

In an embodiment of the invention, the polycationic peptide of the invention is a nucleolin-binding peptide.

The International Patent Application Publication with number WO 2011/031477 A2 offers numerous examples of nucleolin-binding peptides that would be suitable for use in the conjugate of the invention.

In a preferred embodiment of the invention, the nucleolin-binding peptide of the invention is the peptide of sequence SEQ ID NO:47 or the peptide of sequence SEQ ID NO:48.

IV-C. The Third Polypeptide Region of the Conjugate

In a particular embodiment, the polypeptide of the conjugate of the sixth aspect of the invention further comprises a third polypeptide region which is a positively charged amino acid-rich region.

The third polypeptide region which is a positively charged amino acid-rich region and comprised in the polypeptide of the conjugate is also referred to as the "third polypeptide of the conjugate", "third polypeptide region of the conjugate", "the third polypeptide region" or "third polypeptide region comprised in the polypeptide of the conjugate". As understood by a skilled person, the expressions "third polypeptide of the conjugate", "third polypeptide region of the conjugate" or "third polypeptide region comprised in the polypeptide of the conjugate" are interchangeable with "positively charged amino acid-rich region".

The term "positively charged amino acid", "positively charged amino-acid rich region" or "third polypeptide region which is a positively charged amino acid-rich region", as used herein, refers to the polypeptide sequence of the third polypeptide of the conjugate, different from the second polypeptide, region of the conjugate, characterized in that it contains multiple positively charged amino acids. In addition, the positively charged amino acid-rich region may be formed exclusively by positively charged amino acids or may contain other amino acids provided that the overall net charge of the region at pH 7 is positive. Thus, the positively charged amino acid-rich region sequence may comprise 33%, preferably 40%, preferably 45%, preferably 50%, preferably 55%, preferably 60%, preferably 65%, preferably 70%, preferably 75%, preferably 80%, preferably 85%, more preferably 90%, more preferably 95%, even more preferably 99%, yet even more preferably 100% of the amino acid residues of its complete sequence as positively charged amino acids residues.

The positively charged amino acid-rich region may contain only one type of positively charged amino acid or may contain more than one type of positively charged amino acid. In one embodiment, the positively charged amino acid-rich region is a polyhistidine region. In one embodiment, the positively charged amino acid-rich region is a polyarginine region. In one embodiment, the positively charged amino acid-rich region is a polyhistidine region. In one embodiment, the positively charged amino acid-rich region comprises lysine and arginine residues. In one embodiment, the positively charged amino acid-rich region comprises lysine and histidine residues. In one embodiment, the positively charged amino acid-rich region comprises arginine and histidine residues. In one embodiment, the positively charged amino acid-rich region comprises lysine, arginine and histidine residues In some embodiments, the positively charged amino acid-rich region comprises at least 2, at least 3, at least 4, at least 5, at least 6, at least 7, at least 8, at least 9, at least 10, at least 11, at least 12, at least 13, at least 14, or at least 15 positively charged amino acids residues, wherein the positively charged amino acid can be histidine, lysine, arginine or combinations thereof.

In some embodiments, the positively charged amino acid-rich region comprises fewer than 100, fewer than 90, fewer than 80, fewer than 70, fewer than 60, fewer than 50, fewer than 40, fewer than 30, fewer than 29, fewer than 28, fewer than 27, fewer than 26, fewer than 25, fewer than 24, fewer than 23, fewer than 22, fewer than 21, fewer than 20, fewer than 19, fewer than 18, fewer than 17, fewer than 16, fewer than 15, fewer than 14, fewer than 13, fewer than 12, fewer than 11, fewer than 10 or less positively charged amino acids residues, wherein the positively charged amino acid can be histidine, lysine, arginine or combinations thereof.

In some embodiments, the positively charged amino acid-rich region comprises between 2 and 50 amino acids, between 2 and 40 amino acids, between 2 and 30 amino acids, between 2 and 25 amino acids, between 2 and 20 amino acids, between 2 and 10 amino acids or between 2 and 8 amino acids.

In some embodiments, the positively charged amino acid-rich region comprises between 3 and 50 amino acids, between 3 and 40 amino acids, between 3 and 30 amino acids, between 3 and 25 amino acids, between 3 and 20 amino acids, between 3 and 10 amino acids or between 3 and 8 amino acids. In some embodiments, the positively charged amino acid-rich region comprises between 4 and 50 amino acids, between 4 and 40 amino acids, between 4 and 30 amino acids, between 4 and 25 amino acids, between 4 and 20 amino acids, between 4 and 10 amino acids or between 4 and 8 amino acids. In some embodiments, the positively charged amino acid-rich region comprises between 5 and 50 amino acids, between 5 and 40 amino acids, between 5 and 30 amino acids, between 5 and 25 amino acids, between 5 and 20 amino acids, between 5 and 10 amino acids or between 5 and 8 amino acids.

In an embodiment of the invention, the positively charged amino acid-rich region of the conjugate of the invention is a polyhistidine region. In a preferred embodiment of the invention, the polyhistidine region comprises between 2 and 10, preferably 6, contiguous histidine residues.

In an embodiment of the invention, the positively charged amino acid-rich region of the conjugate of the invention is a polyarginine region. In a preferred embodiment of the invention, the polyarginine region comprises between 2 and 10, preferably 6, contiguous arginine residues.

In an embodiment of the invention, the positively charged amino acid-rich region of the fusion protein of the invention is a polylysine region. In a preferred embodiment of the invention, the polylysine region comprises between 2 and 10, preferably 6, contiguous polylysine residues.

In a particular embodiment, the positively charged peptide sequence is RKRKRK (SEQ ID NO. 77), RRRRRR (SEQ ID NO. 78), KKKKKK (SEQ ID NO:79), HHHHHH (SEQ ID NO. 80), RHRHRH (SEQ ID NO. 81), RKRKRKRK (SEQ ID NO. 82), RKRHRK (SEQ ID NO. 83), RKRHRH (SEQ ID NO. 84), RHRHRH (SEQ ID NO. 85) or RKRKRKR (SEQ ID NO:86).

IV-D. Relative Positions of the Elements of the Polypeptide of the Conjugate and Linking Elements The different elements of the polypeptide of the conjugate of the invention (first, second and third polypeptides of the conjugate) can be placed in any relative order provided that the second polypeptide, wherein said polypeptide is preferably a polycationic peptide, and the third polypeptide (or the positively charged amino acid-rich region) are functional on any position of the conjugate and also the first polypeptide remains functional totally or in part (i.e. it substantially maintains the structure of the G2 domain of nidogen-1).

As used herein, the terms "N-terminal end", "N-terminus", and "amino-terminal end" of a polypeptide are indistinct. Equally, the terms "C-terminal end", "C-terminus", and "carboxy-terminal end" are considered equivalent. The terms are of common usage for the person skilled in the art regarding the free moieties of the amino acids at the ends of the polypeptide chains comprised by a protein.

Thus, in an embodiment of the invention, the second polypeptide of the conjugate is located at the N-terminal end of the polypeptide of the conjugate, while the positively charged amino acid-rich region (i.e. the third polypeptide of the conjugate) of the polypeptide is located at the C-terminal end of the polypeptide. In another embodiment of the invention, the positively charged amino acid-rich region of the polypeptide of the conjugate is located at the N-terminal end of the polypeptide, while the second polypeptide region is located at the C-terminal end of the polypeptide. In another embodiment of the invention, the first polypeptide region can be located at either the C-terminal end or the N-terminal end of the polypeptide of the conjugate, while the second polypeptide is in the middle position of the polypeptide and the positively charged amino acid-rich region is at the end of the polypeptide opposite the first polypeptide region, or the positively charged amino acid-rich region is in the middle position of the polypeptide and the second polypeptide is located at the end of the polypeptide opposite the first polypeptide region.

Accordingly, the relative order of the elements of the polypeptide of the conjugate according to the invention, can be:

- N-second polypeptide region-first polypeptide region-positively charged amino acid-rich region-C;
- N-positively charged amino acid-rich region-first polypeptide region-second polypeptide region-C;
- N-second polypeptide region-positively charged amino acid-rich region-first polypeptide region-C;
- N-positively charged amino acid-rich region-second polypeptide region-first polypeptide region-C;
- N-first polypeptide region-second polypeptide region-positively charged amino acid-rich region-C; or
- N-first polypeptide region-positively charged amino acid-rich region-second polypeptide region-C In a particular embodiment, the order of the elements in the polypeptide of the conjugate of the sixth aspect of the invention is any of those indicated above.

In a preferred embodiment, the order of the elements in the polypeptide of the conjugate of the sixth aspect of the invention is N-second polypeptide region-first polypeptide region-positively charged amino acid-rich region-C.

The terms "N-terminal end" and "C-terminal end" do not mean that the components need to be directly conjugated end-to-end, but that they maintain that relative order of positions regardless of the presence of additional elements at the end of either component or intercalated between them, such as linkers/spacers.

Therefore, the polypeptide of the conjugate of the invention comprises the aforementioned elements ((1) second polypeptide region, (2) first polypeptide region and (3) positively charged amino acid-rich region) and these can be conjugated end-to-end but also may include one or more optional peptide or polypeptide "linkers" or "spacers" intercalated between them, linked, preferably by peptidic bond.

According to the invention, the spacer or linker amino acid sequences can act as a hinge region between components (1) and (2) and (2) and (3), allowing them to move independently from one another while maintaining the three-dimensional form of the individual domains, such that the presence of peptide spacers or linkers does not alter the functionality of any of the components (1), (2) and (3). In this sense, a preferred intermediate amino acid sequence according to the invention would be a hinge region characterized by a structural ductility allowing this movement. In a particular embodiment, said intermediate amino acid sequence is a flexible linker. The effect of the linker region is to provide space between the components (1) and (2) and (2) and (3). It is thus assured that the secondary and tertiary structure of component (1), (2) or (3) is not affected by the presence of either of the others. The spacer is of a polypeptide nature. The linker peptide preferably comprises at least 2 amino acids, at least 3 amino acids, at least 5 amino acids, at least 10 amino acids, at least 15 amino acids, at least 20 amino acids, at least 30 amino acids, at least 40 amino acids, at least 50 amino acids, at least 60 amino acids, at least 70 amino acids, at least 80 amino acids, at least 90 amino acids or approximately 100 amino acids.

The spacer or linker can be bound to components flanking the two components of the polypeptide of the conjugates of the invention by means of covalent bonds, preferably by peptide bonds; and also preferably the spacer is essentially afunctional, and/or is not prone to proteolytic cleavage, and/or does not comprise any cysteine residue. Similarly, the three-dimensional structure of the spacer is preferably linear or substantially linear.

The preferred examples of spacer or linker peptides include those that have been used to bind proteins without substantially deteriorating the function of the bound peptides or at least without substantially deteriorating the function of one of the bound peptides. More preferably the spacers or linkers used to bind peptides comprise coiled coil structures.

Preferred examples of linker peptides comprise 2 or more amino acids selected from the group consisting of glycine, serine, alanine and threonine. A preferred example of a flexible linker is a polyglycine linker. The possible examples of linker/spacer sequences include GGSSRSS (SEQ ID NO:39), GGSSRSSS (SEQ ID NO:76), SGGTSGSTSGTGST (SEQ ID NO:49), AGSSTGSSTGPGSTT (SEQ ID NO:50) or GGSGGAP (SEQ ID NO:51). These sequences have been used for binding designed coiled coils to other protein domains [Muller, K. M., Arndt, K. M. and Alber, T., Meth. Enzymology, 2000, 328:261-281]. Further non-limiting examples of suitable linkers comprise the amino acid sequence GGGVEGGG (SEQ ID NO:52), the sequence of 10 amino acid residues of the upper hinge region of murine IgG3 (PKPSTPPGSS, SEQ ID NO:53), which has been used for the production of dimerized antibodies by means of a coiled coil [Pack, P. and Pluckthun, A., 1992, Biochemistry 31:1579-1584], the peptide of sequence APAETKAEPMT (SEQ ID NO:54), the peptide of sequence GAP, the peptide of sequence AAA and the peptide of sequence AAALE (SEQ ID NO:55). In another preferred embodiment, the linker is GGSSRSS (SEQ ID NO:39).

Alternatively, the components of the polypeptide of the conjugates of the invention can be connected by peptides the sequence of which contains a cleavage target for a protease, thus allowing the separation of any of the components. Protease cleavage sites suitable for their incorporation into the polypeptides of the conjugates of the invention include enterokinase (cleavage site DDDDK, SEQ ID NO:56), factor Xa (cleavage site IEDGR, SEQ ID NO:57), thrombin (cleavage site LVPRGS, SEQ ID NO:58), TEV protease (cleavage site ENLYFQG, SEQ ID NO:59), PreScission protease (cleavage site LEVLFQGP, SEQ ID NO:60), inteins and the like.

In a preferred embodiment, the polypeptide at the N-terminal position connects with the polypeptide at the middle position in the polypeptide of the conjugate by a linker, preferably a linker selected from any of the examples of linkers provided above. In another preferred embodiment, the polypeptide at the middle position connects with the polypeptide at the C-terminal position of the polypeptide of the conjugate by a linker, preferably a linker selected from any of the examples of linkers provided above. Thus, in an embodiment of the invention, the second polypeptide is connected to the first polypeptide region through a linker. In another embodiment of the invention, the first polypeptide region is connected to the positively charged amino acid-rich region through a linker. In yet another embodiment of the invention, the second polypeptide is connected to the first polypeptide region through a linker and the first polypeptide region is bound to the positively charged amino acid-rich region through a linker also. Thus in a particular embodiment, the second polypeptide region is connected to the first polypeptide region via a first peptide linker and/or the first polypeptide region is connected to the third polypeptide region via a second peptide linker. In a particular embodiment, the first peptide linker comprises the GGSSRSS sequence (SEQ ID NO:39) sequence, the GGSSRSSS (SEQ ID NO:76), or the GGGNS sequence (SEQ ID NO:40). In a preferred embodiment, it comprises the GGSSRSS sequence (SEQ ID NO:39). In another preferred embodiment, it comprises GGSSRSS (SEQ ID NO:39).

As the person skilled in the art will acknowledge, the linkers connecting the second polypeptide to the first polypeptide region and the first polypeptide region to the positively charged amino acid-rich region may comprise the same sequence or different ones with the aforementioned limitation so that the presence and/or sequence of the linkers does not result in functional alterations of the second polypeptide, the first polypeptide region, and/or the positively charged amino acid-rich region (for instance, but not limited to, due to secondary or tertiary structure modifications of the polypeptide of the conjugate or formation of disulfide bonds).

The aforementioned considerations regarding the relative positions from the N-terminal end to the C-terminal end of the elements of the polypeptide of the conjugate apply also in the presence of linkers between them, independently of the number of them or what elements are placed in-between. Therefore, the possible combinations and relative orders of elements will be the following (wherein the numbering stated above for the elements is retained: (1) second polypeptide, (2) first polypeptide, (3) positively charged amino acid-rich region):

N-(1)-(2)-(3)-C
N-(1)-linker-(2)-(3)-C
N-(1)-(2)-linker-(3)-C
N-(1)-linker-(2)-linker-(3)-C
N-(3)-(2)-(1)-C
N-(3)-linker-(2)-(1)-C
N-(3)-(2)-linker-(1)-C
N-(3)-linker-(2)-linker-(1)-C
N-(2)-(1)-(3)-C
N-(2)-linker-(1)-(3)-C
N-(2)-(1)-linker-(3)-C
N-(2)-linker-(1)-linker-(3)-C
N-(2)-(3)-(1)-C
N-(2)-linker-(3)-(1)-C
N-(2)-(3)-linker-(1)-C
N-(2)-linker-(3)-linker-(1)-C
N-(1)-(3)-(2)-C
N-(1)-(3)-linker-(2)-C
N-(1)-linker-(3)-(2)-C
N-(1)-linker-(3)-linker-(2)-C
N-(3)-(1)-(2)-C
N-(3)-linker-(1)-(2)-C
N-(3)-(1)-linker-(2)-C
N-(3)-linker-(1)-linker-(2)-C In a preferred embodiment of the invention, the linkers of the polypeptide of the conjugate of the invention comprise the sequence GGSSRSS (SEQ ID NO:39) or the GGGNS sequence (SEQ ID NO:40).

In a preferred embodiment, the polypeptide at the N-terminal position connects with the polypeptide at the middle position of the polypeptide of the conjugate through a protease cleavage site, preferably through a protease cleavage site selected from any of the examples of protease cleavage sites provided above. In another preferred embodiment, the polypeptide at the middle position connects with the polypeptide at the C-terminal position of the conjugate through a protease cleavage site, preferably through a protease cleavage site from any of the examples of cleavage sites provided above.

In another embodiment, the second polypeptide is connected to the first polypeptide region through a protease cleavage site. In another embodiment of the invention, the first polypeptide region is connected to the positively charged amino acid-rich region through a protease cleavage site. In yet another embodiment of the invention, the second polypeptide is connected to the first polypeptide region through a protease cleavage site and the first polypeptide region is bound to the positively charged amino acid-rich region through a protease cleavage site also.

As the person skilled in the art will acknowledge, the protease cleavage sites connecting the second polypeptide to the first polypeptide region and the first polypeptide region to the positively charged amino acid-rich region may comprise the same sequence or different ones with the aforementioned limitation so that the presence and/or sequence of the protease cleavage site does not result in functional alterations of the second polypeptide, the first polypeptide region, and/or the positively charged amino acid-rich region (for instance, but not limited to, due to secondary or tertiary structure modifications of the polypeptide of the conjugate or formation of disulfide bonds).

The aforementioned considerations regarding the relative positions from the N-terminal end to the C-terminal end of the elements of the polypeptide of the conjugate apply also in the presence of protease cleavage sites between them, independently of the number of them or what elements are placed in-between. Therefore, the possible combinations and relative orders of elements will be the following (wherein the numbering stated above for the elements is retained: (1) second polypeptide, (2) first polypeptide, (3) positively charged amino acid-rich region):

N-(1)-(2)-(3)-C
N-(1)-protease cleavage site-(2)-(3)-C
N-(1)-(2)-protease cleavage site-(3)-C
N-(1)-protease cleavage site-(2)-protease cleavage site-(3)-C
N-(3)-(2)-(1)-C
N-(3)-protease cleavage site-(2)-(1)-C
N-(3)-(2)-protease cleavage site-(1)-C
N-(3)-protease cleavage site-(2)-protease cleavage site-(1)-C
N-(2)-(1)-(3)-C
N-(2)-protease cleavage site-(1)-(3)-C N-(2)-(1)-protease cleavage site-(3)-C
N-(2)-protease cleavage site-(1)-protease cleavage site-(3)-C
N-(2)-(3)-(1)-C
N-(2)-protease cleavage site-(3)-(1)-C
N-(2)-(3)-protease cleavage site-(1)-C
N-(2)-protease cleavage site-(3)-protease cleavage site-(1)-C
N-(1)-(3)-(2)-C
N-(1)-(3)-protease cleavage site-(2)-C
N-(1)-protease cleavage site-(3)-(2)-C
N-(1)-protease cleavage site-(3)-protease cleavage site-(2)-C
N-(3)-(1)-(2)-C
N-(3)-protease cleavage site-(1)-(2)-C
N-(3)-(1)-protease cleavage site-(2)-C
N-(3)-protease cleavage site-(1)-protease cleavage site-(2)-C In a particular embodiment, the conjugate comprises a linker connecting two polypeptides of the conjugate, and a protease cleavage site connected the other two polypeptides of the conjugate. In this case, the aforementioned considerations regarding the relative positions from the N-terminal end to the C-terminal end of the elements of the conjugate apply also in the presence of linkers and protease cleavage sites between them, independently of the number of them or what elements are placed in-between. Therefore, the possible combinations and relative orders of elements will be the following (wherein the numbering stated above for the elements is retained: (1) second polypeptide, (2) first polypeptide, (3) positively charged amino acid-rich region):

N-(1)-linker-(2)-protease cleavage site-(3)-C
N-(1)-protease cleavage site-(2)-linker-(3)-C
N-(1)-linker-(2)-protease cleavage site-(3)-C
N-(1)-protease cleavage site-(2)-linker-(3)-C
N-(2)-linker-(1)-protease cleavage site-(3)-C
N-(2)-protease cleavage site-(1)-linker-(3)-C
N-(2)-linker-(3)-protease cleavage site-(1)-C
N-(2)-protease cleavage site-(3)-linker-(1)-C
N-(1)-linker-(3)-protease cleavage site-(2)-C
N-(1)-protease cleavage site-(3)-linker-(2)-C
N-(3)-linker-(1)-protease cleavage site-(2)-C
N-(3)-protease cleavage site-(1)-linker-(2)-C In a preferred embodiment, the combinations and relative orders of elements in the polypeptide of the conjugate is N-(1)-linker-(2)-protease cleavage site-(3)-C. Thus, in a preferred embodiment, the second polypeptide is connected to the first polypeptide region through a linker, and the first polypeptide is connected to the third polypeptide region through a protease cleavage site.

In another preferred embodiment, said linker comprises the sequence GGSSRSS (SEQ ID NO:39), GGSSRSSS (SEQ ID NO:76), or the GGGNS sequence (SEQ ID NO:40), preferably the sequence GGSSRSS (SEQ ID NO:39).

In preferred embodiments, the conjugates of the sixth aspect of the invention comprise a polypeptide which comprises the following elements:

TABLE 3

Preferred polypeptides forming part of the conjugates of the invention

| Second polypeptide | first peptide linker | First polypeptide | Third polypeptide |
|---|---|---|---|
| T22 (SEQ ID NO: 27) | GGSSRSS (SEQ ID NO: 39) | Nid (238 amino acids) (SEQ ID NO: 62) | Hexahistidine (SEQ ID NO: 73) |
| T22 (SEQ ID NO: 27) | GGSSRSS (SEQ ID NO: 39) | Nid (236 amino acids) SEQ ID NO: 63 | Hexahistidine (SEQ ID NO: 73) |
| T22 (SEQ ID NO: 27) | GGSSRSS (SEQ ID NO: 39) | Nidomut2 (238 amino acids) as defined in SEQ ID NO: 64 | Hexahistidine (SEQ ID NO: 73) |
| T22 (SEQ ID NO: 27) | GGSSRSS (SEQ ID NO: 39) | NidoMut2 (236 amino acids) as defined in SEQ ID NO: 65 | Hexahistidine (SEQ ID NO: 73) |
| T22 (SEQ ID NO: 27) | GGSSRSS (SEQ ID NO: 39) | NidoMut3 or any of SEQ ID NO: 88-91 or 95-102 | Hexahistidine (SEQ ID NO: 73) |
| T22 (SEQ ID NO: 27) | GGSSRSS (SEQ ID NO: 39) | NidoMut4 | Hexahistidine (SEQ ID NO: 73) |
| T22 (SEQ ID NO: 27) | GGSSRSS (SEQ ID NO: 39) | NidoMut5 or any of SEQ ID NO: 102-105 | Hexahistidine (SEQ ID NO: 73) |
| Optimized EPI-X4 (SEQ ID NO. 29) | GGSSRSS (SEQ ID NO: 39) | Nidomut2 (238 amino acids) as defined in SEQ ID NO: 64 | Hexahistidine (SEQ ID NO: 73) |
| Optimized EPI-X4 to the positively charged region of sequence RKRKRK (SEQ ID NO: 133) | GGSSRSSS (SEQ ID NO: 39) | NidoMut2 (236 amino acids) as defined in SEQ ID NO: 65 | Hexahistidine (SEQ ID NO: 73) |
| Optimized EPI-X4 to the positively charged region of sequence RKRKRK (SEQ ID NO: 133) | GGSSRSS (SEQ ID NO: 39) | NidoMut3 or any of SEQ ID NO: 88-91 or 95-102 | Hexahistidine (SEQ ID NO: 73) |

TABLE 3-continued

Preferred polypeptides forming part of the conjugates of the invention

| Second polypeptide | first peptide linker | First polypeptide | Third polypeptide |
|---|---|---|---|
| Optimized EPI-X4 to the positively charged region of sequence RKRKRK (SEQ ID NO: 133) | GGSSRSS (SEQ ID NO: 39) | NidoMut4 | Hexahistidine (SEQ ID NO: 73) |
| Optimized EPI-X4 to the positively charged region of sequence RKRKRK (SEQ ID NO: 133) | GGSSRSS (SEQ ID NO: 39) | NidoMut5 or any of SEQ ID NO: 102-105 | Hexahistidine (SEQ ID NO: 73) |

In another particular embodiment, a positively charged amino acid, preferably an arginine or a lysine, more preferably a lysine, is comprised between the first polypeptide region and the third polypeptide region of the conjugate of the sixth aspect.

In another preferred embodiment, the polypeptide forming part of the conjugate of the invention comprises, essentially comprises or consists of the amino acid sequence SEQ ID NO:61, optionally containing a methionine at the amino terminus.

In some embodiments, the polypeptide forming part of the conjugate of the invention comprises, essentially comprise or consists of the amino acid sequence of any of SEQ ID NO:61 or 106-124, optionally containing a methionine at the amino terminus.

In a particular embodiment, the agent of interest of the conjugate of the sixth aspect of the invention is a therapeutic agent or an imaging agent.

IV-E. The Agent of Interest

In a particular embodiment, the agent of interest of the conjugate of the sixth aspect of the invention is a therapeutic agent or an imaging agent.

IV-E.1 the Therapeutic Agent

The term “therapeutic agent”, as used herein, is drawn to any compound, without chemical structure limitations, suitable for therapy and/or treatment of a condition, disorder or disease.

The nature of the therapeutic agent is not particularly limiting for the present invention provided it remains active in the conjugate or can be activated once it is delivered to the inside of the cell. Accordingly, any therapeutic agent can be used in the conjugate provided that it shows an activity or can reach an activity once it is delivered to the inside of the cell of at least 100%, at least 90%, at least 80%, at least 70%, at least 60%, at least 50% or less of the activity of the unconjugated therapeutic agent. Alternatively, since the purpose of the invention is to facilitate the action of the therapeutic agent by increasing its selectivity and reducing its off-target effects, it is contemplated that the effects of the therapeutic agent conjugated to the polypeptide of the conjugate may be synergic and exceed the parametrized values already known for the specific therapeutic agent. Accordingly, it is intended that some embodiments of the therapeutic agent conjugated to the polypeptide of the conjugate of the invention also show at least 101%, at least 105%, at least 110%, at least 115%, at least 120%, at least 125%, at least 130%, at least 135%, at least 140%, at least 145%, at least 150%, at least 175%, at least 200%, at least 300%, at least 400%, at least 500%, at least 1000%, or more of the functionality of the therapeutic agent alone.

In an embodiment of the invention, the therapeutic agent conjugated to the polypeptide of the conjugate of the invention is selected from the group consisting of (i) a chemotherapy agent,
(ii) a cytotoxic polypeptide,
(ii) an antiangiogenic polypeptide,
(iii) a polypeptide encoded by a tumor suppressor gene,
(iv) a pro-apoptotic polypeptide,
(v) a polypeptide having anti-metastatic activity,
(vi) a polypeptide encoded by a polynucleotide which is capable of activating the immune response towards a tumor,
(vii) an antiangiogenic molecule, and
(viii) a toxin.

In a particular embodiment, the polypeptide of the conjugate is conjugated to a plurality of therapeutic agents, wherein said plurality of therapeutic agents are the same or different.

(i) Chemotherapy Agent

In a particular embodiment, the therapeutic agent is a chemotherapy agent.

It will be understood that the term “chemotherapeutic agents” refers to anti-cancer agents.

As used herein, an anti-cancer agent is an agent that at least partially inhibits the development or progression of a cancer, including inhibiting in whole or in part symptoms associated with the cancer even if only for the short term.

Several anti-cancer agents can be categorized as DNA damaging agents and these include topoisomerase inhibitors (e.g., etoposide, ramptothecin, topotecan, teniposide, mitoxantrone), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), DNA strand break inducing agents (e.g., bleomycin, doxorubicin, daunorubicin, idarubicin, mitomycin C), anti-microtubule agents (e.g., vincristine, vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), anthracyclines, vinca alkaloids, or epipodophyllotoxins.

Additional examples of anti-cancer agents include without limitation Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Bortezomib (VELCADE™); Brequinar Sodium; Bropirimine;

Busulfan; Cactinomycin; Calusterone; Caracemide; Carbetimer; Carboplatin (a platinum-containing regimen); Carmustine; Carubicin Hydrochloride; Carzelesin; Cedefingol; Chlorambucil; Cirolemycin; Cisplatin (a platinum-containing regimen); Cladribine; Crisnatol Mesylate; Cyclophosphamide; Cytarabine; Dacarbazine; Dactinomycin; Daunorubicin; Decitabine; Dexormaplatin; Dezaguanine; Diaziquone; Docetaxel (TAXOTERE®); Doxorubicin; Droloxifene; Dromostanolone; Duazomycin; Edatrexate; Eflornithine; Elsamitrucin; Enloplatin; Enpromate; Epipropidine; Epirubicin; Erbulozole; Erlotinib (TARCEVA®), Esorubicin; Estramustine; Etanidazole; Etoposide; Etoprine; Fadrozole; Fazarabine; Fenretinide; Floxuridine; Fludarabine; 5-Fluorouracil; Flurocitabine; Fosquidone; Fostriecin; Gefitinib (IRESSA®), Gemcitabine; Hydroxyurea; Idarubicin; Ifosfamide; Ilmofosine; Imatinib mesylate (GLEEVAC®); Interferon alpha-2a; Interferon alpha-2b; Interferon alpha-n1; Interferon alpha-n3; Interferon beta-I a; Interferon gamma-I b; Iproplatin; Irinotecan; Lanreotide; Lenalidomide (REVLLMID® REVIMID®); Letrozole; Leuprolide; Liarozole; Lometrexol; Lomustine; Losoxantrone; Masoprocol; Maytansine; Mechlorethamine; Megestrol; Melengestrol; Melphalan; Menogaril; Mercaptopurine; Methotrexate; Metoprine; Meturedepa; Mitindomide; Mitocarcin; Mitocromin; Mitogillin; Mitomalcin; Mitomycin; Mitosper; Mitotane; Mitoxantrone; Mycophenolic Acid; Nocodazole; Nogalamycin; Ormaplatin; Oxisuran; Paclitaxel; Pemetrexed (ALIMTA®), Pegaspargase; Peliomycin; Pentamustine; Pentomone; Peplomycin; Perfosfamide; Pipobroman; Piposulfan; Piritrexim Isethionate; Piroxantrone; Plicamycin; Plomestane; Porfimer; Porfiromycin; Prednimustine; Procarbazine; Puromycin; Pyrazofurin; Riboprine; Rogletimide; Safingol; Semustine; Simtrazene; Sitogluside; Sparfosate; Sparsomycin; Spirogermanium; Spiromustine; Spiroplatin; Streptonigrin; Streptozocin; Sulofenur; Talisomycin; Tamsulosin; Taxol; Taxotere; Tecogalan; Tegafur; Teloxantrone; Temoporfin; Temozolomide (TEMODAR®); Teniposide; Teroxirone; Testolactone; Thalidomide (THALOMID®) and derivatives thereof; Thiamiprine; Thioguanine; Thiotepa; Tiazofurin; Tirapazamine; Topotecan; Toremifene; Trestolone; Triciribine; Trimetrexate; Triptorelin; Tubulozole; Uracil; Mustard; Uredepa; Vapreotide; Verteporfin; Vinblastine; Vincristine; Vindesine; Vinepidine; Vinglycinate; Vinleurosine; Vinorelbine; Vinrosidine; Vinzolidine; Vorozole; Zeniplatin; Zinostatin; Zorubicin.

In one embodiment, the anti-cancer agent is provided as an oligomer containing several units of the anti-cancer molecule. In one embodiment, the anti-cancer agent is a floxuridine poly- or oligonucleotide, which comprises several floxuridine molecules. The floxuridine poly- or poligonucleotide contains at least 2, 3, 4, 5, 6, 7, 8, 9, 10, 15, 20, 25, 30, 35, 40, 45, 50 or more floxuridine molecules. In a preferred embodiment the floxuridine polynucleotide is a floxuridine pentanucleotide, i.e. an oligonucleotide containing 5 floxuridine molecules.

The anti-cancer agent may be an enzyme inhibitor including without limitation tyrosine kinase inhibitor, a CDK inhibitor, a MAP kinase inhibitor, or an EGFR inhibitor. The tyrosine kinase inhibitor may be without limitation Genistein (4',5,7-trihydroxyisoflavone), Tyrphostin 25 (3,4, 5-trihydroxyphenyl), methylene]-propanedinitrile, Herbimycin A, Daidzein (4',7-dihydroxyisoflavone), AG-126, trans-1-(3'-carboxy-4'-hydroxyphenyl)-2-(2",5"-dihydroxyphenyl) ethane, or HDBA (2-Hydroxy5-(2,5-Dihydroxybenzylamino)-2-hydroxybenzoic acid. The CDK inhibitor may be without limitation p21, p27, p57, p15, p16, p18, or p19. The MAP kinase inhibitor may be without limitation KY12420 ($C_{23}H_{24}O_8$), CNI-1493, PD98059, or 4-(4-Fluorophenyl)-2-(4-methylsulfinyl phenyl)-5-(4-pyridyl) 1H-imidazole. The EGFR inhibitor may be without limitation erlotinib (TARCEVA®), gefitinib (IRESSA®), WHI-P97 (quinazoline derivative), LFM-A12 (leflunomide metabolite analog), ABX-EGF, lapatinib, canertinib, ZD-6474 (ZACTIMA®), AEE788, and AG1458.

The anti-cancer agent may be a VEGF inhibitor including without limitation bevacizumab (AVASTIN®), ranibizumab (LUCENTIS®), pegaptanib (MACUGEN®), sorafenib, sunitinib (SUTENT®), vatalanib, ZD-6474 (ZACTIMA®), anecortave (RETAANE®), squalamine lactate, and semaphorin. The anti-cancer agent may be an antibody or an antibody fragment including without limitation an antibody or an antibody fragment including but not limited to bevacizumab (AVASTIN®), trastuzumab (HERCEPTIN®), alemtuzumab (CAMPATH®, indicated for B cell chronic lymphocytic leukemia), gemtuzumab (MYLOTARG®, hP67.6, anti-CD33, indicated for leukemia such as acute myeloid leukemia), rituximab (RITUXAN®), tositumomab (BEXXAR®, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), edrecolomab (PANOREX®), daclizumab (ZENAPAX®), palivizumab (SYNAGIS® indicated for respiratory conditions such as RSV infection), ibritumomab tiuxetan (ZEVALIN®, indicated for Non-Hodgkin's lymphoma), cetuximab (ERBITUX®), MDX-447, MDX-22, MDX-220 (anti-TAG-72), I0R-C5, 10R-T6 (anti-CD 1), IOR EGF/R3, celogovab (ONCOSCINT® OV 103), epratuzumab (LYMPHOCIDE®), pemtumomab (THERAGYN®), and Gliomab-H (indicated for brain cancer, melanoma).

It is contemplated that in certain embodiments of the invention a protein that acts as an angiogenesis inhibitor is targeted to a tumor. These agents include, in addition to the anti-angiogenic polypeptides mentioned above, Marimastat; AG3340; COL-3, BMS-275291, Endostatin, SU6668, Thalidomide, SU5416, EMD121974, 2-methoxyoestradiol, carboxiamidotriazole, CMlO1, pentosan polysulphate, angiopoietin 2 (Regeneron), herbimycin A, PNU145156E, 16K prolactin fragment, Linomide, thalidomide, pentoxifylline, genistein, TNP470, endostatin, paclitaxel, accutin, angiostatin, cidofovir, vincristine, bleomycin, AGM-1470, platelet factor 4 or minocycline.

Other suitable active agents are DNA cleaving agents. Examples of DNA cleaving agents suitable for inclusion as the cell toxin in the conjugates used in practicing the methods include, but are not limited to, anthraquinone-oligopyrrol-carboxamide, benzimidazole, leinamycin; dynemycin A; enediyne; as well as biologically active analogs or derivatives thereof (i.e., those having a substantially equivalent biological activity). Known analogs and derivatives are disclosed, for examples in Islam et al., J. Med. Chem. 34 2954-61, 1991; Skibo et al., J. Med. Chem. 37:78-92, 1994; Behroozi et al., Biochemistry 35:1568-74, 1996; Helissey et al., Anticancer Drug Res. 11:527-51, 1996; Unno et al., Chem. Pharm. Bull. 45:125-33, 1997; Unno et al., Bioorg. Med. Chem., 5:903-19, 1997; Unno et al., Bioorg. Med. Chem., 5:883-901, 1997; and Xu et al., Biochemistry 37:1890-7, 1998). Other examples include, but are not limited to, endiyne quinone imines (U.S. Pat. No. 5,622, 958); 2,2r-bis(2-aminoethyl)-4-4'-bithiazole [Lee et al., Biochem. Mol. Biol. Int. 40:151-7, 1996]; epillicitine-salen-.copper conjugates [Routier et al., Bioconjug. Chem., 8:789-92, 1997].

Some of the aforementioned chemotherapy agents can be grouped together under a common category as antimetabolites. "Antimetabolite" as used herein, refers to the compounds which inhibit the use of a metabolite that is part of normal metabolism. Antimetabolites are often similar in structure to the metabolite that they interfere with, such as the antifolates that interfere with the use of folic acid. Non-limiting examples of antimetabolites include the following compounds: bleomycin, busulfan, capecitabine, carmustine, carboplatin, chlorodeoxyadenosine, cisplatin, cyclophosphamide, cytarabine, dacarbazine, daunorubicin, docetaxel, doxorubicin, etoposide, fludarabine, fluorouracil, gemcitabine, hydroxyurea, idarubicin, ifosfamide, irinotecan, lomustine, melphalan, mercaptopurine, methotrexate mitomycin, mitoxantrone, oxaliplatin, paclitaxel, procarbazine, SN-38, thioguanine, thiotepa, teniposide vinblastine, vincristine, and vinorelbine.

In a particular embodiment, the anti-cancer agent is an antimetabolite. In another particular embodiment, the antimetabolite is a pyrimidine analogue, or an oligomeric form thereof. In another particular embodiment, the pyrimidine analogue is floxuridine, or a pentameric form thereof.

The term "pyrimidine analog", as used herein, refers to nucleoside analog antimetabolites which mimic the structure of pyrimidines. The pyrimidine analogues interfere with nucleic acid synthesis. Their antiproliferative effect is achieved through incorporation into DNA, causing chain termination and inhibition of DNA synthesis. They can also interfere with enzymes involved in nucleic acid synthesis, such as DNA polymerases and ribonucleotide reductase. Non-limiting examples of pyrimidine analogs include: Azacitidine, 6-Azauracil, Cytarabine, Decitabine, Gemcitabine, Troxacitabine, Floxuridine, Fluorouracil, Capecitabine, Tegafur-uracil.

The term "floxuridine", as used herein, refers to an anti-cancer agent classified as antimetabolite, which is a pyrimidine analog, classified as a deoxyuridine. The IUPAC name of said anti-cancer agent is 5-Fluoro-1-[4-hydroxy-5-(hydroxymethyl)tetrahydrofuran-2-yl]-1H-pyrimidine-2,4-dione.

The expression "oligomeric form thereof", as used herein, refers to a molecule formed by a few repeating units, as opposed to a polymer which is not limited to specific number of units, wherein each unit is termed a monomer. Generally, the number of monomers in an oligomer is between 5 and 100. Thus, an oligomeric form of pyrimidine analogue, refers herein to a molecule formed by a sequence of a few pyrimidine analogues. In a particular embodiment, the oligomeric or polymeric form of pyrimidine analogues refers to a molecule comprising a sequence of at least 2, 3, 4, 5, 6, 7, 8, 9, 10, 15, 20, 25, 30, 35, 40, 45, 50 or more pyrimidine analogs. In another particular embodiment, it refers to a molecule consisting of a sequence of at least 2, 3, 4, 5, 6, 7, 8, 9, 10, 15, 20, 25, 30, 35, 40, 45, 50 or more pyrimidine analogs.

In a particular embodiment, the oligomeric or polymeric form of pyrimidine analogue is a molecule comprising a sequence of at least 2, 3, 4, 5, 6, 7, 8, 9, 10, 15, 20, 25, 30, 35, 40, 45, 50 or more floxuridines. In another particular embodiment, the oligomeric form of pyrimidine analogue is a molecule consisting of a sequence of at least 2, 3, 4, 5, 6, 7, 8, 9, 10, 15, 20, 25, 30, 35, 40, 45, 50 or more floxuridines.

The expression "pentameric form thereof", when referring to a floxuridine analogue, is understood as molecule comprising, or consisting of, a sequence of 5 floxuridines.

(ii) Cytotoxic Polypeptides

As used herein, the term "cytotoxic polypeptide" refers to an agent that is capable of inhibiting cell function. The agent may inhibit proliferation or may be toxic to cells. Any polypeptides that when internalized by a cell interfere with or detrimentally alter cellular metabolism or in any manner inhibit cell growth or proliferation are included within the ambit of this term, including, but not limited to, agents whose toxic effects are mediated when transported into the cell and also those whose toxic effects are mediated at the cell surface. Useful cytotoxic polypeptides include proteinaceous toxins such as bacterial toxins.

Examples of proteinaceous cell toxins useful for incorporation into the conjugates according to the invention include, but are not limited to, type one and type two ribosome inactivating proteins (RIP). Useful type one plant RIPs include, but are not limited to, dianthin 30, dianthin 32, lychnin, saporins 1-9, pokeweed activated protein (PAP), PAP II, PAP-R, PAP-S, PAP-C, mapalmin, dodecandrin, bryodin-L, bryodin, Colicin 1 and 2, luffin-A, luffin-B, luffin-S, 19K-protein synthesis inhibitory protein (PSI), 15K-PSI, 9K-PSI, alpha-kirilowin, beta-kirilowin, gelonin, momordin, momordin-II, momordin-Ic, MAP-30, alpha-momorcharin, beta-momorcharin, trichosanthin, TAP-29, trichokirin; barley RIP; flax RIP, tritin, corn RIP, Asparin 1 and 2 [Stirpe et al., 1992. Bio/Technology 10:405-12]. Useful type two RIPs include, but are not limited to, volkensin, ricin, nigrin-b, CIP-29, abrin, modeccin, ebulitin-[alpha], ebulitin-[beta], ebultin-[gamma], vircumin, porrectin, as well as the biologically active enzymatic subunits thereof [Stirpe et al., 1992. Bio/Technology 10:405-12; Pastan et al., 1992. Annu. Rev. Biochem. 61:331-54; Brinkmann and Pastan, 1994. Biochim. et Biophys. Acta 1198:27-45; and Sandvig and Van Deurs, 1996. Physiol. Rev. 76:949-66].

Examples of bacterial toxins useful as cell toxins include, but are not limited to, shiga toxin and shiga-like toxins (i.e., toxins that have the same activity or structure), as well as the catalytic subunits and biologically functional fragments thereof. These bacterial toxins are also type two RIPs [Sandvig and Van Deurs, 1996. Physiol. Rev. 76:949-66; Armstrong, 1995. J. Infect. Dis., 171:1042-5; Kim et al., 1997. Microbiol. Immunol. 41:805-8; and Skinner et al., 1998. Microb. Pathog. 24:117-22]. Additional examples of useful bacterial toxins include, but are not limited to, *Pseudomonas* exotoxin and Diphtheria toxin [Pastan et al., 1992. Annu. Rev. Biochem. 61:331-54; and Brinkmann and Pastan, 1994. Biochim. et Biophys. Acta 1198:27-45]. Truncated forms and mutants of the toxin enzymatic subunits also can be used as a cell toxin moiety (Pastan et al., Annu. Rev. Biochem. 61:331-54; Brinkmann and Pastan, Biochim. et Biophys. Acta 1198:27-45, 1994; Mesri et al., J. Biol. Chem. 268:4852-62, 1993; Skinner et al., Microb. Pathog. 24:117-22, 1998; and U.S. Pat. No. 5,082,927). Other targeted agents include, but are not limited to the more than 34 described Colicin family of RNase toxins which include colicins A, B, D, E1-9, cloacin DF13 and the fungal RNase, [alpha]-sarcin [Ogawa et al. 1999. Science 283:2097-100; Smarda et al., 1998. Folia Microbiol (Praha) 43:563-82; Wool et al., 1992. Trends Biochem. Sci., 17:266-69].

(iii) Antiangiogenic Polypeptides

Proliferation of tumor cells relies heavily on extensive tumor vascularization, which accompanies cancer progression. Thus, inhibition of new blood vessel formation with anti-angiogenic agents and targeted destruction of existing blood vessels have been introduced as effective and relatively non-toxic approaches to tumor treatment.

The term "anti-angiogenic polypeptide", as used herein, denotes a polypeptide capable of inhibiting angiogenesis. Suitable antiangiogenic polypeptides include, without limitation, angiostatin, endostatin, anti-angiogenic anti-thrombin III, sFRP-4 as described in WO2007115376, and an anti-VEGF antibody such as anibizumab, bevacizumab (AVASTIN®), Fab IMC 1121 and F200 Fab.

(iv) Polypeptides Encoded by a Tumor Suppressor Gene

As used herein, a "tumor suppressor" is a gene or gene product that has a normal biological role of restraining unregulated growth of a cell. The functional counterpart to a tumor suppressor is an oncogene—genes that promote normal cell growth may be known as "proto-oncogenes" A mutation that activates such a gene or gene product further converts it to an "oncogene", which continues the cell growth activity, but in a dysregulated manner Examples of tumor suppressor genes and gene products are well known in the literature and may include PTC, BRCA1, BRCA2, p16, APC, RB, WTl, EXTl, p53, NFl, TSC2, NF2, VHL, ST7, ST14, PTEN, APC, CD95 or SPARC.

(v) Pro-Apoptotic Polypeptides

The term "pro-apoptotic polypeptides", as used herein, refers to a protein which is capable of inducing cell death in a cell or cell population. The overexpression of these proteins involved in apoptosis displaces the careful balance between anti-apoptotic and pro-apoptotic factors towards an apoptotic outcome. Suitable pro-apoptotic polypeptides include, without limitation, pro-apoptotic members of the BCL-2 family of proteins such as BAX, BAK, BOK/MTD, BID, BAD, BIK/NBK, BLK, HRK, BIM/BOD, BNIP3, NIX, NOXA, PUMA, BMF, EGL-I, and viral homologs, caspases such as caspase-8, the adenovirus E4orf4 gene, p53 pathway genes, pro-apoptotic ligands such as TNF, FasL, TRAIL and/or their receptors, such as TNFR, Fas, TRAIL-R1 and TRAIL-R2.

(vi) Polypeptides with Anti-Metastatic Activity

The term "metastasis suppressor" as used herein, refers to a protein that acts to slow or prevent metastases (secondary tumors) from spreading in the body of an organism with cancer. Suitable metastasis suppressors include, without limitation, proteins such as BRMS1, CRSP3, DRGI, KAI1, KISS-1, NM23, a TIMP-family protein and uteroglobin.

(vii) Polypeptides Encoded by a Polynucleotide Capable of Activating the Immune Response Towards a Tumor As used herein, an immunostimulatory polypeptide agent is a polypeptide encoded by a polynucleotide which is capable of activating or stimulating the immune response (including enhancing a pre-existing immune response) in a subject to whom it is administered, whether alone or in combination with another agent. Suitable non-limiting examples of immunostimulatory peptides include flagellin, muramyl dipeptide), cytokines including interleukins (e.g., IL-2, IL-7, IL-15 (or superagonist/mutant forms of these cytokines), IL-12, IFN-gamma, IFN-alpha, GM-CSF, FLT3-ligand, etc.), immunostimulatory antibodies (e.g., anti-CTLA-4, anti-CD28, anti-CD3, or single chain/antibody fragments of these molecules), and the like.

(viii) Antiangiogenic Molecules

It is also contemplated that in certain embodiments the intervening region of the fusion protein of the invention corresponds to a protein that acts as an angiogenesis inhibitor is targeted to a tumor. These agents include, in addition to the anti-angiogenic polypeptides mentioned above, Marimastat; AG3340; COL-3, BMS-275291, Thalidomide, Endostatin, SU5416, SU6668, EMD121974, 2-methoxyoestradiol, carboxiamidotriazole, CMIO1, pentosan polysulphate, angiopoietin 2 (Regeneron), herbimycin A, PNU145156E, 16K prolactin fragment, Linomide, thalidomide, pentoxifylline, genistein, TNP470, endostatin, paclitaxel, accutin, angiostatin, cidofovir, vincristine, bleomycin, AGM-1470, platelet factor 4 or minocycline. Also included are VEGF inhibitors including without limitation bevacizumab (AVASTIN®), ranibizumab (LUCENTIS®), pegaptanib (MACUGEN®), sorafenib, sunitinib (SUTENT®), vatalanib, ZD-6474 (ZACTIMA®), anecortave (RETAANE®), squalamine lactate, and semaphorin.

(ix) Toxins

As used herein, the term "toxins" refers to non-proteinaceous/non-polypeptidic cytotoxic compounds obtained from different organisms, as well as chemically modified derivatives of those same compounds and compounds obtained through chemical synthesis. The compounds of this category with biological origin may be obtained from microorganisms (whether bacteria, archaea, protozoa or unicellular fungi) or pluricellular organisms (pluricellular fungi, plants, or animals, like mollusks). It is intended that the chemical composition and structure of these toxins is not limited in any way beyond their non-polypeptidic nature, therefore one or more amino acids may be part of their structure, whether as part of their basic composition or as result of chemical derivation, as long as all the amino acids participating in the structure are not bound together by peptide bonds.

Examples of toxins suitable for the invention are calicheamycin y1, dolastatin 10, maytansinoid (DM1) and pyrrolobenzodiazepine dimer (PBD).

(x) Additional Therapeutic Agents

In a particular embodiment of the conjugate of the invention, the therapeutic agent is selected from the therapeutic agents indicated in the third column of table 4 below.

TABLE 4

Ligands, and receptors, cells or microorganisms, to which said ligands bind are provided in columns 1 and 2, as in table 1 above. In addition, therapeutic agents to be associated to said ligands for the treatment of a certain disease or disorder are provided in the third column, and the disease or disorder to be treated in the fourth column. The agents to be associated to a certain ligand or group of ligands is provided in the same raw as said ligand or group of ligands. The disease or disorder to be treated by the association of a ligand, or group of ligands, and a therapeutic agent, or a group of therapeutic agents, are provided in the same raw as said ligand/s and therapeutic agent/s.

| Ligand | Cell receptor/cell type or microorganism | Therapeutic agent | Disease or disorder |
|---|---|---|---|
| Folic acid or folic acid targeting ligand, including methotrexate or aminopterin. | Folate receptor in leucocyte | Cytotoxic agent | Leukemia |
| Hyalurinic acid (HA) | CD44 | | |
| Xanthine scaffold, inluding lingaliptin | fibroblast activation protein (FAP) on wound fibroblast cells | Growth factor | Wounds |
| IgG Fc | Protein A in *S. aureus* | antimicrobial agent (antibacterial, antifungal, antiprotozoal or antiviral) | Infections/ sepsis |
| Ligands of Her 2 are well-known in the art, and can be any of those described in Wikman M et al., Protein Eng Des Sel 17: 455-62 (2004); Orlova A et al. Cancer Res 66: 4339-8 (2006); Ahlgren S et al., Bioconjug Chem 19: 235-43 (2008); Feldwisch J et al., JMol Biol 398: 232-47 (2010); US patents with Pat. No.: 5,578,482; 5,856,110; 5,869,445; 5,985,553; 6,333, 169; 6,987,088; 7,019,017; 7,282,365; 7,306,801; 7,435,797; 7,446, 185; 7,449,480; 7,560,111; 7,674,460; 7,815,906; 7,879,325; 7,884, 194; 7,993,650; 8,241,630; 8,349,585; 8,389,227; 8,501,909; 8,512,967; 8,652,474; and U.S. patent application US20110059090A1 | HER2 | Cytotoxic agent | Breast cancer |
| CRPPR peptide | Heart endothelium | NAP -2, TGF-a, ErBb3, VEGF, IGF-1, FGF-2, PDGF, IL-2, CD 19, CD20, and/or CD80/86, prostaglandins (PGE2, PGI2) | Cardiac disease |
| Angiotensin | angiotensin II type 1 (AT1) receptor | NAP-2, TGF-a, ErBb3, VEGF, IGF-1, FGF-2, | Cardiac disease |

TABLE 4-continued

Ligands, and receptors, cells or microorganisms, to which said ligands bind are provided in columns 1 and 2, as in table 1 above. In addition, therapeutic agents to be associated to said ligands for the treatment of a certain disease or disorder are provided in the third column, and the disease or disorder to be treated in the fourth column. The agents to be associated to a certain ligand or group of ligands is provided in the same raw as said ligand or group of ligands. The disease or disorder to be treated by the association of a ligand, or group of ligands, and a therapeutic agent, or a group of therapeutic agents, are provided in the same raw as said ligand/s and therapeutic agent/s.

| Ligand | Cell receptor/cell type or microorganism | Therapeutic agent | Disease or disorder |
|---|---|---|---|
| | | PDGF, IL-2, CD 19, CD20, and/or CD80/86, prostaglandins (PGE2, PGI2) | |
| Ligand for interleukin-6 (IL-6) such as: The S7 peptide described in SU JL et al. Cancer Res. 2019 Jul. 15; 79(14): 3791, and with SEQ ID NO: 66 (LSLITRL) the IL6 ligand described in Weiergraber O et al. FEBS Lett. 1996 Jan. 29; 379(2): 122-6 and with SEQ ID NO: 67 (WQDPHSWNSSFYRLRFELRYRAERSK TFTTW); interleukin-6 receptor (IL-6R); PDGF; angiopoietin; angiopoietin 2; Tie2; SIP; integrins av beta 3, av beta 5, and a5 beta 1; betacellulin; apelin/APJ; erythropoietin; complement factor D; TNFa; HtrA1; a VEGF receptor; ST-2 receptor; and proteins genetically linked to age-related macular degeneration (AMD) risk such as complement pathway components C2, factor B, factor H, CFHR3, C3b, C5, C5a, C3a, HtrA1, ARMS2, TIMP3, HLA, interleukin-8 (IL-8), CX3CR1, TLR3, TLR4, CETP, LIPC, COL10A1, and TNFRSF10A | Cells from the eye, preferably cells from the retinal pigment epithelium. | Anti-VEGF (Pegaptanib Ranibizumab Bevacizumab Aflibercept or conbercept) | intraocular neovascular disease selected from the group consisting of proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, retinal vein occlusion (RVO), including Central Retinal Vein Occlusion (CRVO) and branched retinal vein occlusion (BRVO), corneal neo-vascularization, retinal neo-vascularization, and retinopathy of prematurity (ROP). |
| Opsonins, including vitronectin, fibronectin, complement components such as Clq (including any of its component polypeptide chains A, B and C), complement fragments such as C3d, C3b and C4b, mannose-binding protein, conglutinin, surfactant proteins A and D, C-reactive protein (CRP), alpha2- | Microbe (virus, bacterial cell, fungal cell, protozoa) | antimicrobial agent (antibacterial, antifungal, antiprotozoal, or antiviral | Infections/ sepsis |

TABLE 4-continued

Ligands, and receptors, cells or microorganisms, to which said ligands bind are provided in columns 1 and 2, as in table 1 above. In addition, therapeutic agents to be associated to said ligands for the treatment of a certain disease or disorder are provided in the third column, and the disease or disorder to be treated in the fourth column. The agents to be associated to a certain ligand or group of ligands is provided in the same raw as said ligand or group of ligands. The disease or disorder to be treated by the association of a ligand, or group of ligands, and a therapeutic agent, or a group of therapeutic agents, are provided in the same raw as said ligand/s and therapeutic agent/s.

| Ligand | Cell receptor/cell type or microorganism | Therapeutic agent | Disease or disorder |
|---|---|---|---|
| macroglobulin, and immunoglobulins, for example, the Fc portion of an immunoglobulin | | | |
| Mannose-binding lectin (MBL) | Microbe (virus, bacterial cell, fungal cell, protozoa) | antimicrobial agent (antibacterial, antifungal, antiprotozoal, or antiviral | Infections/ sepsis |

In a particular embodiment of the conjugate of the invention, the second polypeptide region is a ligand selected from the ligands provided in Table 4, and the agent of interest is selected from the therapeutic agents provided in the same row as said ligand in Table 4. Another particular embodiment refers to the conjugate of the invention as defined in the previous embodiments of this section, for use in the treatment of a disease or disorder, wherein said disease or disorder is selected from those provided in Table 4. Another particular embodiment refers to the conjugate of the invention as defined in the previous embodiments of this section, for use in the treatment of a disease or disorder, selected from those provided in the row of table 4, corresponding to the raw where the second polypeptide region of the conjugate is provided.

IV-E.2 Imaging Agent

The term "imaging agent" is used herein to refer to a biocompatible compound, the use of which facilitates the differentiation of different parts of an image, by increasing the contrast between those different regions of the image. The term "imaging agent" thus encompasses agents that are used to enhance the quality of an image that may nonetheless be generated in the absence of such an agent (as is the case, for instance, in MRI), as well as agents that are prerequisites for the generation of an image (as is the case, for instance, in nuclear imaging). Suitable imaging agents include, without limitation, imaging agents for Radionuclide imaging, for computerized tomography, for Raman spectroscopy, for Magnetic resonance imaging (MRI) and for optical imaging.

Imaging agents for radionuclide imaging include iodine 123, technetium 99, indium 111, rhenium 188, rhenium 186, copper 67, iodine 131, yttrium 90, iodine 125, astatine 211, gallium 67, iridium 192, cobalt 60, radium 226, gold 198, cesium 137 and phosphorus 32 ions. Examples of fluorogenic agents include gadolinium and renographin. Examples of paramagnetic ions include chromium (III), manganese (II), iron (III), iron (II), cobalt (II), nickel (H) 3 copper (II), neodymium (III), samarium (III), ytterbium (III), gadolinium (III), vanadium (II), terbium (III), dysprosium (III), holmium (III) and erbium (III) ions.

Imaging agents for optical imaging include, for example, fluorescein, a fluorescein derivative, indocyanine green, Oregon green, a derivative of Oregon green derivative, rhodamine green, a derivative of rhodamine green, an eosin, an erythrosin, Texas red, a derivative of Texas red, malachite green, nanogold sulfosuccinimidyl ester, cascade blue, a coumarin derivative, a naphthalene, a pyridyloxazole derivative, cascade yellow dye, dapoxyl dye. It also includes fluorescent proteins, that refer herein to proteins whose atomic structure allows them to present fluorescence, which is a phenomenon well-known in the art. Non-limiting examples of commonly used fluorescent proteins suitable for the conjugate of the invention, are the green fluorescent protein (GFP, first discovered in *Aequorea victoria*), the red fluorescent protein (RFP), the yellow fluorescent protein (YFP), the blue fluorescent protein (BFP), the cyan fluorescent protein, or any other variant, examples of which can be found in Kremers et al. [Kremers, G-J-et al. 2011. J. Cell Sci. 124:157-160].

Additional non-limiting examples of fluorescent proteins suitable for the conjugate of the invention are the enhanced green fluorescent protein (eGFP), enhanced cyan fluorescent protein CFP (ECFP), enhanced YFP (EYFP), GFPS65T, Emerald, Topaz (TYFP), Venus, Citrine, mCitrine, GFPuv, destabilized EGFP (dEGFP), destabilised ECFP (dECFP), destabilized EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2 (12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. In other embodiments, the imaging agent is a fluorescent protein selected from the group consisting of the mHoneydew, mBanana, mOrange, dTomato, tdTomato, mTangerine, mStrawberry, mCherry, mGrape1, mRaspberry, mGrape2, mPlum [Shaner et al. (2005) Nat. Methods 2:905-909], and the like.

Imaging agent for magnetic resonance imaging apparatus gadolinium chelates, manganese chelates, chromium chelates, $^{19}F$ and iron particles.

MRI imaging agents include complexes of metals selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III).

IV-E.3 Linkage of the Agent of Interest to the Polypeptide of the Conjugate

The polypeptide of the conjugate can be conjugated to a single agent of interest or to a plurality of agents. When a plurality of agents are conjugated to the polypeptide of the conjugate, said agents can be either the same or different. In a particular embodiment, said plurality of agents of interest are therapeutic agents, and they are the same or different therapeutic agents, as defined above. In another particular embodiment, said plurality of agents of interest are imaging agents, and they are the same or different imaging agents, as defined above.

The following applies to any agent of interest, i.e. to a therapeutic, to an imaging agent, to a plurality of therapeutic agents, and to a plurality of imaging agents as just defined. Thus in a particular embodiment, any of the following embodiment addressed to an agent apply to a therapeutic agent by substituting the term "agent" by "therapeutic agent". In another particular embodiment, any of the following embodiments addressed to an agent apply to an imaging agent by substituting the term "agent" by "imaging agent". In another particular embodiment, any of the following embodiments apply to a plurality of therapeutic agents, by substituting the expression "plurality of agents" by "plurality of therapeutic agents", where said plurality of therapeutic agents is as just defined above. In another particular embodiment, any of the following embodiments apply to a plurality of imaging agents, by substituting the expression "plurality of agents" by "plurality of imaging agents", where said plurality of imaging agents is as just defined above.

The agent or agents of interest can be conjugated to any sequence of the polypeptide of the conjugate.

Therefore, in a particular embodiment, the agent of interest is conjugated to the first polypeptide region. In a particular embodiment, it is conjugated to the second polypeptide region of the conjugate. In another particular embodiment, it is conjugated to the third polypeptide region of the conjugate. In another particular embodiment, it is conjugated to any of the linking region between the first and the second polypeptide. In another particular embodiment, it is conjugated to the linking region between the second and the third polypeptide region. In another particular embodiment, it is conjugated to the linking region between the second and the third polypeptide region. In another particular embodiment, it is conjugated to the protease cleavage site between the first and the second polypeptide regions. In another particular embodiment, it is conjugated to the protease cleavage site between the first and the third polypeptide regions. In another particular embodiment, it is conjugated to the protease cleavage site between the second and the third polypeptide regions.

In a particular embodiment, the plurality of agents of interest are conjugated the same polypeptide region of the conjugate. In a preferred embodiment, they are conjugated to the first polypeptide region. In a particular embodiment, they are conjugated to the second polypeptide region of the conjugate. In another particular embodiment, they are conjugated to the third polypeptide region of the conjugate. In another particular embodiment, they are conjugated to all three polypeptide regions of the polypeptide of the conjugate. In another particular embodiment, they are conjugated to the first and the second polypeptide regions of the polypeptide. In another particular embodiment, they are conjugated to the first and third polypeptide regions of the conjugate. In another particular embodiment, they are conjugated to the second and third polypeptide regions of the conjugate.

In another particular embodiment, they are conjugated to the linking regions of the polypeptide of the conjugate. In another particular embodiment, they are conjugated to the linking region between the second and the first polypeptide regions. In another particular embodiment, they are conjugated to the linking region between the first and the third polypeptide regions. In another particular embodiment, they are conjugated to the linking region between the second and the third polypeptide regions. In another particular embodiment, they are conjugated to the protease cleavage sites of the polypeptide of the conjugate. In another particular embodiment, they are conjugated to the protease cleavage site between the second and the first polypeptide regions. In another particular embodiment, they are conjugated to the protease cleavage site between the first and the third polypeptide regions. In another particular embodiment, they are conjugated to the protease cleavage site between the second and the third polypeptide regions. In another particular embodiment, they are conjugated to all the protease cleavage sites of the polypeptide.

In another particular embodiment, they are conjugated to any of the polypeptide regions indicated above and to the linking regions of the polypeptide of the conjugate. In another particular embodiment, they are conjugated to any of the polypeptide regions indicated above and to the linking region between the second and the first polypeptide regions. In another particular embodiment, they are conjugated to any of the polypeptide regions indicated above and to the linking region between the first and the third polypeptide regions. In another particular embodiment, they are conjugated to any of the polypeptide regions indicated above and to the linking region between the second and the third polypeptide regions. In another particular embodiment, they are conjugated to any of the polypeptide regions of the polypeptide indicated above and to all the linking regions of the polypeptide.

In another particular embodiment, they are conjugated to any of the polypeptide regions indicated above and to the protease cleavage sites of the polypeptide of the conjugate. In another particular embodiment, they are conjugated to any of the polypeptide regions indicated above and to the protease cleavage site between the first polypeptide region and the second polypeptide region. In another particular embodiment, they are conjugated to any of the polypeptide regions of the polypeptide and to the protease cleavage site between the first and the third polypeptide region. In another particular embodiment, they are conjugated to any of the polypeptide regions of the polypeptide and to the protease cleavage site between the second and the third polypeptide region. In another particular embodiment, they are conjugated to the polypeptide regions indicated above and to all the cleavage sites of the polypeptide.

In another particular embodiment, they are conjugated to the linking region of the polypeptide and to the protease cleavage site of the polypeptide. In another particular embodiment, they are conjugated to any of the polypeptide regions indicated above, to the linking region and to the protease cleavage site of the polypeptide of the conjugate.

It is intended that the agent of interest, as aforementioned, is conjugated to the polypeptide of the conjugate, without limitation of the position of the conjugation inside the polypeptide with regards to its N-terminal and C-terminal ends. Accordingly, the agent of interest can be conjugated to the polypeptide of the conjugate in an equidistant position with respect to the N-terminal and C-terminal ends or it can be closer to either of them. Hence, the agent of interest can be conjugated to the polypeptide region at a distance of 500, 450, 400, 350, 325, 300, 275, 250, 236, 230, 220, 210, 200, 190, 180, 170, 160, 100, 90, 80, 75, 70, 65, 60, 55, 50, 45, 40, 35, 30, 25, 30, 25, 20, 15, 20, 10, 5, or less amino acid residues from the N-terminal or C-terminal end of said polypeptide, or at the same residue of the N-terminal or C-terminal end of said polypeptide. This paragraph applies to each agent conjugated to the polypeptide, where a plurality of agents are conjugated to the polypeptide of the conjugate.

The only intended limitation in the conjugation position/s of the agent/s of interest is that the agent/s and the elements of the polypeptide are functional and the conjugation of the agent/s does not interfere with the activity of either the agent, the polypeptide or the conjugate.

So, the agent of interest, the second polypeptide, the first polypeptide region and the positively charged amino acid-rich region conserve at least 45%, at least 50%, at least 55%, at least 60%, at least 65%, at least 70%, at least 75%, at least 80%, at least 85%, at least 90%, preferably 95%, more preferably 99%, even more preferably 100% of their functionality with respect to their non-conjugated forms. This also applies regardless of the position of the conjugation in the polypeptide of the conjugate. This paragraph also applies to each of the agents conjugated to the polypeptide where a plurality of agents are conjugated to the polypeptide of the conjugate. It is intended that the agent can either be conjugated directly to a residue of the polypeptide of the conjugate or indirectly through a linking moiety.

Thus, in a particular embodiment, the agent of interest is conjugated to the polypeptide of the conjugate directly. In another particular embodiment, the agent of interest is conjugated to the polypeptide of the conjugate through a linking moiety.

In another particular embodiment, where a plurality of agents are conjugated to the polypeptide of the conjugate, all of them are conjugated directly to a residue of the polypeptide. In another particular embodiment, where a plurality of agents are conjugated to the polypeptide of the conjugate, part of them are conjugated directly to a residue of the polypeptide and the rest are conjugated indirectly through a linking moiety. In another particular embodiment, all the agents are conjugated through a linking moiety.

The expression "linking moiety", or "linker" has already been defined in the second aspect of the invention.

The person skilled in the art will acknowledge that the previous provisions regarding the functionality of the elements of the polypeptide of the conjugate and the agent apply also whenever a coupler mediates the conjugation between an agent of interest and the polypeptide of the conjugate. Therefore, whenever an agent of interest is conjugated to the polypeptide of the conjugate through a linking moiety, said agent of interest, the second polypeptide region, the first polypeptide region and the positively charged amino acid-rich region conserve at least 45%, at least 50%, at least 55%, at least 60%, at least 65%, at least 70%, at least 75%, at least 80%, at least 85%, at least 90%, preferably 95%, more preferably 99%, even more preferably 100% of their functionality with respect to their non-conjugated forms, regardless of the position of the conjugation in the polypeptide of the conjugate, the chemical composition or structure of the linking moiety and the chemical nature of the bond/s between the linking moiety and the agent and between the linking moiety and the polypeptide of the conjugate. This applies to all the agents of interest when a plurality of agents are conjugated to the polypeptide of the conjugate.

In a preferred embodiment of the invention, the linking moiety that mediates the attachment between the agent and the polypeptide of the conjugate is a 6-Maleimidohexanoic acid N-hydroxysuccinimide ester or a 4-maleimido hexanoic acid N-hydroxysuccinimide ester. In another particular embodiment, where a plurality of agents are conjugated to the polypeptide of the conjugate, all the linking moieties that mediate the attachment of the agent/s to the polypeptide of the conjugate are 6-Maleimidohexanoic acid N-hydroxysuccinimide ester or a 4-maleimido hexanoic acid N-hydroxysuccinimide ester. In another particular embodiment, where a plurality of agents are conjugated to the polypeptide of the conjugate, part of the linking moieties that mediate the attachment of the agent/s to the polypeptide of the conjugate are 6-Maleimidohexanoic acid N-hydroxysuccinimide ester or a 4-maleimido hexanoic acid N-hydroxysuccinimide ester.

In another preferred embodiment, the linking moiety that mediates the attachment between the agent and the polypeptide of a conjugate is a moiety which is capable of reacting with the sulfhydryl groups present in the side chain of the polypeptide and an active group in the agent of interest. Suitable linking groups capable of reacting with sulfhydryl groups present in the side chain of the polypeptide include, without limitation, maleimido reagents, haloacetyls, aziridines, acryloyls, arylating agents, vinylsulfones, pyridyl disulfides, TNB-thiols and disulfide reducing agents. Most of these groups conjugate to sulfhydryls by either alkylation (usually the formation of a thioether bond) or disulfide exchange (formation of a disulfide bond).

In some embodiments, the linking moiety contains a spacer region which connects the part of the linking moiety that is connected to the polypeptide forming part of the conjugate and the part of the linking moiety that is connected to the agent of interest. In some embodiments, the linking moiety is connected with the agent of interest by the spacer and the linking moiety connects the spacer-agent of interest with the polypeptide. In one embodiment, the linking moiety is connected with the polypeptide and the linking moiety connects the spacer-polypeptide with the agent of interest.

As used herein the term "spacer" refers to a moiety that connects at least two other moieties with each other. In some embodiments, the spacer is a polymer.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. The monomers may be identical, in which case the polymer is a homopolymer, or may be different, in which case the polymer is a heteropolymer. A heteropolymer may also be referred to as a "copolymer" and includes, for example, alternating copolymers in which monomers of different types alternate, periodic copolymers, in which monomers of different types are arranged in a repeating sequence; statistical copolymers, in which monomers of different types are arranged randomly; block copolymers, in which blocks of different homopolymers consisting of only one type of monomers are linked by a covalent bond; and gradient copolymers, in which the composition of different monomers changes gradually along a polymer chain. In some embodiments, the polymer comprise one or more other moieties, which in certain embodiments are selected from the group consisting of $C_{1\_50}$ alkyl, $C_{2-50}$ alkenyl, $C_{2-50}$ alkynyl, $C_{3\_10}$ cycloalkyl, 3- to 10-membered heterocyclyl, 8- to 11-membered heterobicyclyl, phenyl, naphthyl, indenyl, indanyl, and tetralinyl. In some embodiments, the spacer is a PEG-based spacer.

As used herein, the term "PEG-based" in relation to a spacer means that said spacer comprises PEG. Such PEG-based moiety or reagent comprises at least 10 percent (w/w) PEG, such as at least 20 percent (w/w) PEG, such as at least 30 percent (w/w) PEG, such as at least 40 percent (w/w) PEG, such as at least 50 percent (w/w), such as at least 60 (w/w) PEG, such as at least 70 percent (w/w) PEG, such as at least 80 percent (w/w) PEG, such as at least 90 percent (w/w) PEG, or such as at least 95 percent (w/w) PEG. The remaining weight percentage of the PEG-based moiety or reagent may be other moieties, such as those selected from the group consisting of:

$C_{1\_50}$ alkyl, $C_{2-50}$ alkenyl, $C_{2-50}$ alkynyl, $C_{3\_10}$ cycloalkyl, 3- to 10-membered heterocyclyl, 8- to 11-membered heterobicyclyl, phenyl, naphthyl, indenyl, indanyl, and tetralinyl; branching points, such as —CR<, >C< or —N<; and linkages selected from the group consisting of wherein dashed lines indicate attachment to the remainder of the moiety or reagent, and —R and —$R^a$ are independently of each other selected from the group consisting of —H, and $Ci\__6$ alkyl; and which moieties and linkages are optionally further substituted.

In some embodiments of the invention, the linking moiety binding agent/s to the polypeptide of a conjugate is susceptible to be processed by enzymes present in the cytoplasm, releasing the therapeutic agent from the fusion protein once the therapy agent conjugated to the fusion protein has been internalized in a cell.

Besides, some agents may be polymerized in such a way that multiple copies of the same molecule may be bound together, forming polymers where each monomer of the polymer is one of said molecules. A non-limiting example of such polymers is 5-Fluoro-2'-deoxyUridine (FdU), which result in oligo-FdU. It is intended that some embodiments of the invention may comprise such polymers. Also, it is intended that some other embodiments of the invention may comprise polymers of 2 or more different molecules of agents provided that the agents do not interfere with the physiological or biological effects of each other. The person skilled in the art will recognize that those embodiments of the invention featuring polymers of agents of interest may feature 2, 3, 4, 5, 6, 7, 8, 9, 10, 15, 20, 15, 30, 40, 50 or more molecules polymerized together of 1 or more different agents of interest in a proportion of 1:1, 1:2, 1:3, 1:4, 1:5, 1:6, 1:7, 1:8, 1:9, 1:10, or more.

IV-F. Reporter Proteins

In another embodiment of the invention, the polypeptide of the conjugate of the invention further comprises a reporter protein.

The person skilled in the art will acknowledge the term "reporter protein" as referring to a protein resulting from the expression of a "reporter gene". Reporter proteins are well known and commonly used in the art as markers suitable for multiple purposes, such as location of the expression of the reporter genes in tissues, cells or subcellular locations, protein-protein interactions, transport across the plasmatic membranes or endomembranes, vesicular traffic, ligand-receptor interactions, etcetera.

Useful reporter proteins in the context of the present invention include luciferase-4-monooxygenase from Photinus pyralis, β-galactosidase, thymidine kinase, and the like. The reporter proteins also include fluorescent proteins, which have already been discussed.

The reporter protein comprised by the polypeptide of the conjugate of the invention is directly adjacent to the positively charged amino acid-rich region or separated by a linker. The relative position of the positively charged amino acid-rich region, however, remains as per the aforementioned considerations about the relative position of the elements of the fusion protein. Hence, independently of the position of the positively charged amino acid-rich region in the fusion protein, the fluorescent protein is always adjacent to it, either directly or separated by a linker.

Accordingly, in the embodiments of the invention comprising a fluorescent protein, the possible relative positions of the elements of the polypeptide of the conjugate of the invention would fit the following scheme (wherein RP refers to a reporter protein and the numbering stated above for the elements is retained: (1) second polypeptide region, (2) first polypeptide region, (3) positively charged amino acid region):

N-(1)-(2)-RP-(3)-C
N-(1)-linker-(2)-RP-(3)-C
N-(1)-protease cleavage site-(2)-RP-(3)-C
N-(1)-(2)-linker-RP-(3)-C
N-(1)-(2)-protease cleavage site-RP-(3)-C
N-(1)-linker-(2)-linker-RP-(3)-C
N-(1)-protease cleavage site-(2)-protease cleavage site-RP-(3)-C
N-(1)-linker-(2)-protease cleavage site-RP-(3)-C
N-(1)-protease cleavage site-(2)-linker-RP-(3)-C
N-(3)-RP-(2)-(1)-C
N-(3)-RP-linker-(2)-(1)-C
N-(3)-RP-protease cleavage site-(2)-(1)-C
N-(3)-RP-(2)-linker-(1)-C
N-(3)-RP-(2)-linker-(1)-C
N-(3)-RP-linker-(2)-linker-(3)-C
N-(3)-RP-protease cleavage site-(2)-protease cleavage site-(3)-C
N-(3)-RP-linker-(2)-protease cleavage site-(3)-C
N-(3)-RP-protease cleavage site-(2)-linker-(3)-C
N-(1)-(2)-RP-linker-(3)-C
N-(1)-(2)-RP-protease cleavage site-(3)-C
N-(1)-linker-(2)-RP-linker-(3)-C
N-(1)-protease cleavage site-(2)-RP-protease cleavage site-(3)-C
N-(1)-linker-(2)-RP-protease cleavage site-(3)-C
N-(1)-protease cleavage site-(2)-RP-linker-(3)-C
N-(1)-(2)-linker-RP-linker-(3)-C
N-(1)-(2)-protease cleavage site-RP-protease cleavage site-(3)-C
N-(1)-(2)-linker-RP-protease cleavage site-(3)-C
N-(1)-(2)-protease cleavage site-RP-linker-(3)-C
N-(1)-linker-(2)-linker-RP-linker-(3)-C
N-(1)-protease cleavage site-(2)-protease cleavage site-RP-protease cleavage site-(3)-C
N-(1)-protease cleavage site-(2)-linker-RP-protease cleavage site-(3)-C
N-(1)-protease cleavage site-(2)-protease cleavage site-RP-linker-(3)-C
N-(1)-linker-(2)-protease cleavage site-RP-protease cleavage site-(3)-C
N-(1)-linker-(2)-linker-RP-protease cleavage site-(3)-C
N-(1)-linker-(2)-protease cleavage site-RP-linker-(3)-C
N-(1)-protease cleavage site-(2)-linker-RP-linker-(3)-C
N-(3)-linker-RP-(2)-(1)-C
N-(3)-protease cleavage site-RP-(2)-(1)-C N-(3)-linker-RP-linker-(2)-(1)-C
N-(3)-protease cleavage site-RP-protease cleavage site-(2)-(1)-C
N-(3)-protease cleavage site-RP-linker-(2)-(1)-C
N-(3)-linker-RP-protease cleavage site-(2)-(1)-C
N-(3)-linker-RP-(2)-linker-(1)-C
N-(3)-protease cleavage site-RP-(2)-protease cleavage site-(1)-C
N-(3)-linker-RP-(2)-protease cleavage site-(1)-C
N-(3)-protease cleavage site-RP-(2)-linker-(1)-C
N-(3)-linker-RP-linker-(2)-linker-(3)-C
N-(3)-protease cleavage site-RP-protease cleavage site-(2)-protease cleavage site-(3)-C
N-(3)-linker-RP-protease cleavage site-(2)-protease cleavage site-(3)-C
N-(3)-protease cleavage site-RP-linker-(2)-protease cleavage site-(3)-C
N-(3)-protease cleavage site-RP-protease cleavage site-(2)-linker-(3)-C
N-(3)-linker-RP-linker-(2)-protease cleavage site-(3)-C
N-(3)-linker-RP-protease cleavage site-(2)-linker-(3)-C
N-(3)-protease cleavage site-RP-linker-(2)-linker-(3)-C
N-(2)-(1)-RP-(3)-C
N-(2)-linker-(1)-RP-(3)-C
N-(2)-protease cleavage site-(1)-RP-(3)-C
N-(2)-(1)-linker-RP-(3)-C
N-(2)-(1)-protease cleavage site-RP-(3)-C
N-(2)-linker-(1)-linker-RP-(3)-C
N-(2)-protease cleavage site-(1)-protease cleavage site-RP-(3)-C
N-(2)-linker-(1)-protease cleavage site-RP-(3)-C
N-(2)-protease cleavage site-(1)-linker-RP-(3)-C
N-(2)-RP-(3)-(1)-C
N-(2)-(3)-RP-(1)-C
N-(2)-linker-RP-(3)-(1)-C
N-(2)-protease cleavage site-RP-(3)-(1)-C
N-(2)-linker-(3)-RP-(1)-C
N-(2)-protease cleavage site-(3)-RP-(1)-C
N-(2)-RP-(3)-linker-(1)-C
N-(2)-RP-(3)-protease cleavage site-(1)-C
N-(2)-(3)-RP-linker-(1)-C
N-(2)-(3)-RP-protease cleavage site-(1)-C
N-(2)-linker-RP-(3)-linker-(1)-C
N-(2)-protease cleavage site-RP-(3)-protease cleavage site-(1)-C
N-(2)-linker-RP-(3)-protease cleavage site-(1)-C
N-(2)-protease cleavage site-RP-(3)-linker-(1)-C
N-(2)-linker-(3)RP-linker-(1)-C
N-(2)-protease cleavage site-(3)RP-protease cleavage site-(1)-C
N-(2)-linker-(3)RP-protease cleavage site-(1)-C
N-(2)-protease cleavage site-(3)RP-linker-(1)-C
N-(1)-RP-(3)-(2)-C
N-(1)-(3)-RP-(2)-C
N-(1)-RP-(3)-linker-(2)-C
N-(1)-RP-(3)-protease cleavage site-(2)-C
N-(1)-(3)-RP-linker-(2)-C
N-(1)-(3)-RP-protease cleavage site-(2)-C
N-(1)-linker-RP-(3)-(2)-C
N-(1)-protease cleavage site-RP-(3)-(2)-C
N-(1)-linker-(3)-RP-(2)-C
N-(1)-protease cleavage site-(3)-RP-(2)-C
N-(1)-linker-RP-(3)-linker-(2)-C
N-(1)-protease cleavage site-RP-(3)-protease cleavage site-(2)-C
N-(1)-linker-RP-(3)-protease cleavage site-(2)-C
N-(1)-protease cleavage site-RP-(3)-linker-(2)-C N-(1)-linker-(3)-RP-linker-(2)-C
N-(1)-protease cleavage site-(3)-RP-protease cleavage site-(2)-C
N-(1)-linker-(3)-RP-protease cleavage site-(2)-C
N-(1)-protease cleavage site-(3)-RP-linker-(2)-C
N-RP-(3)-(1)-(2)-C
N-(3)-RP-(1)-(2)-C
N-RP-(3)-linker-(1)-(2)-C
N-RP-(3)-protease cleavage site-(1)-(2)-C
N-(3)-RP-linker-(1)-(2)-C
N-(3)-RP-protease cleavage site-(1)-(2)-C
N-RP-(3)-(1)-linker-(2)-C
N-RP-(3)-(1)-protease cleavage site-(2)-C
N-(3)-RP-(1)-linker-(2)-C
N-(3)-RP-(1)-protease cleavage site-(2)-C
N-RP-(3)-linker-(1)-linker-(2)-C
N-RP-(3)-protease cleavage site-(1)-protease cleavage site-(2)-C
N-RP-(3)-linker-(1)-protease cleavage site-(2)-C
N-RP-(3)-protease cleavage site-(1)-linker-(2)-C
N-(3)-RP-linker-(1)-linker-(2)-C
N-(3)-RP-protease cleavage site-(1)-protease cleavage site-(2)-C
N-(3)-RP-linker-(1)-protease cleavage site-(2)-C
N-(3)-RP-protease cleavage site-(1)-linker-(2)-C IV-G. Preferred Conjugates of the Invention Preferred embodiments of the invention are conjugates in which the components are as defined in the Table 3 above and wherein the agent of interest is one or more copies of a floxuridine or floxuridine pentanucleotide. In a more preferred embodiment, the conjugates defined above result from linkages between an amino group or a thiol group in the side chain of the first region of the polypeptide forming the conjugate and a thiol or hydroxy or phosphate group or amino or carboxy in the therapeutic agent connected or not by a 9 to 35-atom spacer-linker region.

IV-H Stoichiometry of the Conjugates of the Invention

The number of agents of interest which are conjugated to the fusion protein of the invention, while not being particularly limitative, will depend on the number of available residues in the polypeptide of the invention which are available for chemical conjugation with the agent of interest. Since most conjugations occur via amino- or sulfhydryl groups present in the side chains of the amino acids forming part of the polypeptide of the conjugate, the number of agents conjugated to the polypeptide of the conjugate will depend on the number of lysine and arginine residues (for a conjugation via an amino groups in the side chains) or on the number of cysteine residues (for conjugation via sulfhydryl groups in the side chains) as well as on the yield of the conjugation reaction. Thus, in a particular embodiment of the invention, the polypeptide of the conjugate of the invention is conjugated to at least 1, 2, 3, 4, 5, 6, 7, 8, 9, 10, 12, 15, 17, 20, 25, 30 agents of interest.

It will be understood that, in the particular case wherein the agent is provided as a polymer, the number of agents will also depend on the number of the monomers in the polymer. In the particular case of a FdU oligomer, the number of agents of interest in a given conjugate will be the result of multiplying the number of oligomers attached to the polypeptide of the conjugate by the number of monomers. In the preferred case of a FdU pentamer, preferred embodiments include conjugates comprising at least 5, 10, 15, 20, 25, 30, 35, 40, 45, 50, 60, 75, 85, 100, 125, 150 or more therapeutic agents per polypeptide of the invention, corresponding, respectively, to 1, 2, 3, 4, 5, 6, 7, 8, 9, 10, 12, 15, 17, 20, 25 or 30 FdU pentamers conjugated per molecule.

In addition, the nanoparticles according to the invention result from the assembly of multiple copies of the conjugates of the invention. In preferred embodiments, the nanoparticle comprises at least 2, 3, 4, 5, 6, 7, 8, 9, 10, 11, 12, 13, 14, 15, 17, 20, 25, more preferably at least 15 monomers of the conjugate of the invention.

Accordingly, the total number of agents of interest attached to each nanoparticle will depend on (i) the number of agents conjugated to each polypeptide of the conjugate, (ii) the oligomerization state of the agents and (iii) the number of conjugates forming the nanoparticle. In preferred embodiments, the nanoparticle is conjugated to at least 30, 35, 40, 45, 50, 60, 65, 70, 57, 80, 85, 90, 59, 100, 125, 150, 175, 200, 225, 250, 275, 300 agents of interest. In a further preferred embodiment, the nanoparticle is conjugated to at least 30, 35, 40, 45, 50, 60, 65, 70, 57, 80, 85, 90, 59, 100, more preferably at least 60 molecules of FdU pentamer.

In a certain embodiment, all the terms and embodiments described in the first, second, third, fourth and fifth aspects of the invention are equally applicable to the sixth aspect of the invention V—Method for Preparing the Conjugates of the Invention In a seventh aspect, the invention relates to a method to prepare the conjugate of the sixth aspect of the invention comprising the steps of:

(i) providing the polypeptide of the conjugate of the sixth aspect of the invention comprising the G2 domain of nidogen-1 or a functionally equivalent variant thereof and (ii) contacting said polypeptide with an activated form of the agent of interest of the conjugate according to the sixth aspect of the invention which is capable of reacting with at least one group in the polypeptide and wherein the contacting is carried out under conditions adequate for the formation of a bond between the reactive group in the agent of interest and the group in the polypeptide In another embodiment, the invention relates to a method to prepare the conjugates of the sixth aspect of the invention comprising the steps of:

(i) providing the polypeptide of the conjugate of the sixth aspect of the invention comprising the G2 domain of nidogen-1 or a functionally equivalent variant thereof wherein the polypeptide is provided in an activated form and (ii) contacting said polypeptide with the agent of interest which is capable of reacting with the reactive group in the polypeptide, wherein said contacting is carried out under conditions adequate for the formation of a bond between the reactive group in the polypeptide and the group in the agent of interest The person skilled in the art will recognize that “reactive group”, as used herein, refers to any moiety of a molecule which is capable of chemically reacting with another moiety from another molecule in such a fashion so as to bind the two molecules together, usually with the release of one or more additional molecules. Many such reactions are known in the art such as the formation of the peptide bond between a carboxyl and an amine group being one non-limiting example among them.

“Activated”, as used herein when referring to a molecule, refers to a modified version of the molecule which contains a chemical modification whereby said molecule is capable to chemically react in a manner not previously present in the molecule (for instance, the activation adds a reactive group not present previously, allowing for a bond that was unfeasible before) or with an increased reactivity (meaning that the reaction of the molecule with another molecule requires a lower activation energy than in the inactivated state). The present invention contemplates the possibility of activating the agent of interest of the conjugate and then contacting the activated agent with the polypeptide of the conjugate or of activating the polypeptide of the conjugate and then contacting the activated polypeptide with the agent of interest. In both cases, the activation of the polypeptide or of the agent of interest is usually carried out by reacting the molecule to be activated with a reagent that introduces the reactive group in the molecule to be activated. Examples of reactive groups that allow the agent of interest of the conjugate or the polypeptide of the conjugate to be activated include, but are not limited, to carboxyl, amine, imine, thiol, sulfone, hydroxyl, sulfate, and phosphate moieties, among many others which are commonly known to the person skilled in the art. The activated form of the agent of interest of the conjugate is also herein referred to as the “activated agent of interest”. The activated form of the polypeptide of the conjugate is also herein referred to as the “activated polypeptide”. The reactive group or groups in the activated polypeptide is or are located in the regions of the polypeptide where the agent of interest is/are to be conjugated, as described in the sixth aspect of the invention. Therefore, in a particular embodiment, the reactive group is located: in the first polypeptide region, in the second polypeptide region, in the third polypeptide region, in the linker/s between any of said polypeptide regions, or in the protease cleavage site/s between said polypeptide regions of the conjugate. In another particular embodiment, the reactive groups are located: in the first polypeptide region, and/or in the second polypeptide region, and/or in the third polypeptide region, and/or in the linkers between any of said polypeptide regions, and/or in the protease cleavage sites between said polypeptide regions of the conjugate.

In a preferred embodiment, it is/they are located in the first polypeptide region comprised in the polypeptide of the conjugate. In a particular embodiment the reactive groups are located in the first polypeptide region of the conjugate and also in other regions comprised in the polypeptide of the conjugate of the sixth aspect just mentioned.

In those embodiments of the invention wherein a linking moiety mediates the bond between the polypeptide and the agent of interest of the conjugate, the linking moiety is a bifunctional cross-linker and, more preferably, a heterobifunctional cross-linker, that reacts with the groups in the agent of interest and in the polypeptide of the conjugate, either sequentially (either reacting with the activated agent first and then with the polypeptide, or first with the polypeptide and then with the activated agent) or simultaneously, using among other linkages such as thioethers, amide bonds, carbon-nitrogen double bonds, or linkages generated by cycloaddition as disclosed in Kalia J et al. Advances in bioconjugation. Curr Org Chem 2010 Jan. 14 (2): 138-147). As a way of example typical thiol-reactive functional groups include iodoacetamides, maleimides, and disulfides. In addition, a protein can be treated with a small molecule or surface displaying an activated ester (e.g., an N-hydroxysuccinimidyl ester) to form amide bonds with the amino groups on lysine side chains and the N terminus. In another embodiment, the linking moiety is a heterobifunctional cross-linker which contains reactive groups capable of reacting with a thiol group and with an amino group. In one embodiment, the heterobifunctional cross-linker is 6-maleimidohexanoic acid N-hydroxysuccinimide ester.

In a preferred embodiment, the linking moiety reacts in a first step with the activated agent of interest and in a second step with the polypeptide of the conjugate. In another embodiment, the linking moiety reacts in a first step with the polypeptide of the conjugate and, in a second step, with the agent of interest.

It is intended that the step of contacting the polypeptide of the conjugate of the sixth aspect of the invention with the activated form of the agent of interest is carried out in a medium which favors the reaction establishing the bond between them. Media suitable for the reactions are commonly known to the person skilled in the art, including aqueous buffers and non-aqueous buffers. It is also intended that solid supports can be used in conjunction with the media for any of the reaction steps conducing to the synthesis of the activated agent and the conjugation of the polypeptide of the conjugate, and the agent of interest, as well as the linking moiety in the embodiments that include one. Furthermore, it is intended that the method for the preparation of the conjugates between the polypeptide and the therapeutic agent is not limited to comprise the polypeptide, the activated agent of interest, and the linking moiety, but that some embodiments include also the use of one or more catalysts and co-factors in the reaction.

Thus, in one embodiment of the invention, the activated form of the agent of interest contains a group which reacts with at least one of the side chains in the polypeptide of the conjugate, preferably in the first polypeptide region comprised in the polypeptide of the conjugate. As a skilled person will understand "a side chain in the polypeptide" refers to a side chain in an amino acid residue of the polypeptide sequence.

In another preferred embodiment said residue is an external lysine. In a further preferred embodiment of the invention, the group of the activated agent of interest, preferably the chemotherapeutic agent, which reacts with at least one of the side chains in the polypeptide of the conjugate is a thiol group.

In an even more preferred embodiment of the invention, the activated therapeutic agent is an activated chemotherapeutic agent, more preferably a thiol-functionalized oligo-floxuridine.

In a preferred embodiment, the linking moiety is 6-maleimidohexanoic acid N-hydroxysuccinimide ester, and mediates the conjugation between the activated agent and the side chain in the polypeptide of the conjugate indicated in the previous embodiments of this section. In a yet more preferred embodiment, the linking moiety 6-maleimido-hexanoic acid N-hydroxysuccinimide ester is bound in a first step to the agent of interest, preferably the activated FdU, yet more preferably FdU functionalized with a sulfhydryl, and in a second step to the side chain in the polypeptide of the conjugate, more preferably to external lysines of the polypeptide of the conjugate, even more preferably to external lysines of the first polypeptide region of the conjugate of the invention.

In another preferred embodiment of the invention, the activated therapeutic agent is an activated chemotherapeutic agent, more preferably an amino-functionalized oligo-floxuridine.

In a preferred embodiment, the linking moiety is 6-maleimidohexanoic acid N-hydroxysuccinimide ester, and mediates the conjugation between the activated agent and the side chain in the polypeptide of the conjugate indicated in the previous embodiments of this section. In a yet more preferred embodiment, the linking moiety 6-maleimido-hexanoic acid N-hydroxysuccinimide ester is bound in a first step to the agent of interest, preferably the activated FdU, yet more preferably FdU functionalized with a amino, and in a second step to the side chain in the polypeptide of the conjugate, more preferably to external cysteines of the polypeptide of the conjugate, even more preferably to external cysteines of the first polypeptide region of the conjugate of the invention.

In another preferred embodiment of the invention, the activated therapeutic agent is an activated chemotherapeutic agent, more preferably a carboxy-functionalized oligo-floxuridine.

In a preferred embodiment, the activated FdU, yet more preferably FdU functionalized with an activated form of carboxylic acid, reacts the carboxyl group in the agent of interest and with the reactive group in the polypeptide (e.g. an amino group which is capable of forming an amide group with the carboxyl group in the agent of interest) to the side chain in the polypeptide of the conjugate, more preferably to external lysines of the polypeptide of the conjugate, even more preferably to external lysines of the first polypeptide region of the conjugate of the invention.

In a further preferred embodiment, the agent of interest and, more preferably, FdU or the pentameric form thereof is functionalized with an amino group and the linking moiety is a bifunctional reagent that reacts with the amino group in the agent of interest and with the reactive group in the polypeptide. In some embodiments, the bifunctional reagent contains a moiety that reacts with an amino group (e.g. a carboxylate group which is capable of forming an amide group with the amino group in the agent of interest) and a moiety that reacts with a sulfhydryl group in the side chain of the protein (e.g. a maleimide group, which is capable of forming a thioeter with the sulfhydryl group in the side chain of the polypeptide).

In a further preferred embodiment, the agent of interest and, more preferably, FdU or the pentameric form thereof is functionalized with a carboxyl group and the linking moiety is a bifunctional reagent that reacts with the carboxyl group in the agent of interest and with the reactive group in the polypeptide. In some embodiments, the bifunctional reagent contains a moiety that reacts with the carboxyl group (e.g. an amino group which is capable of forming an amide group with the carboxyl group in the agent of interest) and a moiety that reacts with a sulfhydryl group in the side chain of the protein (e.g. a maleidimide group, which is capable of forming a thioeter with the sulfhydryl group in the side chain of the polypeptide) or with an amino group in the protein.

Figure 6:
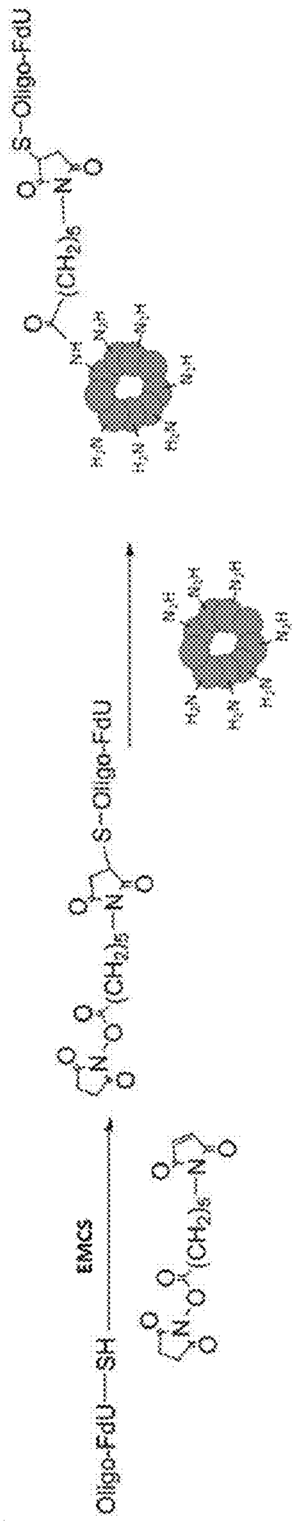
FIG. 6 shows T22-NIDOmut2-H6 nanoparticles conjugation with oligo-FdU. (Panel A) Schematic representation of the covalent binding of a thiol conjugated oligo 5'-(FdU) 5-hexaethyleneglycolthiol-3' (oligo-FdU-SH) though protein lysine amines using a 6-Maleimidohexanoic acid N-hydroxysuccinimide ester (EMCS) bifunctional linker in a two-step reaction. (Panel B) MALDI-TOF mass spectrometry spectrum of T22-NIDOmut2-H6-FdU nanoconjugates. (Panel C) Volume size distribution of T22-NIDOmut2-H6-FdU nanoconjugates determined by DLS.
Figure 6:
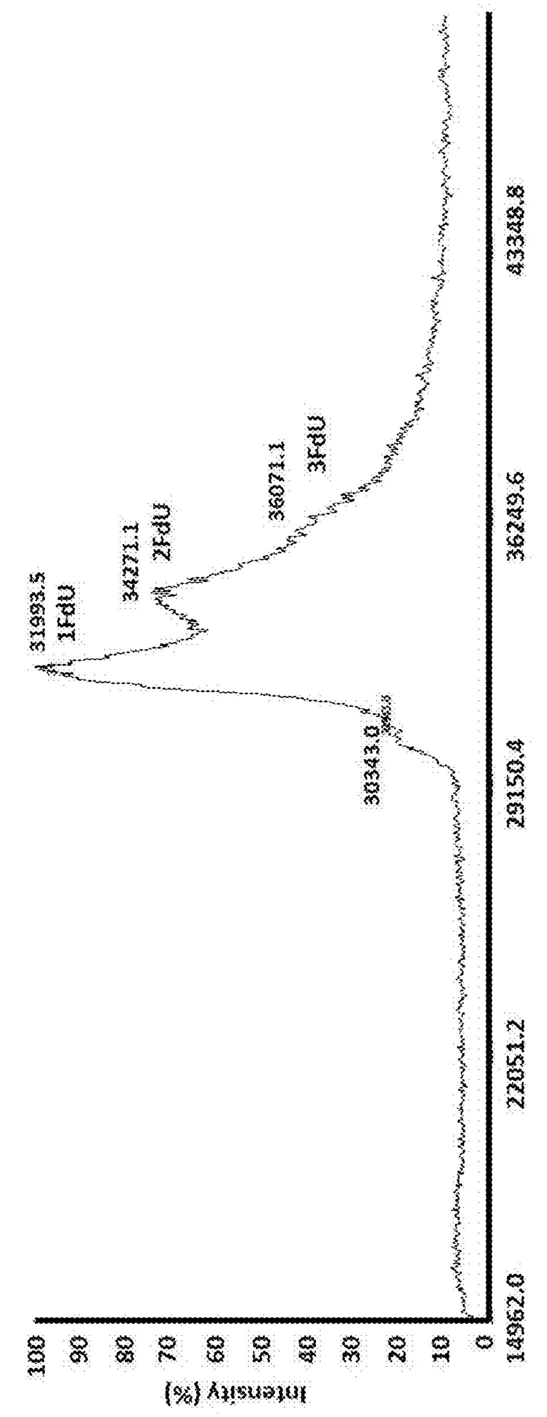
Figure 6:
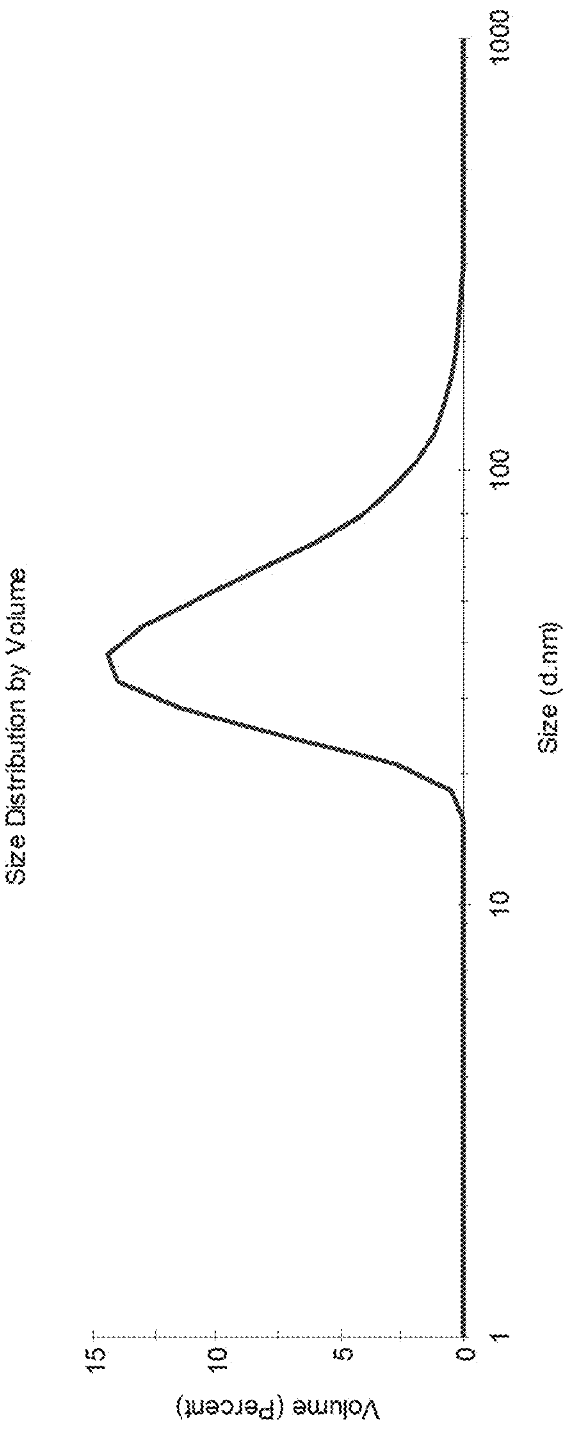

Additional linkers that can be used in the context of the present invention between the agent of interest and the polypeptide include those which are commonly used to prepare antibody-drug conjugates, such as those disclosed in Leung et al. (Antibodies 2020, 9, 2; doi:10.3390/antib9010002) (see FIG. 6) as well as those disclosed in Bargh et al. (Chem. Soc. Rev., 2019, DOI: 10.1039/c8cs00676h), the contents of which are hereby incorporated by reference.

Thus, in one embodiment of the invention, the activated form of the polypeptide of the conjugate contains a group which reacts with at least one moiety in the agent of interest. In a further preferred embodiment of the invention, the group of the agent of interest, preferably the chemotherapeutic agent, which reacts with the activated polypeptide of the conjugate is a thiol group.

In an even more preferred embodiment of the invention, the activated polypeptide of the conjugate is obtained by reacting one or more amino groups in the side chains of the polypeptide with a bifunctional reagent comprising an activated carboxyl group, such as a N-hydroxysuccinimide group. In one embodiment, the bifunctional reagent contains a second activated carboxyl group that can be reacted with an amino, thiol or hydroxyl group within the agent if interest.

In a further preferred embodiment, the linking moiety is 6-maleimidohexanoic acid N-hydroxysuccinimide ester and mediates the conjugation between an amino group in the polypeptide of the conjugate and a thiol group in the agent of interest. In a yet more preferred embodiment, the linking moiety 6-maleimidohexanoic acid N-hydroxysuccinimide ester is bound in a first step to the polypeptide of the conjugate, more preferably to external lysines of the polypeptide of the conjugate and in a second step to the agent side chain, preferably to the thiol group of the activated agent.

In a further preferred embodiment, the linking moiety is 6-maleimido hexanoic acid N-hydroxysuccinimide ester and mediates the conjugation between a thiol group in the polypeptide of the conjugate and an amino group in the agent of interest. In a yet more preferred embodiment, the linking moiety 6-maleimido hexanoic acid N-hydroxysuccinimide ester is bound in a first step to the polypeptide of the conjugate, more preferably to external Cysteines of the polypeptide of the conjugate and in a second step to the agent of interest, preferably to the amino group in the agent of interest.

In a further preferred embodiment, the linking moiety is 6-maleimido hexanoic acid N-hydroxysuccinimide ester and mediates the conjugation between a thiol group in the polypeptide of the conjugate and an amino group in the agent of interest. In a yet more preferred embodiment, the linking moiety 6-maleimido hexanoic acid N-hydroxysuccinimide ester is bound in a first step to the agent of interest, preferably to the amino group in the agent of interest. And in a second step to the polypeptide of the conjugate, more preferably to the thiol group of external Cysteines of the polypeptide of the conjugate.

In a certain embodiment, all the terms and embodiments described in the previous aspects of the invention are equally applicable to the seventh aspect of the invention VI—Polypeptides of the Invention Containing Antagonistic CXCR4 Ligands The authors of the present invention have observed that a fusion protein comprising an antagonistic CXCR4 ligand and the G2 domain of nidogen-1 or a variant form thereof are capable of targeting and penetrating CXCR4-expressing cells. Moreover, when this fusion protein is further modified by the presence of a polycationic region, the fusion protein spontaneously assembles into nanoparticles that are also capable of targeting and penetrating CXCR4-expressing cells and inducing apoptosis in CXCR4-expressing cells.

Accordingly, in another aspect, the invention relates to a polypeptide (also known as second polypeptide of the invention, fusion protein of the invention, CXCR4-antagonistic polypeptide of the invention) which comprises (i) a first region comprising the G2 domain of nidogen-1 or a functionally equivalent variant thereof and (ii) a second region which comprises an antagonistic CXCR4 ligand.

The first region has been defined above in the context of the first polypeptide of the invention and in the context of the first region of the polypeptides forming part of the conjugates of the invention and applies equally to the second polypeptide of the invention. In some embodiments, the first region is a functionally equivalent variant of the G2 domain of nidogen-1, wherein said functionally equivalent variant of the G2 domain of nidogen-1 is any of the variants defined above in the first polypeptide of the invention. In some embodiments, the first region comprises amino acids 430 to 667 with respect to the sequence of human nidogen-1 defined in the UniProt database with accession number P14543-1. In some embodiments, the functionally equivalent variant of the domain G2 of nidogen-1 forming part of the first region comprises a mutation in one or more amino acid residues at positions 459, 468, 639, 650, 543, 545, 449, 525, 561, 618, 619, 151, 604, 638, 641, 469 and 518 with respect to the numbering of the sequence of human nidogen-1 defined under the UniProt database with accession number P14543-1 (version dated Jul. 7, 2009). Thus, in another particular embodiment, the polypeptide of the conjugate of the sixth aspect of the invention is a functionally equivalent variant of the domain G2 of nidogen-1 comprising a mutation in one or more amino acid residues at positions 459, 468, 639, 650, 543, 545, 449, 525, 561, 618, 619, 151, 604, 638, 641, 469 and 518 with respect to the numbering of the sequence of human nidogen-1 defined under the UniProt database with accession number P14543-1 (version dated Jul. 7, 2009). In some embodiments, the nidogen G2 domain variant that can be included in the first polypeptide region include, without limitation, any of the nidogen G2 domain variants defined above in the context of the first aspect of the invention including the variant carrying the NIDOmut2, NIDOmut3, the NIDOmut3-V45T, the NIDOmut3_V121Q, the NIDOmut3-F157E, the NIDOmut3-V215T, the NIDOmut4, the NIDOmut4_T215V, the NIDOmut5, NIDOmut3-V176T, the NIDOmut3-1200T, the NIDOmut3-V236Y, the NIDOmut3-L237T, the NIDOmut3-S65I, the NIDOmut3-R114I, the NIDOmut3-C214S, the NIDOmut3-S65I_R114I, the NIDOmut5-S65I_R114I, the NIDOmut3-S65I_R114I and the NIDOmut5-S65I_R114I as defined, respectively, as SEQ ID NO:64, 65 and 87 to 104.

The second region of the second polypeptide of the invention comprises an antagonistic CXCR4 ligand. The term "antagonistic CXCR4 ligand", as used herein, refers to any polypeptide, peptide or peptide mimetic that is capable of specifically binding to CXCR4 and diminishes, inhibits, or prevents biological activity of the said molecule in response to its interaction with an agonist. In one embodiment, the antagonistic CXCR4 ligand is a competitive antagonist, i.e. an antagonist that reversibly binds to CXCR4 at the same binding site (active site) as the endogenous ligand or agonist, without necessarily activating the receptor.

Suitable methods for determining whether a given peptide is capable of binding to CXCR4 have been defined above in the context of the conjugates of the invention and are equally applicable for the instant polypeptides. In some embodiments, the second region is capable of specifically binding to CXCR4 with a dissociation constant (KD) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M or less than $10^{-15}$ M. Methods to determine if a polypeptide is capable of binding to a target molecule, as well as to determine the dissociation constant of said binding are provided in the definition of "specifically binding" in the second aspect of the invention.

Suitable antagonists for use according to the present invention are characterized in that compete for binding to CXCR4 by its natural ligand CXCL12 with an IC50 of not more than 0.1 μM, not more than 0.2 μM, not more than 0.3 μM, not more than 0.4 μM, not more than 0.5 μM, not more than 0.6 μM, not more than 0.7 μM, not more than 0.8 μM, not more than 0.9 μM, not more than 1 μM, not more than 2 μM, not more than 3 μM, not more than 4 μM, not more than 5 μM, not more than 6 μM, not more than 7 μM, not more than 8 μM, not more than 9 μM, not more than 10 μM, not more than 15 μM, not more than 20 μM, not more than 30 μM, not more than 40 μM, not more than 50 μM, not more than 60 μM, not more than 70 μM, not more than 80 μM, not more than 90 μM or not more than 100 μM.

Suitable methods for determining whether a molecule is an antagonistic CXCR4 ligand are, for example, the methods shown in Zirafi et al. (Cell Rep. 2015, 11, 737), the contents of which are hereby incorporated by reference. These methods include assays based on the detection of the ability of the antagonist to inhibit binding of CXCL12 to CXCR4 (for determination on whether the molecule is a ligand) as well as those methods based on the detection of the ability of the molecule to block $Ca^{2+}$ release from CXCR4-expressing cells such as HEX293 cells, based on the ability of the molecule to block CXCL12-directed transwell migration of Jurkat T cells and/or based on the detection of the ability of the molecule to block CXCL12-induced migration of human CD34+ stem cells (for determination of whether the molecule act as an antagonist).

In some embodiments, the second region of the polypeptide carrying the antagonistic CXCR4 ligand according to the invention further comprises a positively-charged amino acid region.

The positively charged peptide sequence may contain only one type of positively charged amino acid or may contain more than one type of positively charged amino acid. In one embodiment, the positively charged peptide sequence is a polyarginine region. In one embodiment, the positively charged peptide sequence is a polylysine region. In one embodiment, the positively charged peptide sequence is a polyhistidine region. In one embodiment, the positively charged peptide sequence comprises lysine and arginine residues. In one embodiment, the positively charged peptide sequence comprises lysine and histidine residues. In one embodiment, the positively charged peptide sequence comprises arginine and histidine residues. In one embodiment, the positively charged peptide sequence comprises lysine, arginine and histidine residues.

In some embodiments, the positively charged peptide sequence comprises at least 2, at least 3, at least 4, at least 5, at least 6, at least 7, at least 8, at least 9, at least 10, at least 11, at least 12, at least 13, at least 14, or at least 15 positively charged amino acids residues, wherein the positively charged amino acids can be arginine, lysine, histidine, or combinations thereof.

In some embodiments, the positively charged peptide sequence comprises fewer than 100, fewer than 90, fewer than 80, fewer than 70, fewer than 60, fewer than 50, fewer than 40, fewer than 30, fewer than 29, fewer than 28, fewer than 27, fewer than 26, fewer than 25, fewer than 24, fewer than 23, fewer than 22, fewer than 21, fewer than 20, fewer than 19, fewer than 18, fewer than 17, fewer than 16, fewer than 15, fewer than 14, fewer than 13, fewer than 12, fewer than 11, fewer than 10, fewer than 9, fewer than 8, fewer than 7, fewer than 6, fewer than 5, fewer than 4, fewer than 3 or less positively charged amino acids residues, wherein the positively charged amino acids can be arginine, lysine, histidine, or combinations thereof.

In some embodiments, the positively charged peptide sequence comprises between 2 and 50 amino acids, between 2 and 40 amino acids, between 2 and 30 amino acids, between 2 and 25 amino acids, between 2 and 20 amino acids, between 2 and 10 amino acids, between 2 and 8 amino acids, between 3 and 7 amino acids, between 4 and 7 amino acids, or between 5 and 7 amino acids.

In some embodiments, the positively charged peptide sequence comprises between 3 and 50 amino acids, between 3 and 40 amino acids, between 3 and 30 amino acids, between 3 and 25 amino acids, between 3 and 20 amino acids, between 3 and 10 amino acids or between 3 and 8 amino acids. In some embodiments, the positively charged peptide sequence comprises between 4 and 50 amino acids, between 4 and 40 amino acids, between 4 and 30 amino acids, between 4 and 25 amino acids, between 4 and 20 amino acids, between 4 and 10 amino acids or between 4 and 8 amino acids. In some embodiments, the positively charged peptide sequence comprises between 5 and 50 amino acids, between 5 and 40 amino acids, between 5 and 30 amino acids, between 5 and 25 amino acids, between 5 and 20 amino acids, between 5 and 10 amino acids or between 5 and 8 amino acids.

In another embodiment, the positively charged peptide sequence comprises 3, 4, 5, 6, 7, 8, 9, 10 amino acids, preferably 6 amino acids.

In an embodiment of the invention, the positively charged peptide sequence comprises arginine and lysine residues. In a preferred embodiment of the invention, the positively charged peptide sequence comprises between 1 and 5 arginines, preferably 3 arginines, and between 1 and 5 lysines, preferably 3 lysines.

In an embodiment of the invention, the positively charged peptide sequence comprises arginine and histidine residues. In a preferred embodiment of the invention, the positively charged peptide sequence comprises between 1 and 5 arginines, preferably 3 arginines, and between 1 and 5 histidines, preferably 3 histidines.

In an embodiment of the invention, the positively charged peptide sequence comprises lysine and histidine residues. In a preferred embodiment of the invention, the positively charged peptide sequence comprises between 1 and 5 lysines, preferably 3 lysines, and between 1 and 5 histidines, preferably 3 histidines.

In an embodiment of the invention, the positively charged peptide sequence of the conjugate of the invention is a polyarginine region. In a preferred embodiment of the invention, the polyarginine region comprises between 2 and 10, preferably 6, contiguous arginine residues.

In an embodiment of the invention, the positively charged amino acid-rich region of the conjugate of the invention is a polylysine region. In a preferred embodiment of the invention, the polylysine region comprises between 2 and 10, preferably 6, contiguous lysine residues.

In an embodiment of the invention, the positively charged amino acid-rich region of the fusion protein of the invention is a polyhistidine region. In a preferred embodiment of the invention, the polyhistidine region comprises between 2 and 10, preferably 6, contiguous polyhistidine residues.

In a particular embodiment, the positively charged peptide sequence is RKRKRK (SEQ ID NO. 77), RRRRRR (SEQ ID NO. 78), KKKKKK (SEQ ID NO:79), HHHHHH (SEQ ID NO. 80), RHRHRH (SEQ ID NO. 81), RKRKRKRK (SEQ ID NO. 82), RKRHRK (SEQ ID NO. 83), RKRHRH (SEQ ID NO. 84) or RHRHRH (SEQ ID NO. 85)

In a preferred embodiment, the positively charged peptide sequence is attached to the N- or to the C-terminal end of the sequence of the optimized EPI-X4 (SEQ ID NO. 29), preferably to the C-terminal end of the optimized EPI-X4 sequence (SEQ ID NO. 29). In a preferred embodiment, the positively charged peptide sequence is attached to the N- or to the C-terminal end of the sequence of the EPI-X4 (SEQ ID NO. 132, preferably to the C-terminal end of the sequence EPI-X4 (SEQ ID NO. 132).

In some embodiments, the second polypeptide of the invention further comprises a third polypeptide region which is a positively charged amino acid-rich region. Suitable positively charged amino acid-rich region that can act as third region of the second polypeptide of the invention are as defined above in respect of the third polypeptide region of the conjugates according to the invention. In preferred embodiments, the positively charged amino acid-rich region is a polyhistidine region. In a preferred embodiment of the invention, the polyhistidine region comprises between 2 and 10, preferably 6, contiguous histidine residues. In preferred embodiments, the positively charged amino acid-rich region is a polyarginine region. In a preferred embodiment of the invention, the polyarginine region comprises between 2 and 10, preferably 6, contiguous arginine residues. In preferred embodiments, the positively charged amino acid-rich region is a polylysine region. In a preferred embodiment of the invention, the polyarginine region comprises between 2 and 10, preferably 6, contiguous lysine residues.

In preferred embodiments, the positively charged amino acid rich region comprises or consists of the sequences RKRKRK (SEQ ID NO. 77), RRRRRR (SEQ ID NO. 78), KKKKKK (SEQ ID NO:79), HHHHHH (SEQ ID NO. 80), RHRHRH (SEQ ID NO. 81), RKRKRKRK (SEQ ID NO. 82), RKRHRK (SEQ ID NO. 83), RKRHRH (SEQ ID NO. 84) or RHRHRH (SEQ ID NO. 85).

In some embodiment, the first, second and third region of the second polypeptide of the invention are located within the second polypeptide of the invention in the following order:

N-First polypeptide region-Second polypeptide region-Third polypeptide region-C;
N-First polypeptide region-Third polypeptide region-Second polypeptide region-C;
N-Second polypeptide region-First polypeptide region-Third polypeptide region-C;
N-Second polypeptide region-Third polypeptide region-First polypeptide region-C
N-Third polypeptide region-First polypeptide region-Second polypeptide region-C;
N-Third polypeptide region-Second polypeptide region-First polypeptide region-C.

Therefore, the elements of the second polypeptide of the invention can be connected end-to-end but also may include one or more optional peptide or polypeptide "linkers" or "spacers" intercalated between them, linked, preferably by peptidic bond. The linker peptide or peptides preferably comprise at least 2 amino acids, at least 3 amino acids, at least 5 amino acids, at least 10 amino acids, at least 15 amino acids, at least 20 amino acids, at least 30 amino acids, at least 40 amino acids, at least 50 amino acids, at least 60 amino acids, at least 70 amino acids, at least 80 amino acids, at least 90 amino acids or approximately 100 amino acids. Preferred examples of linker peptides comprise 2 or more amino acids selected from the group consisting of glycine, serine, alanine and threonine. A preferred example of a flexible linker is a polyglycine linker. The possible examples of linker/spacer sequences include GGSSRSS (SEQ ID NO:39), GGSSRSSS (SEQ ID NO:76), SGGTSGSTSGTGST (SEQ ID NO:49), AGSSTGSSTGPGSTT (SEQ ID NO:50) or GGSGGAP (SEQ ID NO:51). These sequences have been used for binding designed coiled coils to other protein domains [Muller, K. M., Arndt, K. M. and Alber, T., Meth. Enzymology, 2000, 328:261-281]. Further non-limiting examples of suitable linkers comprise the amino acid sequence GGGVEGGG (SEQ ID NO:52), the sequence of 10 amino acid residues of the upper hinge region of murine IgG3 (PKPSTPPGSS, SEQ ID NO:53), which has been used for the production of dimerized antibodies by means of a coiled coil [Pack, P. and Pluckthun, A., 1992, Biochemistry 31:1579-1584], the peptide of sequence APAETKAEPMT (SEQ ID NO:54), the peptide of sequence GAP, the peptide of sequence AAA and the peptide of sequence AAALE (SEQ ID NO:55). In a preferred embodiment, the linker is GGSSRSS (SEQ ID NO:39).

In some embodiment, depending on the presence of a linker connecting the different regions of the second polypeptide of the invention and depending on the order of elements forming the second polypeptide of the invention, the second polypeptide of the invention can have the following arrangements of elements (wherein the numbering stated above for the elements is as follows: (1) first region polypeptide, (2) second polypeptide region, (3) third polypeptide region:

N-(1)-(2)-(3)-C
N-(1)-linker-(2)-(3)-C
N-(1)-(2)-linker-(3)-C
N-(1)-linker-(2)-linker-(3)-C
N-(3)-(2)-(1)-C
N-(3)-linker-(2)-(1)-C
N-(3)-(2)-linker-(1)-C
N-(3)-linker-(2)-linker-(1)-C
N-(2)-(1)-(3)-C
N-(2)-linker-(1)-(3)-C
N-(2)-(1)-linker-(3)-C
N-(2)-linker-(1)-linker-(3)-C
N-(2)-(3)-(1)-C
N-(2)-linker-(3)-(1)-C
N-(2)-(3)-linker-(1)-C
N-(2)-linker-(3)-linker-(1)-C
N-(1)-(3)-(2)-C
N-(1)-(3)-linker-(2)-C
N-(1)-linker-(3)-(2)-C
N-(1)-linker-(3)-linker-(2)-C
N-(3)-(1)-(2)-C
N-(3)-linker-(1)-(2)-C
N-(3)-(1)-linker-(2)-C
N-(3)-linker-(1)-linker-(2)-C Preferred fusion proteins having antagonistic CXCR4 ligands are as defined in the following Table

TABLE 5

Preferred fusion proteins having antagonistic CXCR4 ligands

| First region | first peptide linker | Second region | Third region |
|---|---|---|---|
| Optimized EPI-X4 (SEQ ID NO: 29) | GGSSRSS (SEQ ID NO: 39) | GFP | Hexahistidine (SEQ ID NO: 73) |
| Optimized EPI-X4 coupled to the positively charged region of sequence RKRKRK (SEQ ID NO: 131) | GGSSRSS (SEQ ID NO: 39) | GFP | Hexahistidine (SEQ ID NO: 73) |

TABLE 5-continued

Preferred fusion proteins having antagonistic CXCR4 ligands

| First region | first peptide linker | Second region | Third region |
|---|---|---|---|
| Optimized EPI-X4 (SEQ ID NO: 29) | GGSSRSS (SEQ ID NO: 39) | NIDOmut2, NIDOmut3, the NIDOmut3-V45T, the NIDOmut3_V121Q, the NIDOmut3-F157E, the NIDOmut3-V215T, the NIDOmut4, the NIDOmut4_T215V, the NIDOmut5, NIDOmut3-V176T, the NIDOmut3-I200T, the NIDOmut3-V236Y, the NIDOmut3-L237T, the NIDOmut3-S65I, the NIDOmut3-R114I, the NIDOmut3-C214S, the NIDOmut3-S65I_R114I, the NIDOmut5-S65I_R114I, the NIDOmut3-S65I_R114I and the NIDOmut5-S65I_R114I | Hexahistidine (SEQ ID NO: 73) |
| Optimized EPI-X4 coupled to the positively charged region of sequence RKRKRK (SEQ ID NO: 131) | GGSSRSS (SEQ ID NO: 39) | NIDOmut2, NIDOmut3, the NIDOmut3-V45T, the NIDOmut3_V121Q, the NIDOmut3-F157E, the NIDOmut3-V215T, the NIDOmut4, the NIDOmut4_T215V, the NIDOmut5, NIDOmut3-V176T, the NIDOmut3-I200T, the NIDOmut3-V236Y, the NIDOmut3-L237T, the NIDOmut3-S65I, the NIDOmut3-R114I, the NIDOmut3-C214S, the NIDOmut3-S65I_R114I, the NIDOmut5-S65I_R114I, the NIDOmut3-S65I_R114I and the NIDOmut5-S65I_R1141 | Hexahistidine (SEQ ID NO: 73) |

VII—Nanoparticles of the Invention and Methods for their Preparation

In an additional aspect, the invention relates to a method to prepare nanoparticles comprising multiple copies of the conjugate according to the sixth aspect of the invention comprising placing a preparation of said conjugate under conditions adequate for the assembly of a plurality of copies of the conjugate into a nanoparticle.

The term "conjugate" has been defined above in the context of the conjugates according to the invention and are equally applicable to the present method.

In another aspect, the invention relates to a method for preparing a nanoparticle comprising multiple copies of the conjugate according to the sixth aspect of the invention comprises (i) placing a plurality of polypeptides each comprising 1. a first polypeptide region which is the G2 domain of nidogen-1 or a functionally equivalent variant thereof,
2. a second polypeptide region which is capable of specifically binding to a target of interest wherein said second polypeptide is a polycationic peptide and
3. a third polypeptide region which is a positively charged amino acid-rich region, wherein the polycationic peptide and the positively charged amino acid-rich region are located at the ends of the polypeptide and wherein the polypeptide is provided in an activated form, wherein said activated form of the polypeptide contains a reactive group, wherein said placing is carried out under conditions adequate for the formation of a nanoparticle containing a plurality of copies of the polypeptide and (ii) contacting the nanoparticle obtained in step (i) with an activated form of the agent of interest which contains a group which is capable of reacting with the reactive group in the polypeptide, wherein said contacting is carried out under conditions adequate for the formation of a bond between the reactive group in the polypeptide and the group in the agent of interest.

The terms "first polypeptide region", "second polypeptide region" and "third polypeptide region" have been defined above in the context of the polypeptides forming the conjugates of the invention and are equally applicable to the method for obtaining nanoparticles comprising multiple copies of the conjugate.

The term "conditions adequate for the formation of a nanoparticle containing a plurality of copies of the polypeptide", as used herein, refer to any conditions that are suitable for the incorporation of a substantial percentage of the polypeptides in the sample into nanoparticles. In one embodiment, the conditions involve incubating the conjugates or polypeptides to be assembled into a low salt buffer.

As the person skilled in the art will recognize, "nanoparticles" are microscopic particles whose size is measured in nanometers. The nanoparticles of the invention comprise the nanoparticles that result from the aggregation of multiple copies of the conjugate, or of the polypeptide of the conjugate, of the sixth aspect of the invention as defined in the previous section. In the methods (i) and (ii) above, the conjugates or polypeptide of the conjugate of the sixth aspect of the invention used for the preparation of the nanoparticles are thermodynamically favored to form non-covalent electrostatic unions and spontaneously aggregate in the conditions of the low salt buffer. In a particular embodiment, said thermodynamically favored conjugates or polypeptides of the conjugate of the sixth aspect of the invention, comprise the first, second and third polypeptide regions comprised in the polypeptide of the conjugate of the sixth aspect of the invention. In a particular embodiment, said polypeptides, or the polypeptides comprised in said conjugates, are as the polypeptides defined in the sixth aspect of the invention, wherein the second polypeptide region is a polycationic peptide, located at the N-terminus of the first polypeptide region, and the third polypeptide region is located at the C terminus of the first polypeptide region of the conjugate.

In a particular embodiment, the conditions adequate for the assembly of a plurality of copies of the conjugate into a nanoparticle in the method (i) of the eighth aspect of the invention, comprise an incubation in a low salt buffer. In another particular embodiment, the condition adequate for the assembly of a plurality of copies of the polypeptide into a nanoparticle in the method (ii) of the eighth aspect of the invention, comprise an incubation in a low salt buffer.

It will be understood that the expression "low salt buffer" comprises any buffer solution resulting from the dissolution of one or more salts in water with the capability to moderate changes in pH, wherein the amount of dissolved salt or salts results in an osmolarity lower or equal to that of the physiological fluids, such as the cytoplasm or the extracellular medium, for instance. Thus, the low salt buffer is understood to keep pH and osmolarity inside the range of physiological values and will be used inside the range of physiological temperatures.

The person skilled in the art will recognize that the range of physiological temperatures can oscillate between 15 and 45°C, more preferably between 2° and 40°C, even more preferably between 25 and 39°C, yet even more preferably between 3° and 37°C The person skilled in the art will also acknowledge that the osmolarity of the low salt buffer will be in the range between 100 and 400 milli-osmoles/L (mOsm/L), preferably between 150 and 350 mOsm/L, more preferably between 200 and 300 mOsm/L, even more preferably between 225 and 275 mOsm/L.

In some embodiments, the low salt buffer has a pH of between pH 4 and pH 7, preferably between pH 5 and pH 6, more preferably is of about pH 5.3, pH 6.5 or pH 7.2.

In some embodiments, the low salt buffer is selected from the group consisting of a carbonate buffer, a citrate buffer, an acetate buffer, a Tris buffer and a phosphate buffer. Low salt buffers suitable for the invention, for instance, are the Tris-dextrose buffer (20 mM Tris+5% dextrose, pH 7.4), the Tris-NaCl buffer (20 mM Tris, 500 NaCl, pH 7.4), the PBS-glycerol buffer (phosphate buffered saline, PBS, pH 7.4, which is well known in the art, +10% glycerol), Tris Buffered Saline (TBS)-dextrose (20 mM Tris-HCl buffer pH 7.5, well known in the art, 200 NaCl, +5% dextrose), Tris Buffered Saline TWEEN® 20 (TBST) buffer (10 mM Tris-HCl pH 7.5, 200 mM NaCl, +0.01% TWEEN® 20), or any physiological buffer known in the art with a pH not lower than 6.

In one embodiment, the low salt buffer further comprises Polysorbate 80 and/or sucrose. In yet another embodiment, the sucrose in the low salt buffer is found at a concentration of between 20 mg/ml and 100 mg/ml, more preferably of between 50 mg/ml and 90 mg/ml, preferably of 70 mg/ml.

In one embodiment, the low salt buffer is a citrate buffer that comprises Polysorbate 80 (0.4 mg/ml), sucrose (80 mg/ml), sodium citrate 2-hydrate (2.7 mg/ml) and citric acid anhydrous (0.146 mg/ml) and has a pH of about 6.5.

In one embodiment, the low salt buffer is an acetate buffer that comprises sucrose (70 mg/ml), glacial acetic acid (0.12 mg/ml), sodium acetate 3-hydrate (2.45 mg/ml) and has a pH of about 5.3.

In another embodiment, the low salt buffer is a phosphate buffer that comprises Polysorbate 80 (0.05 mg/ml), sucrose (50 mg/ml), sodium phosphate monobasic 1-hydrate (0.22 mg/ml), sodium phosphate dibasic anhydrous (0.49 mg/ml) and has a pH of about 7.2.

In some embodiments, the low salt buffer suitable for carrying out the method for obtaining nanoparticles is the A9 buffer which comprises sucrose at a concentration between 40 mg/ml and 100 mg/ml, preferably of 80 mg/ml, polysorbate 80 at a concentration between 0.01 mg/ml and 10 mg/ml, preferably of 4 mg/ml, sodium citrate 2-hydrate at a concentration of 2.7 mg/ml, citric acid anhydrous at a concentration of 0.146 mg/ml and wherein the pH of the buffer is between pH 5 and pH 9, preferably between pH 7 and pH 8, more preferably is pH 6.5.

In some embodiments, the low salt buffer suitable for carrying out the method for obtaining nanoparticles is the B6 buffer that comprises:

sucrose at a concentration between 50 and 90, preferably of 70 mg/ml, glacial acetic acid at a concentration between 0.05 mg/ml and 25 mg/ml, preferably of 0.12 mg/ml, sodium acetate 3-hydrate at a concentration between 1 mg/ml and 4 mg/ml, preferably of 2.45 mg/ml, wherein the pH of the B6 buffer is between pH_4 and pH_7, preferably between pH_5 and pH_6, more preferably is pH_5.3.

In some embodiments, the low salt buffer suitable for carrying out the method for obtaining nanoparticles is the D1 buffer that comprises:

sucrose at a concentration between 40 mg/ml and 60 mg/ml, preferably of 50 mg/ml, polysorbate 80 at a concentration between 0.01 mg/ml and 1 mg/ml, preferably of 0.05 mg/ml, sodium phosphate monobasic 1-hydrate at a concentration between 0.1 mg/ml and 0.5 mg/ml, preferably of 0.22 mg/ml sodium phosphate dibasic anhydrous at a concentration between 0.2 mg/ml and 1 mg/ml, preferably of 0.49 mg/ml, wherein the pH of the sucrose buffer D1 is between pH 5 and pH 9, preferably between pH_7 and pH 8, more preferably is pH_7.2

The inventors additionally produced biparatopic nanoparticles by allowing the oligomerization of two types fusion proteins: a first type of fusion proteins comprising the T22 CXCR4 ligand and a scaffold protein and a second type of fusion proteins comprising the EPI-X4 antagonistic CXCR4 ligand and the same scaffold protein. These biparatopic nanoparticles showed higher levels of internalization in CXCR4+ cells in vitro than nanoparticles formed by a single type of fusion protein, being either the fusion protein comprising the T22 CXCR4 ligand or the fusion protein comprising the EPI-X4 CXCR4 ligand alone. Upon administration to the mouse model, the biparatopic nanoparticles also showed higher levels of internalization in the tumor cells and a higher number of apoptotic bodies in the tumoral cells than the any of the two types of monoparatopic nanoparticles comprising a single type of fusion protein.

In another aspect, the invention relates to a method to prepare biparatopic nanoparticles comprising multiple copies of two different types of conjugates according to the sixth aspect of the invention, wherein the sequence of the second polypeptide of the first type of conjugate is different from the sequence of the second polypeptide of the second type of conjugate, said method comprising placing a preparation of said two types of conjugates in a low salt buffer.

In a ninth aspect, the invention relates to a method for preparing a biparatopic nanoparticle comprising multiple copies of a first type of conjugate and multiple copies of a second type of conjugate, wherein the first and second types of conjugates of the invention and wherein the first and the second type of conjugates differ in the sequence of the polycationic peptide, said method comprising contacting a preparation of said first type of conjugate with a preparation of said second type of conjugate under conditions adequate for the assembly of a plurality of copies of the two types of conjugates into a nanoparticle.

In another embodiment, the invention relates to a method for preparing a biparatopic nanoparticle comprising multiple copies of a first type of conjugate and multiple copies of a second type of conjugates according to the invention, wherein the sequence of the polycationic peptide of the first type of conjugate is different from the sequence of the polycationic peptide of the second type of conjugate, said method comprising i. contacting a preparation of a first polypeptide with a preparation of a second polypeptide wherein the first type and second polypeptides comprise
  (i) a first polypeptide region which is the G2 domain of nidogen-1 or a functionally equivalent variant thereof,
  (ii) a second polypeptide region which is capable of specifically binding to a target of interest wherein said second polypeptide is a polycationic peptide and the sequence of the polycationic peptide of one polypeptide is different from the sequence of the polycationic peptide of the other polypeptide,
  (iii) a third polypeptide region which is a positively charged amino acid-rich region,
  wherein the polycationic peptide and the positively charged amino acid-rich region are located at the ends of the polypeptides,
  wherein the polypeptides are provided in an activated form, wherein said activated form of the polypeptides contains a reactive group, wherein said placing is carried out under conditions adequate for the formation of a nanoparticle containing a plurality of copies of polypeptides and
ii. contacting the nanoparticle obtained in step I with an activated form of the agent of interest which contains a group which is capable of reacting with the reactive group in each polypeptide, wherein said contacting is carried out under conditions adequate for the formation of a bond between the reactive group in the polypeptides and the group in the agent of interest.

As used herein, the term "biparatopic nanoparticle", refers to nanoparticles which are formed by at least two types of conjugates, wherein the two types of conjugates contain polypeptides that differ in the nature of the sequence which is specifically binding to a target of interest, being these sequences either ligands for different receptors or, more preferably, two different ligands for the same receptor.

Suitable conjugates that can be used as first type or second types of conjugates in the above methods are as defined above in the context of the conjugates according to the invention. In some embodiments, the first region of the polypeptide forming the conjugate is selected from the group consisting of NIDOmut2, NIDOmut3, the NIDOmut3-V45T, the NIDOmut3_V121Q, the NIDOmut3-F157E, the NIDOmut3-V215T, the NIDOmut4, the NIDOmut4_T215V, the NIDOmut5, NIDOmut3-V176T, the NIDOmut3-1200T, the NIDOmut3-V236Y, the NIDOmut3-L237T, the NIDOmut3-S65I, the NIDOmut3-R114I, the NIDOmut3-C214S, the NIDOmut3-S65I_R114I, the NIDOmut5-S65I_R114I, the NIDOmut3-S65I_R114I and the NIDOmut5-S65I_R114I as defined, respectively, as SEQ ID NO:64, 65 and 87 to 104. In some embodiments, the second region of the polypeptide forming the conjugate is a CXCR4 ligand, more preferably the T22 peptide having the sequence RRWCYRKCYKGYCYRKCR (SEQ ID NO:25), the V1 peptide (SEQ ID NO:26), the CXCL12 peptide (SEQ ID NO:27), the vCCL2 peptide (SEQ ID NO:28) and the optimized EPI-X4 sequence (SEQ ID NO:29) or the EPI-X4 sequence (SEQ ID NO:132), wherein the EPI-X4 sequence or the optimized EPI-X4 sequence may be provided as a fusion with a polycationic peptide, preferably the peptide having the sequence RKRKRK (SEQ ID NO. 77). In some embodiments, the third region of the polypeptide forming part of the conjugates is a positively charged amino acid-rich region selected from the group consisting of RKRKRK (SEQ ID NO. 77), RRRRRR (SEQ ID NO. 78), KKKKKK (SEQ ID NO:79), HHHHHH (SEQ ID NO. 80), RHRHRH (SEQ ID NO. 81), RKRKRKRK (SEQ ID NO. 82), RKRHRK (SEQ ID NO. 83), RKRHRH (SEQ ID NO. 84) or RHRHRH (SEQ ID NO. 85).

In some embodiments, both the first and second type of conjugates used in the methods for preparing biparatopic nanoparticles contain CXCR4 ligands, being said ligands the T22 peptide having the sequence RRWCYRKC YKGYCYRKCR (SEQ ID NO:25) and the and the optimized EPI-X4 sequence (SEQ ID NO:29) or the EPI-X4 sequence (SEQ ID NO:132), wherein the optimized EPI-X4 sequence or the EPI-X4 sequence may be provided as a fusion with a polycationic peptide, preferably the peptide having the sequence RKRKRK (SEQ ID NO:77).

In the methods for preparing biparatopic nanoparticles described above, the conjugates or polypeptide of the two types of conjugates used for the preparation of the nanoparticles are thermodynamically favored to form non-covalent electrostatic unions and spontaneously aggregate in the conditions of the low salt buffer. Suitable conditions for the assembly into a biparatopic nanoparticle of the plurality of copies of the two conjugates in the methods for the preparation of biparatopic nanoparticles are similar to the conditions adequate for the assembly of a plurality of copies of the conjugate into a nanoparticle in the methods according to the eighth aspect of the invention.

In one embodiment, the low salt buffer further comprises Polysorbate 80 and/or sucrose. In yet another embodiment, the sucrose in the low salt buffer is found at a concentration of between 20 mg/ml and 100 mg/ml, more preferably of between 50 mg/ml and 90 mg/ml, preferably of 70 mg/ml.

In one embodiment, the low salt buffer is a citrate buffer that comprises Polysorbate 80 (0.4 mg/ml), sucrose (80 mg/ml), sodium citrate dihydrate (2.7 mg/ml) and citric acid anhydrous (0.146 mg/ml) and has a pH of about 6.5.

In one embodiment, the low salt buffer is an acetate buffer that comprises sucrose (70 mg/ml), glacial acetic acid (0.12 mg/ml), sodium acetate 3-hydrate (2.45_mg/ml) and has a pH of about 5.3.

In another embodiment, the low salt buffer is a phosphate buffer that comprises Polysorbate 80 (0.05 mg/ml), sucrose (50 mg/ml), sodium phosphate monobasic 1-hydrate (0.22 mg/ml), sodium phosphate dibasic anhydrous (0.49 mg/ml) and has a pH of about 7.2.

In preferred embodiment, the buffer used in the methods for obtaining the biparatopic nanoparticles is selected from the group comprising the A9 buffer, the B6 buffer and the D1 buffer, the composition of which has been described above.

In a preferred embodiment of the invention, the low salt buffer adequate for the assembly of a plurality of copies of the polypeptides of the conjugate into a nanoparticle in the method (ii) of the eighth aspect of the invention is selected from the group consisting of a carbonate buffer, a Tris buffer and a phosphate buffer.

In a particularly preferred embodiment of the invention, the low salt buffer of the method (ii) of the eighth aspect of the of the invention is a carbonate buffer that comprises sodium bicarbonate at a concentration between 100 and 300 nM. In another particularly preferred embodiment of the invention, the low salt buffer of the method (ii) eighth aspect of the invention is a Tris buffer that comprises Tris at a concentration of between 10 and 30 nM. In another particularly preferred embodiment of the method (ii) eighth aspect of the invention, the low salt buffer of the invention is a phosphate buffer that comprises $Na_2HPO_4$ and $NaH_2PO_4$ at a total concentration of between 5 mM and 20 mM.

In an even more preferred embodiment of the invention, the low salt buffer of the method (ii) eighth aspect of the invention further comprises dextrose and/or glycerol.

In a yet more preferred embodiment of the invention, the low salt buffer of the method (ii) eighth aspect of the invention has a pH between 6.5 and 8.5.

In a tenth aspect, the invention relates to nanoparticles comprising multiple copies of a conjugate according to the invention or multiple copies of a polypeptide comprising an antagonistic CXCR4 ligand according to the invention or a nanoparticle that has been obtained by any of the methods explained above. It will be understood that these nanoparticles are formed by a single type of conjugate or by a single type of polypeptide and that, accordingly, they are monospecific (i.e. all the conjugates or polypeptides forming the nanoparticle bind to a single type of target molecule) and monoparatopic (i.e. all the conjugates or polypeptides forming the nanoparticle bind to the same region in the target molecule).

Thus, the nanoparticles of the invention comprise aggregates of multiple copies of the conjugates of the sixth aspect of the invention, which result from the electrostatic interaction between regions in their structures favoring their non-covalent binding and coupling in physiological conditions. Since the method of the invention for the preparation of nanoparticles comprises placing a preparation of the conjugates, or of polypeptides of the conjugates, of the sixth aspect of the invention in a low salt buffer, it is understood that the nanoparticles thus formed comprise also an aggregate of multiple copies of the conjugates of the sixth aspect of the invention.

In a particular embodiment, the conjugates are as the conjugates defined in the sixth aspect of the invention, wherein the second polypeptide region of the conjugate is a polycationic peptide, located at the N-terminus of the first polypeptide region of the conjugate, and the third polypeptide region of the conjugate is located at the C terminus of the first polypeptide region of the conjugate.

In some embodiments, the nanoparticles according to the invention are characterized in that the polycationic peptide of the conjugates forming the nanoparticles is a CXCR4 ligand. In some embodiments, the polycationic region of the conjugate or of the polypeptide forming the nanoparticle is selected from the group consisting of the sequence RRWCYRKCYKGYCYRKCR (SEQ ID NO:25), the V1 peptide (SEQ ID NO:26), the CXCL12 (SEQ ID NO:27) peptide, the vCCL2 (SEQ ID NO:28) and functionally equivalent variant thereof. In some embodiments, wherein the nanoparticles result from the assembly of multiple copies of polypeptides comprising an antagonistic CXCR4 ligand according to the invention, the antagonistic CXCR4 ligand is the optimized EPI-X4 sequence (SEQ ID NO:29), the EPI-X4 sequence (SEQ ID N: 132) or a functionally equivalent variant thereof. In some embodiments, the EPI-X4 sequence (SEQ ID NO:29) or the optimized EPI-X4 sequence is joined to a RKRKRK (SEQ ID NO:77) sequence.

In an eleventh aspect, the invention relates to a biparatopic nanoparticle that comprises multiple copies of a first type of conjugates and of a second type of conjugates according to the invention wherein the first and second types of conjugates differ in the polycationic peptide. In some embodiments, the nanoparticles according to the invention are characterized in that the polycationic peptide of the first type of conjugates and of the second type of conjugates forming the nanoparticles is a CXCR4 ligand. In some embodiments, the polycationic region of the conjugate or of the polypeptide forming the nanoparticle is selected from the group consisting of the sequence RRWCYRKCY KGYCYRKCR (SEQ ID NO:25), the V1 peptide (SEQ ID NO:26), the CXCL12 (SEQ ID NO:27) peptide, the vCCL2 (SEQ ID NO:28) and functionally equivalent variant thereof. In some embodiments, wherein the nanoparticles result from the assembly of multiple copies of polypeptides comprising an antagonistic CXCR4 ligand according to the invention, the antagonistic CXCR4 ligand is the optimized EPI-X4 sequence (SEQ ID NO:29), the EPI-X4 sequence (SEQ ID NO:132) or a functionally equivalent variant thereof. In some embodiments, the optimized EPI-X4 sequence (SEQ ID NO:29) or the EPI-X4 sequence I (SEQ ID NO:132) is joined to a RKRKRK (SEQ ID NO:77) sequence.

In a twelfth aspect, the invention relates to a biparatopic nanoparticle that comprises multiple copies of a conjugate according to the invention wherein the polycationic region is a CXCR4 ligand and multiple copies of a polypeptide comprising an antagonistic CXCR4 ligand according to the invention. It will be understood that the conjugate and the polypeptide comprising an antagonistic CXCR4 ligand bind to different regions within CXCR4 and hence, despite being monospecific, they are biparatopic.

In some embodiments, the CXCR4 ligand included in the conjugates of the biparatopic nanoparticles is selected from the group consisting of the peptide that comprises the sequence RRWCYRKCYKGYCYRKCR (SEQ ID NO:25), the VI peptide (SEQ ID NO:26) the CXCL12 peptide (SEQ ID NO:27), the vCCL2 peptide (SEQ ID NO:28), the optimized EPI-X4 sequence (SEQ ID NO:29), the EPI-X4 sequence (SEQ ID N: 132) and a functionally equivalent variant thereof.

In some embodiments, the CXCR4 antagonistic ligand included in the polypeptides forming the biparatopic nanoparticles is the optimized EPI-X4 sequence (SEQ ID NO:29) and a functionally equivalent variant thereof. In some embodiments, the optimized EPI-X4 sequence (SEQ ID NO:29) is provided forming part of a polycationic region resulting from the fusion of the EPI-X4 sequence to the RKRKRK (SEQ ID NO:77) sequence.

In one embodiment, the biparatopic nanoparticle according to the invention is formed by conjugates according to the invention in which the polycationic peptide comprises the sequence RRWCYRKCYKGYCYRKCR and by polypeptides comprising an CXCR4 antagonistic ligand in which the CXCR4 antagonistic ligand the is the optimized EPI-X4 sequence (SEQ ID NO:29), optionally forming part of a fusion peptide with a polycationic sequence, preferably, the RKRKRK (SEQ ID NO:77) sequence.

Preferred forms of the biparatopic nanoparticles according to the present invention are formed by any of the preferred conjugates defined in Table 3 and any of the preferred fusion proteins comprising an antagonistic ligand as defined in Table 5. In some embodiments, the first type of conjugates forming part of the biparatopic nanoparticles (those exemplified in Table 3) do not contain an agent of interest as defined above. In some embodiments, the first type of conjugates forming part of the biparatopic nanoparticles contain an agent of interest, which is preferably any of those defined above in the context of the conjugates of the invention, more preferably floxuridine and even more preferably a floxuridine pentamer.

In a particular embodiment, the expressions "polypeptide of the nanoparticle", "first polypeptide of the nanoparticle", "second polypeptide of the nanoparticle", "polycationic peptide of the nanoparticle", "CXCR4 ligand of the nanoparticle", "third polypeptide of the nanoparticle", "polypeptide regions of the nanoparticle", "agent of interest of the nanoparticle", "linking moiety between the agent of interest and the nanoparticle", or "positively charged peptide sequence", refer to the corresponding component of the nanoparticle that is part of the conjugates assembled in the nanoparticles of the invention. Thus, said components are as defined above in the context of the conjugates of the invention, and thus, are as the corresponding parts of the conjugates of the invention.

The person skilled in the art will acknowledge that the size of the nanoparticles of the invention, including the biparatopic nanoparticles of the invention, can be in the range between 1 and 1000 nm, more preferably between 2.5 and 500 nm, even more preferably between 5 and 250 nm, and yet even more preferably between 10 and 100 nm.

In a preferred embodiment of the invention, the nanoparticles of the invention have a diameter between 10 and 100 nm. In another preferred embodiment, the biparatopic nanoparticles of the invention have a diameter between 10 and 100 nm.

As it will be noted by a person skilled in the art, the biparatopic nanoparticles of the invention are considered one of the nanoparticles of the invention. Therefore, in a preferred embodiment, when referring to "the nanoparticle of the invention", or to "the nanoparticle", the biparatopic nanoparticles as defined herein are also designated.

In a certain embodiment, all the terms and embodiments described in the first, second, third, fourth, fifth, sixth, and seventh aspects of the invention, are equally applicable to the eighth aspect of the invention. In another embodiment, all the terms and embodiments described in the first, second, third, fourth, fifth, sixth, seventh and eighth aspects of the invention, are equally applicable to the ninth aspect of the invention.

VIII—Medical Uses of the Conjugates and the Nanoparticles of the Invention

In a twelfth aspect, the invention relates to a conjugate or a nanoparticle according to the invention for use in medicine. In another aspect, the invention relates to the use of a conjugate or a nanoparticle according to the invention for the treatment of a patient suffering from a disease that responds to the therapeutic agent forming part of the conjugate of the invention.

As used herein, the terms "treat", "treatment" and "treating" refer to the reduction or amelioration of the progression, severity and/or duration of a condition, disorder or disease, or the amelioration of one or more symptoms (preferably, one or more discernible symptoms) of a condition, disorder or disease. The terms "treat", "treatment" and "treating" also refer to the amelioration of at least one measurable physical parameter of a condition, disorder or disease not necessarily discernible by the patient. Furthermore, "treat", "treatment" and "treating" refer also to the inhibition of the progression of a condition, disorder or disease, either physically by, e.g., stabilization of a discernible symptom, physiologically by, e.g., stabilization of a physical parameter, or both. "Treat", "treatment" and "treating" may refer, too, to the reduction or stabilization of the condition, disorder or disease.

It will be understood by the person skilled in the art that by use in medicine, the conjugate or nanoparticle of the invention can be administered to a patient in order to induce a therapeutic response.

The therapeutic response comprises the suppression, reduction or arrest of the causes of the pathological condition or the disease suffered by a patient; the elimination, reduction, arrest or amelioration of the symptoms of the condition or disease; or the extinction, arrest or slowing down of the progression of the condition or disease in the patient.

The person skilled in the art will acknowledge that the conjugate or nanoparticle of the invention suitable for use in medicine may be presented accompanied by a pharmaceutically acceptable carrier. As used herein, the term "pharmaceutically acceptable carrier" means a non-toxic, inert solid, semi-solid or liquid filler, diluent, encapsulating material or formulation auxiliary of any type. Remington's Pharmaceutical Sciences. Ed. by Gennaro, Mack Publishing, Easton, Pa., 1995 discloses various carriers used in formulating pharmaceutical compositions and known techniques for the preparation thereof.

Accordingly, the compositions comprising the conjugate or nanoparticle of the invention and a pharmaceutically acceptable carrier are pharmaceutical compositions.

The pharmaceutical compositions of this invention can be administered to a patient by any means known in the art including oral and parenteral routes. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

VII.A—Use of the Conjugate or the Nanoparticle of the Invention in the Treatment of Cancer Another embodiment of the invention relates to the conjugate or the nanoparticle of the invention, or their corresponding pharmaceutical compositions, wherein the polypeptide of the conjugate, or at least a polypeptide of the nanoparticle, comprises a sequence which is capable of specifically interacting with a receptor on a cell surface and promoting the internalization of the conjugate, or the nanoparticle, into the cell, wherein said cell expressing the receptor is a tumor cell present in cancer for use in the treatment of cancer.

In a particular embodiment, the agent of interest of said conjugates for use, or of said nanoparticles for use, or of the conjugates or nanoparticles of the corresponding pharmaceutical compositions for use, is a therapeutic agent selected from the group consisting of (i) A chemotherapy agent,
(ii) a cytotoxic polypeptide,
(iii) an antiangiogenic polypeptide,
(iv) a polypeptide encoded by a tumor suppressor gene,
(v) a pro-apoptotic polypeptide,
(vi) a polypeptide having anti-metastatic activity,
(vii) a polypeptide encoded by a polynucleotide which is capable of activating the immune response towards a tumor and
(viii) an antiangiogenic molecule.
(ix) a toxin.

As used herein, the terms "treat", "treatment" and "treating" refer to the reduction or amelioration of the progression, severity and/or duration of cancer, or the amelioration of one or more symptoms (preferably, one or more discernible symptoms) of cancer. The terms "treat", "treatment" and "treating" also refer to the amelioration of at least one measurable physical parameter of cancer, such as growth of a tumor, not necessarily discernible by the patient. Furthermore, "treat", "treatment" and "treating" refer also to the inhibition of the progression of cancer, either physically by, e.g., stabilization of a discernible symptom, physiologically by, e.g., stabilization of a physical parameter, or both. "Treat", "treatment" and "treating" may refer, too, to the reduction or stabilization of tumor size or cancerous cell count.

The term "cancer" refers to a group of diseases involving abnormal, uncontrolled cell growth and proliferation (neoplasia) with the potential to invade or spread (metastasize) to other tissues, organs or, in general, distant parts of the organism; metastasis is one of the hallmarks of the malignancy of cancer and cancerous tumors. The abnormal growth and/or proliferation of cancerous cells is the result of a combination of genetic and environmental factors that alter their normal physiology. The growth and/or proliferation abnormalities of cancerous cells result in physiological disorders and, in many cases, death of the individual, due to the dysfunctionality or loss of functionality of the cell types, tissues and organs affected.

The term "cancer" includes, but is not restricted to, cancer of the breast, prostate, lung, ovarian, colon, colorectal, pancreatic, kidney, brain, non-Hodgkin's lymphoma, chronic lymphocytic leukemia. heart, small intestine, spleen, kidney, bladder, head, neck, skin, bone, bone marrow, blood, thymus, womb, testicles, hepatobiliary system and liver; in addition to tumors such as, but not limited to, adenoma, angiosarcoma, astrocytoma, epithelial carcinoma, germinoma, glioblastoma, glioma, hemangioendothelioma, hemangiosarcoma, hematoma, hepatoblastoma, leukemia, lymphoma, medulloblastoma, melanoma, neuroblastoma, hepatobiliary cancer, osteosarcoma, retinoblastoma, rhabdomyosarcoma, sarcoma and teratoma. Furthermore, this term includes acrolentiginous melanoma, actinic keratosis adenocarcinoma, adenoid cystic carcinoma, adenomas, adenosarcoma, adenosquamus carcinoma, astrocytic tumors, Bartholin gland carcinoma, basal cell carcinoma, bronchial gland carcinoma, capillary carcinoid, carcinoma, carcinosarcoma, cholangiocarcinoma, cystadenoma, endodermal sinus tumor, endometrial hyperplasia, endometrial stromal sarcoma, endometrioid adenocarcinoma, ependymal sarcoma, Ewing sarcoma, focal nodular hyperplasia, germ cell tumors, glioblastoma, glucagonoma, hemangioblastoma, hemangioendothelioma, hemangioma, hepatic adenoma, hepatic adenomatosis, hepatocellular carcinoma, hepatobiliary cancer, insulinoma, intraepithelial neoplasia, squamous cell intraepithelial neoplasia, invasive squamous-cell carcinoma, large cell carcinoma, leiomyosarcoma, melanoma, malignant melanoma, malignant mesothelial tumor, medulloblastoma, medulloepithelioma, mucoepidermoid carcinoma, neuroblastoma, neuroepithelial adenocarcinoma, nodular melanoma, osteosarcoma, papillary serous adenocarcinoma, pituitary tumors, plasmacytoma, pseudosarcoma, pulmonary blastoma, renal cell carcinoma, retinoblastoma, rhabdomyosarcoma, sarcoma, serous carcinoma, microcytic carcinoma, soft tissue carcinoma, somatostatin secreting tumor, squamous carcinoma, squamous cell carcinoma, undifferentiated carcinoma, uveal melanoma, verrucous carcinoma, vipoma, Wilm tumor, intracerebral cancer, head and neck cancer, rectal cancer, astrocytoma, glioblastoma, microcytic cancer and non-microcytic cancer, metastatic melanoma, androgen-independent metastatic prostate cancer, androgen-dependent metastatic prostate cancer and breast cancer.

Thus, in a preferred embodiment of the invention, the therapeutic agent is selected from the group consisting of (i) A chemotherapy agent,
(ii) a cytotoxic polypeptide,
(iii) an antiangiogenic polypeptide,
(iv) a polypeptide encoded by a tumor suppressor gene,
(v) a pro-apoptotic polypeptide,
(vi) a polypeptide having anti-metastatic activity,
(vii) a polypeptide encoded by a polynucleotide which is capable of activating the immune response towards a tumor and
(viii) an antiangiogenic molecule.
(ix) a toxin In a particular embodiment of the invention, the therapeutic agent is an antitumor peptide selected from the group consisting of the BH3 domain of BAK, PUMA, GW-H1, and the active segment of diphtheria toxin I, and the *Pseudomonas aeruginosa* exotoxin A.

As used herein "BAK" refers to the well-known pro-apoptotic factor belonging to the Bcl-2 protein family that triggers programmed cell death by caspase-dependent apoptotic pathway through inactivating anti-apoptotic proteins, permeabilizing the mitochondrial membrane, and consequently, releasing cytochrome C and other mitochondrial cell death factors. [as seen in Llambi, F. et al. 2011. Mol. Cell, 44:517-31]. In one embodiment, BAK refers to full length BAK (SEQ ID NO:67). In other embodiment, BAK refers to any truncated form thereof containing the functional BH3 domain (SEQ ID NO:68).

As used herein, "PUMA" refers to a protein characterized by a full sequence corresponding to SEQ ID NO:69) which is a (Bcl-2 homology 3) BH3-only protein that triggers cell death by interacting with pro and antiapoptotic proteins of the Bcl-2 family.

As used herein, GW-H1 refers to a polypeptide having the sequence of SEQ ID NO:46 which exerts its cytolytic activity by folding into an amphipathic helix.

Diphtheria toxin I (produced by the bacteria of the species *Corynebacterium diphtheriae*) (SEQ ID NO:70) and the exotoxin of *P. aeruginosa* (SEQ ID NO:71) belong to the family of ADP-ribosilating toxins. Both toxins are proteins that act on eukaryotic Elongation Factor-2 (eEF-2), basically inhibiting the translational activity of the cell that incorporates them and inducing apoptosis. The structure of both toxins presents a receptor-binding domain (that binds to a surface receptor of the cell and induces endocytosis; heparin binding epidermal growth factor precursor in the case of diphtheria toxin, CD91 in the case of the exotoxin A), a translocation domain, and a catalytic domain that performs the action on eEF-2 (an overview is provided in Shapira, A. & Benhar, I., 2010, Toxins, 2:2519-2583).

In an even more preferred embodiment of the invention, the polycationic peptide of the conjugate of the invention or of the nanoparticle of the invention is a CXCR4 ligand, and the cancer targeted to be treated with the conjugate or the nanoparticle of the invention is characterized in that it comprises cells which express the CXCR4 receptor. In a more preferred embodiment, the cells cancer cells that express or overexpress CXCR4 are metastatic stem cells. The term "metastatic stem cells", as used herein, refers to cells that are responsible for metastasis initiation and metastasis maintenance In a yet more preferred embodiment of the invention, the CXCR4 ligand of the conjugate or of the nanoparticle of the invention is selected from the group comprising the T22 peptide (SEQ ID NO:25), the VI peptide (SEQ ID NO:26), the CXCL12 peptide (SEQ ID NO:27), the vCCL2 peptide (SEQ ID NO:28), the optimized EPI-X4 sequence (SEQ ID NO:29), the EPI-X4 sequence (SEQ ID NO:132) or a functionally equivalent variant thereof.

In another more preferred embodiment of the invention, the cancer to be treated with the conjugate or the nanoparticle of the invention is selected from the group consisting of pancreatic and colorectal cancer.

In another preferred embodiment of the invention, the conjugate and the nanoparticle of the invention are used for the treatment of cancerous tumor, wherein the cancerous tumor is a primary tumor or a metastasis.

In a certain embodiment, all the terms and embodiments described in the previous aspects of the invention, are equally applicable to the twelfth aspect of the invention.

VII.B—Use of the Conjugate or of the Nanoparticle of the Invention in the Treatment of Bacterial Infections Another embodiment of the invention relates to the conjugate or of the nanoparticle of the invention for use in the treatment of a disease caused by a bacterial infection.

As used herein, the terms "treat", "treatment" and "treating" refer to the reduction or amelioration of the progression, severity and/or duration of a bacterial infection, or the amelioration of one or more symptoms (preferably, one or more discernible symptoms) of a bacterial infection. The terms "treat", "treatment" and "treating" also refer to the amelioration of at least one measurable physical parameter of a bacterial infection, such as presence of bacterial toxins, not necessarily discernible by the patient. Furthermore, "treat", "treatment" and "treating" refer also to the inhibition of the progression of a bacterial infection, either physically by, e.g., stabilization of a discernible symptom, physiologically by, e.g., stabilization of a physical parameter, or both. "Treat", "treatment" and "treating" may refer, too, to the reduction or stabilization of the bacterial cell count.

The term "bacteria", as used herein, refers to Prokaryotes of the domain Bacteria. Non-limiting examples of bacterial genera that may be used in the method of the present invention include: *Actinomyces, Bacillus, Bacteroides, Bartonella, Bordetella, Borrelia, Brucella, Burkholderia, Campylobacter, Chlamydia, Clostridium, Corynebacterium, Coxiella, Ehrlichia, Enterococcus, Eschrichia, Francisella, Haemophilus, Helicobacter, Klebsiella, Legionella, Leptospira, Listeria, Moraxella, Mycobacterium, Mycoplasma, Neisseria, Nocardia, Pseudomonas, Rickettsia, Salmonella, Shigella, Staphylococcus, Streptobacillus, Streptococcus, Treponema, Ureaplasma, Vibrio* and *Yersinia*. Individual Prokaryotes of the domain Bacteria are denominated bacterium.

The invention contemplates the suitability of the fusion protein, the polynucleotide, the vector, the host cell, or the nanoparticle for the treatment of infections of bacteria such as *Neisseria* spp, including *N. gonorrhea* and *N. meningitides, Streptococcus pyogenes Streptococcus agalactiae, Streptococcus mutans; Haemophilus ducreyi; Moraxella* spp., including *M. catarrhalis*, also known as *Branhamella catarrhalis Bordetella* spp., including *B. pertussis, B. parapertussis* and *B. bronchiseptica, Mycobacterium* spp., including *M. tuberculosis, M. bovis, M. leprae, M. avium, M. paratuberculosis, M. smegmatis; Legionella* spp, including *L. pneumophila, Escherichia* spp., including enterotoxic *E. coli*, enterohemorragic *E. coli* and enteropathogenic *E. coli, Vibrio* spp, including *V. cholera, Shigella* spp., including *S. sonnei, S. dysenteriae, S. flexnerii; Yersinia* spp., including *Y. enterocolitica, Y. pestis, Y. pseudotuberculosis; Campylobacter* spp., including *C. jejuni, Salmonella* spp., including *S. typhi, S. enterica* and *S. bongori, Listeria* spp., including *L. monocytogenes; Helicobacter* spp., including *H. pylori, Pseudomonas* spp., including *P. aeruginosa; Staphylococcus* spp., including *S. aureus, S. epidermidis; Enterococcus* spp., including *E. faecalis, E. faecium; Clostridium* spp., including *C. tetani, C. botulinum, C. difficile, Bacillus* spp., including *B. anthracis; Corynebacterium* spp., including *C. diphtheria, Borrelia* spp., including *B. burgdorferi, B. garinii, B. afzelii, B. andersonfi, B. hermsii, Ehrlichia* spp., including *E. equi* and the agent of the Human Granulocytic Ehrlichiosis; *Rickettsia* spp., including *R. rickettsii; Chlamydia* spp., including *C. trachomatis, Chlamydia pneumoniae, C. psittaci*; Leptospira spp., including *L. interrogans; Treponema* spp., including *T. pallidum, T. denticola, T. hyodysenteriae, Mycobacterium tuberculosis, Streptococcus* spp., including *S. pneumoniae, Haemophilus* spp., including *H. influenzae* type B, and non typeable *H. influenza*, among others and without limitation.

VII.C—Use of the Conjugate or of the Nanoparticle of the Invention in the Treatment of Viral Infections Another embodiment of the invention, relates to the conjugate or of the nanoparticle of the invention, wherein the polycationic peptide is capable of specifically interacting with a receptor on the cell surface of a cell infected by a virus causing an infection; and wherein the intervening polypeptide region is an antiviral agent, for use in the treatment of a disease caused by a viral infection.

As used herein, the terms "treat", "treatment" and "treating" refer to the reduction or amelioration of the progression, severity and/or duration of a viral infection, or the amelioration of one or more symptoms (preferably, one or more discernible symptoms) of a viral infection. The terms "treat", "treatment" and "treating" also refer to the amelioration of at least one measurable physical parameter of a bacterial infection, such as viral titer, not necessarily discernible by the patient. Furthermore, "treat", "treatment"

and "treating" refer also to the inhibition of the progression of a viral infection, either physically by, e.g., stabilization of a discernible symptom, physiologically by, e.g., stabilization of a physical parameter, or both. "Treat", "treatment" and "treating" may refer, too, to the reduction or stabilization of the viral titer.

The term "virus", as used herein, refers to a small infectious agent that can replicate only inside the living cells of organisms. Non-limiting examples of viral families that may be used in the method of the present invention include Adenoviridae, African swine fever-like viruses, Arenaviridae, Arteriviridae, Astroviridae, Baculoviridae, Birnaviridae, Bunyaviridae, Caliciviridae, Circoviridae, Coronaviridae, Deltavirus, Filoviridae, Flaviviridae, Hepadnaviridae, Hepeviridae, Herpesviridae, Orthomyxoviridae, Paramyxoviridae, Picomaviridae, Poxyviridae, Reoviridae, Retroviridae and Rhabdoviridae.

Examples of viral infections that the fusion protein, the polynucleotide, the vector, the host cell, or the nanoparticle of the invention are suitable to treat include those of Human Immunodeficiency Virus (HIV-1), human herpes viruses, like HSV1 or HSV2, cytomegalovirus, especially Human, Epstein Barr virus, Varicella Zoster Virus, hepatitis virus such as hepatitis B virus, hepatitis C virus, paramyxoviruses such as Respiratory Syncytial virus, parainfluenza virus, rubella virus, measles virus, mumps virus, human papilloma viruses, flaviviruses (e.g. Yellow Fever Virus, Dengue Virus, Tick-borne encephalitis virus, Japanese Encephalitis Virus), Influenza virus, rotavirus, and the like.

In an even more preferred embodiment of the invention, the antiviral agent of the fusion protein, the polynucleotide, the vector, the host cell, or the nanoparticle of the invention is selected from the group consisting of (i) A cytotoxic polypeptide, (ii) A pro-apoptotic polypeptide, (iii) A polypeptide encoded by a suicide gene; and (iv) An antiretroviral polypeptide Cytotoxic polypeptides (i), pro-apoptotic polypeptides (ii) and polypeptides encoded by a suicide gene have already been discussed in the section corresponding to the fusion protein.

Antiretroviral agents are one subtype of the antiviral class of antimicrobials. Antiretroviral agents are used specifically for treating viral infections caused by retroviruses. Retroviruses comprise the Retroviridae family of viruses, which includes genera such as Alpharetrovirus, Betaretrovirus, and Lentivirus, to name a few. They are characterized by being single-stranded, positive-sense RNA-genome viruses. Retroviruses generate, through their own reverse transcriptase, a double stranded DNA copy of their genome that integrates in the genome of their host cell. The person skilled in the art will recognize that "antiretroviral agents" comprises any molecules or compounds capable of interfering with the normal replication cycle of a retrovirus at any of its stages. Thus, an antiretroviral polypeptide (iv), as used herein refers to a polypeptide with antiretroviral properties.

Antiretroviral polypeptides suitable for the invention are, for instance, "entry inhibitors", also known as "fusion inhibitors", peptides which interfere with the binding, fusion and entry of the retrovirus to the host cell. Examples of this group are efuvirtide, a biomimetic peptide that competes with the fusion machinery of HIV-1, and peptide T, a peptide that blocks chemokine receptors CCR2 and CCR5.

Also comprised as entry inhibitors are antibodies specific against the receptors used by retroviruses to fuse with the cell. Non-limiting examples of these receptors suitable to be blocked with antibodies, are CD4, CCR2, CCR5, and CXCR4.

The term "antibody", as used herein, refers to a glycoprotein that exhibits specific binding activity for a particular protein, which is referred to as "antigen". The term "antibody" comprises whole monoclonal antibodies or polyclonal antibodies, or fragments thereof, and includes human antibodies, humanised antibodies, chimeric antibodies and antibodies of a non-human origin. "Monoclonal antibodies" are homogenous, highly specific antibody populations directed against a single site or antigenic "determinant". "Polyclonal antibodies" include heterogeneous antibody populations directed against different antigenic determinants.

As used herein, the antibodies suitable for the invention encompass not only full length antibodies (e.g., IgG), but also antigen-binding fragments thereof, for example, Fab, Fab', F(ab')2, Fv fragments, human antibodies, humanised antibodies, chimeric antibodies, antibodies of a non-human origin, recombinant antibodies, and polypeptides derived from immunoglobulins produced by means of genetic engineering techniques, for example, single chain Fv (scFv), diabodies, heavy chain or fragments thereof, light chain or fragment thereof, VH or dimers thereof, VL or dimers thereof, Fv fragments stabilized by means of disulfide bridges (dsFv), molecules with single chain variable region domains (Abs), minibodies, scFv-Fc, and fusion proteins comprising an antibody, or any other modified configuration of the immunoglobulin molecule that comprises an antigen recognition site of a desired specificity. The antibody of the invention may also be a bispecific antibody. An antibody fragment may refer to an antigen binding fragment. An antibody includes an antibody of any class, namely IgA, IgD, IgE, IgG (or sub-classes thereof), and IgM, and the antibody need not be of any particular class.

Thus, a yet more preferred embodiment of the invention relates to the fusion protein, polynucleotide, vector, host cell, or nanoparticle of the invention, wherein the polycationic peptide is a CXCR4 ligand, and wherein the cell is an HIV-infected cell, for use in the treatment of HIV infection.

A yet even more preferred embodiment of the invention relates to the fusion protein, the polynucleotide, the vector, the host cell, or nanoparticle of the invention, wherein the CXCR4 ligand is selected from the group consisting of SEQ ID NO:5, SEQ ID NO:6, SEQ ID NO:7 and SEQ ID NO:8 or a functionally equivalent variant thereof for use in the treatment of a viral infection.

VII.D—Use of the Conjugate or of the Nanoparticle of the Invention in the Treatment of Neurodegenerative Diseases In another embodiment of the invention relates to the conjugate or of the nanoparticle of the invention, wherein the polycationic peptide is a peptide capable of crossing the blood-brain barrier, and wherein the intervening polypeptide region is a chaperone or an inhibitor of protein aggregation, for use in the treatment of a neurodegenerative disease.

Protein aggregation is a biological phenomenon which results from the accumulation of misfolded proteins, whether intra- or extracellularly. The resulting protein aggregates can originate diseases and, in fact, it has been found their involvement in a wide range of diseases known as amyloidoses. The amyloidoses comprise several well-studied neurodegenerative diseases, like ALS, Alzheimer's, Parkinson's and prion disease.

Suitable chaperones or inhibitors of protein aggregation are as defined above. Diseases that can be treated using the fusion proteins, nanoparticles, vectors or host cells according to the invention include Alzheimer's disease, Pick's disease, Alpha1-antitrypsin deficiency, Parkinson's disease and other synucleinopathies, Creutzfeldt-Jakob disease, Retinal ganglion cell degeneration in glaucoma, Cerebral β-amyloid angiopathy, Prion diseases, Tauopathies, Frontotemporal lobar degeneration, Type II diabetes, Amyotrophic lateral sclerosis, Huntington's disease and other trinucleotide repeat disorders, Familial Danish dementia, Familial English dementia, Hereditary cerebral hemorrhage with amyloidosis, Alexander disease, Seipinopathies, Familial amyloidotic neuropathy, Senile systemic amyloidosis, Lysozyme amyloidosis, Fibrinogen amyloidosis, Dialysis amyloidosis, Inclusion body myositis/myopathy, Cataracts, Retinitis pigmentosa with rhodopsin mutations, Medullary thyroid carcinoma, Cardiac atrial amyloidosis, Pituitary prolactinoma, Hereditary lattice corneal dystrophy, Cutaneous lichen amyloidosis, Mallory bodies, Corneal lactoferrin amyloidosis, Pulmonary alveolar proteinosis, Odontogenic tumor amyloid, Seminal vesicle amyloid, Apolipoprotein C2 amyloidosis, Apolipoprotein C3 amyloidosis, Lect2 amyloidosis, Insulin amyloidosis, Galectin-7 amyloidosis (primary localized cutaneous amyloidosis), Corneodesmosin amyloidosis, Enfuvirtide amyloidosis, Cystic Fibrosis, Sickle cell disease, Hereditary cerebral hemorrhage with amyloidosis, AL amyloidosis AH amyloidosis, AA amyloidosis, Aortic medial amyloidosis, ApoAI amyloidosis, ApoAII amyloidosis, ApoAIV amyloidosis and Familial amyloidosis of the Finnish type.

Accordingly, a preferred embodiment of the invention relates to the conjugate or to the nanoparticle of the invention, wherein the intervening polypeptide region is a chaperone or an inhibitor of protein aggregation, for use in the treatment of a neurodegenerative disease, wherein the polycationic peptide capable of crossing the blood-brain barrier is selected from the group consisting of Seq-1-7, Seq-1-8, and Angiopep-2-7.

IX—Method for Imaging a Target Cell

In another aspect, the invention is addressed to a method allowing detecting the presence of a specific cell, or group of cells, within a cell sample, by means of the use of the conjugates or the nanoparticles of the invention.

Therefore, in an thirteenth aspect, the invention relates to a method for the imaging of a target cell which comprises specific binding sites for one or more components of the conjugate according to the sixth aspect of the invention, or of the nanoparticle according to the ninth aspect of the invention, the method comprising (i) contacting a sample containing said cell with a conjugate according to the sixth aspect of the invention or with a nanoparticle according to the tenth or to the eleventh aspect of the invention under conditions adequate for the binding of the conjugate or of the nanoparticle to the cell and wherein the agent of interest is an imaging agent and (ii) Imaging the cell by detecting the signal provided by the imaging agent.

The expression "method for the imaging", as used herein, refers to any method allowing to visualize a target cell within a cell sample, by increasing the contrast between the parts of an image of the sample that comprise the target cell/s and the parts of the image that do not comprise said cell/s. This increase in the contrast is generally mediated by means of an imaging agent, as it has been defined in section IV-E.2 above. In a particular embodiment, the imaging agent is any of those specified in said section.

The term "target cell", as used herein, refers to a cell showing at least one characteristic of interest associated to the presence of a specific binding site in the surface of said target cells. In a particular embodiment, said cell is any of the cells comprising the cell receptors specified in the sixth aspect of the invention.

In a preferred embodiment, the cell expresses or overexpresses the CXCR4 receptor. In another preferred embodiment, the target cell is a cancer cell from any of the cancers specified in the definition of "cancer" in the sixth aspect of the invention. Preferably, said cell is a cell from breast cancer, prostate cancer, lung cancer, ovarian cancer, colon cancer, colorectal cancer, pancreatic cancer, kidney cancer, brain cancer, non-Hodgkin's lymphoma and chronic lymphocytic leukemia.

The term "binding site", as used herein, refers to any pair of a binding pair, wherein the other part of the binding pair is one of the components of the conjugate or nanoparticles of the invention, preferably the second polypeptide of the conjugate or of the nanoparticle of the invention. The expression "binding pair" refers to a molecule that can interact and bind to another molecule resulting in a binding complex, wherein the first and second components are bound to each other by means of non-covalent bonds, such as hydrogen bonds, hydrophobic interactions, van der Waals bonds, ionic bonds or a combination thereof. A binding pair can be part of any type of interaction such as protein/protein interaction, peptide/protein interaction, protein region/protein interaction, antigen/antibody, antigen/antibody fragment or hapten/anti-hapten. The terms "binding", or "bound" have been defined in the second aspect of the invention.

In a particular embodiment, the binding site is any of the targets of interest specified in section IV-B above. In another particular embodiment, it is a cell receptor. In a particular embodiment, it is a cell receptor selected from those specified in section IV-B above. In particular embodiment, it is the CXCR4 receptor. As understood by a skilled person, said targets of interest, as well as the cell receptors, are not necessarily specific for the binding of the second polypeptide of the conjugate of the invention, or of the nanoparticles of the invention. Said targets of interest can be specific for the binding of any component of the conjugate or of the nanoparticle of the invention, or even for the binding of more than one component of the conjugates or nanoparticles.

In a particular embodiment, the target cell comprises more than one binding site, wherein some of the binding sites are specific for the binding of one component of the conjugate, and the rest of binding sites are specific for the binding of at least another component of the conjugate of the invention, or of the nanoparticles of the invention.

As understood by a skilled person, the components of the conjugate or of the nanoparticle of the invention can be: the first, second, and third polypeptide regions of the conjugate of the invention, or of the nanoparticle of the invention, the linking moieties between said polypeptide regions, the protease cleavage sites between said polypeptide regions, the agent of interest of the polypeptides or the nanoparticles of the invention, or the linking moieties between the agent of interest and the polypeptide of the conjugate of the invention, or of the nanoparticle of the invention.

In a particular embodiment, the one or more components of the conjugate or of the nanoparticle that bind to the binding site in the target cell is the second polypeptide of the conjugate, or of the nanoparticle of the invention, wherein said polypeptide is as defined in the sixth aspect of the invention. In a particular embodiment, said second polypeptide is a polycationic peptide. In a preferred embodiment, the polycationic peptide is a CXCR4 ligand. In a more preferred embodiment, it is a CXCR4 ligand selected from the group of CXCR4 ligands specified in section IV-B. (i).

In a preferred embodiment of the imaging method of the invention, the target cell expresses or overexpressed CXCR4 and the one or more components of the conjugate or of the nanoparticle of the invention is a polycationic peptide and is a ligand of CXCR4. In a preferred embodiment, said ligand is selected from the CXCR4 ligands specified in section IV-B (i).

As it will be understood by a skilled person, when the nanoparticle is a biparatopic nanoparticle, the one or more components of the two different conjugates of the nanoparticle that bind to the binding site in the target cell is the second polypeptide of each of the conjugates forming the biparatopic nanoparticle of the invention, wherein said polypeptides are different between the different conjugates of the biparatopic nanoparticle and selected form those defined in the sixth aspect of the invention.

In a particular embodiment, the second polypeptide region of one of the two conjugates of the biparatopic nanoparticle is a polycationic peptide. In a preferred embodiment, the polycationic peptide is a CXCR4 ligand. In a more preferred embodiment, it is a CXCR4 ligand selected from the group of CXCR4 ligands specified in section IV-B. (i). In another particular embodiment, the second polypeptide region of both conjugates of the biparatopic nanoparticle is a polycationic peptide. In a preferred embodiment, the polycationic peptide of both conjugates is a CXCR4 ligand. In a more preferred embodiment, the polycationic peptide of both conjugates is a CXCR4 ligand selected from the group of CXCR4 ligands specified in section IV-B. (i), wherein each of the polycationic peptides is different. IN a preferred embodiment, the polycationic peptide of one of the conjugates of the biparatopic nanoparticles is the T22 peptide (SEQ ID NO. 25, RRWCYRKCYKGYCYRKCR). In another preferred embodiment, the polycationic peptide of one of the conjugates of the biparatopic nanoparticle is the optimized EPI-X4 sequence (SEQ ID NO. 29). In a more preferred embodiment, the polycationic peptide of one of the conjugates of the biparatopic nanoparticles is the T22 peptide (SEQ ID NO. 25, RRWCYRKCYKGYCYRKCR), and the polycationic peptide of the other conjugate of the biparatopic nanoparticle is the optimized EPI-X4 sequence (SEQ ID NO. 29).

The term "sample" or "biological sample", as used herein, refers to biological material isolated from an organism, preferably a subject. The biological sample of the thirteenth aspect of the invention contains any biological material suitable for detecting target cells present in the sample. The biological sample can comprise cell and/or non-cell material of the subject. The sample can be isolated from any suitable tissue or biological fluid such as, for example a tissue biopsy, solid tumor biopsy, blood, saliva, cerebrospinal fluid, urine, stool, bone marrow, a nipple aspirate, a solid tumor biopsy, plasma, serum, cerebrospinal liquid (CSF), feces, a buccal or buccal-pharyngeal swab, semen, a surgical specimen, a specimen obtained from a biopsy, and a tissue sample embedded in paraffin.

The sample is contacted with the conjugates of the invention or the nanoparticles of the invention under conditions adequate for the binding of the conjugate or the nanoparticle to the binding site of the cell. The expression "under conditions adequate for binding" means that the conditions preferably include diluting the conjugates or the nanoconjugates with solutions that are not toxic for the cells, such as BSA or phosphate buffered saline (PBS). These added agents also tend to assist in the reduction of nonspecific background.

The "suitable" or "adequate" conditions also mean that the incubation is at a temperature or for a period of time sufficient to allow effective binding. The conjugates or nanoparticles of the invention are incubated for any suitable time, for instance at least 5 min, at least 15 min, at least 30 min, at least 1 hour, at least 2 hours, at least 4 hours. They are performed at temperatures allowing the survival of the cells and the binding of the conjugates or nanoparticles to the binding sites. Preferably, said temperature is in the order of 15-45°C, preferably 25°C, more preferably 37°C, or at room temperature.

After said incubation, the excess of conjugates and/or nanoparticles in the sample are removed by methods well-known by an expert in the field and include the use of a suitable medium, such as PBS. The medium may contain a detergent such as TWEEN® 20. It may be washed for any suitable time, e.g. 1 to 30 minutes or 3 to 10 minutes for each wash. Washing may include gentle shaking or rocking of the carrier of said cell. The washing temperature is such that the cell can survive and binding is not disrupted. For example, it can be between 15-45°C, preferably 25°C, more preferably 37°C, or at room temperature. Suitable protocols for washing complexes formed by a polypeptide bound to a binding site in a cell, i.e formed by the conjugate or the nanoparticle of the invention bound to the binding site of the target cell, are well known in the art.

Imaging the cell in the sample involves detecting the signal emitted by the imaging agent present in the conjugates or nanoconjugates present in the sample. As understood by a skilled person, after the washing step, said conjugates and nanoconjugates are primarily those bound to the binding site of the target cells present in the sample. Thus, detecting the signal emitted by the imaging agents in the sample indirectly allows detecting the target cells present in the sample. The technique used to detect the imaging agent will depend on the imaging agent used. Said techniques are well-known by an expert in the field, and may comprise the use of a microscope coupled to a camera capable to detect the specific imaging agent. For instance, if the imaging agent is fluorescent agent, it might comprise the use of a fluorescent microscope, if the imaging agent is a radionucleotide, it might comprise the use of a radioluminescence microscope, or a single-cell radioluminescence microscope. Adequate methods to detect a specific type of imaging agent are well known in the art and are of the type indicated in section IV-B.1 for each group of imaging agent specified in this section.

In a particular embodiment, the imaging method allows to determine the target cells present in the sample and also the amount of said target cells in the sample. As understood by a skilled person, it allows to compare the amount of target cells present in sample with the amount of cells present in a control sample.

In a certain embodiment, all the terms and embodiments described in the previous aspects of the invention, are equally applicable to the thirteenth aspect of the invention.

X—Methods for Identifying a Polypeptide that Binds to a Target Peptide

The polypeptide according to the first aspect of the invention is capable of presenting heterologous peptides which are inserted in one or more of the loop regions AB, BC, CD, DE, EF, FG, GH, HI, IJ and JK. These variant polypeptides can be provided as a peptide library wherein different polypeptides are presented by different members of the library. These libraries can be used for the identification of peptides which are capable of biding to a target polypeptide by selecting those members of the library which bind to the target polypeptide and determining the sequence of the peptide within the member of the polypeptide library which is responsible for the binding. Thus, in another aspect, the invention is addressed to a method for the identification of a polypeptide that binds to a target peptide.

In a fourteenth aspect, the invention relates to a method for identifying a polypeptide that binds to a target peptide, said method comprising:

i) contacting a target peptide with the polypeptide display library according to the second aspect of the invention under conditions that allow a polypeptide to interact with the target peptide,
ii) recovering those members of the library that have specifically interacted with the target peptide, and
iii) identifying the sequence of the polypeptide that interacts with the target peptide.

The term "target peptide", as used herein, refers to any peptide of interest, with no function, sequence or structure limitation.

The expression "under conditions that allow a polypeptide to interact with the target peptide" refers to conditions allowing the target peptide and the members of the polypeptide library to maintain their integrity, so that at least the tertiary structure of the polypeptides of the library and of the target peptides is maintained and thus, the polypeptide of the library that has binding affinity for the target peptide specifically binds to the target peptide. Said conditions involves diluting the members of the library in a certain buffer allowing the polypeptide to maintain its integrity. Said buffers are well-known by an expert in the field and can include BSA, bovine gamma globulin (BGG), phosphate buffered saline (PBS), or Tris-buffered saline (TBS). Said conditions also imply that the polypeptide and the target peptide are incubated for a period of time and a temperature adequate for said specific binding to take place effectively. Said conditions are well-known by an expert in the field, and typically include 1 to 4 hours of incubation, at temperatures preferably in the order of 15-45°C, preferably 25°C, more preferably 37°C, or at room temperature or may be overnight at 4°C The term "member of the polypeptide library" has been defined in the first aspect of the invention. Thus, in a particular embodiment, the member of the library is the polypeptide of the library as defined in the second aspect of the invention. In another particular embodiment, it is the complex comprising a polypeptide of the first aspect of the invention, directly linked to a nucleic acid encoding it, as defined in the second aspect of the invention. In another particular embodiment, it is a microorganism comprising the polypeptide of the library as defined in the second aspect of the invention.

The terms "binding" and "specifically binding" have been defined in the first aspect of the invention. In a particular embodiment, the term "binds" and "interacts" in the context in the present aspect are interchangeable. In another particular embodiment, the method is addressed to identify a polypeptide that specifically binds to a target peptide, wherein the polypeptide is considered to specifically bind a target peptide if the binding affinity between said polypeptide and target peptide is of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M or less than $10^{-15}$ M.

In a particular embodiment, the target peptide if immobilized in a solid support.

Non-limiting exemplary solid supports include polymers (such as agarose, sepharose, cellulose, nitrocellulose, alginate, Teflon, latex, acrylamide, nylon, plastic, polystyrene, silicone, etc.), glass, silica, ceramics, and metals. Such solid supports may take any form, such as particles (including microparticles), sheets, dip-sticks, gels, filters, membranes, microfiber strips, tubes, wells, plates (such as microplates, including 6-well plates, 24-well plates, 96-well plates, 384-well plates, etc.), fibers, capillaries, combs, pipette tips, microarray chips, etc. In some embodiments, the biotin-binding moiety is associated with the surface of a solid support. In some embodiments, the surface of the solid support comprises an irregular surface, such as a porous, particulate, fibrous, webbed, or sintered surface.

In some embodiments, a solid support is selected from a microplate, a microarray chip, and a microparticle. In some embodiments, a solid support is at least partially composed of a polymer. In some embodiments, a microparticle solid support comprises monodisperse or polydisperse spherical beads. Monodisperse microparticles are substantially uniform in size (i.e., they have a diameter standard deviation of less than 5 percent), while polydisperse microparticles vary in size. In some embodiments, microparticles are composed of the same polymer throughout, or are core-shell polymers, in which the core of the microparticle is composed of one polymer, and the outer layer (or "shell") is composed of another. In some embodiments, microparticles are magnetic.

In some embodiments, the target peptide is attached to a solid support through a linker moiety. In a particular embodiment, said linker comprises a protease cleavage site.

In a second step of the method, the member or members of the library which are specifically bound to the target peptide are recovered. It will be understood that, in order to identify in step (ii) those polypeptides which bind specifically to the target polypeptide, a separate binding reaction (hereinafter referred to as "negative selection step") should be carried out in parallel in which the target polypeptide is contacted with the non-variant or naturally occurring form of the polypeptide which is found in the library. Preferably, said non-variant or naturally occurring form is identical to the member of the library but wherein the loop region has not been modified by the insertion of an heterologous peptide or polypeptide. Only if the target polypeptide binds to the member of the polypeptide display library but not to the non-variant or naturally occurring form thereof, then the member of the polypeptide library will be selected as capable of specifically binding to the target polypeptide. Thus, by way of illustration, if the polypeptide library is formed by variegated forms of the human nidogen G2 domain as defined in SEQ ID NO:62 or 63 in which one or more of the loop regions AB, BC, CD, DE, EF, FG, GH, HI, IJ and JK are modified by the insertion of an heterologous peptide, then the negative selection step used to exclude peptides which do not bind specifically to the heterologous peptide will be carried out using the polypeptides of SEQ ID NO:62 or 63 respectively. The polypeptide library may be formed by variegated forms of the human nidogen G2 domain containing one or more mutations at positions 459, 468, 639, 650, 543, 545, 449, 525, 561, 618, 619, 151, 604, 638, 641, 469 and 518 wherein the numbering corresponds to that of the full-length human nidogen-1 defined under the UniProt database with accession number P14543-1 (version dated Jul. 7, 2009). In some embodiments, the polypeptide library is formed by variegated forms of the nidogen G2 domain containing one or more of mutations H459A, R468N, F639S, R650A, H543K, H545N, V449T, V525Q, V619T, F561E, C618S, S469I, R518I as defined above. Suitable nidogen G2 domain variants that can be used in the polypeptide library include, without limitation, any of the nidogen G2 domain variants defined above in the context of the previous aspects of the invention including the variant carrying the NIDOmut2, NIDOmut3, the NIDOmut3-V45T, the NIDOmut3_V121Q, the NIDOmut3-F157E, the NIDOmut3-V215T, the NIDOmut4, the NIDOmut4_T215V, the NIDOmut5, NIDOmut3-V176T, the NIDOmut3-1200T, the NIDOmut3-V236Y, the NIDOmut3-L237T, the NIDOmut3-S65I, the NIDOmut3-R114I, the NIDOmut3-C214S, the NIDOmut3-S65I_R114I, the NIDOmut5-S65I_R114I, the NIDOmut3-S65I_R114I and the NIDOmut5-S65I_R114I as defined, respectively, as SEQ ID NO:64, 65 and 87 to 104 and in which one or more of the loop regions AB, BC, CD, DE, EF, FG, GH, HI, IJ and JK are modified by the insertion of an heterologous peptide, then the negative selection step used to exclude peptides which do not bind specifically to the heterologous peptide will be carried out using the polypeptides defined above but lacking the heterologous peptide.

For that purpose, the target peptide is first washed to remove the members of the library that have not bound to the target peptide. Washing conditions are well-known by an expert in the field and include the use of a suitable medium, such as PBS. The medium may contain a detergent such as TWEEN® 20. It may be washed for any suitable time, e.g. 1 to 30 minutes or 3 to 10 minutes for each wash. Washing may include gentle shaking or rocking of the carrier of said target peptide. The washing temperature is such that the binding between the target peptide and the polypeptide of the library is not disrupted. For example, it can be between 15 and 45°C or between 3° and 40°C Typically, it is about 37°C or room temperature.

Once the target peptide has been washed, the members of the library bound to the target peptide are recovered. Said recovery may consist on eluting the polypeptide of the library bound to the target peptides. Different techniques can be used for said elution. For instance, elution can be carried by incubating the complex "target peptide-member of the library" under low pH conditions that disrupt the binding between both, such as at a pH between 3 and 6, preferably at a pH 4. Elution may also be carried by incubating the complex with DTT. Alternatively, the whole complex of the polypeptide and the target peptide can be recovered. For instance, when the target peptide is immobilized in the target support, said immobilization can be mediated by means of a linker that comprises a protease cleavage site, which is cleaved to recover to the whole complex. Said methods are well-known by an expert in the field.

In a particular embodiment, steps i) and ii) are repeated at least once, at least twice, at least three times, at least four times, at least 5 times, at least 6 times, at least 7 times at least 10 times, preferably at least 2 times. In each of said repetitions, the members of the polypeptide library used in step i) correspond to the members recovered in step ii).

Thus, in another particular embodiment, steps i) and ii) of the method of the fourteenth aspect are repeated at least once, at least twice, at least three times, at least four times, at least 5 times, at least 6 times, at least 7 times at least 10 times, preferably at least 2 times, wherein the polypeptide library used in step i) in each repetition is formed by the members of the library recovered in step (ii).

In a third step, the polypeptide of the library is identified. Identification of the polypeptide involves determining the sequence of the polypeptide of the library.

Said determination can be mediated by several methods. For instance, it can simply consist on determining the sequence of said polypeptide, by any technique well-known by a skilled person, such as mass spectrometry.

In case where the member of the library is a polypeptide of the library as a phenotype is directly or indirectly linked to a nucleic acid as a genotype corresponding to said phenotype, as defined in the second aspect of the invention, the determination of the sequence of the polypeptide of the library can also consist on sequencing said nucleic acid. As indicated in the definition of the "genotype" referred in the second aspect of the invention, said nucleic acid encodes, or comprises a sequence encoding, the polypeptide of the library directly or indirectly linked to it. Methods to determine the sequence of a nucleic acid directly or indirectly linked to a polypeptide are well known by an expert in the field. For instance, they might simply involve amplifying the sequence of said nucleic acid by PCR or in case the nucleic acid is an RNA molecule, by reverse transcriptase followed by PCR (RT-PCR). The amplified cDNA is then sequenced by well-known techniques for a skilled person. Non-limiting examples of said sequencing techniques include the well-known Sanger method, pyrosequencing, sequencing by synthesis or sequencing by ligation. Alternatively it might comprise a first step where the nucleic acids are isolated from the polypeptide of the library to which they are directly or indirectly linked, and then, the nucleic acids are amplified by PCR or RT-PCR and sequenced, as previously described. Techniques to separate a nucleic acid from a polypeptide are well-known by a skilled person. Non/limiting examples of said techniques include any technique allowing the disruption of the interaction of a polypeptide with other molecules, or simply the degradation of a polypeptide. These techniques include an incubation with dithiothreitol (DTT), with a detergent such as sodium dodecyl sulfate (SDS), with proteinases such as proteinase K to degrade the proteins, or simply an incubation at high temperatures to denature the proteins so that the binding of any polypeptide to the nucleic acids is disrupted, preferably between 40-95°C, more preferably at 60°C The nucleic acids are then isolated from the proteins by well-known techniques, such as phenol/chloroform, silica methods, or guanidinium thiocyanate-phenol-chloroform extraction when the nucleic acid is RNA. In case where the nucleic acid is indirectly linked to the polypeptide and is comprised within a cell from a microorganism, such as for example a bacteria or a yeast cell, the separation of the nucleic acid might comprise techniques allowing to degrade the cell membrane. Said techniques are also well-known by an expert in the field and may for instance consist on any of the techniques indicated above to disrupt the interaction of a polypeptide with another molecule. Some of the methods referred above to separate the nucleic acids from the polypeptides are described in more detail in Kelly M. Elkins, 2013, Forensic DNA Biology.

Thus, in a particular embodiment, identifying the sequence of the polypeptide that interacts with the target peptide comprises determining the sequence of said peptide. In another particular embodiment, it comprises determining the sequence of the nucleic acid directly or indirectly linked to it and encoding it.

In a particular embodiment, several polypeptides of the library are capable to specifically bind to the target peptide. In this case, the method is for identifying polypeptides that bind to a target peptide, and step iii) of the method consists on identifying the sequence of the polypeptides that interact with the target peptide. The same methods provided above for the identification of the sequence of one polypeptide are also applicable for the identification of the sequence of several polypeptides. Thus, in a particular embodiment, the identification of the sequence of the polypeptides that interact with the target peptide comprises determining the sequence to the nucleic acid directly or indirectly linked to each of them.

In another particular embodiment, after step ii), the method comprises an additional step wherein the recovered members of the library are amplified. Said amplification might consist on transforming host organisms with the members of the polypeptide library recovered, or simply amplifying the members of the library recovered. For instance, in case the member of the library is a microorganism as escribed in the second aspect of the invention and capable to replicate upon infection of an organism, such as a phage, a bacteriophage, or a virus, the members of the library recovered in step ii) can be amplified by cultivating bacteria that have been infected by said members of the library. In case said members are microorganisms as described in the second aspect of the invention that are capable to replicate, such as bacteria or yeast, the amplification of the members of the library can simply consist on cultivating said microorganisms.

Therefore, in a particular embodiment, the method for identifying a polypeptide, or polypeptides, that bind/s to a target peptide comprises:

i) contacting a target peptide with the polypeptide display library according to the second aspect of the invention under conditions that allow a polypeptide to interact with the target peptide,
ii) recovering those members of the library that have interacted with the target peptide,
iii) amplifying the members of the library that have been recovered in step ii)
iv) identifying the sequence of the polypeptide/s that interact/s with the target peptide.

In a particular embodiment, where steps i)-iii) are repeated at least once, at least twice, at least three times, at least four times, at least 5 times, at least 6 times, at least 7 times at least 10 times, preferably at least 2 times, wherein the polypeptide library used in step i) in each repetition is formed by the members of the library recovered in step (ii) and amplified in step iii).

In a certain embodiment, all the terms and embodiments described in the previous aspects of the invention, are equally applicable to the fourteenth aspect of the invention.

XI—Use of the Polypeptide of the First Aspect of the Invention

As indicated in the first aspect of the invention, the polypeptides of this aspect are suitable for incorporating heterologous peptide or peptides within one or more of the loop regions, either as insertion in the loop regions or replacing partially or completely the loop regions. These variant polypeptides can then be used to present the heterologous peptide or peptides, which can be defined as "peptides of interest". Thus, in a fifteenth aspect, the invention relates to the use of a polypeptide according to the first aspect of the invention, for presenting a peptide, wherein said peptide is found in one of the loop regions.

The expression "for presenting", as used herein, refers to the capacity of the polypeptide to bring the heterologous peptide into proximity of an element of interest. The term "peptide of interest", as used herein, is not limited by any function, sequence or structural characteristic, besides the fact that it can be found in one of the loop regions of the polypeptide of the first aspect of the invention. In one embodiment, the heterologous polypeptide is inserted within one or more of the loop regions, i.e. the loop region conserves all the amino acids found in the cognate loop domain in SEQ ID NO:62 or SEQ ID NO:63 but the heterologous polypeptide is inserted between two consecutive amino acids. In another embodiment, the heterologous polypeptide within one or more of the loop regions is found as an insertion within the loop region which replaces the partially or completely the sequence of the loop domain. In another embodiment, wherein more than one peptide is presented in different loops of the polypeptide of the invention, one or more of the peptides may be located as insertions in the loop regions and one or more of the peptides can be found replacing part or the complete loop regions.

The length of the heterologous polypeptide or peptides to be presented is not particularly limitative. Thus, the heterologous polypeptide may comprise at least two, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100 or more amino acids.

In a particular embodiment, the peptide of interest is any of the agents of interest defined in the sixth aspect of the invention, preferably, it is a therapeutic agent as defined in section IV-E.1, in particular, a cytotoxic polypeptide, an antiangiogenic polypeptide, a polypeptide encoded by a tumor suppressor gene, a pro-apoptotic polypeptide, polypeptide having anti-metastatic activity, a polypeptide encoded by a polynucleotide which is capable of activating the immune response towards a tumor, an antiangiogenic molecule or a toxin.

The terms "binds" and "specifically binds" have been defined in the first aspect of the invention. Methods to determine the binding between a polypeptide and a target molecule as well as the KD of a binding complex have been provided in said definition in the first aspect of the invention. In a particular embodiment, the specific binding between the peptide of interest and the at last one loop region of the polypeptide has a Kd of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M or less than $10^{-15}$ M.

In a particular embodiment, the element of interest to which the polypeptide of the first aspect presents, or brings, the peptide of interest, is a cell. In a preferred embodiment, it is a cell in a sample. In another particular embodiment, it is a cell isolated from a tissue or organism from which it derives. In another particular embodiment, said element of interest is another peptide, protein, or nucleic acid in a sample.

The term "sample" has been defined in the thirteenth aspect of the invention. The sample referred in the present aspect contains the element of interest, wherein said element is preferably as specified above.

In a particular embodiment, the invention relates to a non-therapeutic use of a polypeptide according to the first aspect of the invention, for presenting a peptide, wherein said peptide is found in one of the loop regions.

In a certain embodiment, all the terms and embodiments described in the previous aspects of the invention, are equally applicable to the fifteenth aspect of the invention.

XII—Method for Determining the Presence of a Target Peptide in a Sample

As indicated in the previous aspect, the polypeptide of the first aspect of the invention is capable of specifically binding to a target molecule or target peptide. Therefore, it might be useful for determining the presence of said peptide in a sample.

Thus, in a sixteenth aspect, the invention relates to a method for determining the presence of a target peptide in a sample comprising:

(i) contacting the proteins present in the sample with a polypeptide according to the first aspect of the invention, wherein the sequence of at least one of the loop regions in the polypeptide is a sequence that is capable of specifically binding to the target peptide, (ii) determining if there is an interaction between the target peptide and the polypeptide, wherein if there is an interaction between the polypeptide and the target peptide, then the target peptide is present in the sample.

The term "sample" has been defined in the thirteenth aspect of the invention. The sample of the fourteenth aspect of the invention contains any biological material suitable for detecting peptides present in the sample.

The expression "target peptide", as used herein, is not limited by any functional, sequence or structural characteristic, besides the fact that it specifically binds to the sequence of at least one of the loop region of a polypeptide of the first aspect of the invention.

In a particular embodiment, the target peptide is that of the thirteenth aspect of the invention, and the polypeptide is that identified in said aspect as specifically binding to said target peptide.

The specifically binding between said sequence of at least one loop region and the target peptide has a KD of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M or less than $10^{-15}$ M. The term "specifically binding" has been defined in the first aspect of the invention. Methods to determine the binding between a polypeptide and a target peptide have also been provided in the first aspect of the invention.

Contacting the proteins present in a sample with a polypeptide of the first aspect capable to specifically bind to the target peptide, is generally a matter of simply mixing the polypeptide with the sample under conditions that allow a polypeptide to interact with a target peptide. Thus, in a particular embodiment, step i) of the method is carried under said conditions. The expression "under conditions that allow a polypeptide to interact with a target peptide" has been defined in the fourteenth aspect of the invention. Said definition applies to the present aspect of the invention by substituting the term "member of the library", or "polypeptide of the library", by "polypeptide of the first aspect".

Determining if there is an interaction, i.e. the formation of a polypeptide-target peptide complex, can be done in a number of ways.

On one side, this may be done by first attaching the target peptide to a solid support by means of a specific antibody attached to said support and specific for said peptide, or of an antibody specific for a tag present in said peptide, such as a histidine tag or biotin. Then, the polypeptide of the first aspect is added, and excess reagent is washed off. The presence of the polypeptide of the first aspect in the solid support is then determined. Various blocking and washing steps may be utilized as it is known in the art. The washing conditions can be any of those specified in the fourteenth aspect of the invention. As understood by a skilled person, after the washing steps, the polypeptide of the first aspect detected is that bound to the target peptide. Thus, the detection of the polypeptide of the first aspect is an indirect indication of the binding of the polypeptide to the target peptide, and thus of the presence of said peptide in the sample.

Techniques to detect the presence of a polypeptide or peptide in a sample are well-known by an expert in the field. For instance, the polypeptide can be labelled and said label detected. Said label can be any radioactive, fluorescent, biological or enzymatic tags. Methods to detect said labels are well-known by an expert in the field. Patents concerning the use of such labels include U.S. Pat. Nos. 3,817,837; 3,850,752; 3,939,350; 3,996,345; 4,277,437; 4,275,149 and 4,366,241. Alternatively, one may find additional advantages through the use of a secondary binding ligand such as a first and second antibody and/or a biotin/avidin ligand binding arrangement, as it is known in the art. Non-limiting examples of techniques based on the use of a secondary ligand to detect a polypeptide in a sample include Western blot or immunoblot, ELISA (Enzyme-Linked Immunosorbent Assay) or RIA (Radioimmunoassay).

On the other side, determining if there is an interaction can be done by first attaching the polypeptide of the first aspect to a solid support, by means of an antibody attached to said solid support and specific for said polypeptide. Then, the sample suspected to comprise the target peptide is added, and excess reagent is washed off. Finally, the presence of the peptide of interest in the solid support is determined.

The rest of steps can be the same as those indicated above in case the target peptide is immobilized in a solid support, except that the part of the polypeptide-target peptide complex that is detected in the present case is the target peptide, by means of a label (as those indicated above) attached to the target peptide or of a secondary ligand (as those indicated above) specific for the target peptide. Thus, in this case, the detection of the target peptide is an indirect indication of the binding of the polypeptide to the target peptide, and thus of the presence of said peptide in the sample.

As well-known by an expert in the field, any of the techniques specified above allowing determining the presence of a polypeptide or of a peptide in a sample or attached to a solid support, also allow determining the amount of said polypeptide or peptide in said sample or attached to said solid support. Therefore, the method for determining the presence of a target peptide in a sample allows not only determining the presence of the target peptide, but also the amount of the polypeptide-target peptide complexes formed and thus the amount of target peptide in the sample.

Thus, in a particular embodiment, the invention also relates to a method for determining the amount of a target peptide in a sample comprising:

i) contacting the proteins present in the sample with a polypeptide according to the first aspect of the invention, wherein the sequence of at least one of the loop regions in the polypeptide is a sequence that is capable of specifically binding to the target peptide, under condition allowing a polypeptide-target peptide complex to form, ii) determining the amount of the polypeptide-target peptide complexes formed, wherein the amount of polypeptide-target peptide complexes formed indicates the amount of target peptide in the sample.

The expression "under condition allowing a polypeptide-target peptide complex to form", as used herein, refers to the same conditions that allow a polypeptide to interact with a target peptide indicated above.

In a particular embodiment of the fourteenth aspect, the polypeptide of the first aspect is immobilized in a solid support. In a particular embodiment, said solid support is any of those specified in the fourteenth aspect of the invention. In a particular embodiment, the polypeptide is attached to the solid support through a linker moiety.

In another particular embodiment of the fourteenth aspect, the target peptide is immobilized in a solid support. In a particular embodiment, said solid support is any of those specified in the fourteenth aspect of the invention. In a particular embodiment, the polypeptide is attached to the solid support through a linker moiety.

In a certain embodiment, all the terms and embodiments described in the previous aspects of the invention, are equally applicable to the sixteenth aspect of the invention.

In another embodiment, the terms "consists" and "comprises", "consisting" and "comprising", used in any of the aspects and embodiment of the invention are interchangeable.

Sequence Overview

TABLE 6

Sequence overview

| SEQ ID NO | Sequence |
|---|---|
| 1 | Loop region AB (GSSQVP) |
| 2 | Loop region BC (MNHG) |
| 3 | Loop region CD (PETVGYSLLPLAPVGGIIGWMFAVEQDGFKNGFSITGG) |
| 4 | Loop region DE (VGHPGN) |
| 5 | Loop region EF (GIDEHGH) |
| 6 | Loop region FG (PQIPFGS) |
| 7 | Loop region HI (EPERDGASP) |
| 8 | Loop region IJ (FQECVHDDSRPALPS) |
| 9 | Loop region JK (NQEEK) |
| 10 | beta strand A (QRVNGKVKGRIFV) |
| 11 | beta strand B (IVFENTDLHSYVV) |
| 12 | beta strand C (RSYTAIS) |
| 13 | beta strand D (EFTRQAEVTF) |
| 14 | beta strand E (LVIKQRFS) |
| 15 | beta strand F (LTIDTELEGRV) |
| 16 | beta strand G (SVHIEPYTELYHYS) |
| 17 | beta strand H (VITSSSTREYTVT) |
| 18 | beta strand I (SRIYTYQWRQTIT) |
| 19 | beta Strand J (TQQLSVDSVFVLY) |
| 20 | beta strand K (ILRYALSNSIG) |
| 21 | α1 (TVGYSL) |
| 22 | α2 (PVGGIIGWM) |
| 23 | α3 (GFSIT) |
| 24 | CαD (TIPE) |
| 25 | T22(RRWCYRKCYKGYCYRKCR) |
| 26 | V1 peptide (LGASWHRPDKCCLGYQKRPLP) |
| 27 | CXCL12<br>(KPVSLSYRCPCRFFESHVARANVKHLKILNTPNCALQIVARLKNNNRQVCIDPKLKWIQEYLEKALN |
| 28 | vCCL2<br>LGASWHRPDKCCLGYQKRPLPQVLLSSWYPTSQLCSKPGVIFLTKRGRQVCADKDWVKKLMQQLPVTA) |
| 29 | Optimized EPI-X4<br>IVRWSKKVPCVSIVRWSKKVPCVS |

TABLE 6-continued

Sequence overview

| SEQ ID NO | Sequence |
|---|---|
| 30 | Arg-rich sequence (RRRRRRRRR) |
| 31 | Arg-rich sequence (RRRGRGRRR) |
| 32 | Arg-rich sequence (RARGRGRRR) |
| 33 | Arg-rich sequence (RARGRGGGA) |
| 34 | A5G27 (RLVSYNGIIFFLK) |
| 35 | FNI/II/V (WQPPRARITGYIIKYEKPGSPPREVVPRPRPGVTEATITGLEPGTEYTIYVIALKNNQKSEPLIGRKKT) |
| 36 | Seq-1-7 (KYLAYPDSVHIWRKRKRK) |
| 37 | Seq-1-8 (KYLAYPDSVHIWRKRKRKR) |
| 38 | Angiopep-2-7 (TFFYGGSRGKRNNFKTEEYRKR) |
| 39 | Linker region (GGSSRSS) |
| 40 | Linker region (GGGNS) |
| 41 | T140 (RRX$_1$CYRKX$_2$PYRX$_3$CR) |
| 42 | TN14003 (RRX$_1$CYX$_2$KX$_3$PYRX$_4$CR) |
| 43 | TC14012 (RRX$_1$CYEKX$_2$PYRX$_3$CR) |
| 44 | TE14011 (RRX$_1$CYX$_2$KX$_3$PYRX$_4$CR) |
| 45 | TZ14011 (RRX$_1$CYX$_2$KX$_3$PYRX$_4$CR) |
| 46 | GW-H1 peptide (GYNYAKKLANLAKKFANALW) |
| 47 | nucleolin-binding peptide 1 (KDEPQRRSARLSAKPAPPKPEPKPKKAPAKK) |
| 48 | nucleolin-binding peptide 2 (KDEPQRRSARLSAKPAPPKPEPKPKKAPAKKRKRKRKRK) |
| 49 | Linker region (SGGTSGSTSGTGST) |
| 50 | Linker region (AGSSTGSSTGPGSTT) |
| 51 | Linker region (GGSGGAP) |
| 52 | Linker region (GGGVEGGG) |
| 53 | Linker region (PKPSTPPGSS) |
| 54 | Linker region (APAETKAEPMT) |
| 55 | Cleavage site (AAALE) |
| 56 | Cleavage site (DDDDK) |
| 57 | Cleavage site (IEDGR) |
| 58 | Cleavage site (LVPRGS) |
| 59 | Cleavage site (ENLYFQG) |
| 60 | Cleavage site (LEVLFQGP) |
| 61 | T22-NIDOmut2-H6<br>RRWCYRKCYKGYCYRKCRGGSSRSSSPQRVNGKVKGRIFVGSSQVPIVFENTDLASYVVMNHGNSYTAISTIPETVG<br>YSLLPLAPVGGIIGWMFAVEQDGFKNGFSITGGEFTRQAEVTFVGHPGNLVIKCIRFSGIDEHGHLTIDTELEGRVPQI<br>PFGSSVHIE<br>PYTELYHYSTSVITSSSTREYTVTEPERDGASPSRIYTYQWRQTITFQECVHDDSRPALPSTCIQLSVDSVSVLYNCIEEKI<br>LAYALSNSIGPVREGSPDAKHHHHHH |

TABLE 6-continued

| Sequence overview | |
|---|---|
| SEQ ID NO | Sequence |
| 62 | Native human nidogen-1 G2 domain<br>SPQRVNGKVKGRIFVGSSQVPIVFENTDLHSYWMNHGRSYTAISTIPETVGYSLLPLAPVGGIIGWMFAVEQDGFKNG<br>FSITGGEFTRQAEVTFVGHPGNLVIKQRFSGIDEHGHLTIDTELEGRVPQIPFGSSVHIEPYTELYHYSTSVITSSSTREYT<br>VTEPERDGASPSRIYTYQWRQTITFQECVHDDSRPALPSTQQLSVDSVFVLYNQEEKILRYALSNSIGPVREGSPDA |
| 63 | Native human nidogen-1 G2 domain lacking SP dipeptide.<br>QRVNGKVKGRIFVGSSQVPIVFENTDLHSYVVMNHGRSYTAISTIPETVGYSLLPLAPVGGIIGWMFAVEQDGFKNG<br>FSITGGEFTRQAEVTFVGHPGNLVIKQRFSGIDEHGHLTIDTELEGRVPQIPFGSSVHIEPYTELYHYSTSVITSSSTREYT<br>VTEPERDGASPSRIYTYQWRQTITFQECVHDDSRPALPSTQQLSVDSVFVLYNQEEKILRYALSNSIGPVREGSPDA |
| 64 | Human nidogen-1 G2 domain carrying H459A., R468N, F639S and R650A mutations (NIDOmut2).<br>SPQRVNGKVKGRIFVGSSQVPIVFENTDLASYVVMNHGNSYTAISTIPETVGYSLLPLAPVGGIIGWMFAVECIDGFKNG<br>FSITGGEFTRQAEVTFVGHPGNLVIKQRFSGIDEHGHLTIDTELEGRVPQIPFGSSVHIEPYTELYHYSTSVITSSSTREYT<br>VTEPERDGASPSRIYTYQWRQTITFQECVHDDSRPALPSTQQLSVDSVSVLYNQEEKILAYALSNSIGPVREGSPDA |
| 65 | Human nidogen-1 G2 domain carrying H459A., R468N, F639S and R650A mutations and lacking SP dipeptide.<br>QRVNGKVKGRIFVGSSQVPIVFENTDLASYVVMNHGNSYTAISTIPETVGYSLLPLAPVGGIIGWMFAVEQDGFKNG<br>FSITGGEFTRQAEVTFVGHPGNLVIKQRFSGIDEHGHLTIDTELEGRVPQIPFGSSVHIEPYTELYHYSTSVITSSSTREYT<br>VTEPERDGASPSRIYTYQWRQTITFQECVHDDSRPALPSTQQLSVDSVSVLYNQEEKILAYALSNSIGPVREGSPDA |
| 66 | T22-G2-H6<br>RRWCYRKCYKGYCYRKCRGGSSRSS<br>SPQRVNGKVKGRIFVGSSQVPIVFENTDLHSYVVMNHGRSYTAISTIPETVGYSLLPLAPVGGIIGWMFAVEQDGFKNG<br>FSITGGEFTRQAEVTFVGHPGNLVIKQRFSGIDEHGHLTIDTELEGRVPQIPFGSSVHIEPYTELYHYSTSVITSSSTREYT<br>VTEPERDGASPSRIYTYQWRQTITFQECVHDDSRPALPSTQQLSVDSVFVLYNQEEKILRYALSNSIGPVREGSPDA<br>KHHHHHH |
| 67 | BAK |
| 68 | BAK BH3 domain |
| 69 | PUMA |
| 70 | Diphtheria toxin I |
| 71 | exotoxin of *P. aeruginosa* |
| 72 | P14543-1 of the Uniprot Database (version dated Jul. 7, 2009) |
| 73 | Hexahistidine (HHHHHH) |
| 74 | IL-6 ligand (LSLITRL) |
| 75 | IL-6 ligand (WQDPHSWNSSFYRLRFELRYRAERSKTFTTW) |
| 76 | Linker region (GGSSRSSS) |
| 77 | Positively charged peptide region (RKRKRK) |
| 78 | Positively charged peptide region (RRRRRR) |
| 79 | Positively charged peptide region (KKKKKK) |
| 80 | Positively charged peptide region (HHHHHH) |
| 81 | Positively charged peptide region (RHRHRH) |
| 82 | Positively charged peptide region (RKRKRKRK) |
| 83 | Positively charged peptide region (RKRHRK) |
| 84 | Positively charged peptide region (RKRHRH) |
| 85 | Positively charged peptide region (RHRHRH) |
| 86 | Positively charged peptide region (RKRKRKR) |
| 87 | NIDOmut3<br>SPQRVNGKVKGRIFVGSSQVPIVFENTDLASYWMNHGNSYTAISTIPETVGYSLLPLAPVGGIIGWMFAVEQDGFK<br>NGFSITGGEFTRQAEVTFVGHPGNLVIKQRFSGIDEKGNLTIDTELEGRVPCIIPFGSSVHIEPYTELYHYSTSVITSSSTR<br>EYTVTEPERDGASPSRIYTYQWRQTITFQECVHDDSRPALPSTQQLSVDSVSVLYNQEEKILAYALSNSIGPVREGSPDA |

TABLE 6-continued

Sequence overview

| SEQ ID NO | Sequence |
|---|---|
| 88 | NIDOmut3_V45T<br>SPQRVNGKVKGRIFVGSSQTPIVFENTDLASYWMNHGNSYTAISTIPETVGYSLLPLAPVGGIIGWMFAVEQDGFK<br>NGFSITGGEFTRQAEVTFVGHPGNLVIKQRFSGIDEKGNLTIDTELEGRVPQIPFGSSVHIEPYTELYHYSTSVITSSSTR<br>EYTVTEPERDGASPSRIYTYQWRQTITFQECVHDDSRPALPSTQQLSVDSVSVLYNQEEKILAYALSNSIGPVREGSPDA |
| 89 | NIDOmut3_V121Q<br>SPQRVNGKVKGRIFVGSSQVPIVFENTDLASYVVMNHGNSYTAISTIPETVGYSLLPLAPVGGIIGWMFAVEQDGFK<br>NGFSITGGEFTRQAEVTFQGHPGNLVIKQRFSGIDEKGNLTIDTELEGRVPQIPFGSSVHIEPYTELYHYSTSVITSSSTR<br>EYTVTEPERDGASPSRIYTYQWRQTITFQECVHDDSRPALPSTQQLSVDSVSVLYNQEEKILAYALSNSIGPVREGSPDA |
| 90 | NIDOmut3_F157E<br>SPQRVNGKVKGRIFVGSSQVPIVFENTDLASYWMNHGNSYTAISTIPETVGYSLLPLAPVGGIIGWMFAVEQDGFK<br>NGFSITGGEFTRQAEVTFVGHPGNLVIKQRFSGIDEKGNLTIDTELEGRVPCIIPEGSSVHIEPYTELYHYSTSVITSSSTR<br>EYTVTEPERDGASPSRIYTYQWRQTITFQECVHDDSRPALPSTQQLSVDSVSVLYNQEEKILAYALSNSIGPVREGSPDA |
| 91 | NIDOmut3_V215T<br>SPQRVNGKVKGRIFVGSSQVPIVFENTDLASYVVMNHGNSYTAISTIPETVGYSLLPLAPVGGIIGWMFAVEQDGFK<br>NGFSITGGEFTRQAEVTFVGHPGNLVIKQRFSGIDEKGNLTIDTELEGRVPQIPFGSSVHIEPYTELYHYSTSVITSSSTR<br>EYTVTEPERDGASPSRIYTYQWRQTITFQECTHDDSRPALPSTQQLSVDSVSVLYNQEEKILAYALSNSIGPVREGSPDA |
| 92 | NIDOmut4<br>SPQRVNGKVKGRIFVGSSQTPIVFENTDLASYWMNHGNSYTAISTIPETVGYSLLPLAPVGGIIGWMFAVEQDGFK<br>NGFSITGGEFTRQAEVTFQGHPGNLVIKQRFSGIDEKGNLTIDTELEGRVPCIIPEGSSVHIEPYTELYHYSTSVITSSSTR<br>EYTVTEPERDGASPSRIYTYQWRQTITFQECTHDDSRPALPSTQQLSVDSVSVLYNQEEKILAYALSNSIGPVREGSPDA |
| 93 | NIDOmut4_T215V<br>SPQRVNGKVKGRIFVGSSQTPIVFENTDLASYVVMNHGNSYTAISTIPETVGYSLLPLAPVGGIIGWMFAVEQDGFK<br>NGFSITGGEFTRQAEVTFQGHPGNLVIKQRFSGIDEKGNLTIDTELEGRVPQIPEGSSVHIEPYTELYHYSTSVITSSSTR<br>EYTVTEPERDGASPSRIYTYQWRQTITFQECVHDDSRPALPSTQQLSVDSVSVLYNQEEKILAYALSNSIGPVREGSPDA |
| 94 | NIDOmut5<br>SPQRVNGKVKGRIFVGSSQTPIVFENTDLASYVVMNHGNSYTAISTIPETVGYSLLPLAPVGGIIGWMFAVEQDGFK<br>NGFSITGGEFTRQAEVTFQGHPGNLVIKQRFSGIDEKGNLTIDTELEGRVPCIIPEGSSVHIEPYTELYHYSTSVITSSSTR<br>EYTVTEPERDGASPSRIYTYQWRQTITFQESTHDDSRPALPSTOCILSVDSVSVLYNCIEEKILAYALSNSIGPVREGSPDA |
| 95 | NIDOmut3_V176T<br>SPQRVNGKVKGRIFVGSSQVPIVFENTDLASYWMNHGNSYTAISTIPETVGYSLLPLAPVGGIIGWMFAVEQDGFK<br>NGFSITGGEFTRQAEVTFVGHPGNLVIKQRFSGIDEKGNLTIDTELEGRVPQIPFGSSVHIEPYTELYHYSTSTITSSSTR<br>EYTVTEPERDGASPSRIYTYQWRQTITFQECVHDDSRPALPSTQCILSVDSVSVLYNQEEKILAYALSNSIGPVREGSPDA |
| 96 | NIDOmut3_I200T<br>SPQRVNGKVKGRIFVGSSQVPIVFENTDLASYWMNHGNSYTAISTIPETVGYSLLPLAPVGGIIGWMFAVEQDGFK<br>NGFSITGGEFTRQAEVTFVGHPGNLVIKQRFSGIDEKGNLTIDTELEGRVPQIPFGSSVHIEPYTELYHYSTSVITSSSTR<br>EYTVTEPERDGASPSRTYTYQWRQTITFQECVHDDSRPALPSTQQLSVDSVSVLYNQEEKILAYALSNSIGPVREGSPDA |
| 97 | NIDOmut3_V236Y<br>SPQRVNGKVKGRIFVGSSQVPIVFENTDLASYVVMNHGNSYTAISTIPETVGYSLLPLAPVGGIIGWMFAVEQDGFK<br>NGFSITGGEFTRQAEVTFVGHPGNLVIKQRFSGIDEKGNLTIDTELEGRVPQIPFGSSVHIEPYTELYHYSTSVITSSSTR<br>EYTVTEPERDGASPSRIYTYQWRQTITFQECVHDDSRPALPSTQQLSVDSVSYLYNQEEKILAYALSNSIGPVREGSPDA |
| 9 | NIDOmut3_L237T<br>SPQRVNGKVKGRIFVGSSQVPIVFENTDLASYVVMNHGNSYTAISTIPETVGYSLLPLAPVGGIIGWMFAVEQDGFK<br>NGFSITGGEFTRQAEVTFVGHPGNLVIKQRFSGIDEKGNLTIDTELEGRVPQIPFGSSVHIEPYTELYHYSTSVITSSSTR<br>EYTVTEPERDGASPSRIYTYQWRQTITFQECVHDDSRPALPSTQQLSVDSVSVTYNQEEKILAYALSNSIGPVREGSPDA |
| 99 | NIDOmut3_S65I<br>SPQRVNGKVKGRIFVGSSQVPIVFENTDLASYVVMNHGNIYTAISTIPETVGYSLLPLAPVGGIIGWMFAVEQDGFKN<br>GFSITGGEFTRQAEVTFVGHPGNLVIKQRFSGIDEKGNLTIDTELEGRVPQIPFGSSVHIEPYTELYHYSTSVITSSSTREY<br>TVTEPERDGASPSRIYTYQWRQTITFQECVHDDSRPALPSTQQLSVDSVSVLYNQEEKILAYALSNSIGPVREGSPDA |
| 100 | NIDOmut3_R114I<br>SPQRVNGKVKGRIFVGSSQVPIVFENTDLASYVVMNHGNSYTAISTIPETVGYSLLPLAPVGGIIGWMFAVEQDGFK<br>NGFSITGGEFTIQAEVTFVGHPGNLVIKQRFSGIDEKGNLTIDTELEGRVPQIPFGSSVHIEPYTELYHYSTSVITSSSTRE<br>YTVTEPERDGASPSRIYTYQWRQTITFQECVHDDSRPALPSTQQLSVDSVSVLYNQEEKILAYALSNSIGPVREGSPDA |
| 101 | NIDOmut3_C214S<br>SPQRVNGKVKGRIFVGSSQVPIVFENTDLASYVVMNHGNSYTAISTIPETVGYSLLPLAPVGGIIGWMFAVEQDGFK<br>NGFSITGGEFTRQAEVTFVGHPGNLVIKQRFSGIDEKGNLTIDTELEGRVPQIPFGSSVHIEPYTELYHYSTSVITSSSTR<br>EYTVTEPERDGASPSRIYTYQWRQTITFQESVHDDSRPALPSTQQLSVDSVSVLYNQEEKILAYALSNSIGPVREGSPDA |
| 102 | NIDOmut3_S65I_R114I<br>SPQRVNGKVKGRIFVGSSQVPIVFENTDLASYVVMNHGNIYTAISTIPETVGYSLLPLAPVGGIIGWMFAVEQDGFKN<br>GFSITGGEFTIQAEVTFVGHPGNLVIKQRFSGIDEKGNLTIDTELEGRVPQIPFGSSVHIEPYTELYHYSTSVITSSSTREY<br>TVTEPERDGASPSRIYTYQWRQTITFQECVHDDSRPALPSTQQLSVDSVSVLYNQEEKILAYALSNSIGPVREGSPDA |

TABLE 6-continued

| Sequence overview | |
|---|---|
| SEQ ID NO | Sequence |
| 103 | NIDOmut5_S65I_R114I<br>SPQRVNGKVKGRIFVGSSQTPIVFENTDLASYVVMNHGNIYTAISTIPETVGYSLLPLAPVGGIIGWMFAVEQDGFKN<br>GFSITGGEFTIQAEVTFQGHPGNLVIKQRFSGIDEKGNLTIDTELEGRVPCIIPEGSSVHIEPYTELYHYSTSVITSSSTREY<br>TVTEPERDGASPSRIYTYQWRQTITFQESTHDDSRPALPSTQCILSVDSVSVLYNQEEKILAYALSNSIGPVREGSPDA |
| 104 | NIDOmut5_S65I<br>SPQRVNGKVKGRIFVGSSQTPIVFENTDLASYVVMNHGNIYTAISTIPETVGYSLLPLAPVGGIIGWMFAVEQDGFKN<br>GFSITGGEFTRQAEVTFQGHPGNLVIKQRFSGIDEKGNLTIDTELEGRVPCIIPEGSSVHIEPYTELYHYSTSVITSSSTRE<br>YTVTEPERDGASPSRIYTYQWRQTITFQESTHDDSRPALPSTQCILSVDSVSVLYNCIEEKILAYALSNSIGPVREGSPDA |
| 105 | NIDOmut5_R114I<br>SPQRVNGKVKGRIFVGSSQTPIVFENTDLASYVVMNHGNSYTAISTIPETVGYSLLPLAPVGGIIGWMFAVEQDGFK<br>NGFSITGGEFTIQAEVTFQGHPGNLVIKQRFSGIDEKGNLTIDTELEGRVPQIPEGSSVHIEPYTELYHYSTSVITSSSTRE<br>YTVTEPERDGASPSRIYTYQWRQTITFQESTHDDSRPALPSTQQLSVDSVSVLYNQEEKILAYALSNSIGPVREGSPDA |
| 106 | T22-NIDOmut3-H6<br>RRWCYRKCYKGYCYRKCRGGSSRSS<br>SPQRVNGKVKGRIFVGSSQVPIVFENTDLASYVVMNHGNSYTAISTIPETVGYSLLPLAPVGGIIGWMFAVEQDGFK<br>NGFSITGGEFTRQAEVTFVGHPGNLVIKQRFSGIDEKGNLTIDTELEGRVPQIPFGSSVHIEPYTELYHYSTSVITSSSTR<br>EYTVTEPERDGASPSRIYTYQWRQTITFQECVHDDSRPALPSTCIQLSVDSVSVLYNCIEEKILAYALSNSIGPVREGSPD<br>AKHHHHHH |
| 107 | T22-NIDOmut3_V45T-H6<br>RRWCYRKCYKGYCYRKCRGGSSRSSSPQRVNGKVKGRIFVGSSQTPIVFENTDLASYVVMNHGNSYTAISTIPETVGY<br>SLLPLAPVGGIIGWMFAVEQDGFKNGFSITGGEFTRQAEVTFVGHPGNLVIKQRFSGIDEKGNLTIDTELEGRVPQIP<br>FGSSVHIEPYTELYHYSTSVITSSSTREYTVTEPERDGASPSRIYTYQWRQTITFQECVHDDSRPALPSTCICILSVDSVSV<br>LYNQEEKILAYALSNSIGPVREGSPDAKHHHHHH |
| 108 | T22-NIDOmut3_V121Q-H6<br>RRWCYRKCYKGYCYRKCRGGSSRSSSPQRVNGKVKGRIFVGSSQVPIVFENTDLASYVVMNH<br>GNSYTAISTIPETVGYSLLPLAPVGGIIGWMFAVEQDGFKNGFSITGGEFTRQAEVTFQGHPGN<br>LVIKQRFSGIDEKGNLTIDTELEGRVPQIPFGSSVHIEPYTELYHYSTSVITSSSTREYTVTEPERD<br>GASPSRIYTYQWRQTITFQECVHDDSRPALPSTQQLSVDSVSVLYNQEEKILAYALSNSIGPVR<br>EGSPDAKHHHHHH |
| 109 | T22-NIDOmut3_F157E-H6<br>RRWCYRKCYKGYCYRKCRGGSSRSSSPQRVNGKVKGRIFVGSSQVPIVFENTDLASYVVMNH<br>GNSYTAISTIPETVGYSLLPLAPVGGIIGWMFAVEQDGFKNGFSITGGEFTRQAEVTFVGHPGN<br>LVIKQRFSGIDEKGNLTIDTELEGRVPQIPEGSSVHIEPYTELYHYSTSVITSSSTREYTVTEPERD<br>GASPSRIYTYQWRQTITFQECVHDDSRPALPSTQQLSVDSVSVLYNQEEKILAYALSNSIGPVR<br>EGSPDAKHHHHHH |
| 110 | T22-NIDOmut3_V215T-H6<br>RRWCYRKCYKGYCYRKCRGGSSRSSSPQRVNGKVKGRIFVGSSQVPIVFENTDLASYVVMNHGNSYTAISTIPETVG<br>YSLLPLAPVGGIIGWMFAVEQDGFKNGFSITGGEFTRQAEVTFVGHPGNLVIKClRFSGIDEKGNLTIDTELEGRVPQI<br>PFGSSVHIEPYTELYHYSTSVITSSSTREYTVTEPERDGASPSRIYTYQWRQTITFQECTHDDSRPALPSTQQLSVDSVS<br>VLYNQEEKILAYALSNSIGPVREGSPDAKHHHHHH |
| 111 | T22-NIDOmut4-H6<br>RRWCYRKCYKGYCYRKCRGGSSRSSSPQRVNGKVKGRIFVGSSQTPIVFENTDLASYVVMNHGNSYTAISTIPETVGY<br>SLLPLAPVGGIIGWMFAVEQDGFKNGFSITGGEFTRQAEVTFCIGHPGNLVIKQRFSGIDEKGNLTIDTELEGRVPQIP<br>EGSSVHIEPYTELYHYSTSVITSSSTREYTVTEPERDGASPSRIYTYCIWRCITITFCIECTHDDSRPALPSTCICILSVDSVSV<br>LYNQEEKILAYALSNSIGPVREGSPDAKHHHHHH |
| 112 | T22-NIDOmut4_T215V-H6<br>RRWCYRKCYKGYCYRKCRGGSSRSSSPQRVNGKVKGRIFVGSSQTPIVFENTDLASYVVMNH<br>GNSYTAISTIPETVGYSLLPLAPVGGIIGWMFAVEQDGFKNGFSITGGEFTRQAEVTFQGHPGN<br>LVIKQRFSGIDEKGNLTIDTELEGRVPQIPEGSSVHIEPYTELYHYSTSVITSSSTREYTVTEPERD<br>GASPSRIYTYQWRQTITFQECVHDDSRPALPSTQQLSVDSVSVLYNQEEKILAYALSNSIGPVR<br>EGSPDAKHHHHHH |
| 113 | T22-NIDOmut5-H6<br>RRWCYRKCYKGYCYRKCRGGSSRSSSPQRVNGKVKGRIFVGSSQTPIVFENTDLASYVVMNHGNSYTAISTIPETVGY<br>SLLPLAPVGGIIGWMFAVEQDGFKNGFSITGGEFTRQAEVTFQGHPGNLVIKClRFSGIDEKGNLTIDTELEGRVPQIP<br>EGSSVHIEPYTELYHYSTSVITSSSTREYTVTEPERDGASPSRIYTYQWRQTITFQESTHDDSRPALPSTQQLSVDSVSVL<br>YNQEEKILAYALSNSIGPVREGSPDAKHHHHHH |
| 114 | T22-NIDOmut3_V176T-H6<br>RRWCYRKCYKGYCYRKCRGGSSRSSSPQRVNGKVKGRIFVGSSQVPIVFENTDLASYVVMNHGNSYTAISTIPETVG<br>YSLLPLAPVGGIIGWMFAVEQDGFKNGFSITGGEFTRQAEVTFVGHPGNLVIKCIRFSGIDEKGNLTIDTELEGRVPQI<br>PFGSSVHIEPYTELYHYSTSTITSSSTREYTVTEPERDGASPSRIYTYQWRQTITFQECVHDDSRPALPSTQQLSVDSVS<br>VLYNQEEKILAYALSNSIGPVREGSPDAKHHHHHH |

TABLE 6-continued

Sequence overview

Figure 13A:
FIG. 13A shows the design of NidoMut2 peptide. Similarity of human and mouse Nidogen G2 domain: Amino acid alignment between Human Nidogen 1 (P14543 from Uniprot Database, version dated Jul. 7, 2009) and Mouse Nidogen 1 (P10493 from Uniprot Database version 27 Jul. 2011) proteins analyzed by Clustal Omega (EMBL-EMI). Black lines indicate the start and finish point of the G2 β-barrel domain. "*" indicates an amino acid match, ":" indicates amino acids with strong similar properties and "." indicates amino acids with weak similar properties.

| SEQ ID NO | Sequence |
|---|---|
| 115 | T22-NIDOmut3_I200T-H6<br>RRWCYRKCYKGYCYRKCRGGSSRSSSPQRVNGKVKGRIFVGSSQVPIVFENTDLASYVVMNHGNSYTAISTIPETVG<br>YSLLPLAPVGGIIGWMFAVEQDGFKNGFSITGGEFTRQAEVTFVGHPGNLVIKCIRFSGIDEKGNLTIDTELEGRVPQI<br>PFGSSVHIEPYTELYHYSTSVITSSSTREYTVTEPERDGASPSRTYTYQWRQTIITFQECVHDDSRPALPSTQCILSVDSVS<br>VLYNQEEKILAYALSNSIGPVREGSPDAKHHHHHH |
| 116 | T22-NIDOmut3_V236Y-H6<br>RRWCYRKCYKGYCYRKCRGGSSRSSSPQRVNGKVKGRIFVGSSQVPIVFENTDLASYVVMNHGNSYTAISTIPETVG<br>YSLLPLAPVGGIIGWMFAVEQDGFKNGFSITGGEFTRQAEVTFVGHPGNLVIKQRFSGIDEKGNLTIDTELEGRVPQI<br>PFGSSVHIEPYTELYHYSTSVITSSSTREYTVTEPERDGASPSRIYTYQWRQTITFQECVHDDSRPALPSTCICILSVDSVS<br>YLYNQEEKILAYALSNSIGPVREGSPDAKHHHHHH |
| 117 | T22-NIDOmut3_L237T-H6<br>RRWCYRKCYKGYCYRKCRGGSSRSSSPQRVNGKVKGRIFVGSSQVPIVFENTDLASYVVMNHGNSYTAISTIPETVG<br>YSLLPLAPVGGIIGWMFAVEQDGFKNGFSITGGEFTRQAEVTFVGHPGNLVIKQRFSGIDEKGNLTIDTELEGRVPCll<br>PFGSSVHIEPYTELYHYSTSVITSSSTREYTVTEPERDGASPSRIYTYQWRQTITFCZECVHDDSRPALPSTCICILSVDSVS<br>VTYNQEEKILAYALSNSIGPVREGSPDAKHHHHHH |
| 118 | T22-NIDOmut3_S65I-H6<br>RRWCYRKCYKGYCYRKCRGGSSRSSSPQRVNGKVKGRIFVGSSQVPIVFENTDLASYVVMNHGNIYTAISTIPETVGY<br>SLLPLAPVGGIIGWMFAVEQDGFKNGFSITGGEFTRQAEVTFVGHPGNLVIKQRFSGIDEKGNLTIDTELEGRVPQIP<br>FGSSVHIEPYTELYHYSTSVITSSSTREYTVTEPERDGASPSRIYTYQWRQTITFQECVHDDSRPALPSTCICILSVDSVSV<br>LYNQEEKILAYALSNSIGPVREGSPDAKHHHHHH |
| 119 | T22-NIDOmut3_R114I-H6<br>RRWCYRKCYKGYCYRKCRGGSSRSSSPQRVNGKVKGRIFVGSSQVPIVFENTDLASYVVMNHGNSYTAISTIPETVG<br>YSLLPLAPVGGIIGWMFAVEQDGFKNGFSITGGEFTIQAEVTFVGHPGNLVIKQRFSGIDEKGNLTIDTELEGRVPOIP<br>FGSSVHIEPYTELYHYSTSVITSSSTREYTVTEPERDGASPSRIYTYQWRQTITFQECVHDDSRPALPSTQQLSVDSVSV<br>LYNQEEKILAYALSNSIGPVREGSPDAKHHHHHH |
| 120 | T22-NIDOmut3_C214S-H6<br>RRWCYRKCYKGYCYRKCRGGSSRSSSPQRVNGKVKGRIFVGSSQVPIVFENTDLASYVVMNHGNSYTAISTIPETVG<br>YSLLPLAPVGGHGWMFAVEODGFKNGFSITGGEFTROAEVTFVGHPGNLVIKQRFSGIDEKGNLTIDTELEGRVPOI<br>PFGSSVHIEPYTELYHYSTSVITSSSTREYTVTEPERDGASPSRIYTYQWRQTITFQESVHDDSRPALPSTQOLSVDSVS<br>VLYNQEEKILAYALSNSIGPVREGSPDAKHHHHHH |
| 121 | T22-NIDOmut3_S65I_R114I-H6<br>RRWCYRKCYKGYCYRKCRGGSSRSSSPORVNGKVKGRIFVGSSQVPIVFENTDLASYVVMNHGNIYTAISTIPETVGY<br>SLLPLAPVGGIIGWMFAVEODGFKNGFSITGGEFTIOAEVTFVGHPGNLVIKORFSGIDEKGNLTIDTELEGRVPOIPF<br>GSSVHIEPYTELYHYSTSVITSSSTREYTVTEPERDGASPSRIYTYQWRQTITFOECVHDDSRPALPSTOQLSVDSVSVL<br>YNQEEKILAYALSNSIGPVREGSPDAKHHHHHH |
| 122 | T22-NIDOmut5_S65I_R114I-H6<br>RRWCYRKCYKGYCYRKCRGGSSRSSSPQRVNGKVKGRIFVGSSQTPIVFENTDLASYVVMNHGNIYTAISTIPETVGY<br>SLLPLAPVGGIIGWMFAVEQDGFKNGFSITGGEFTIOAEVTFOGHPGNLVIKORFSGIDEKGNLTIDTELEGRVPOIPE<br>GSSVHIEPYTELYHYSTSVITSSSTREYTVTEPERDGASPSRIYTYQWRQTITFOESTHDDSRPALPSTQOLSVDSVSVLY<br>NQEEKILAYALSNSIGPVREGSPDAKHHHHHH |
| 123 | T22-NIDOmut5_S65I-H6<br>RRWCYRKCYKGYCYRKCRGGSSRSSSPQRVNGKVKGRIFVGSSQTPIVFENTDLASYVVMNHGNIYTAISTIPETVGY<br>SLLPLAPVGGIIGWMFAVEQDGFKNGFSITGGEFTRQAEVTFQGHPGNLVIKQRFSGIDEKGNLTIDTELEGRVPQIP<br>EGSSVHIEPYTELYHYSTSVITSSSTREYTVTEPERDGASPSRIYTYQWRQTITFQESTHDDSRPALPSTQQLSVDSVSVL<br>YNQEEKILAYALSNSIGPVREGSPDAKHHHHHH |
| 124 | T22-NIDOmut5_R114I-H6<br>RRWCYRKCYKGYCYRKCRGGSSRSSSPQRVNGKVKGRIFVGSSOTPIVFENTDLASYVVMNHGNSYTAISTIPETVGY<br>SLLPLAPVGGilGWMFAVEQDGFKNGFSiTGGEFTIQAEVTFQGHPGNLVIKQRFSGiDEKGNLTIDTELEGRVPQIPE<br>GSSVHIEPYTELYHYSTSVITSSSTREYTVTEPERDGASPSRIYTYQWRQTITFOESTHDDSRPALPSTQQLSVDSVSVLY<br>NQEEKILAYALSNSIGPVREGSPDAKHHHHHH |
| 125 | Human Nidogen G2 domain shown in FIG. 13A<br>HQQHPQVIDVDEVEETGVVFSYNTDSRQTCANNRHQCSVHAECRDYATGFCCSCVAGYTG<br>NGRQCVAEGSPQRVNGKVKGRIFVGSSQVPIVFENTDLHSYVVMNHGRSYTAISTIPETV<br>GYSLLPLAPVGGIIGWMFAVEQDGFKNGFSITGGEFTRQAEVTFVGHPGNLVIKQRFSGI<br>DEHGHLTIDTELEGRVPQIPFGSSVHIEPYTELYHYSTSVITSSSTREYTVTEPERDGAS<br>PSRIYTYQWRQTITFQECVHDDSRPALPSTQQLSVDSVFVLYNQEEKILRYALSNSIGPV<br>REGSPDALQNPCYIGTHGCDTNAACRPGPRTQFTCECSIGFRGDGRTCYDIDECSEQPSV<br>(human sequence in FIG.13A) |
| 126 | Mouse Nidogen G2 domain shown in FIG. 13A<br>PQHHPQVIDVDEVEETGVVFSYNTGSQQTCANNRHQCSVHAECRDYATGFCCRCVANYTGNG<br>RQCVAEGSPQRVNGKVKGRIFVGSSQVPVVFENTDLHSYVVMNHGRSYTAISTIPETVGY<br>SLLPLAPIGGIIGWMFAVEQDGFKNGFSITGGEFTRQAEVTFLGHPGKLVLKQQFSGIDE |

TABLE 6-continued

Sequence overview

| SEQ ID NO | Sequence |
|---|---|
| | HGHLTISTELEGRVPQIPYGASVHIEPYTELYHYSSSVITSSSTREYTVMEPDQDGAAPS<br>HTHIYQWRQTITFQECAHDDARPALPSTQQLSVDSVFVLYNKEERILRYALSNSIGPVRD<br>GSPDALQNPCYIGTHGCDSNAACRPGPGTQFTCECSIGFRGDGQTCYDIDECSEQPSR<br>(mouse sequence in Fig,. 13A) |
| 127 | Human Nidogen (UniProt P14534)<br>MLASSSRIRAAWTRALLLPLLLAGPVGCLSRQELFPFGPGQGDLELEDGDDFVSPALELS<br>GALRFYDRSDIDAVYVTTNGIIATSEPPAKESHPGLFPPTFGAVAPFLADLDTTDGLGKV<br>YYREDLSPSITQRAAECVHRGFPEISFQPSSAVVVTWESVAPYQGPSRDPDQKGKRNTFQ<br>AVLASSDSSSYAIFLYPEDGLQFHTTFSKKENNQVPAVVAFSQGSVGFLWKSNGAYNIFA<br>NDRESVENLAKSSNSGQQGVWVFEIGSPATTNGVVPADVILGTEDGAEYDDEDEDYDLAT<br>TRLGLEDVGTTPFSYKALRRGGADTYSVPSVLSPRRAATERPLGPPTERTRSFQLAVETF<br>HQQHPQVIDVDEVEETGVVFSYNTDSRQTCANNRHQCSVHAECRDYATGFCCSCVAGYTG<br>NGRQCVAEGSPQRVNGKVKGRIFVGSSQVPIVFENTDLHSYVVMNHGRSYTAISTIPETV<br>GYSLLPLAPVGGHGWMFAVEQDGFKNGFSITGGEFTRQAEVTFVGHPGNLVIKQRFSGI<br>DEHGHLTIDTELEGRVPQIPFGSSVHIEPYTELYHYSTSVITSSSTREYTVTEPERDGAS<br>PSRIYTYQWRQTITFQECVHDDSRPALPSTQQLSVDSVFVLYNQEEKILRYALSNSIGPV<br>REGSPDALQNPCYIGTHGCDTNAACRPGPRTQFTCECSIGFRGDGRTCYDIDECSEQPSV<br>CGSHTICNNHPGTFRCECVEGYQFSDEGTCVAVVDQRPINYCETGLHNCDIPQRAQCIYT<br>GGSSYTCSCLPGFSGDGQACQDVDECQPSRCHPDAFCYNTPGSFTCQCKPGYQGDGFRCV<br>PGEVEKTRCQHEREHILGAAGATDPQRPIPPGLFVPECDAHGHYAPTQCHGSTGYCWCVD<br>RDGREVEGTRTRPGMTPPCLSTVAPPIHQGPAVPTAVIPLPPGTHLLFAQTGKIERLPLE<br>GNTMRKTEAKAFLHVPAKVIIGLAFDCVDKMVYWTDITEPSIGRASLHGGEPTTIIRQDL<br>GSPEGIAVDHLGRNIFWTDSNLDRIEVAKLDGTQRRVLFETDLVNPRGIVTDSVRGNLYW<br>TDWNRDNPKIETSYMDGTNRRILVQDDLGLPNGLTFDAFSSQLCWVDAGTNRAECLNPSQ<br>PSRRKALEGLQYPFAVTSYGKNLYFTDWKMNSVVALDLAISKETDAFQPHKQTRLYGITT<br>ALSQCPQGHNYCSVNNGGCTHLCLATPGSRTCRCPDNTLGVDCIEQK<br>(sequence in FIG. 13B) |
| 128 | T22-NIDOmut2-H6 (Sequence in FIG. 13B)<br>RRWCYRKCYKGYCYRKCRGGSSRSSSPQRVNGKVKGRIFVGSSQVPIVFENTDLASYVVMNHGNSYTAISTIPETVG<br>YSLLPLAPVGGilGWMFAVEQDGFKNGFSITGGEFTRQAEVTFVGHPGNLVIKQRFSGIDEKGNLTIDTELEGRVPQI<br>PFGSSVHIEPYTELYHYSTSVITSSSTREYTVTEPERDGASPSRIYTYQWRQTITFQECVHDDSRPALPSTQQLSVDSVS<br>VLYNQEEKILAYALSNSIGPVREGSPDAKHHHHHH |
| 129 | EPIX-4-(RK)-GFP-H6<br>IVRWSKKVPCVSIVRWSKKVPCVSRKRKRKGGSSRSSSKGEELFTGVVPILVELDGDVNGHKF<br>SVSGEGEGDATYGKLTLKFICTTGKLPVPWPTLVTTLTYGVQCFSRYPDHMKRHDFFKSAMPE<br>GYVQERTISFKDDGNYKTRAEVKFEGDTLVNRIELKGIDFKEDGNILGHKLEYNYNSHNVYIT<br>ADKQKNGIKANFKIRHNIEDGSVQLADHYQQNTPIGDGPVLLPDNHYLSTQSALSKDPNEKRD<br>HMVLLEFVTAAGITHGMDELYHHHHHH (Sequence in FIG. 20) |
| 130 | GFP<br>SKGEELFTGVVPILVELDGDVNGHKFSVSGEGEGDATYGKLTLKFICTTGKLPVPWPTLVTTLTYGVQCFSRYPDHMK<br>RHDFFKSAMPEGYVQERTISFKDDGNYKTRAEVKFEGDTLVNRIELKGIDFKEDGNILGHKLEYNYNSHNVYITADKQ<br>KNGiKANFKIRHNIEDGSVQLADHYQQNTPIGDGPVLLPDNHYLSTQSALSKDPNEKRDHMVLLEFVTAAGITHGM<br>DELY |
| 131 | Optimized EPI-X4 coupled to RKRKRK positively charged peptide region<br>IVRWSKKVPCVSIVRWSKKVPCVSRKRKRK |
| 132 | EPI-X4<br>ILVRYTKKVPQVSTPTL |
| 133 | EPI-X4 coupled to RKRKRK positively charged peptide region<br>ILVRYTKKVPQVSTPTL RKRKRK |

The invention will be described by way of the following examples which are to be considered as merely illustrative and not limitative of the scope of the invention.

EXAMPLES

Production and Purification of Protein Nanoparticles

Plasmid vectors encoding T22-GFP-H6, T22-STM-H6 and T22-NIDOmut2-H6, with SEQ ID NO. 61, modular proteins were transformed in *Escherichia coli* (*E. coli*) expression system and different proteins produced Over Night (O/N) in Luria Broth (LB) medium upon induction with isopropyl β-D-1-thiogalactopyranoside (IPTG) at early exponential growth phase. The NIDOmut2 peptide corresponds to the peptide with SEQ ID NO:61. Cells were then harvested by centrifugation (5 min at 5000 g), resuspended in wash buffer (20 mM Tris, 500 mM NaCl, 10 mM Imidazole pH-8) in presence of protease inhibitors (Complete EDTA-Free, Roche) and disrupted in a French Press (2-3 rounds at 1100 psi). Cell soluble fractions were then separated by centrifugation (45 min at 15.000 g) and soluble proteins purified by Immobilized Metal Affinity Chromatography (IMAC). For that soluble fractions were charged in immobilized Nickel containing HITRAP™ Chelating HP columns (GE Healthcare) and proteins eluted by a linear gradient of Elution buffer (20 mM Tris, 500 mM NaCl, 500 mM Imidazole pH=8) in a ÄKTA™ pure system (GE Healthcare). Purified proteins were finally dialyzed against sodium carbonate buffer (166 mM $NaCO_3H$ pH=8) for T22-STM-H6 and T22-NIDOmut2-H6 or sodium carbonate with salt buffer (166 mM $NaCO_3H$, 333 mM NaCl, pH=8) for T22-GFP-H6.

Protein purity was determined by polyacrylamide gel electrophoresis (SDS-PAGE) and western blot immunostaining with monoclonal anti-His antibody (Santa Cruz Biotechnology). Protein integrity was verified by MALDI-TOF mass spectrometry, protein amount quantified by Bradford's assay and Nanoparticles size determined by Dynamic Light Scattering.

Production of Nanoconjugates

Protein-FdU nanoconjugates were generated by covalent binding of protein nanoparticles with oligomers containing five units of 5'-(FdU) 5-hexaethyleneglycolthiol-3' (FdU) through protein lysine amines using a 6-Maleimidohexanoic acid N-hydroxysuccinimide ester (EMCS) bifunctional linker. For that thiol conjugated FdU oligomers were first reacted with the Maleimide group in the EMCS bifunctional linker in a 1:1 molar ratio at Room Temperature (RT) for 10 min adding ester groups. Subsequently, active ester groups containing FdU molecules were then reacted with external lysine-amine groups within protein nanoparticles in a 1:5 molar ratio Over Night at RT. Finally, protein-FdU nanoconjugates were dialyzed against their respective storage buffers to remove non reacted free oligo-FdU molecules. Final conjugated products were characterized by MALDI-TOF mass spectrometry and Dynamic Light Scattering and conjugated FdU/protein molar ratio was calculated by UV light absorbance at 260 nm (wavelength at which our FdU oligomers absorbs light with a molar extinction coefficient of 44500 $M^{-1}\cdot cm^{-1}$) in a UV-visible light spectrophotometer. All nanoconjugates incorporated an average of 2-10 oligo FdU molecules per proteins unit and maintained their parental average nanoparticle size.

T22-NIDOmut2-H6 NPs Fluorescence Labelling

T22-NIDOmut2-H6 molecules were covalently labelled with ATTO488™ fluorescent molecules for intracellular tracking. For that, ester conjugated ATTO488™ molecules (Sigma) were reacted with external lysine-amine groups in T22-NIDOmut2-H6 molecules at 1:2 (protein:dye molecule) for 1 h at RT. Then labelled nanoparticles were dialyzed against their storage buffer (Sodium Carbonate buffer) at 4°C O/N in order to remove non-conjugated free ATTO488™ molecules. Labelled nanoparticles were finally characterized by MALDI-TOF mass spectrometry and Dynamic Light Scattering.

Dynamic Light Scattering

Volume size distribution of all protein nanoparticles and nanoconjugates were determined by Dynamic Light Scattering (DLS) at 633 nm in a Zetasizer Nano ZS (Malvern Instruments) in triplicate. All nanoparticles and nanoconjugates were within nanometric range and showed average nanoparticles sizes between 10-50 nm.

Nanoparticles CXCR4-Dependent Internalization

CXCR4 receptor specific internalization was studied with labelled T22-NIDOmut2-H6-ATTO488™ nanoparticles over CXCR4+ Human Cervix HeLa cells. For that, HeLa cells acquired at ATCC (CCL-2) were cultured on 24 well plates in MEM alpha medium (Gibco) supplemented with 10% fetal bovine serum (Gibco) in a humidified atmosphere at 37°C and 5% $CO_2$ until reaching a 70% confluence. Then labelled T22-NIDOmut2-H6-ATTO488™ nanoparticles were incubated with Hela cells in serum-free OPTIPRO™ medium (Gibco) supplemented with L-glutamine for different times and concentrations. Cells fluorescence was then analyzed in a FACS-CANTO™ flow cytometer (Becton Dickinson) using an argon ion laser at 488 nm (for ATTO488™ molecule excitation) and a D detector (530/30 nm filter) after a "harsh" trypsin digestion designed to complete remove protein externally attached to cells.

For competition assays, cells were pre-incubated with the CXCR4 specific antagonist AMD3100 (octahydrochloride hydrate-Sigma) for 1 h before the addition of labelled T22-NIDOmut2-H6-ATTO488™ nanoparticles.

Confocal Laser Microscopy

Labelled T22-NIDOmut2-H6-ATTO488™ nanoparticles' intracellular localization was also studied in Hela cells by Confocal Laser Microscopy. For that, HeLa cells were cultured in MatTek culture dishes (MatTek Corp.) in MEM alpha medium supplemented with 10% Fetal bovine serum until reaching 70% of confluence. Then labelled T22-NIDOmut2-H6-ATTO488™ nanoparticles were incubated with HeLa cells in serum-free OPTIPRO™ medium (Gibco) supplemented with L-glutamine for different times and concentrations. Cells membranes and nuclei were then stained with CELLMASK™ DeepRed and Hoescht (Molecular Probes) respectively for 10 min before being washed with PBS. Living cells were finally recorded in a Leica TCS-SP5 confocal laser scanning microscope (Leica Microsystems) using a Apo63x/1.4 (oil HC x PL APO lambda blue) objective and a blue diode (405 nm), Argon laser (488 nm) and HeNe laser (633 nm) to visualize cell nuclei, cells membranes and labelled nanoparticles respectively.

MTT

In-Vitro cell cytotoxicity of FdU containing nanoconjugates (T22-GFP-H6-FdU, T22-STM-H6-FdU, T22-NIDOmut2-H6-FdU) were evaluated over CXCR4+ HeLa cells with luminescent cells viability assays. For that, HeLa cells were cultured on 96-well plates in 90 ul of MEM alpha medium supplemented with 10% Fetal bovine serum for 24 h. Then 10 ul of different concentrations of FdU containing protein nanoconjugates where added and incubated for additional 48 h. Finally, cell viability was determined by Cell-Titer-Glo Luminiscent Cell Viability Assay (Promega) following supplier's instructions.

Generation of the CXCR4+ Colorectal Cancer Model

All in vivo procedures were approved by the Hospital de Sant Pau Animal Ethics Committee and performed according to European Council directives. Five-week-old female NSG (NOD.Cg-Prkdescid Il2rgtm 1Wjl/SzJ) mice weighing between 18 and 20 g (Charles River, L-Abreslle, France) and maintained in specific-pathogen-free (SPF) conditions, were used to generate the CXCR4 overexpressing (CXCR4+) subcutaneous (SC) colorectal (CRC) xenograft mouse model to study the antitumor effect of the nanoconjugates. To that purpose, we used the patient-derived M5 colorectal tumor tissue, perpetuated as a tumor line in donor animals. Thus, 10 mg of M5 SC CRC tumor tissue obtained from these animals were and implanted in the subcutis of NSG mice.

Antitumor Effect of the Nanoconjugates in the M5 CXCR4+ SC CRC Model

Once the tumors reached a volume within the 120-200 $mm^3$ range, mice were randomly allocated in four groups, one Control (K, n=4) and three experimental: T22-STM-FdU (n=4); T22-NIDOmut2-FdU (n=4) and T22-GFP-FdU (n=4). All experimental groups received intravenous injections of the corresponding nanoconjugate, in a repeated dose schedule following a dosage regime of 20 μg, every 3 days, per 5 doses. The control group received 200 μl of 166 mM $NaHCO_3$ pH 8.0, following the same schedule. The antitumor effect was evaluated as inhibition of tumor growth, measuring the evolution of tumor volume along time, by registering every three days the longer (D) and shorter (d) tumor diameters with a caliper. Tumor volume was calculated using the ellipsoid formula, Volume=½ (D×d2). Fourteen days after the initiation of the nanoconjugate administration, mice were euthanized, the subcutaneous tumors taken for the evaluation of apoptotic induction, whereas the liver and kidney tissues were processed for histological analysis. Mouse body weight was registered over the experimental period 2 times a week.

Evaluation of Apoptotic Induction in Tumor and Histology in Normal Tissues

Tumor, liver and kidney tissues were collected and fixed with 4% formaldehyde in phosphate-buffered solution for 24 h and then embedded in paraffin for histological analysis. Apoptotic induction analyses were performed in 4 µm thick sections of tumors at the end of the experiment (two days after the last nanoconjugate dose) that were processed for hematoxylin and eosin (H&E) staining. Apoptotic induction was evaluated by counting the number of cell death bodies in H&E stained tumor slices per 10 high-power fields (magnification 400×), in blinded samples evaluated by two independent researchers. Liver and kidney were also taken for histopathological analysis. Representative pictures were taken using Cell/\B software (Olympus Soft Imaging v 3.3, Nagano, Japan).

Determination of Intrinsic Fluorescence

Fluorescence spectra were recorded in a Cary Eclipse spectrofluorimeter (Agilent Technologies, Mulgrave, Australia). A quartz cell with 10 mm path length and a thermostated holder was used. The excitation and emission slits were set at 5 nm. Excitation wavelength ($\lambda_{ex}$) was set at 295 nm. Emission spectra were acquired within a range from 310 to 450 nm. The protein concentration was 0.2 mg/mL in carbonate buffer (166 mM $NaCO_3H$, pH 8). In order to evaluate the conformation stability against heating we obtained the fluorescence spectra at each temperature at a 1°C/min scan rate and we calculated the Centre of Spectral Mass (CSM) for each spectrum. CSM is a weighted average of the fluorescence spectrum peak. Also it is related with the relative exposure of the Trp to the protein environment. The maximum red-shift in the CSM of the Trp, is compatible with a large solvent accessibility (Li, T. M.; et al., Biochemistry 1976, 15, 5571-80; Ruan, K and Weber, G, Biochemistry 1989, 28 (5), 2144-53 and Mohana-Borges, R. et al., Proceedings of the National Academy of Sciences of the United States of America 1999, 96 (14), 7888-93) and the protein unfolding.

The Centre of Spectral Mass (CSM) was calculated for each of the fluorescence emission according to Eq. 1 (Lakowicz, J. R.; et al., 1991, *Biophys Chem* 39 (1), 79-84), where $I_i$ is the fluorescence intensity measure at the wavelength $\lambda_i$.

$$\lambda = \frac{\sum \lambda_i \cdot I_i}{\sum I_i} \quad \text{(i)}$$

Unfolding Temperature Determination

Midpoint unfolding temperature ($T_m$) was determined as the temperature value that correspond to the inflexion point of the CSM vs T° curve. We also determined the $T_{onset}$ as the temperature where the CSM value begins to increase.

Statistical Analysis

Mann-Whitney U tests were used for pairwise comparisons of the differences in tumor volume or the number of apoptotic bodies between groups. Differences were considered significant at $p<0.05$ All statistical analyses were performed using SPSS version 11.0 package (IBM, NY, USA), and values were expressed as mean±standard error of the mean (SEM).

Obtention and Characterization of New Protein Clones: T22-NIDOmut3-H6 and all its Further Derivatives T22-NIDOmut3_V45T-H6, T22-NIDOmut3_V121Q-H6, T22-NIDOmut3_F157E-H6, T22-NIDOmut3_V215T-H6, T22-NIDOmut4_T215V-H6, T22-NIDOmut4-H6, and T22-NIDOmut5-H6

Genes encoding for the new T22-NIDOmut3-H6 and all its further derivatives T22-NIDOmut3_V45T-H6, T22-NIDOmut3_V121Q-H6, T22-NIDOmut3_F157E-H6, T22-NIDOmut3_V215T-H6, T22-NIDOmut4_T215V-H6, T22-NIDOmut4-H6, and T22-NIDOmut5-H6 were provided by Geneart (Thermo Fisher) and subcloned into pET26b plasmids (Novagen). Protein-encoding plasmids were transformed into *Escherichia coli* BL21 DE3 (Novagen) strains and the protein was produced overnight (O/N) at 20°C in Luria Broth (LB) medium upon induction with 0.1 mM isopropil-β-D-1-tiogalactopyranoside (IPTG). Cells were then harvested by centrifugation (15 min at 5000 g) and resuspended in wash buffer (20 mM Tris, 500 mM NaCl, 10 mM Imidazole, pH 8) in presence of protease inhibitors (COMPLETE™ EDTA-Free, Roche). Cells were then disrupted in an EmulsiFlex-C5 system (Avestin) by 3 rounds at 8000 psi. The soluble fraction of the cell lysate, containing the proteins, was separated by centrifugation (45 min at 15000 g) and then charged into a HISTRAP™ HP column (GE Healthcare) for purification by immobilized metal affinity chromatography (IMAC) in an ÄKTA™ pure system (GE Healthcare). Protein elution was achieved applying a lineal gradient of elution buffer (20 mM Tris, 500 mM NaCl, 500 mM Imidazole, pH 8). Purified protein fractions were then dialyzed against sodium carbonate (166 mM $NaCO_3H$, pH 8). Protein purity was determined by SDS-PAGE gel electrophoresis and subsequent western-blot immunodetection using anti-His monoclonal antibody (Santa Cruz Biotechnology). Protein integrity was also determined by MALDI-TOF mass spectrometry. Final protein concentration was determined by Bradford's assay and Nanodrop.

For the stability study in other buffers, purified protein fractions were dialyzed against chosen FDA-approved buffer and carbonate as control. Protein concentration was initially set at 2.0 mg/ml in carbonate buffer and dialysed into 0.5 ml of each new buffer. Samples were centrifuged for 15 min 15000 g to remove precipitate and the remaining soluble protein concentration was determined by Bradford's assay and Nanodrop.

Morphometric Characterization of Proteins T22-NIDOmut3-H6 and all its Further Derivatives Volume size distribution of protein nanoparticles was determined in a Zetasizer Nano ZS (Malvern Instruments) by Dynamic Light Scattering (DLS) at 633 nm in triplicates.

Oligo-FdU Conjugation for Proteins Used in Experiments Addressed to the Analysis of Proteins T22-NIDOmut3-H6 and all its Further Derivative T22-NIDOmut3-H6 and T22-NIDOmut2-H6 were covalently linked to oligo 5-Fluoro-2'-deoxyuridine (oligoFdU) molecules through the amine groups of exposed lysines in a two-step reaction using a bi-functional linker. To that end, TCEP was first added to cleave the S—S bond protecting the thiol group of the oligoFdU molecules and the product was cleaned of impurities using NAP-10 sephadex gravity columns (GE Healthcare). Then, thiol-oligoFdU molecules were reacted to a 6-Maleimidohexanoic acid N-hydroxysuccinimide ester bifunctional linker (EMCS) by thiol-maleimide reaction in a 1:1 molar ratio for 30 min at room temperature. Resulting hydroxysuccinimide-functionalized oligoFdU molecules were finally reacted to amino groups of external lysines, in a 1:5 molar ratio 5 h at R.T. and subsequently purified using ZEBA™ Spin Desalting Columns (Thermo Scientific) and dialyzed against carbonate buffer in order to remove non-covalently bonded oligoFdU molecules. Reaction efficiency was finally checked by MALDI-TOF mass spectrometry and conjugated oligoFdU molecules determined by FdU absorbance at 260 nm in a UV/visible light spectrophotometer using molar extinction coefficient (ε: 43500 M−1 cm−1). Absorbance values were corrected by subtracting the baseline 260 nm absorbance of the non-conjugated protein at an equivalent concentration.

In Vitro Cell Viability Assay Performed for the Analysis of New Proteins T22-NIDOmut3-H6 and all its Further Derivative HeLa cells (ATCC, CCL-2) were incubated in opaque 96-well plates in 90 μl of MEM alpha medium (Gibco) containing 10% of Fetal bovine serum (Gibco) in humidified atmosphere and 5% $CO_2$ at 37°C Then, 10 μl of T22-NIDOmut3-H6-FdU and T22-NIDOmut2-H6-FdU nanoconjugates were added along with the control T22-NIDOmut3-H6 at 25 nM final concentration and incubated for additional 48 h. Cell viability was finally tested by CELLTITER-GLO® Luminescent Cell Viability Assay (Promega) in a Victor 3 luminescent plate reader (Perkin Elmer). All samples were analyzed in triplicate and data expressed as mean % of viability (related to control cells)+/−standard error.

Protein Design, Production, and Purification of EPIX4-(RK)-GFP-H6, T22-GFP-H6 and T22-BFP-H6 Proteins Synthetic genes encoding the modular proteins were designed in-house. The EPIX-4 sequence used was the optimized dimeric version with higher receptor affinity. In the case of EPIX4-(RK)-GFP-H6, a six cationic amino acid sequence (RKRKRK) was added after the EPIX-4 ligand to favor protein self-assembling. Also, between EPIX-4 and the protein scaffold GFP a flexible linker (GGSSRSS) was added conferring the ligand accessibility to bind CXCR4 receptor. The gene codon usage was optimized for *E. coli* to be inserted into the plasmid pET22b (Novagen) and the construct was provided by Geneart (ThermoFisher). The recombinant versions of the vector were transformed in *E. coli* BL21 (DE3) (F-ompT hsdSB (rB-, mB-) gal dcm DE3) (Novagen). The encoded proteins were produced in Luria-Bertani (LB) media in 500 mL cell Erlenmeyer flasks at 20°C overnight (O/N) upon addition of 0.1 mM IPTG (Isopropyl β-d-1-thiogalactopyranoside). When the $OD_{550}$ of the cell culture reached around 0.5, bacterial cells were harvested and centrifuged at 7000 rpm, for 15 min at 4°C The cell pellet was resuspended in Wash Buffer (20 mM Tris-HCl, 500 mM NaCl, 40 mM imidazole pH=8) in presence of protease inhibitor cocktail COMPLETE™ EDTA-Free (Roche). Bacterial cells were disrupted with French Press for three rounds at 1200 PSI, centrifuged (45 min, 15000 g, 4°C) and soluble fraction purified by affinity chromatography with a HISTRAP™ Chelating HP column in an AKTA™ purifier FPLC, (GE Healthcare). After the samples were filtered (0.22 μm) and injected into the column, the fractions to be collected were eluted with elution buffer approximately (20 mM Tris-HCl, 500 mM NaCl, 500 mM imidazol pH 8). Purified protein fractions were dialyzed against carbonate buffer (166 mM $NaCO_3H$, pH 8). In addition, the CXCR4-targeted protein T22-GFP-H6 and T22-BFP-H6 were produced and purified for the formation of biparatopic nanoparticles as previously described (U. Unzueta et al., Nanotechnology 2017, 28, 505102). BFP corresponds to the protein provided in the GenBank database under accession number EF064258.1.

Protein Characterization of EPIX4-(RK)-GFP-H6, T22-GFP-H6 and/or T22-BFP-H6 Proteins The integrity of the recombinant proteins was checked by mass spectrometry (MALDI-TOF), TGX (Tris-Glycine eXtended) Stain-Free acrylamide gels electrophoresis (Bio-Rad) and Western Blot analysis using anti-His monoclonal antibody (1:1000; Santa Cruz, ref. 57598). Protein concentration was determined by Bradford (Biorad) assay with an Albumin (Roche) standard curve. GFP fluorescence emission (510 nm) was determined on purified proteins with a Cary Eclipse fluorescence spectrophotometer (Agilent Technologies) using an excitation wavelength of 450 nm. The volume and size distribution of nanoparticles were measured by dynamic light scattering (DLS) at 633 nm through a Zetasizer Nano ZS (Malvern Instruments) using quartz cuvettes.

Ultrastructural Characterization of the Nanoparticles Produced with EPIX4-(RK)-GFP-H6, T22-GFP-H6 and/or T22-BFP-H6 Proteins Size and shape of protein nanoparticles at nearly state were evaluated with a field emission scanning electron microscope (FESEM) Merlin (Zeiss). Protein samples were directly deposited over silicon wafers, excess of liquid blotted with Whatman filter paper, air dried and observed without coating in a FESEM Zeiss Merlin operating and 1 kV and equipped with a high resolution in-lens secondary electron detector. Representative images of nanoparticles were taken at a range of high magnifications (from 80.000× to 300.000×).

Cell Culture, Flow Cytometry and Cytotoxicity Assay with EPIX4-(RK)-GFP-H6, T22-GFP-H6 and/or T22-BFP-H6 Proteins Experiments were performed in CXCR4+ cervical and colorectal cell lines (HeLa and SW1417, respectively). HeLa cells were cultured in Eagle's Minimum Essential Medium (Gibco) and SW1417 in Dulbecco's Modified Eagle's Medium (Gibco). Both cell lines were supplemented with 10% fetal bovine serum (Gibco) and incubated in a humidified atmosphere at 37°C and 5% (HeLa) or 10% (SW1417) of $CO_2$.

For testing protein internalization, cells were seeded in 24-well plates (Nunc) (30000 cells·wells$^{-1}$) for 24 h. Briefly, the medium was removed, and cells were washed with PBS. Then protein was incubated at 1 and 2 M, diluted in OPTIPRO™ medium supplemented with L-Glutamine and incubated at different times, at suitable cell line conditions. Then, harsh trypsin digestion (1 mg ml$^{-1}$ for 15 min) (Gibco) was carried out to remove protein particles bound to the outer size of the cell membranes. Intracellular green fluorescence was analyzed by flow cytometry on an FACS-Calibur system (Becton Dickinson) using a 15 mW air-cooled argon ion laser at 488 nm excitation. Fluorescence emission was measured with a D detector (530/30 nm band pass filter), and manually corrected by the specific fluorescence of purified protein, to get data representative of the amount of internalized protein for comparative purposes. For competition assays, a specific CXCR4 antagonist AMD3100 (octahydrochloride hydrate, Sigma-Aldrich) was added 1 h before nanoparticles addition in a 1:10 (protein: AMD3100) molar ratio. All experiments were done by triplicate.

Production and Characterization of Biparatopic Nanoparticles

T22-GFP-H6, T22-BFP-H6 and EPIX4-(RK)-GFP-H6 protein nanoparticles (at 1.5 mg ml$^{-1}$) were disassembled by different methods. In T22-GFP-H6 and T22-BFP-H6 samples, we added NaCl (500 mM $Na^+$ final concentration) and imidazole (300 mM final concentration) and in EPIX4-(RK)-GFP-H6 we added 0.2% SDS, all of them into carbonate buffer (166 mM $NaCO_3H$, pH 8) for 2 h. at RT.

T22-GFP-H6/EPIX4-(RK)-GFP-H6 and T22-BFP-H6/EPIX4-(RK)-GFP-H6 biparatopic nanoparticles were generated by mixing the building blocks respectively in a 1:1 molar ratio, and subsequently dialyzing them against carbonate buffer (166 mM $NaCO_3H$, pH 8). We performed and exhaustive dialysis (4 changes every 30 min at RT, 1 change O/N at 4°C and finally, 4 changes every 30 min). T22-BFP-H6/EPIX4-(RK)-GFP-H6 biparatopic nanoparticles were used for FRET and confocal microscopy experiments and T22-GFP-H6/EPIX4-(RK)-GFP-H6 for FESEM, cell culture and in vivo experiments.

To determine if EPIX4-(RK)-GFP-H6 is capable to form heterogeneous nanoparticles, carrying at the same time EPIX4-(RK)-GFP-H6 and T22-BFP-H6 protein, FRET analysis was performed. Fluorescence emission of protein nanoparticles was measured in a Cary Eclipse fluorescence spectrophotometer (Agilent Technologies) upon excitation at 387 nm. The emission was collected from 400-600 nm.

Confocal Assay for Experiments that Involve the Use of EPIX4-(RK)-GFP-H6, T22-GFP-H6 and/or T22-BFP-H6 Proteins HeLa cells were grown on Mat-Tek plates (25,000 cells·wells$^{-1}$) in Eagle's Minimum Essential Medium (Gibco) supplemented with 10% foetal bovine serum (Gibco) at 37°C and 5% for 24 h. Then, 2 μM of protein nanoparticles were added in OPTIPRO™ medium supplemented with L-Glutamine and incubated for 24 h at suitable cells conditions. Upon protein exposure cell nuclei were labelled with 5 μg ml$^{-1}$ Hoechst 33342 (Thermo) and the plasma membrane with 2.5 μg ml$^{-1}$ CELLMASK™ Deep Red (Thermo) for 10 min at room temperature. Confocal images were collected on an inverted TCS SP5 Leica Spectral confocal microscope (Leica) using 63× (1.4 NA) oil immersion objective lenses. Excitation was reached via a 405 nm blue diode laser (nucleic acids), 488 nm line of an argon ion laser (nanoparticles) and 633 nm line of a HeNe laser (Cell membrane). The confocal pinhole was set to 1 Airy unit and z-stacks acquisition intervals were selected to satisfy Nyquist sampling criteria. Confocal images were processed using the Surpass Module in Imaris X64 v.7.2.1. software (Bitplane).

Statistical Analyses for Experiments that Involve the Use of EPIX4-(RK)-GFP-H6, T22-GFP-H6 and/or T22-BFP-H6 Proteins Pairwise comparisons of cell internalization, competition assay and number of apoptotic and mitotic foci in the affected organs were made with Tukey's tests. All statistical tests were performed using GraphPad Prism version 8.0. All quantitative values both in vitro and in vivo experiments were expressed as mean±standard error of mean ($\bar{x}$±SEM). Differences among groups were considered significant at $p<0.05$.

Example 1: Characterization of the T22-NIDOmut2-H6 Protein Nanoparticles

Figure 12:
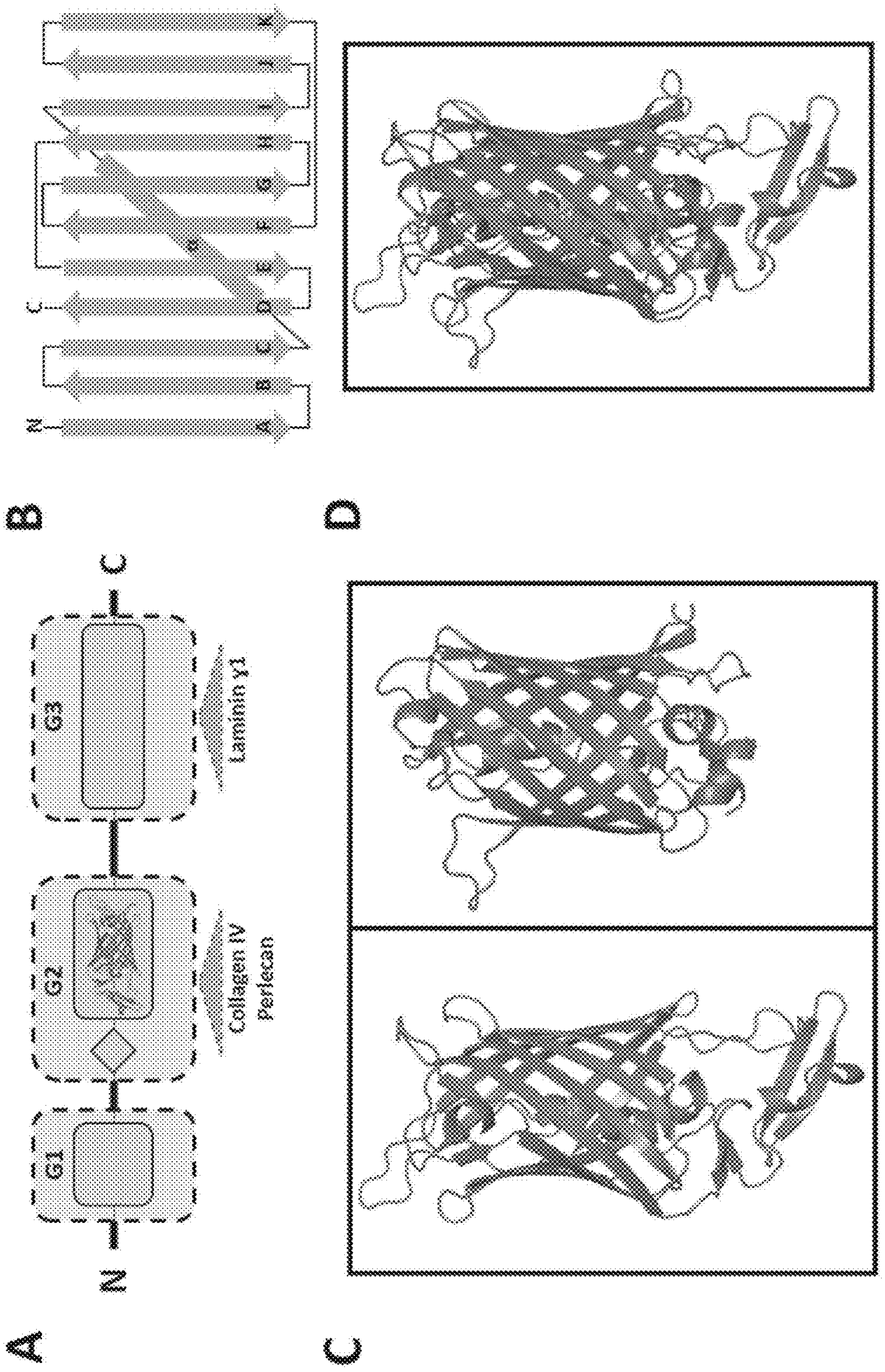
FIG. 12 shows the structure of Nidogen G2 domain. (Panel A) Schematic representation of multi-domain human Nidogen 1 protein and its interactions with natural ligands. β-barrel structure within G2 domain is depicted. (Panel B) Secondary structure of Nidogen G2 β-barrel domain showing β-sheets (A-K) and the α-helix (α). (Panel C) Cartoon representation of the Tertiary β-barrel structure of Nidogen G2 (1GL4 accession number of RCSB PDB database, version 1.2 from the 13 Jul. 2011) on the left panel and Green fluorescent protein (1QYO accession number of RCSB PDB database chain A, version 1.2 from the 13 Jul. 2011) on the right panel. (Panel D) Superposition of Nidogen G2 and GFP β-barrel structures.

Human Nidogen (P14543) is a 136.4 kDa structural protein from the basement membranes that naturally binds collagen IV, perlecan and laminin with high affinity. This protein consists of 3 globular domains that play a key role in the control of the extracellular matrix formation during development by probably linking collagen IV and laminin networks. G2 domain contains an 11-stranded β-barrel with a central α-helix (FIG. 12 Panel A, Panel B) with the same folding as green fluorescent protein from *Aequorea victoria* (FIG. 12 Panel C, Panel D).

In a first step, in order to generate a GFP-like human protein scaffold, a superposition of the mouse Nidogen G2 crystal structure (1GL4), and GFP β-barrel (1Q4A) was performed to select the exact G2 domain sequence which structure perfectly superposes, discarding non-matching domain fragments. A mouse Nidogen sequence as it is currently the only available resolved structure and is highly homologous in sequence to human Nidogen G2 (FIG. 13A). In this sense, the designed human Nidogen protein was decided to start at Ser430 as it is the first superposed residue on both structures (backbone rmsd=1.67) and previous Gly429, being a very flexible amino acid, could produce unwanted folding patterns of preceding N-terminal ligands. Therefore, the designed protein encompasses Ser430-Ala667 amino acids of Human Nidogen (with accession number P14543 in Uniprot Database version dated Jul. 7, 2009) and has SEQ ID NO. 62.

In a second step, in order to produce a biologically neutral protein scaffold, we decided to selectively mutate different residues implicated in the Nidogen G2 domain interaction with described natural ligands such as perlecan. Amino acids His456, Arg650, R468 and F639 were mutated. As shown in FIG. 13B, selected residues were completely buried by perlecan when interacting with G2 β-barrel according to this model, confirming their implication in the interaction hotspot (FIG. 13B).

Finally, from supramolecular organization point-of-view, residues proposed to be implicated in protein-protein contacts in GFP-based nanoparticle model were found to be highly similar (same group) in its relative Nidogen β-barrel structure suggesting that they could also be a homologous interaction point upon Nidogen-derived building blocks oligomerization. In this sense, selected amino acids, candidates to be mutated, although being slightly overlapping with proposed protein interaction area (specifically F639), introduced mutation (F639S) favors this protein-protein contact point. Therefore, any possible effect of Nidogen G2 mutations over its future oligomerization capacity was discarded. Considering all these analysis, the following mutations were incorporated in Ser430-Ala667 sequence of human Nidogen with accession number P14543 in Uniprot Database version dated Jul. 7, 2009 (SEQ ID NO. 72): H459A, R468N, F639S and R650A and was named NIDOmut2 (FIG. 13B) and is shown as SEQ ID NO:64.

Figure 2:
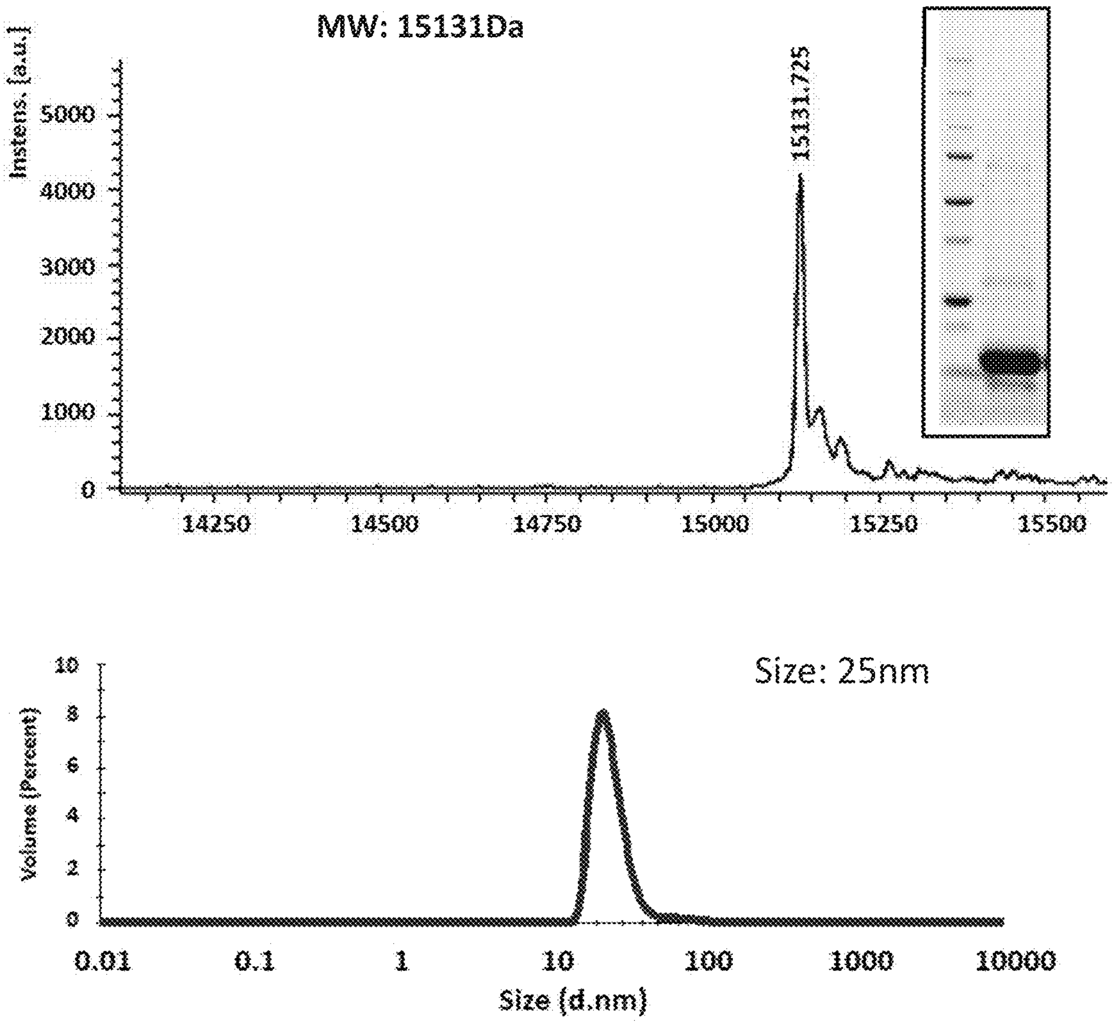
FIG. 2 shows the characterization of T22-STM-H6 (Panel A), T22-NIDOmut2-H6 (Panel B) and T22-GFP-H6 (Panel C) nanoparticles. MALDI-TOF mass spectrometry spectrum is shown in (Top), Western-blot immunodetection using anti-His monoclonal antibody is shown in the (inset) and Volume size distribution measured by DLS is shown (bottom) for each nanoparticle.
Figure 2:
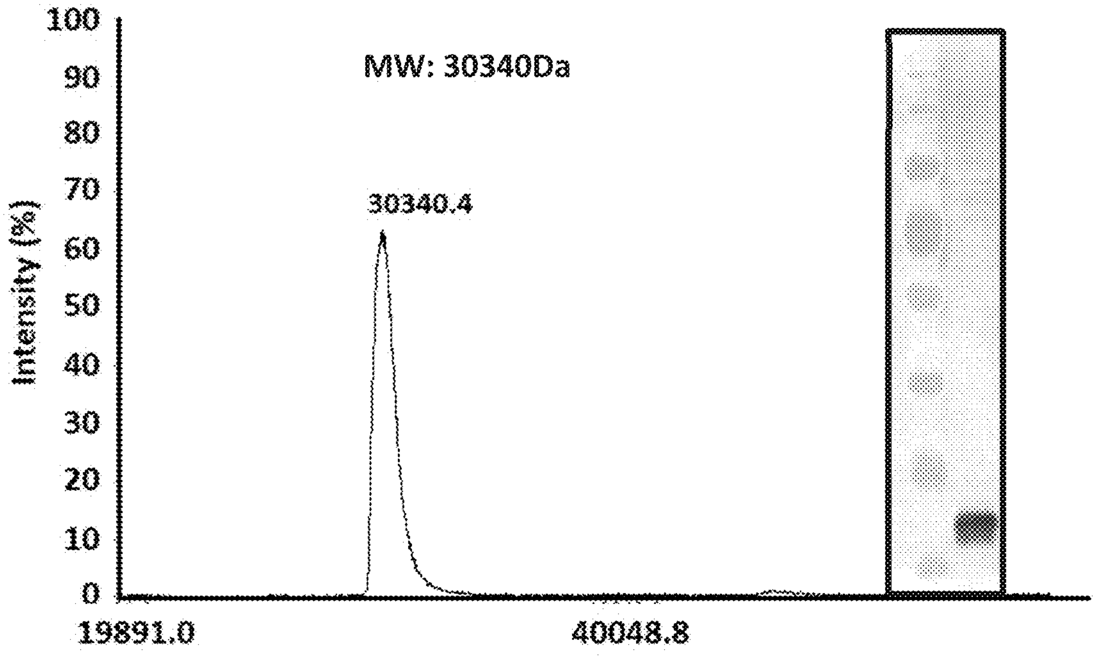
Figure 2:
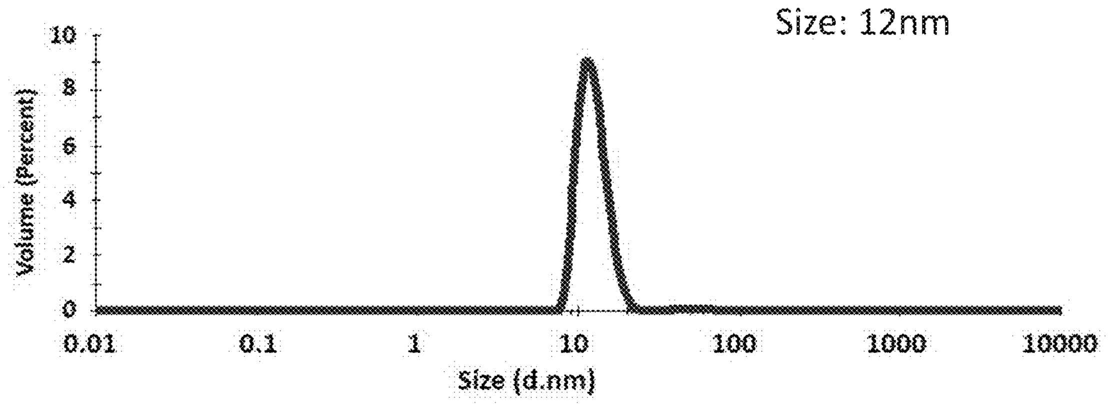
Figure 2:
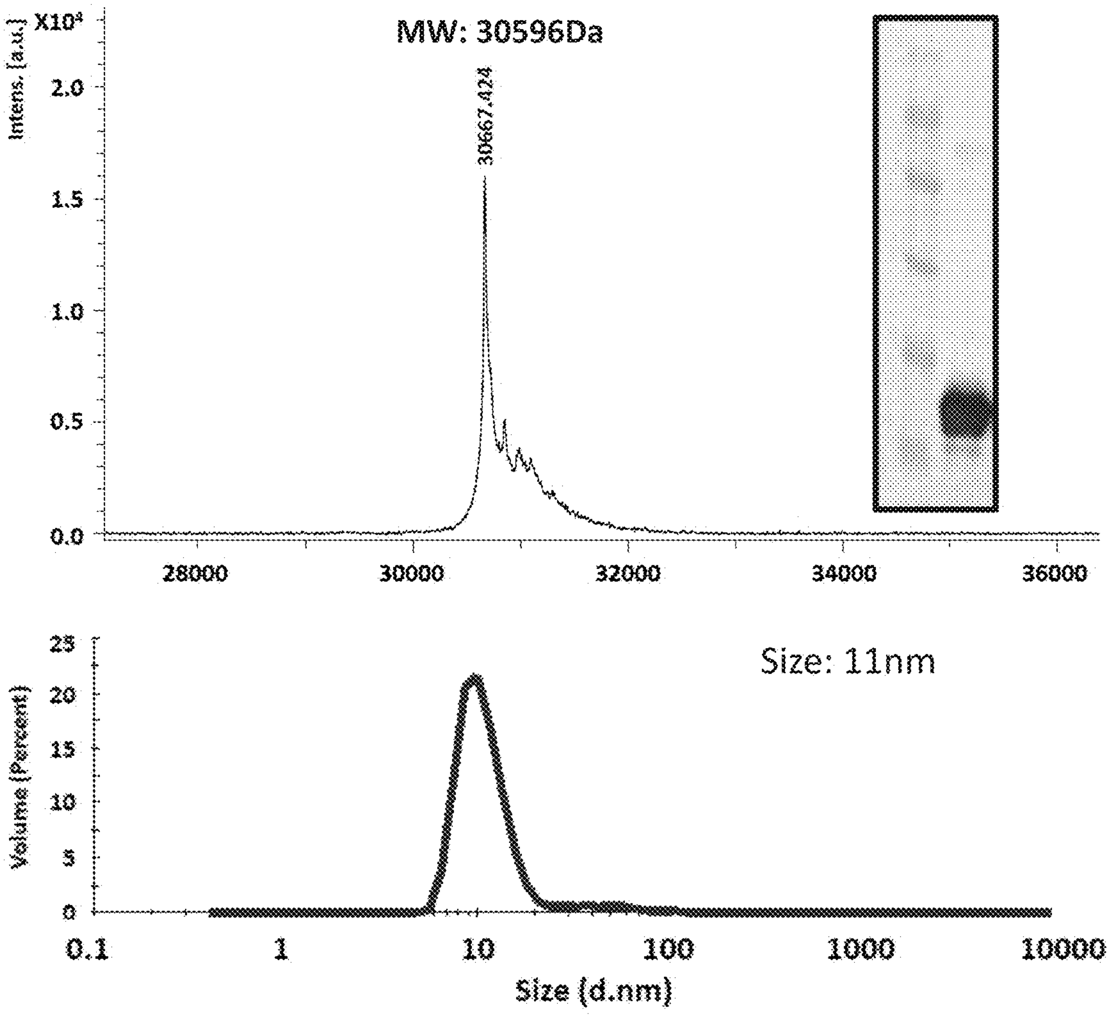
Figure 3:
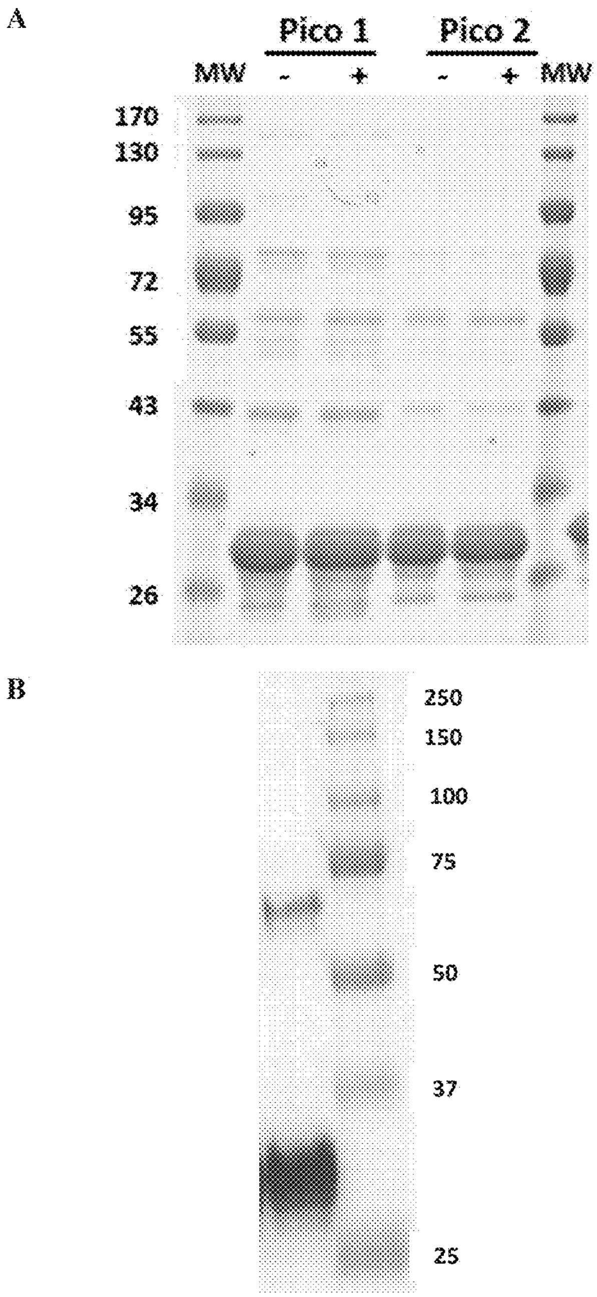
FIG. 3 shows the characterization of T22-NIDOmut2-H6 Nanoparticles characterization. (Panel A) Coomassie-blue staining of T22-NIDOmut2-H6 purification peaks 1 (Pico1) and peak 2 (Pico2) in Carbonate (−) and Carbonate+Salt (+) buffers upon SDS-PAGE electrophoresis. (Panel B) Western-blot immunodetection of T22-NIDOmut2-H6 protein by anti-His monoclonal antibody. (Panel C) Volume size distribution of T22-NIDOmut2-H6 nanoparticles determined by DLS. (Panel D) MALDI-TOF mass spectrometry spectrum of T22-NIDOmut2-H6 protein.
Figure 3:
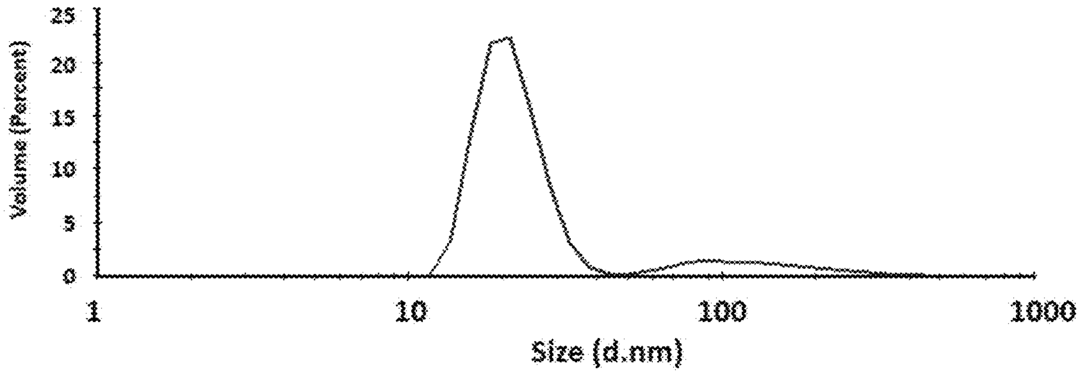
Figure 3:
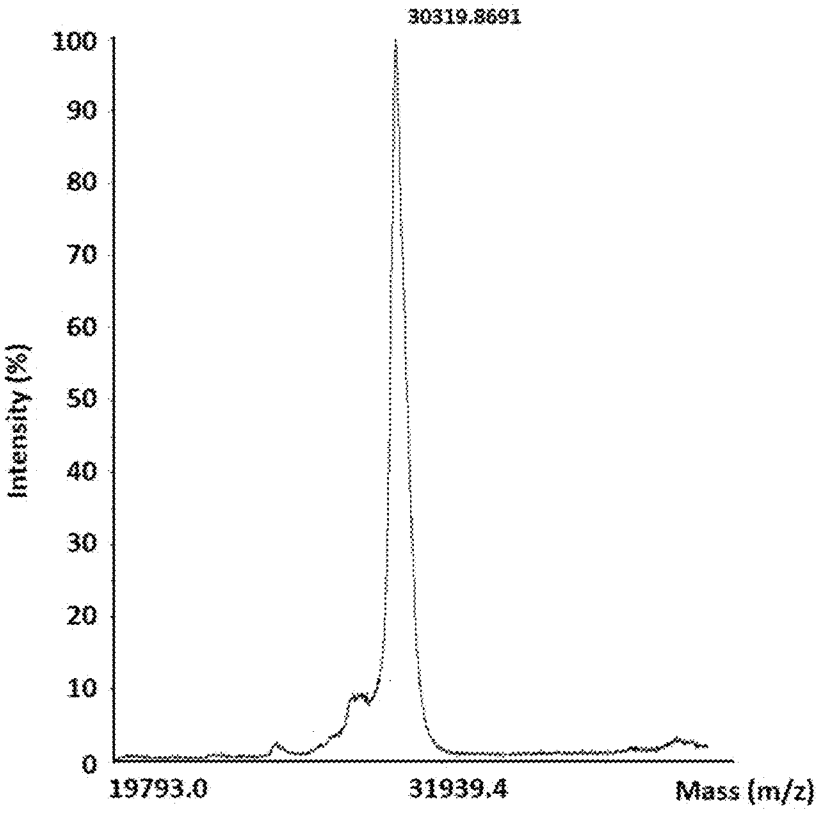
Figure 4:
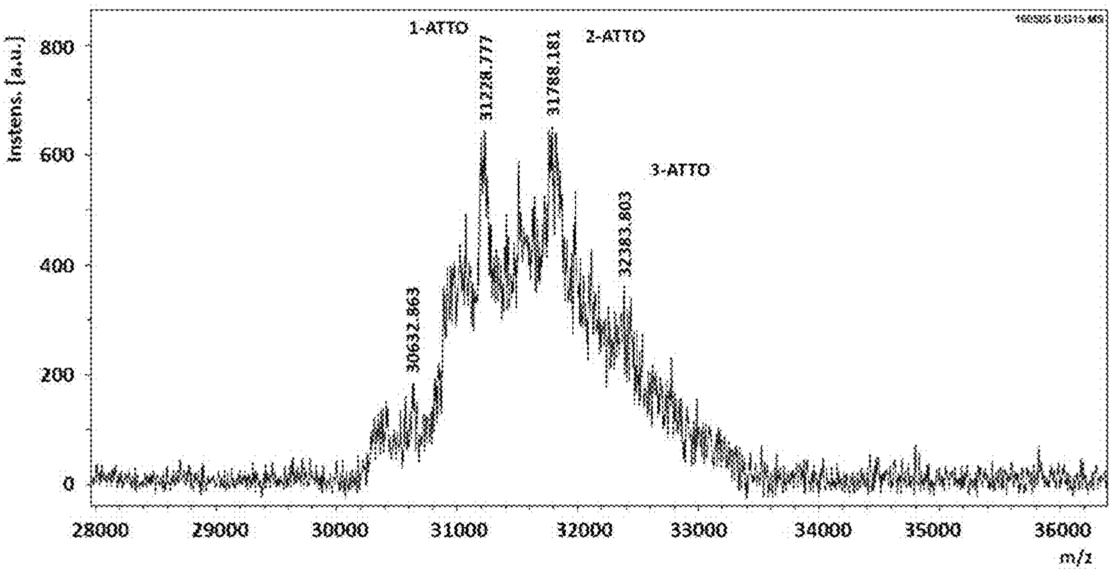
FIG. 4 shows T22-NIDOmut2-H6 labelling. (Panel A) MALDI-TOF mass spectrometry spectrum of labeled T22-NIDOmut2-H6-ATTO488 protein. Each peak over 30.3 kDa correspond to an additional ATTO molecule incorporation. (Panel B) Volume size distribution of T22-NIDOmut2-H6-ATTO488 nanoparticles determined by DLS.
Figure 4:
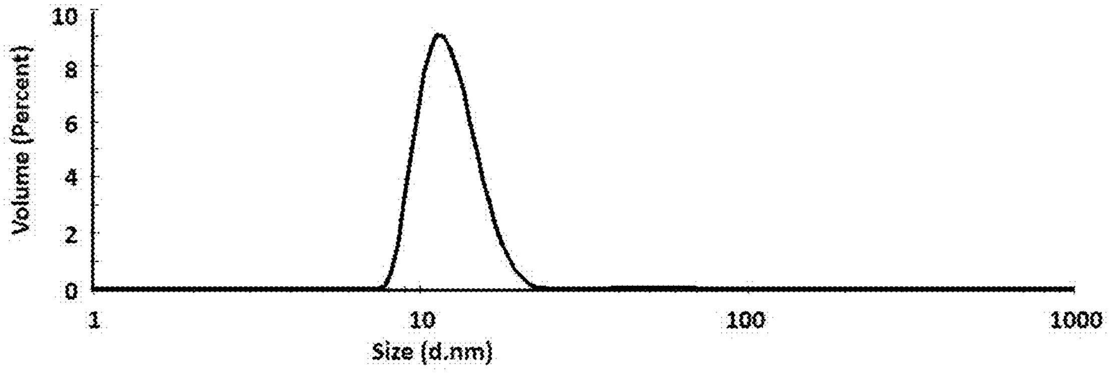

Genetic engineering allows rational design and recombinant production of modular self-assembling proteins. In this example, three different modular proteins containing 1) a N-terminal cationic CXCR4-specific ligand (T22), 2) a structurally stable and biologically neutral protein scaffold namely mutated human Nidogen-1 G2 domain (NIDOmut2, with SEQ ID NO. 64), Stefin A Triple Mutant protein (STM) or Green Fluorescent Protein (GFP) and 3) a C-terminal poly-Histidine have been designed and produced in a recombinant way (T22-NIDOmut2-H6 with SEQ ID NO. 61, T22-STM-H6 and T22-GFP-H6) in *E. coli*. Produced proteins were successfully purified by IMAC affinity chromatography were full-length and pure proteins were obtained as determined by MALDI-TOF mass spectrometry and western-blot immunodetection. All of them self-assemble in regular size nanoparticles in a range of 25 nm for T22-STM-H6, 12 nm for T22-NIDOmut2-H6 and 11 nm for T22-GFP-H6 as determined by Dynamic Light Scattering (FIG. 2 and FIG. 3). T22-NIDOmut2-H6 protein, which shows a molecular mass of 30.3 kDa, was successfully labelled with an ATTO488 fluorescent dye molecule for intracellular tracking purposes as determined by MALDI-TOF mass spectrometry where additional peaks (with molecular mass additions around 600 Da) are detected, corresponding each peak to the acquisition of an additional ATTO488 molecule (FIG. 4).

Example 2: T22-NIDOmut2-H6 with SEQ ID NO. 61 CXCR4-Dependent Internalization

Figure 5:
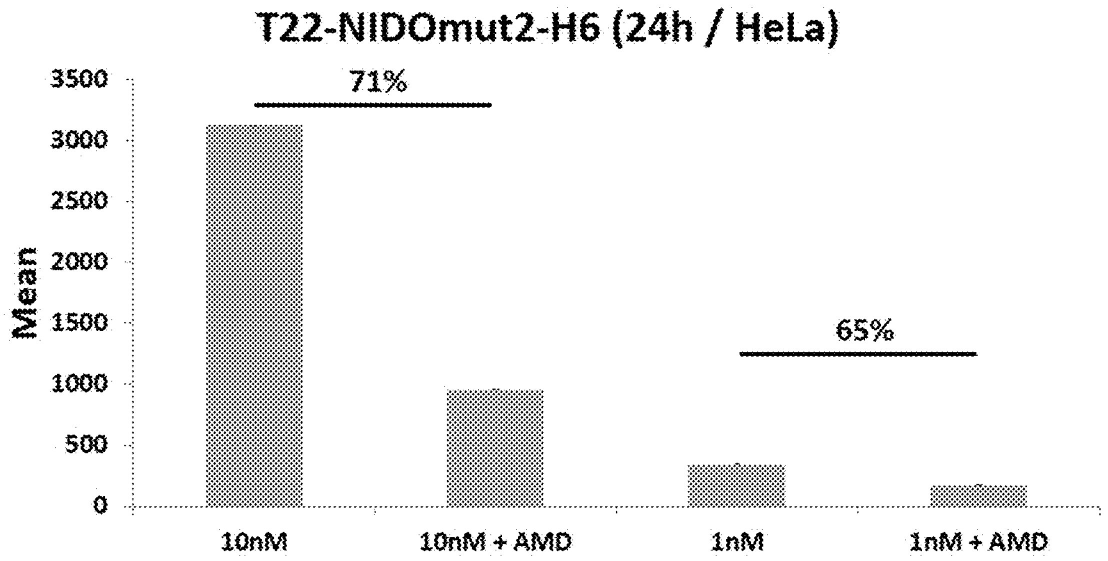
FIG. 5 shows the CXCR4-specific internalization of the T22-NIDOmut2-H6 protein in CXCR4+ cells. (Panel A) Labelled T22-NIDOmut2-H6-ATTO488 nanoparticles internalization and competition (+AMD) upon incubation for 24 h over HeLa cells (CXCR4+) at different concentrations (1 nM and 10 nM). The % of cell uptake inhibition in presence of the CXCR4 receptor antagonist AMD3100 (+AMD) is indicated. (Panel B) Confocal laser microscopy images of HeLa cells incubated in presence of 25 nM of T22-NIDOmut2-H6-ATTO488 for 24 h. Cell nuclei were stained by HOECHST®, cell membranes by CELLMASK™ and punctuated pattern inside cells correspond to protein nanoparticles.
Figure 5:
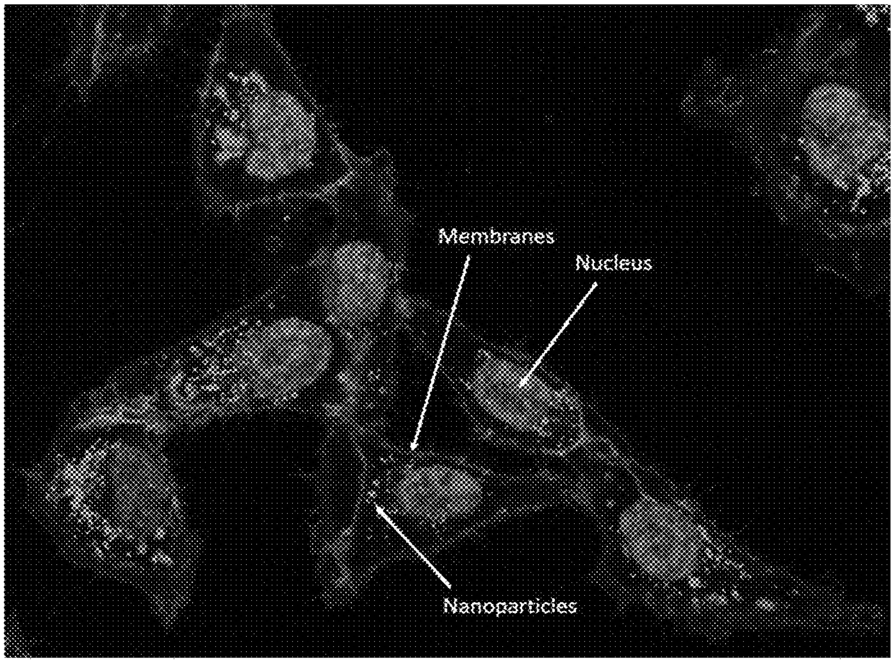

Labelled T22-NIDOmut2-H6-ATTO488 nanoparticles can be internalized into HeLa cells in a CXCR4-dependent process as determined by intracellular fluorescence accumulation measured in a flow cytometer (FIG. 5). HeLa are tumor cells that highly overexpress CXCR4 receptor. CXCR4-mediated nanoparticles uptake is demonstrated by competition assays where the pre-incubation of Hela cells with a CXCR4-specific antagonist AMD3100 efficiently prevents T22-NIDOmut2-H6-ATTO488 internalization. Confocal laser microscopy image shows punctuated intracellular perinuclear accumulation of T22-NIDOmut2-H6-ATTO488 nanoparticles within CXCR4+ HeLa cells.

Example 3: Characterization of T22-NIDOmut2-H6-FdU Nanoconjugates

Figure 7:
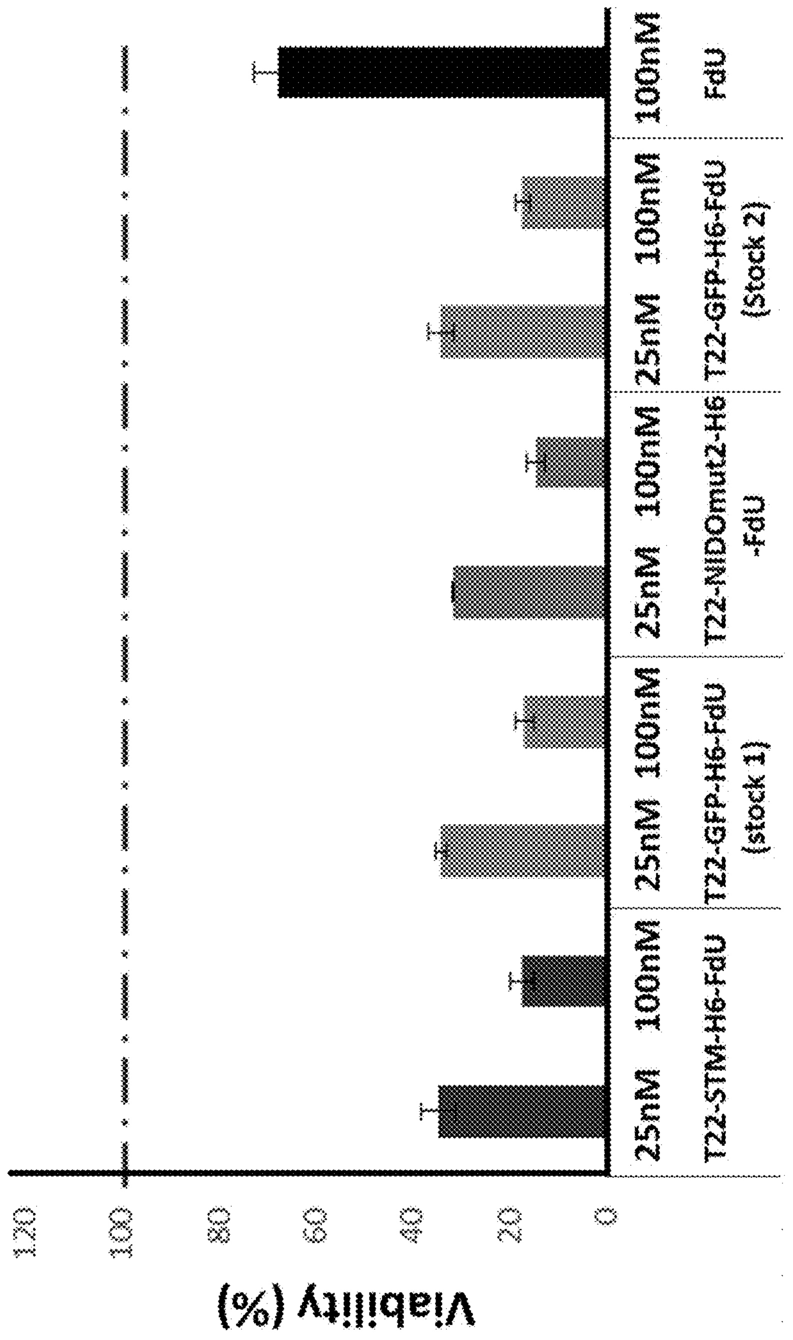
FIG. 7 shows cytotoxicity of oligo-FdU conjugated nanoparticles over CXCR4+ cells. Graph shows the viability (%) of HeLa cells (CXCR4+) upon incubation in presence of 25 nM or 100 nM of T22-STM-H6-FdU, T22-NIDOmut2-H6-FdU or two different stocks of T22-GFP-H6-FdU nanoconjugates and 100 nM of free oligo-FdU (FdU) for 48 h measured by a MTT viability test assay.

Characterization of T22-NIDOmut2-H6-FdU nanoconjugates was performed by MALDI-TOF mass spectrometry where additional peaks over 30.3 kDa (with mass increments around 2 kDa) corresponding to additional oligo-FdU molecules incorporation are detected. In figure-6B, peaks corresponding up to 3-oligoFdU molecules incorporation can be detected. T22-NIDOmut2-H6-FU nanoconjugates maintain their nanometric nanoparticle size range as determined by Dynamic Light Scattering. T22-NIDOmut2-H6-FdU show similar cytotoxic activity than T22-STM-H6-FdU or T22-GFP-H6-FdU nanoconjugates over CXCR4+ HeLa cells in-vitro as determined by MTT cells viability assay (FIG. 7). Incubation of HeLa cells in presence of different concentrations (25 nM and 100 nM) of the three different nanoconjugates resulted in a very efficient cell viability inhibition with IC50s in nanomolar range (IC50<25 nM) that in all cases were significantly more efficient than equimolar concentration of free oligo-FdU (FIG. 7).

Example 4: T22-NIDOmut2-H6-FdU Nanoconjugate Shows Higher Antitumor Effect in the CXCR4+ M5 SC CRC Model than T22-STM-H6-FdU or T22-GFP-H6-FdU The CXCR4+ M5 CRC model was used to assess the relative potency of the three compared nanoconjugates (T22-STM-H6-FdU, T22-NIDOmut2-H6-FdU and T22-GFP-H6-FdU), because it displays high CXCR4-overexpression. This feature is highly relevant to discriminate the potency of the three nanoconjugates that are capable of targeting CXCR4+ cancer cells and, therefore, capable of selectively eliminating CXCR4+ CRC stem cells.

Figure 8:
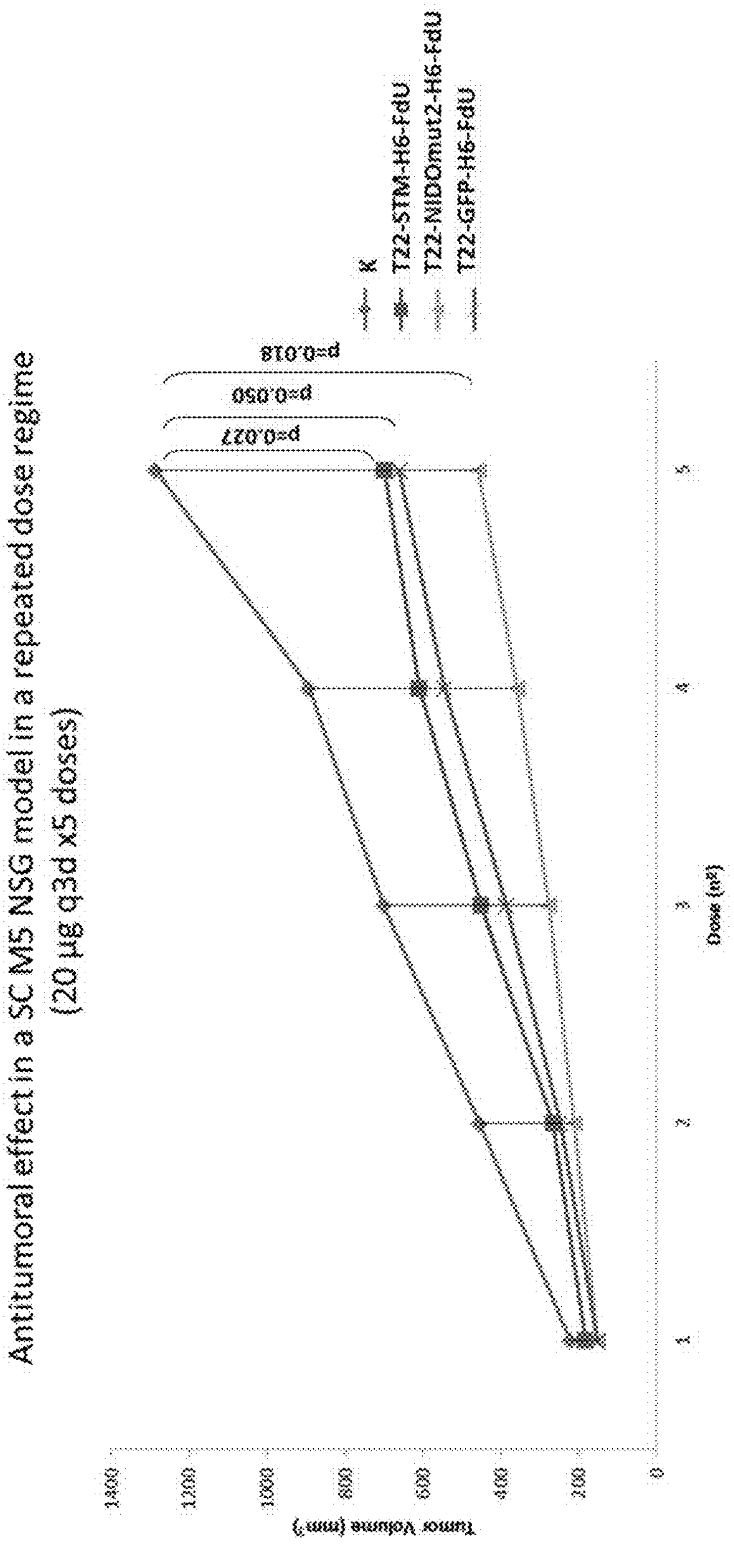
FIG. 8 shows that the T22-NIDOmut2-H6-FdU nanoconjugate induces higher growth inhibition than T22-STM-H6-FdU or T22-GFP-H6-FdU in a CXCR4+ tumor model. The Graphic displays the evolution of tumor volume along time for each nanoconjugate-treated group (n=4) at a dosage of 20 μg q3d×5 doses, and its comparison with Buffer-treated (K, n=4) in the CXCR4+ M5 subcutaneous (SC) colorectal cancer (CRC) model.

After repeated intravenous administration of the nanoconjugates at a 20 μg q3dx5 dosage regime, all three nanoconjugates induced a significant reduction in tumor growth, as measured by tumor volume along time, in comparison to vehicle-treated animals. Reduction in tumor size was more pronounced after T22-NIDOmut2-H6-FdU nanoconjugate treatment than after T22-STM-H6-FdU or T22-GFP-H6-FdU treatment. Moreover, at the end of the experiment the reduction in tumor volume ($mm^3$) was significantly higher (p=0.018) for T22-NIDOmut2-H6-FdU (456.5±134.9) as compared to the tumor volume in the control group (1285.2±149.4) than the difference registered for T22-STM-H6-FdU (699.2±144.6, p=0.027) or that registered for T22-GFP-H6-FdU (661.2±169.2, p=0.050) (FIG. 8).

Figure 9:
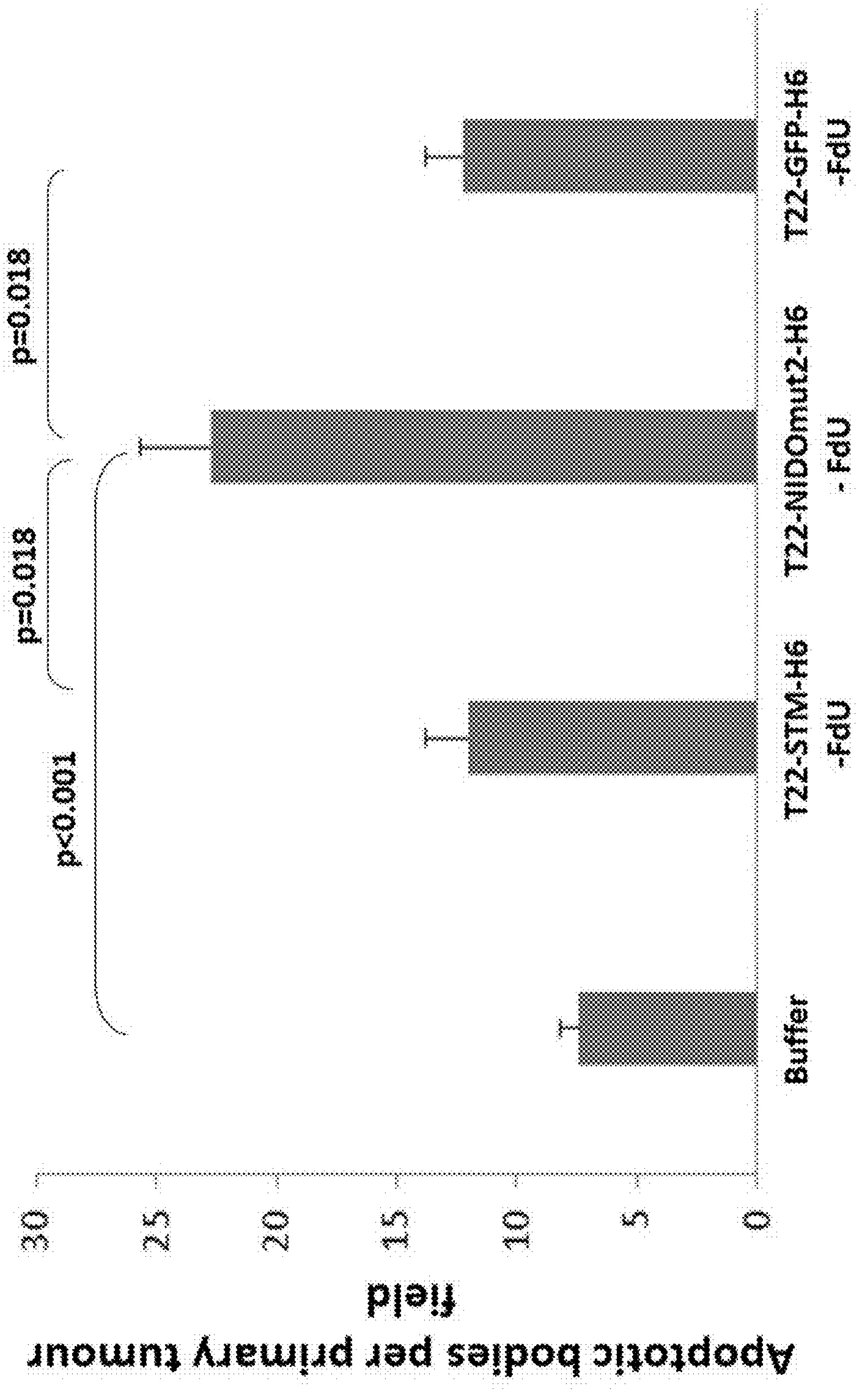
FIG. 9 shows a higher apoptotic induction by the T22-NIDOmut2-H6-FdU nanoconjugate in CXCR4+ M5 tumor tissue than T22-STM-H6-FdU or T22-GFP-H6-FdU. (Panel A) Graphic display of the number of apoptotic bodies observed in tumor sections in Buffer- or nanoconjugate-treated tumors at the end of the experiment. (Panel B) Representative microphotographs of H&E-stained sections identifying the apoptotic figures (Black arrows) observed in each compared group.
Figure 9:
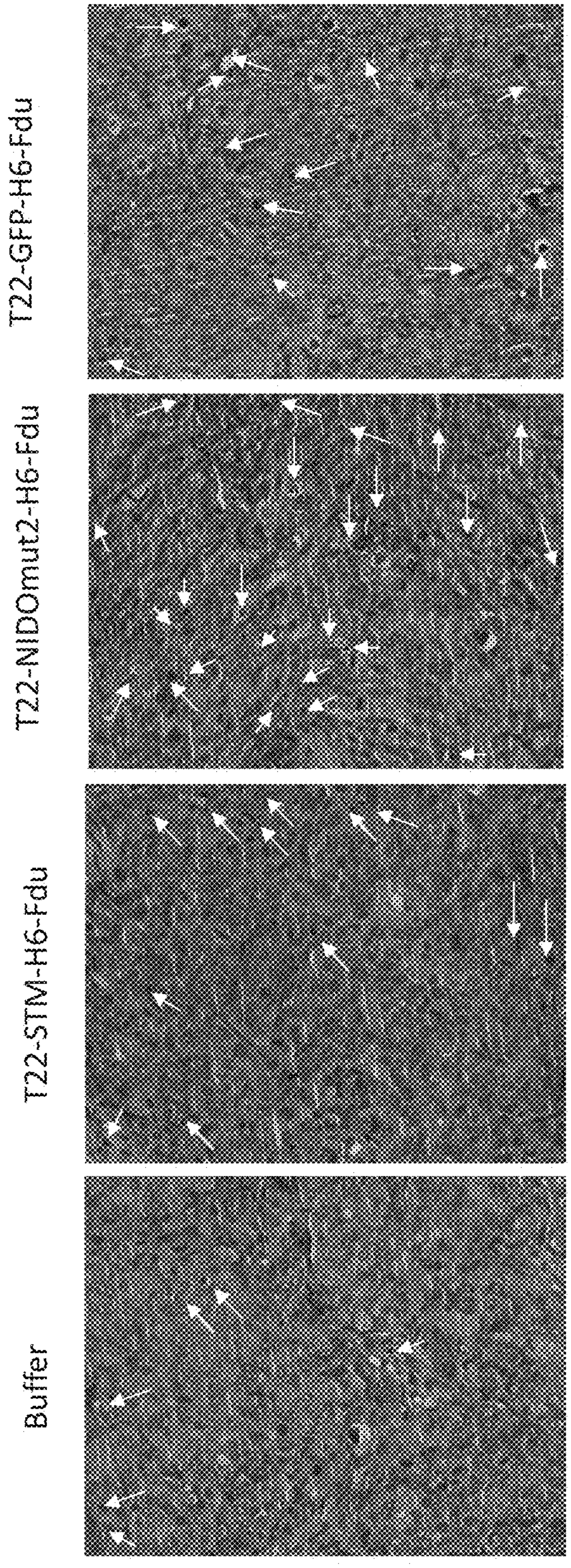
Figure 10:
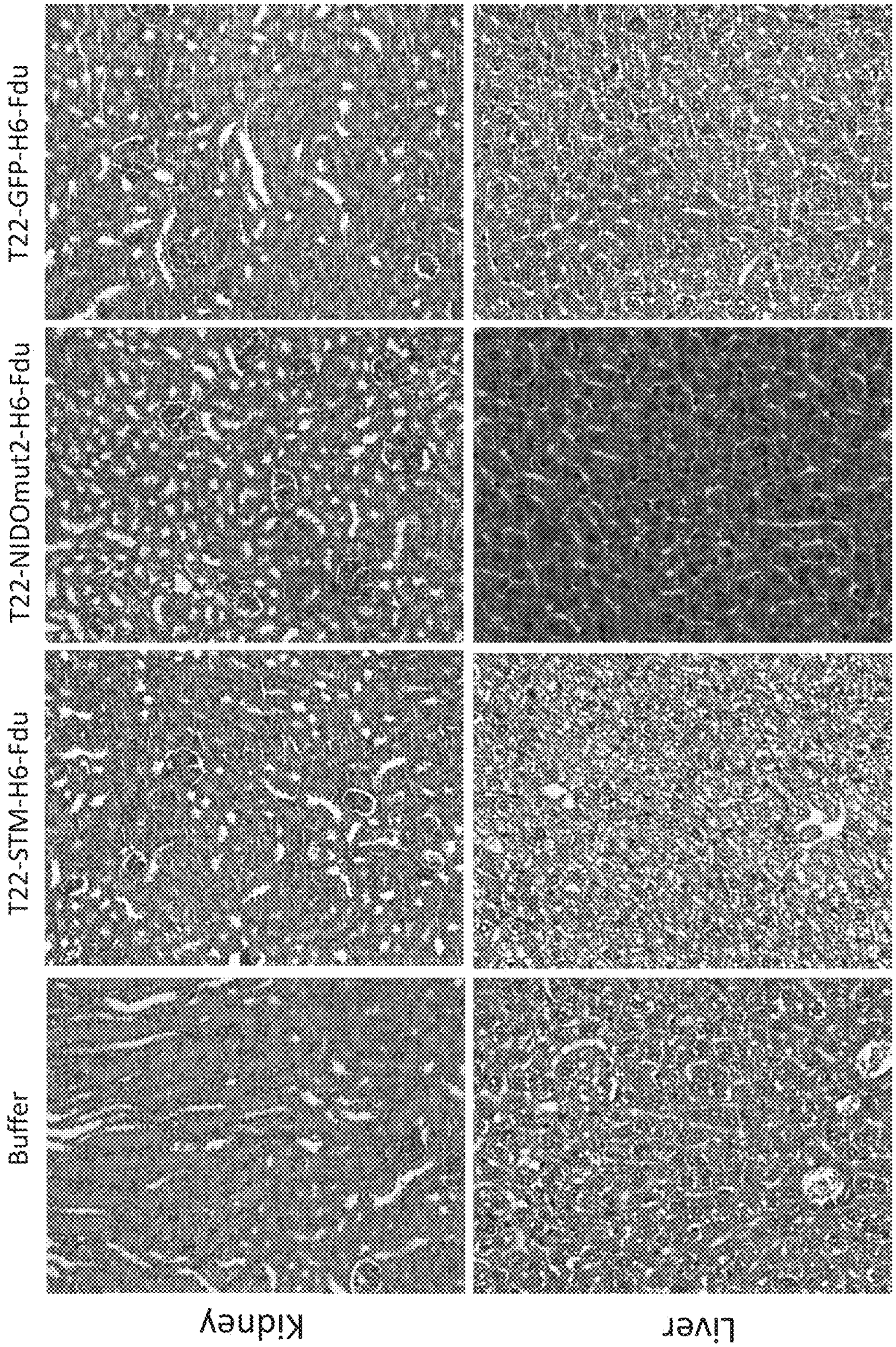
FIG. 10 shows a lack of histological alterations in kidney or liver among the compared groups. Representative H&E-stained sections of kidney and liver tissues showing lack of altered architecture or histology (no inflammation or apoptotic figures observed) in both organs at the end of treatment in control buffer-treated or nanoconjugate-treated mice.

Example 5: T22-NIDOmut2-H6-FdU Nanoconjugate Shows Higher Potency as Inductor of Apoptosis than T22-STM-H6-FdU or T22-GFP-H6-FdUin the CXCR4+M5 SC CRC Model The evaluation of apoptotic induction in 10 high-power fields of H&E stained tumor tissue sections, at mouse sacrifice two days after the last nanoconjugate dose, yielded a significantly higher number of apoptotic figures for T22-NIDOmut2-H6-FdU (22.7±2.9, p<0.001), as compared to those registered in the control vehicle-treated group (7.4±0.8), or those counted in T22-STM-H6-FdU-treated (12.0±1.7, p=0.018) or T22-GFP-H6-FdU-treated (12.3=1.5, p=0.018) tumors (FIG. 9 Panels A and B). In contrast, no significant differences in apoptotic induction were observed between T22-STM-H6-FdU or T22-GFP-H6-FdU-treated tumor and control tumors In summary, T22-NIDOmut2-H6-FdU nanoconjugate induces a significantly more potent antitumor effect than T22-STM-H6-FdU or T22-GFP-H6-FdU nanoconjugates. This finding and the fact that it also induces a significantly higher number of apoptosis figures in treated tumors than the other two nanoconjugates indicates that the nanoconjugate incorporating the mutated G2 domain of human Nidogen protein, described above, is the selected protein to be used for the development and clinical translation of this nanoconjugate. Importantly, the potent antitumor activity displayed by the T22-NIDOmut2-H6-FdU nanoconjugate is observed in the absence of toxicity in normal organs, including the lack of histological alterations in liver or kidney at the end of treatment (FIG. 10), which determines its significantly higher therapeutic index, as compared to the other two nanoconjugates.

Figure 11:
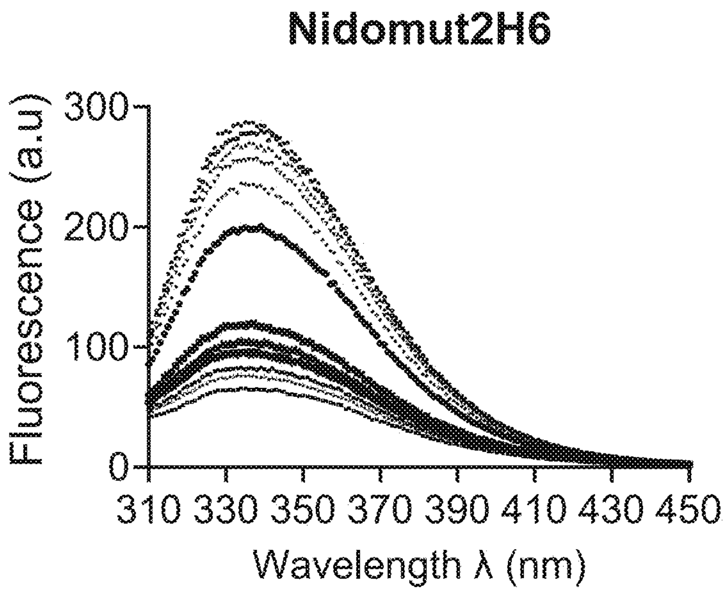
FIG. 11 shows the correlation between intrinsic Fluorescence vs temperature for isolated hexahistidine-tagged versions of the human nidogen G2 domain, of the human nidogen G2 containing the H459A., R468N, F639S and R650A mutations and for stefin (Panel A). Arrow indicates the heating of the sample. Unfolding curves for Nidomut2H6 (Panel B), NidoWTH6 (Panel C) and STMH6 (Panel D) with CSM values as a function of temperature. CSM values were calculated from experiment exemplified with FIG. 1, Panel A, and performed for each protein. Black and grey arrows indicate the $T_m$ and $T_{onset}$ values, respectively.
Figure 11:
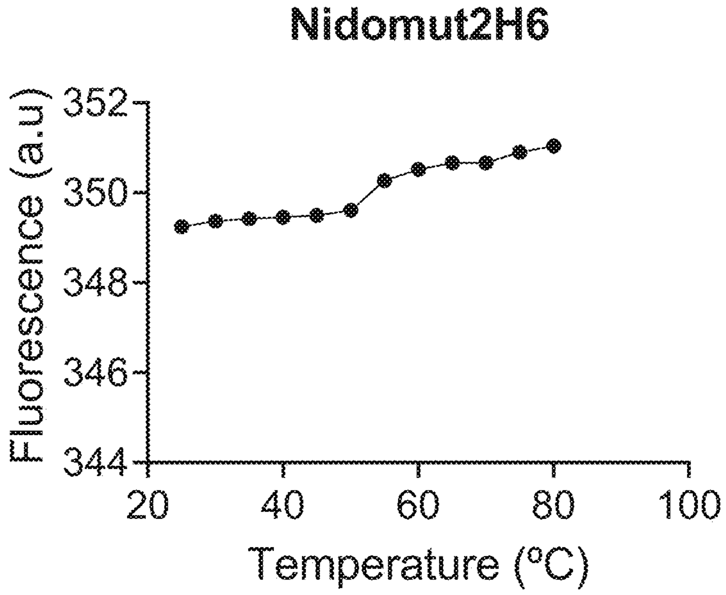
Figure 11:
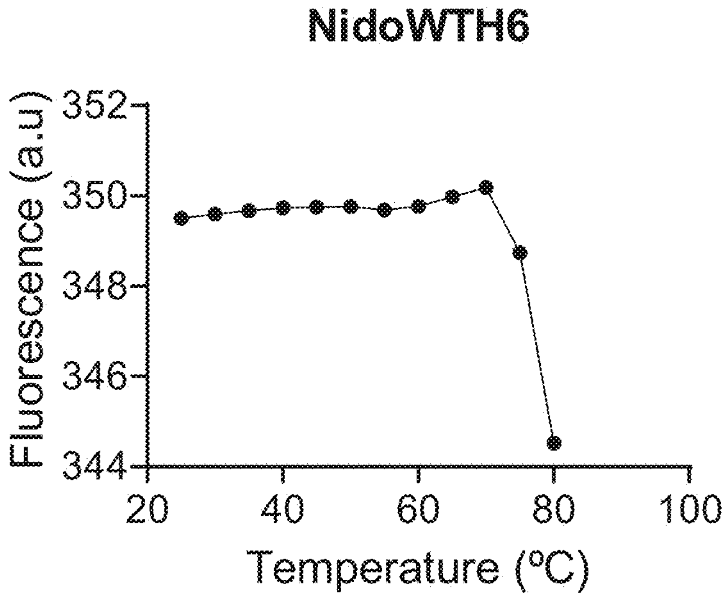
Figure 11:
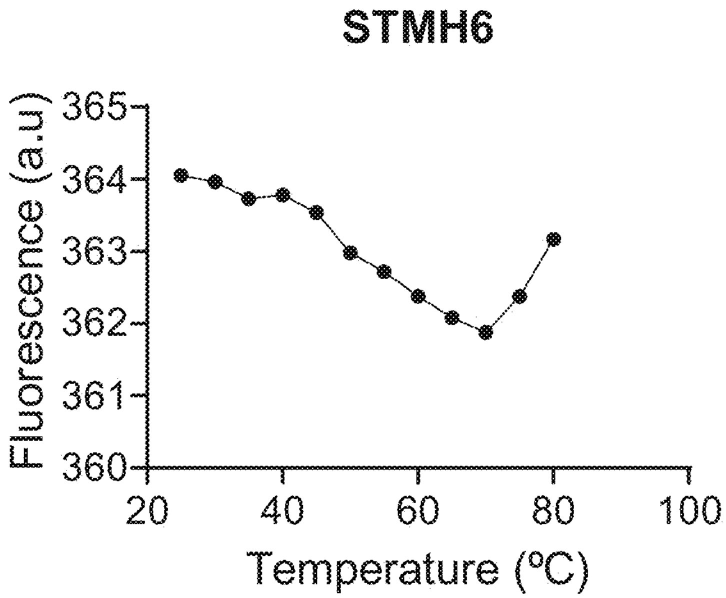

Example 6: The Isolated Native G2 Domain of Nidogen with SEQ ID NO. 62 as well as the NIDOmut2 Variant Containing H459A, R468N F639S and R650A Mutations with SEQ ID NO. 64 are Thermostable Polypeptides The midpoint unfolding temperature ($T_m$) from NidoWTH6 and STMH6 samples could not be determined as the maximal unfolding state was not reached in the temperature range studied. This behavior has also been described for T22-GFP-H6 (Sánchez, J M et al., Biomacromolecules, 2018, 19:3788-3797; doi:10.1021/acs.biomac.8b00924), a highly stable protein. On the other hand a $T_m$=55°C from Nidomut2H6 was acquired but in this case two thermal transitions were observed. Once again the higher $T_m$ could not be obtained (FIG. 11). Alternatively we suggest a $T_m$ value (Table 7, numbers in italic format) assuming that the maximal CSM values represent the unfolding state of the protein.

TABLE 7

| Protein unfolding parameters | | | | |
|---|---|---|---|---|
| Proteins | $T_m$ | $T_{onset,1}$ | $T_{onset,2}$ | Source |
| STMH6 | ≅76° C.* | 70° C. | | |
| NidoWTH6 | ≅65° C.* | 60° C. | | |
| Nidomut2H6 | 55° C. | 50° C. | 70° C. | |
| T22-GFP-H6 | | 75° C. | | Sanchez et al, 2018 (ibid.) |
| Human Collagen Type I | 40.3° C. | 38.2° C. | | Leikina et al, (PNAS, 2002, 31314-1318) |
| HSA | 63° C. | | | Picó. G (Int. J. Biol. Macromol. 1997, 20: 63-7) |

(*$T_m$ value assuming that the maximal CSM values represent the entirely unfolding state of the protein)

All the proteins analyzed could be described as thermostable ($T_m$>65°C) and mesostable ($T_m$<65°C) proteins[4] all of them are more stable than the human collagen type I (Leikina et al, (PNAS, 2002, 31314-1318) and with comparable $T_m$ values to human serum albumin (HAS) (Picó, G (Int. J. Biol. Macromol. 1997, 20:63-7).

Figure 14:
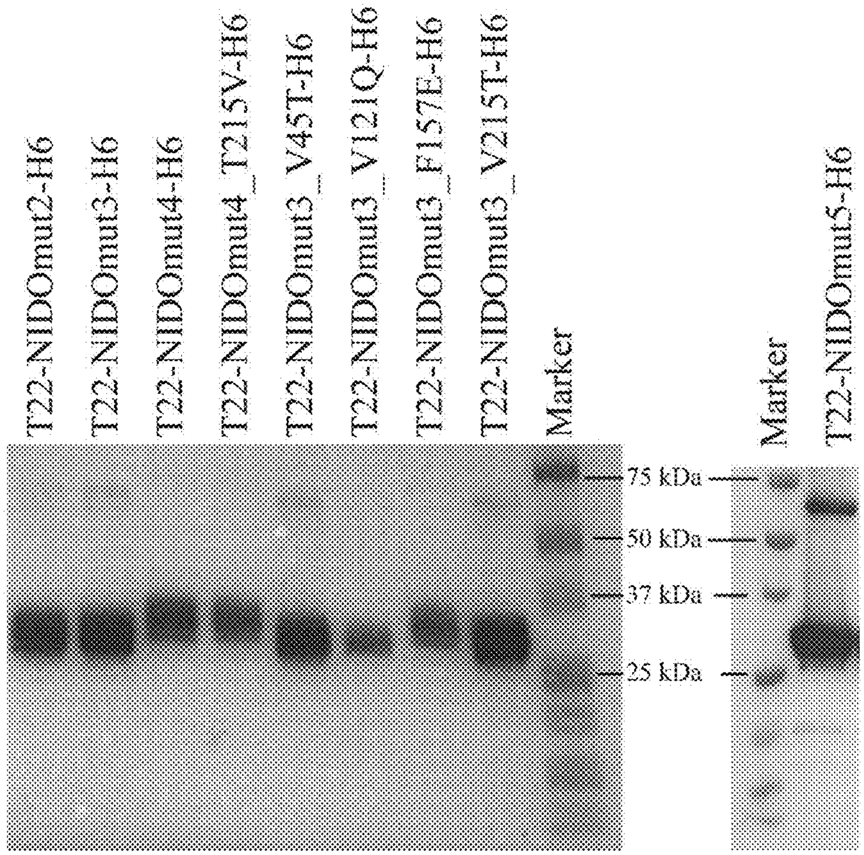
FIG. 14 shows the Western blots of the soluble fraction of cell lysates of the expression test of the proteins indicated in the figure.

Example 7. Expression Test of Proteins T22-NIDOmut3-H6 and all its Further Derivatives An expression test was carried out as a first approach to evaluate the viability and quality of each new mutant protein T22-NIDOmut3-H6, T22-NIDOmut3_V45T-H6, T22-NIDOmut3_V121Q-H6, T22-NIDOmut3_F157E-H6, T22-NIDOmut3_V215T-H6, T22-NIDOmut4_T215V-H6, T22-NIDOmut4-H6, and T22-NIDOmut5-H6 with the exception of T22-NIDOmut5-H6, which was produced and purified directly. All cultures were grown in 20 mL of LB culture media and reached ODs of 3.3-4.5 after O/N induction. Each protein was successfully detected via western blot of the cell lysates (FIG. 14). Molecular weight was within the expected marker bands and it was noted that proteins containing incorporated the mutation F157E (T22NIDOmut3_F157E-H6, T22-NIDOmut4_V215T-H6 and T22-NIDOmut4) exhibited a slightly higher band. Study of T22-NIDOmut3_V121Q-H6 and T22-NIDOmut3_F157E-H6 was halted at this point because the main fraction of these proteins was produced in an insoluble form.

Figure 15:
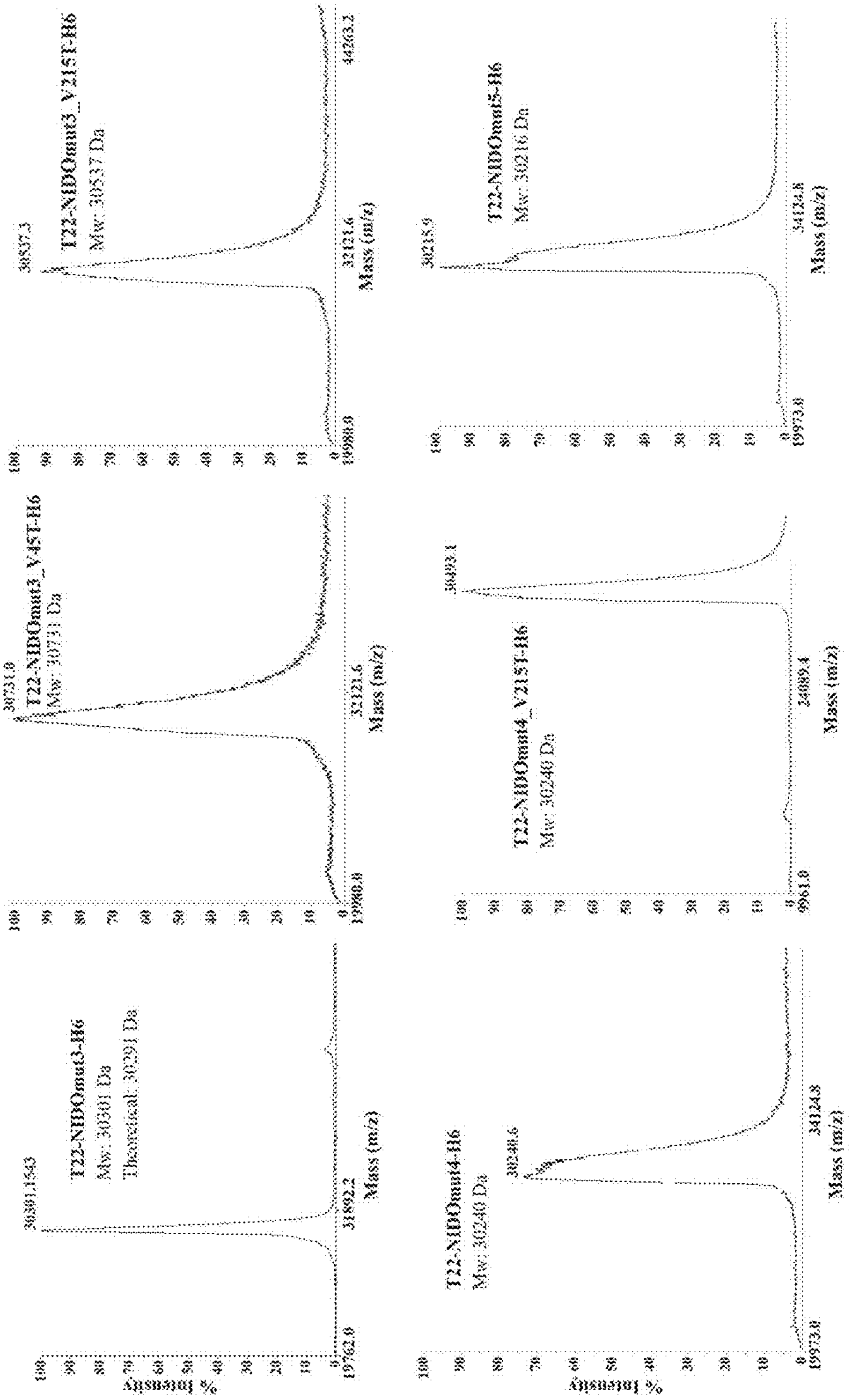
FIG. 15 shows the MALDI-TOF mass spectrometry spectrum of the selected candidate proteins indicated in each panel of the figure after the expression test. Theoretical size of all proteins is approximately 30.3 kDa.

Example 8. Protein Production Scaled-Up of T22-NIDOmut3-H6 and all its Further Derivatives Following this test, protein production was scaled to 500 mL of LB media in 2 L Erlenmeyer flasks and purification was performed via metal affinity chromatography. Yield is provided in Table 8. Proteins were purified efficiently (>95% purity) and their integrity was corroborated again via SDS-PAGE/western blot and MALDI-TOF (FIG. 15). All proteins were stable after dialysis in 133 mM $NaCO_3H$ buffer.

TABLE 8

| Culture growth (OD) and protein yield of the protein mutants derived from T22-NIDOmut2-H6. | | |
|---|---|---|
| Mutant | Culture growth (OD) | Protein yield (mg/L) |
| T22-NIDOmut3-H6 | 4.10-5.32 | 14-24 |
| T22-NIDOmut3_45-H6 | 3.52 | 9 |
| T22-NIDOmut3_121-H6 | 4.07 | Not purified |

TABLE 8-continued

| Culture growth (OD) and protein yield of the protein mutants derived from T22-NIDOmut2-H6. | | |
|---|---|---|
| Mutant | Culture growth (OD) | Protein yield (mg/L) |
| T22-NIDOmut3_157-H6 | 4.13 | Not purified |
| T22-NIDOmut3_215-H6 | 4.52 | 15 |
| T22-NIDOmut4_215-H6 | 3.28 | 26 |
| T22-NIDOmut4-H6 | 2.60-3.78 | 12-24 |
| T22-NIDOmut5-H6 | 3.17-3.54 | 20-28 |

Example 9. Size Distribution of Resulting Nanoparticles

Figure 16:
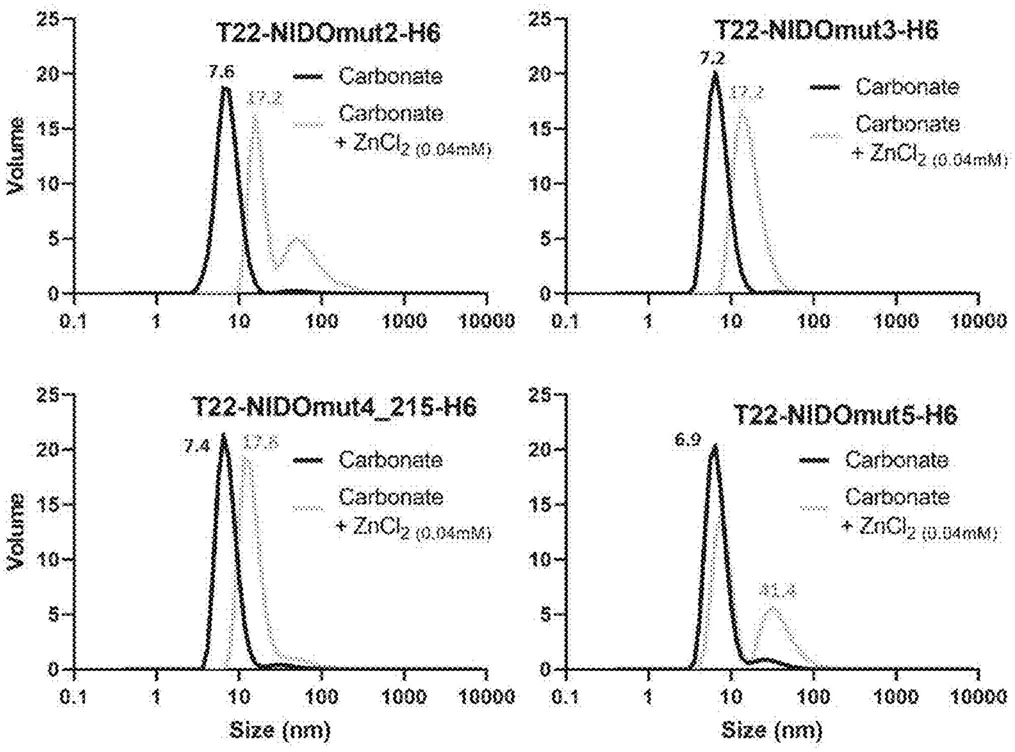
FIG. 16 shows the volume size distribution of T22-NIDOmut2-H6, T22-NIDOmut3-H6, T22-NIDOmut4 T215V-H6 and T22-NIDOmut5-H6 proteins and their nanoparticles, as determined by DLS.
Figure 17:
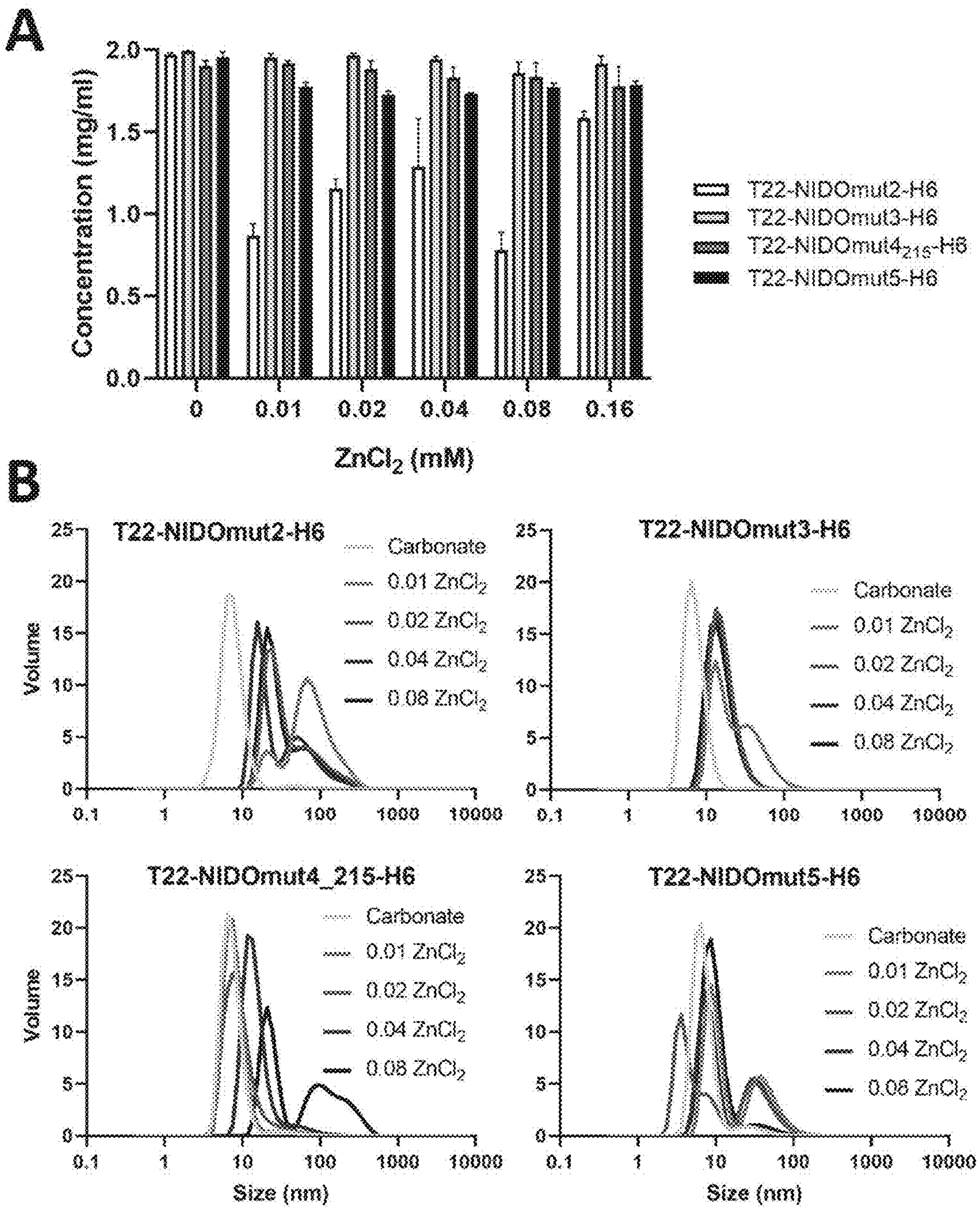
FIG. 17 Panel A shows the precipitation profiles of T22-NIDOmut2-H6, T22-NIDOmut3-H6, T22-NIDOmut4 T215V-H6 and T22-NIDOmut5-H6 after incubation with increasing concentrations of $ZnCl_2$. Panel B. Volume size distribution of T22-NIDOmut2-H6, T22-NIDOmut3-H6, T22-NIDOmut4 T215V-H6 and T22-NIDOmut5-H6 nanoparticles assembled at different $ZnCl_2$ concentrations, as determined by DLS.

T22-NIDOmut3-H6, T22-NIDOmut4_T215V-H6 and T22-NIDOmut5-H6 were selected to proceed with the characterization due to their best production yields (24, 26 and 28 mg/L, respectively). At this point, volume-size distribution of each candidate was studied via DLS (FIG. 16). All three candidates were equivalent to the original T22-NIDOmut2-H6 in size before and after assembly into nanoparticles with $ZnCl_2$ (0.04 mM). Only T22-NIDOmut5-H6 exhibited nanoparticles of higher size, but well within the desired nanoscale (10-100 nm range). Precisely because Zn is used to mediate this assembly, it was deemed appropriate to perform a precipitation assay against increasing concentrations of $ZnCl_2$, up to 0.16 mM, (FIG. 17, Panel A) to test whether the new proteins were resistant to Zn-induced precipitation or not. It was demonstrated that all new proteins derived from T22-NIDOmut3-H6 inherited the ability to remain soluble when in contact with Zn, as opposed to the control T22-NIDOmut2-H6, which exhibited losses up to 66% of the initial soluble protein. Furthermore, nanoparticle size evaluation conducted at most of the previous Zn concentrations (FIG. 17, Panel B) revealed that T22-NIDOmut3-H6 nanoparticles are the ones assembled with a lowest dispersion at a stable size of 17 nm.

Example 10. Stability Study in Buffers

The stability of resulting proteins was studied in three FDA-approved buffers, and carbonate as control buffer. To this end, T22-NIDOmut2-H6 (control), T22-NIDOmut3-H6 and T22-NIDOmut5-H6 were further assessed to study whether the overall stability and solubility could be improved after dialysis in more complex buffers. The composition of the selected three FDA-approved buffers are provided in Table 9.

TABLE 9

| Dialysis buffer composition. | |
|---|---|
| Code | Composition |
| A9 | Polysorbate 80 (0.4 mg/ml), sucrose (80 mg/ml), sodium citrate 2-hydrate (2.7 mg/ml), citric acid anhydrous (0.146 mg/ml), pH 6.5. |
| B6 | Sucrose (70 mg/ml), glacial acetic acid (0.12 mg/ml), sodium acetate 3-hydrate (2.45 mg/ml), pH 5.3. |
| D1 | Polysorbate 80 (0.05 mg/ml), sucrose (50 mg/ml), sodium phosphate monobasic 1-hydrate (0.22 mg/ml), sodium phosphate dibasic anhydrous (0.49 mg/ml), pH 7.2. |

After dialysis with the aforementioned buffers, precipitation was evident in most of the conditions, including the sodium bicarbonate control (Table 10). However, T22-NIDOmut2-H6 and T22-NIDOmut3-H6 remained highly soluble in buffer B6 while buffer A9 proved to be the best suited for T22-NIDOmut5-H6.

TABLE 10

Soluble protein loss due to precipitation evaluating the FDA-approved buffers.

| Sample | Buffer | % Precipitation (Bradford) | % Precipitation (Nanodrop) |
|---|---|---|---|
| T22-NIDOmut2-H6 | Carbonate | 17.6 | 23.9 |
| | A9 | 12.7 | 29.0 |
| | B6 | None | None |
| | D1 | 84.1 | 86.5 |
| T22-NIDOmut3-H6 | Carbonate | 17.6 | 24.5 |
| | A9 | 10.25 | 15.4 |
| | B6 | 5.4 | None |
| | D1 | 83.6 | 84.3 |
| T22-NIDOmut5-H6 | Carbonate | 60.4 | 24.2 |
| | A9 | None | None |
| | B6 | 15.4 | 26.6 |
| | D1 | 50.1 | 62.4 |

Figure 18:
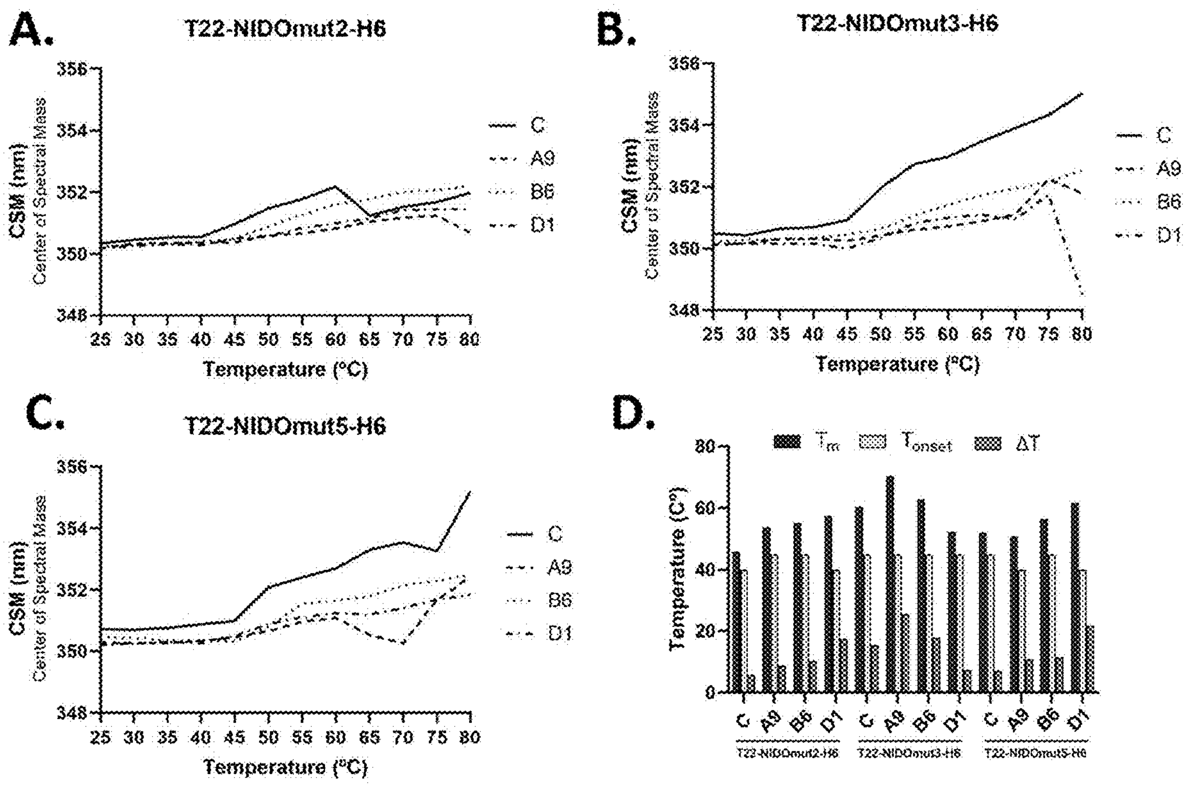
FIG. 18 Panels A-C show CSM profiles of T22-NIDOmut2-H6, T22-NIDOmut3-H6 and T22-NIDOmut5-H6 in carbonate buffer and three FDA-approved buffers (A9, B6, D1). Panel D. Graphical representation of key indicators (Tm, Tonset and ΔT) for each of the tested buffers.

Intrinsic fluorescence of each protein was used to assess unfolding parameters linked to temperature. CSM profiles (FIG. 18, Panels A to C) suggested that all three FDA-approved buffers contributed to a better stability of the protein than the regular carbonate buffer (133 mM NaCO3H, pH 8). This trend is evident in Panels A-C, where the continuous line belonging to carbonate buffer (C) is maintained at higher CSM values than the rest of buffers throughout most temperature points. This trend indicates that buffers A9, B6 and D1 retain the proteins in a more compact state. To assess which buffers are actually providing better stability to each of the proteins, key indicators were extracted from each CSM graph and represented in FIG. 18, Panel D. Ideal candidates should exhibit high values of all three indexes Tm, Tonset and ΔT. Comparing the 3 protein candidates, T22-NIDOmut3-H6 shows the highest values, firstly for buffer A9 and secondly for B6. Considering together precipitation and stability data the best choice for this protein is buffer B6, with good stability indices and showing almost no precipitation in dialysis. Second protein with better stability indexes is T22-NIDOmut5-H6, delivering buffer D1 with the best profile in terms of stability and precipitation.

Example 11-Drug Conjugates

Figure 19:
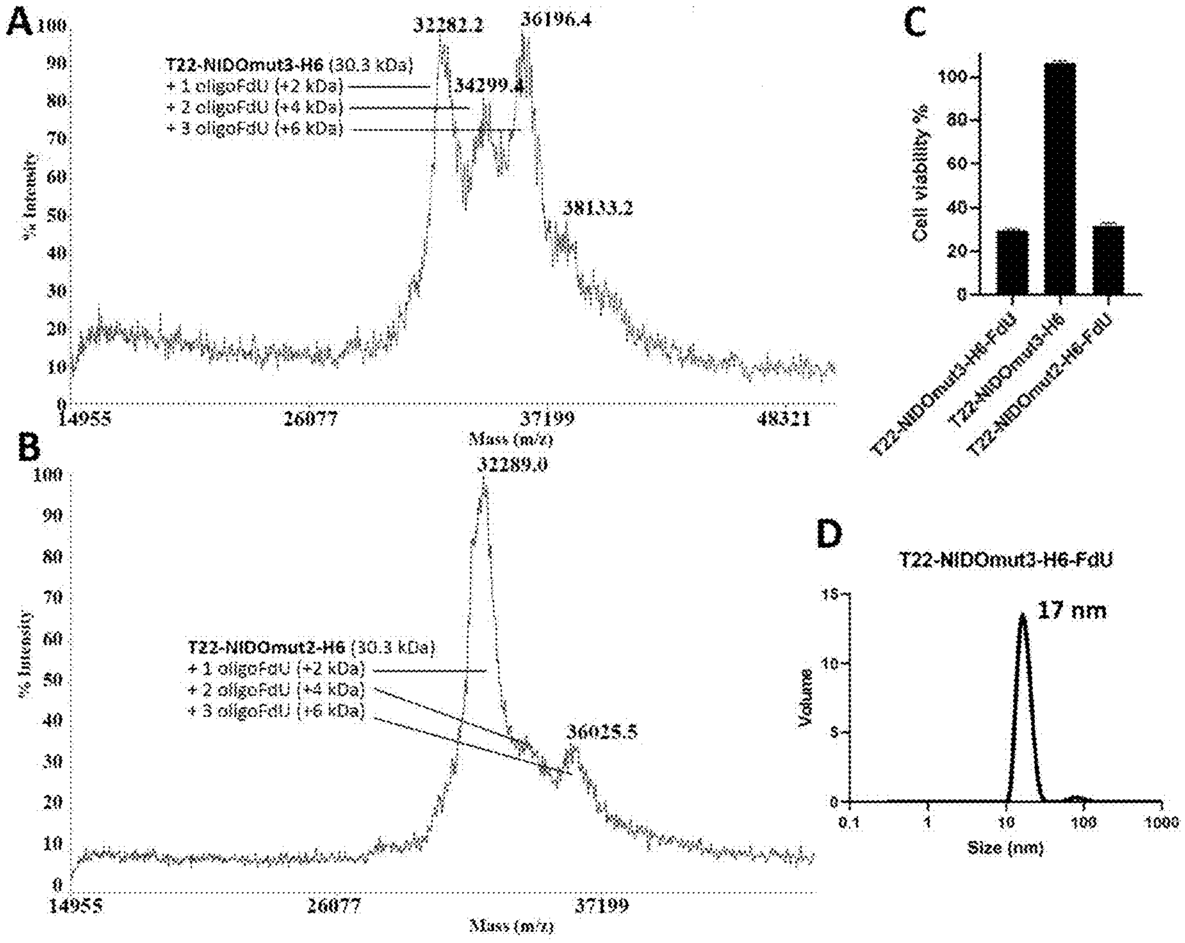
FIG. 19 Panels A-B show the MALDI-TOF mass spectrometry spectrum of T22-NIDOmut3-H6-FdU and T22-NIDOmut2-H6-FdU. Each peak with additional 2 kDa over the protein weight (30.3 kDa) belongs to a conjugated protein with an extra oligoFdU attached. Panel C. Cytotoxicity assay after 48 h incubation of the T22-NIDOmut3-H6-FdU nanoconjugate along with a non-conjugated negative control and the reference T22-NIDOmut2-H6-FdU positive control. Panel D. Volume size distribution of T22-NIDOmut3-H6-FdU.

T22-NIDOmut3-H6 and T22-NIDOmut2-H6 were conjugated to oligoFdU using a similar procedure and identical molar ratios. OligoFdU and protein quantification of the clean conjugated samples indicated payloads of 1.79 and 0.96 FdU/protein, respectively for T22-NIDOmut3-H6 and T22-NIDOmut2-H6. Payload estimation and conjugation efficacy were confirmed via MALDI-TOF (FIG. 19, Panels A and B). Both nanoconjugates had similar cytotoxic efficacy in vitro (CXCR4+ HeLa cell line, at 25 nM concentration of nanoconjugate drug). Remarkably, the same protein concentration of non-conjugated protein T22-Nidomut3-H6 did not cause any cytoxicity (FIG. 19, Panel C). 22-NIDOmut3-H6-FdU assembly into nanoparticles is attained in carbonate buffer with 2 mM $ZnCl_2$; nanoparticle size remains at 17 nm as seen with the non-conjugated version of the protein (FIG. 19, Panel D).

Example 12. Nanoparticle EPIX4-RK-GFP-H6

The capacity of the human ligand EPI-X4 was tested as a tumour-homing peptide in protein-based self-assembling nanoparticles, and also, its potential, together with T22, to form biparatopic nanoparticles to target and internalize into CXCR4-overexpressing tumour cells.

To address this purpose, we have performed a rational protein design to display the EPI-X4 peptidic sequence (FIG. 20, Panel A), with the aim to generate self-assembling protein vehicles with suitable size for cancer therapy. An optimized EPI-X4 tandem version with higher receptor affinity and serum stability was placed at the N-terminal of H6-tagged GFP. The combination of a cationic peptide at amino terminus plus the polyhistidine (H6) carboxy terminal favors the controlled protein assembling in nanoparticles of around 10-80 nm in size, via divalent cation coordination; ideal size for improving enhanced permeability and retention (EPR) effect and cell uptake, but also to minimize renal filtration (kidney cut-off around 6-8 nm). The EPI-X4 polypeptidic sequence has only 25% of cationic residues. Therefore, additional cationic amino acids (RKRKRK) [21] were incorporated into EPI-X4 to reach the 50% in an alternative presentation of EPI-X4 (FIG. 20, Panel A).

Figure 20:
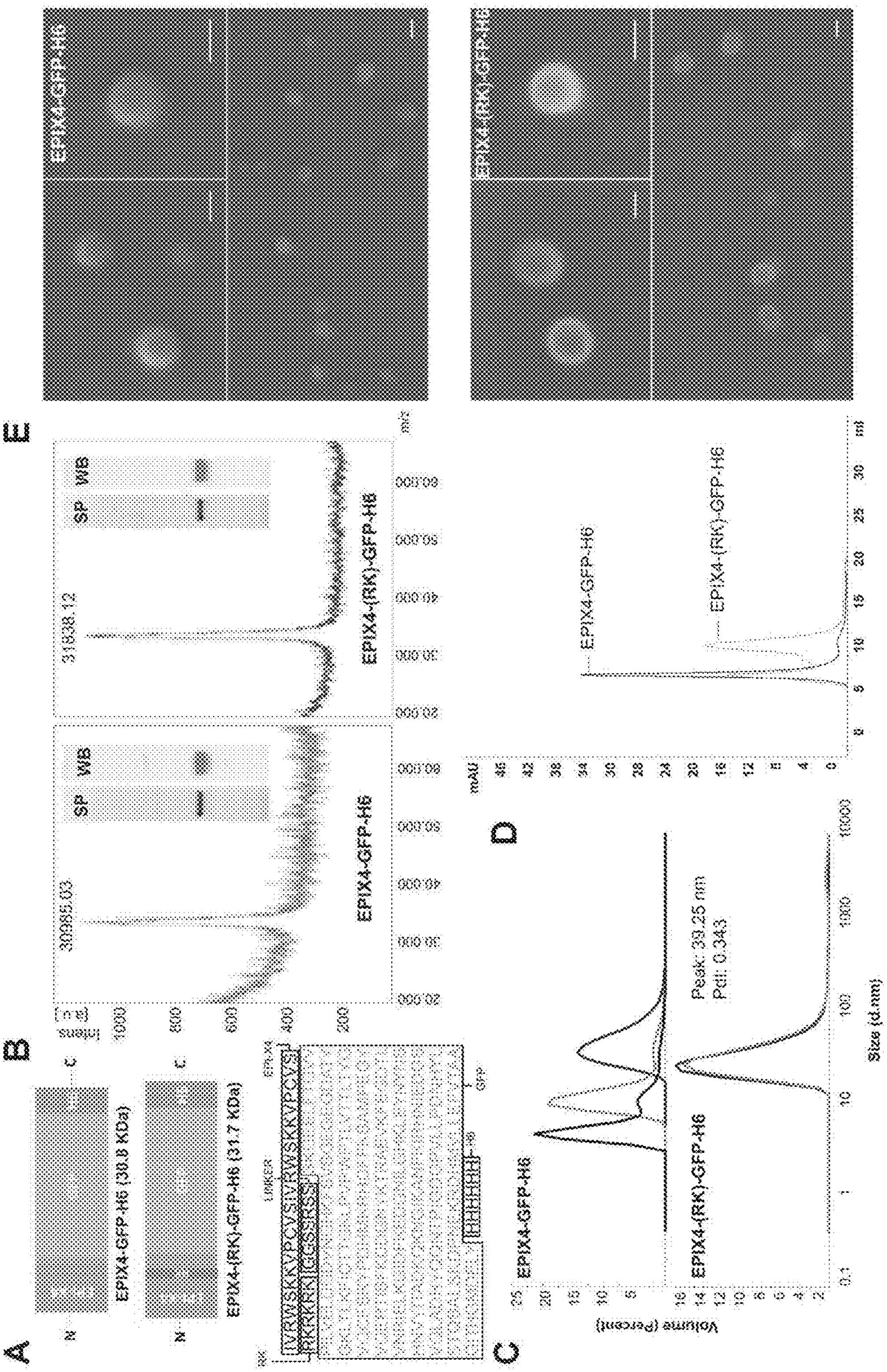
FIG. 20 shows structural and functional characterization of EPI-X4-based NPs. Panel A. Scheme of the modular protein EPIX4-GFP-H6 (top) and EPIX4-(RK)-GFP-H6 (down) and amino acid sequence of the second one. Panel B. Mass spectroscopy analysis of EPIX4-GFP-H6 (left) and EPIX4-(RK)-GFP-H6 (right). The molecular mass of proteins upon purification is shown by SDS-PAGE and Western blot (Anti-His). Panel C. Hydrodynamic size and pdi (polydispersion index), determined by Dynamic Light Scattering (DLS). Values of peak size (mean) are indicated (in nm). Panel D. Size exclusion chromatography (SEC) of EPIX4-GFP-H6 (black) and EPIX4-(RK)-GFP-H6 (grey) using a Superdex 200 increase 10/300GL column E. Representative FESEM (direct deposition) of EPIX4-GFP-H6 (top) and EPIX4-(RK)-GFP-H6 (down) protein NPs. Size bars represent 50 nm. Panel E. Confocal images of HeLa cells exposed to EPIX4-GFP-H6 (top) and EPIX4-(RK)-GFP-H6 (bottom) for 24 h, showing cell nuclei, cell membrane, and internalized NPs. Size bars represent 10 μm. All data are presented as mean±SEM.

Two versions of the protein (namely EPIX4-GFP-H6 and EPIX4-(RK)-GFP-H6) were efficiently produced in *Escherichia coli* and purified as pure full-length polypeptides with expected molecular masses (FIG. 20, Panel B). While the parental version (EPIX4-GFP-H6) reached an unstable oligomerization in form of nanoparticulate entities of different sizes (from monomeric or dimeric forms of 4.8-8 nm to nanoparticles of 10 and 50 nm), the protein version carrying the extra cationic sequence (EPIX4-(RK)-GFP-H6) spontaneously self-assembled as regular nanoparticles of around 40 nm (Pdi=0.343) (FIG. 20, Panels C and D). In agreement, and fully supporting these results, FESEM examinations showed toroid (ring-shaped) materials with ultrastructural morphometry (FIG. 20, Panel E), that confirmed the measurements obtained by Dynamic light scattering (DLS) and Size-exclusion chromatography (SEC).

When exposed to cultured CXCR4+ HeLa cells, only EPIX4-(RK)-GFP-H6 efficiently penetrated target cells and accumulated intracellularly by a specific receptor entry, that was confirmed through its inhibition by the chemical CXCR4 antagonist AMD3100 (FIG. 20, Panel F). In addition, confocal images fully supported these data, showing the intracellular location of EPIX4-(RK)-GFP-H6 without protein attached to the cell membrane (FIG. 20, Panel G). EPIX-4 ligand has been previously described as receptor internalization antagonist by its interaction with the CXCR4 second extracellular loop. The rational addition of a cationic sequence after EPIX-4 promotes protein self-assembling, and it also might mimic the mechanism of action of the natural ligand (CXCL12). The interaction between a set of arginine residues and the CXCR4 N-terminal facilitates the rapid binding and efficient anchoring on the receptor, that favors cellular internalization.

Example 13. Biparatopic Nanoparticles

Figure 21:
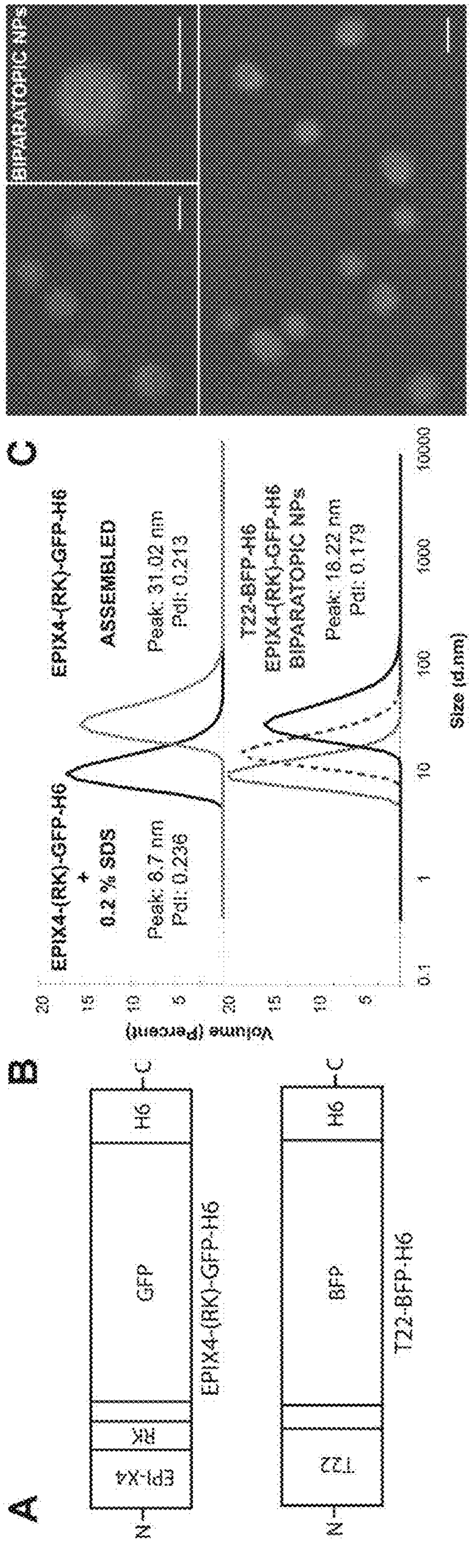
FIG. 21 shows biparatopic nanoparticles formation and characterization. Panel A. Scheme of the hybrid NPs forming proteins EPIX4-(RK)-GFP-H6 (top) and T22-BFP-H6 (down). Panel B. Controlled EPIX4-(RK)-GFP-H6 dissasembled by 0.2% SDS (black) and assembled removing SDS by dialysis (grey); determined by Dynamic Light Scattering (DLS) (top). Hydrodynamic size comparison of T22-BFP-H6 (grey), EPIX4-(RK)-GFP-H6 (black) and Biparatopic NP (dashed grey) (down). Values of peak size (mean) are indicated (in nm) and Pdi (polydispersion index). Panel C. Representative FESEM (direct deposition) of Biparatopic NPs. Size bars represent 50 nm. Panel D. FRET analysis of biparatopic NP formation. Samples of biparatopic NPs, T22-BFP-H6 and EPIX4-(RK)-GFP-H6 monomers mixture and T22-BFP-H6 and EPIX4-(RK)-GFP-H6 NPs mixture were excited with the 405 nm line and the emission was collected from 350-650 nm. BFP was used as donor fluorochrome and GFP as acceptor. Panel E. Time course kinetics of cell internalization of EPIX4-(RK)-GFP-H6, T22-GFP-H6 and Biparatopic NPs (1 μM) in CXCR4+ HeLa cells (left) and SW1417 (right). Intracellular fluorescence was corrected by specific fluorescence to render values representative of protein amounts. Significant differences ($p<0.05$) between Biparatopic NPs and both proteins forming them are depicted by *, significant differences between Biparatopic NPs and EPIX4-(RK)-GFP-H6 are depicted by #. Panel F. Uptake inhibition in Hela cells exposed to 1 μM for 1 h, mediated by the CXCR4 antagonist AMD3100 (always at an excess molar ratio of 10:1). & indicates significant difference between NPs and the inhibition promoted by AMD3100 ($p\leq0.001$).
Figure 21:
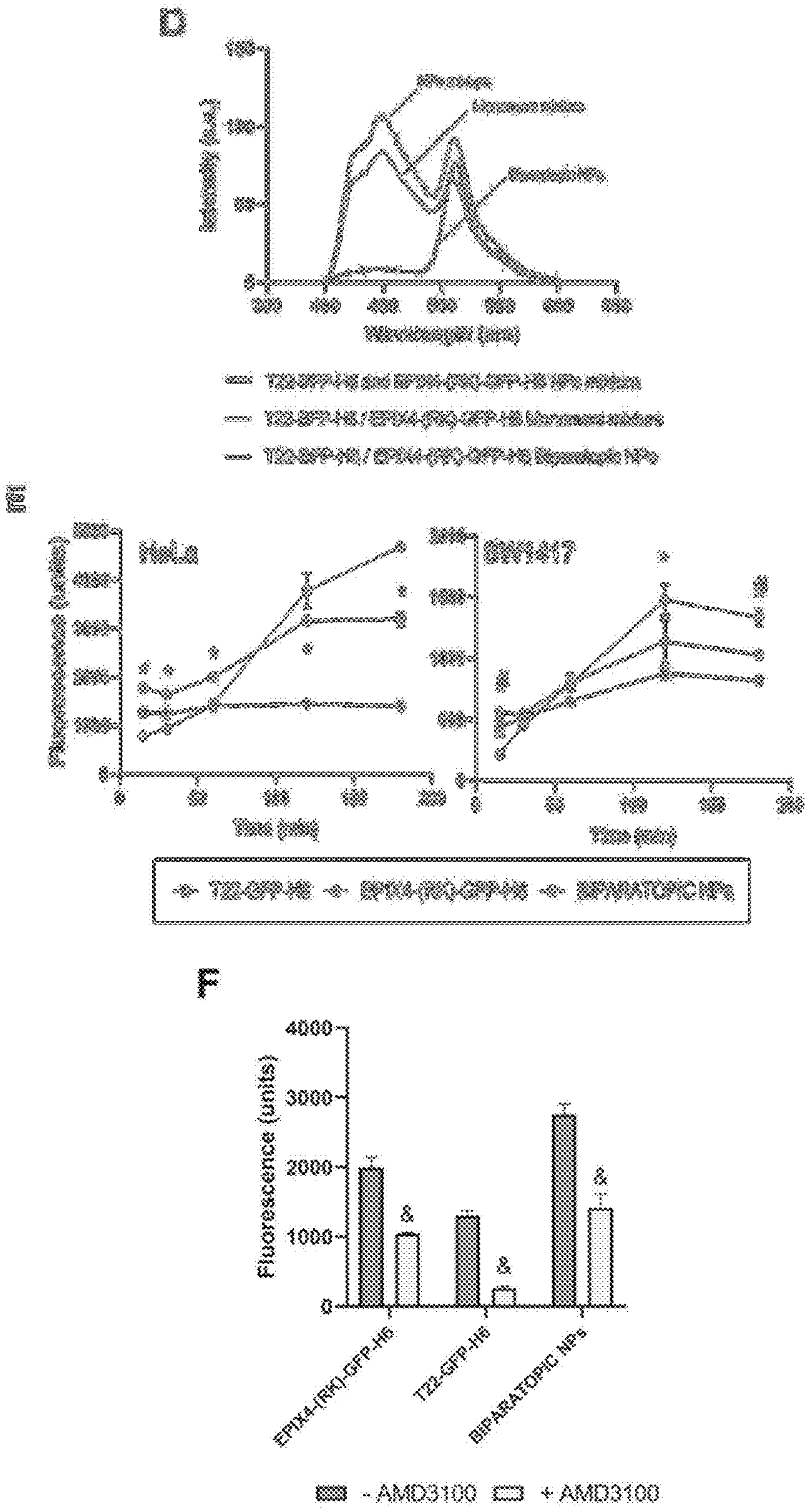

The combination of different cell-ligands in the same construct is an appealing approach in cancer therapy, which might dramatically increase cell specificity and avoid the development of drug resistance. EPIX4-(RK)-GFP-H6 protein nanoparticles could be disassembled to building blocks of 8.7 nm by using a mild detergent and reassembled by dialysis to materials of the same size of the parental nanoparticle (FIG. 21, Panel B). In addition, biparatopic nanoparticles were successfully generated by mixing disassembled entities of EPIX4-(RK)-GFP-H6 with T22-BFP-H6, both CXCR4-targeted proteins (FIG. 21, Panel A). The resulting biparatopic nanoparticles presented a monodisperse population (PdI=0.179) of about 18 nm (FIG. 21, Panel B) morphologically indistinguishable (FIG. 21, Panel C) from the original EPIX4-(RK)-GFP-H6 (FIG. 1, Panel E) or T22-BFP-H6 (U. Unzueta et al., Nanotechnology 2017, 28, 505102). Also, the presence of both proteins in the same entity was corroborated by Förster resonance energy transfer (FRET) (from blue to green fluorescence), as determined by comparing fluorescence emission scans of different protein monomers against biparatopic nanoparticles upon excitation at 387 nm. In this last case, when BFP is excited at 387 nm, the fluorescence emission energy of BFP is transferred to GFP chromophore only observing GFP fluorescence emission at 510 nm (FIG. 21, Panel D).

To evaluate the biological properties of biparatopic nanoparticles, CXCR4+ cells lines (the cervix cancer HeLa and the human colorectal SW1417 cell lines) were exposed at different times to the nanoparticles produced. Biparatopic nanoparticles keep the cell targeting properties (FIG. 21, Panel E) without losing receptor specificity (FIG. 21, Panel F). Regarding cell uptake, T22-GFP-H6 has high uptake at short times, while EPIX4-(RK)-GFP-H6 at longer times; biparatopic nanoparticles combine the uptake behavior of both, being the cell uptake even better at short times (FIG. 21, Panel E). Confocal microscopy confirms the cell internalization and green and blue proteins co-localization supports the occurrence of biparatopic nanoparticle formation.

Figure 22:
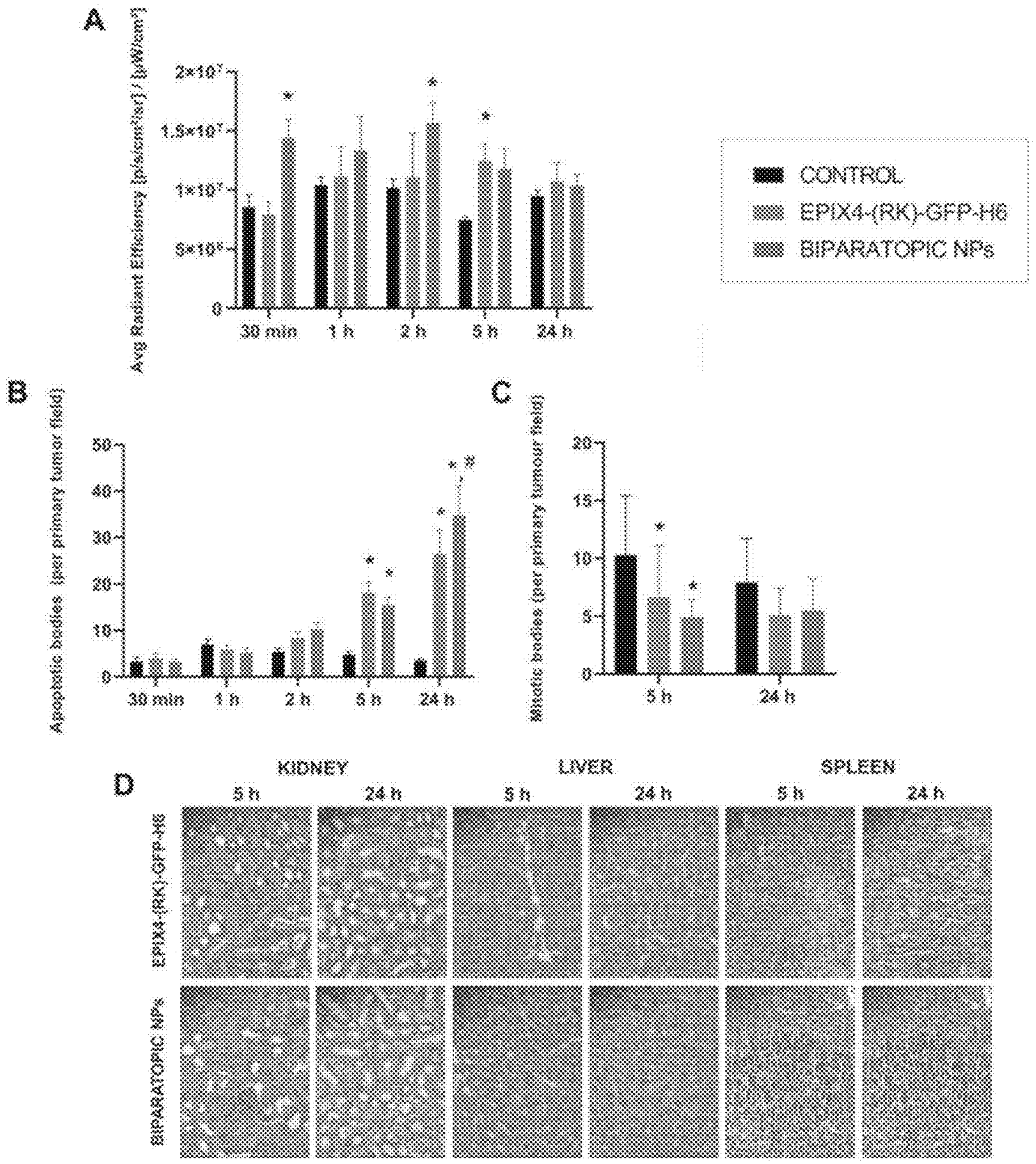
FIG. 22 shows in vivo biodistribution and toxicity assessment in a subcutaneous mouse model of CXCR4+human colorectal cancer. Panel A. Quantification of emitted fluorescence (measured as FLI ratio) at different times in tumours. Panel B. Number of apoptotic cell bodies after nanoparticle administration. Significant differences ($p<0.05$) between EPIX4-(RK)-GFP-H6 or Biparatopic NPs against the control are depicted by *, significant differences between Biparatopic NPs and EPIX4-(RK)-GFP-H6 are depicted by #. Panel C. Mitotic bodies after nanoparticles administration. Significant differences between EPIX4-(RK)-GFP-H6 or Biparatopic NPs against are depicted (* $p<0.05$). Panel D. Lack of systemic toxicity in kidney, liver, kidney and spleen by histological analysis of tissue sections (H&E) 5 and 24 h after treatment. All pictures were taken at 400×. All data are presented as mean±SEM

At this stage, to assess in detail the potential of the targeted nanoparticles, in vivo biodistribution analyses were performed in CXCR4+ mouse model of patient-derived M5 colorectal cancer. Upon systemic administration, mice were treated with a single dose of 200 μg at different times (0.5 1, 2, 5 and 24 h). Biparatopic nanoparticles elicited a much faster tumour accumulation than EPIX4-(RK)-GFP-H6 nanoparticles reaching higher levels of intracellular material at shorter times (from 0.5 to 2 h) as predicted by in vitro analysis (FIG. 21, Panel F). Meanwhile, EPIX4-(RK)-GFP-H6 showed a progressive accumulation, that peaked at 5 h, and remained relatively stable at least for 24 h (FIG. 22, Panel A). When analyzing normal tissues, fluorescence was undetectable in non-tumoral tissues for all nanoparticle versions, indicating the exquisite in vivo specificity of the CXCR4-targeting. Interestingly, the absence of fluorescence in kidney at longer times is an indicator that this heteromeric oligomeric platform retains the nanoparticle stability in vivo as the parental version does (Table 11). In addition, histopathological analyses corroborate the lack of systemic toxicity neither in CXCR4-tissues (kidney and liver) or CXCR4+ (spleen) (FIG. 22, Panel D).

In addition, throughout time, it was observed a dramatic increase of apoptotic events, with a drop in the number of mitotic cells in the tumour samples, being both significant at 5 h (FIG. 22, Panel C). The rapid uptake of biparatopic nanoparticles provoked higher levels of receptor internalization than the other material versions. This fact elicits a substantially higher number of apoptotic bodies at 24 h (FIG. 22, Panel B). Longer administration of these nanoparticles could trigger cell death by sustained caspase-3 activation (M. V. Céspedes et al., Sci Rep 2016, 6, 35765) which could also be enhanced by either chemotherapy conjugation (M. V. Céspedes, et al., EMBO Mol Med 2018, 10) or by toxic protein fusion. (R. Díaz et al., Small 2018, 14, e1800665; L. Sánchez-García et al., J Control Release 2018, 274, 81).

Taken together, all these observations strongly support the high potential of EPI-X4 as a human tumour-homing peptide. The proper protein engineering resulted into regular and stable protein nanoparticles with a potent CXCR4-targeting in vivo. In addition, the plasticity of this protein material permitted to combine with another CXCR4 targeted protein in a structurally robust biparatopic nanoparticle type, with high penetrability at short times and maintaining the parental specificity and biodistribution pattern.

Regarding the antitumor activity of the biparatopic nanoparticles, the results suggest that the multivalent display of the ligands EPI-X4 and T22, which are both CXCR4 antagonists, and most likely interact with different CXCR4 domains, are probably responsible for the faster rate of internalization and the enhanced induction of apoptosis in the biparatopic setting. Thus, the peak, reached 24 h post-treatment, of around 30 apoptotic figures per 400× magnification tumor field, are of a similar magnitude for cell death induction as shown in previous results in colorectal tumor models after treatment with nanoparticles based on T22 that incorporate potent cytotoxic agents, such as Floxuridine or the catalytic domain of bacterial toxins (L. Sánchez-García et al., J Control Release 2018, 274, 81; M. V. Céspedes, et al., J Control Release 2020, 320, 96).

TABLE 11

Biodistribution of CXCR4-targeted protein nanoparticles upon systemic administration. Fluorescence emitted by normal organs after the administration at the analyzed times of 300 μg of each nanoparticle, expressed as mean ± SE of radiant efficiency (×106; [p s −1 cm −2 sr −1)]/μW cm −2

| | 30 min | | 1 h | | 2 h | | 5 h | | 24 h | |
|---|---|---|---|---|---|---|---|---|---|---|
| | Liver | Kidney | Liver | Kidney | Liver | Kidney | Liver | Kidney | Liver | Kidney |
| CONTROL | 4.59 ± 0.9 | 3.24 ± 0.1 | 4.35 ± 0.0 | 3.62 ± 0.7 | 4.57 ± 0.2 | 3.73 ± 0.3 | 4.78 ± 0.3 | 4.3 ± 0.4 | 4.48 ± 1.3 | 4.48 ± 1.8 |
| EPIX4-(RK)-GFP-H6 | 7.14 ± 0.6 | 7.14 ± 0.7 | 4.93 ± 0.3 | 4.93 ± 0.4 | 4.46 ± 0.1 | 4.46 ± 0.4 | 4.53 ± 0.2 | 4.53 ± 2.2 | 5.36 ± 0.2 | 5.36 ± 2.2 |
| BIPARATOPIC NPs | 7.02 ± 0.5 | 7.02 ± 0.8 | 4.73 ± 0.2 | 4.73 ± 1.1 | 4.64 ± 0.4 | 4.64 ± 0.5 | 3.93 ± 0.3 | 3.93 ± 1.9 | 4.38 ± 2.0 | 4.38 ± 2.2 |

The invention claimed is:

1. A polypeptide variant of the G2 domain of nidogen-1 comprising the amino acid sequence set forth in SEQ ID NO: 94.

2. A conjugate comprising, (A) a polypeptide scaffold comprising (i) the polypeptide variant of the G2 domain of nidogen-1 of claim 1, (ii) a positively charged amino acid-rich region, and (iii) a polycationic peptide comprising a CXCR4 ligand, and (B) an anticancer agent conjugated to the polypeptide scaffold, wherein the CXCR4 ligand promotes internalization of the conjugate by cells expressing the CXCR4 receptor on their surface following binding of the conjugate to said receptor.

3. The conjugate of claim 2, wherein the CXCR4 ligand comprises the sequence RRWCYRKCYKGYCYRKCR (SEQ ID NO:25).

4. The conjugate of claim 2, wherein the positively charged amino acid-rich region is a polyhistidine region, wherein the polyhistidine region comprises 2-10 contiguous histidine residues.

5. The conjugate of claim 4, wherein the positively charged amino acid-rich region is a hexahistidine.

6. The conjugate of claim 2, wherein (i) the polycationic peptide is covalently attached to the N-terminus of the polypeptide variant of the G2 domain of nidogen-1, and the positively charged amino acid-rich region is covalently attached to the C-terminus of the polypeptide variant of the G2 domain of nidogen-1, or (ii) the positively charged amino acid-rich region is covalently attached to the N-terminus of the polypeptide variant of the G2 domain of nidogen-1, and the polycationic peptide is covalently attached to the C-terminus of the polypeptide variant of the G2 domain of nidogen-1.

7. The conjugate of claim 2, wherein the anticancer agent is conjugated to the polypeptide variant of the G2 domain of nidogen-1.

8. The conjugate of claim 2, wherein the anticancer agent is connected to the polypeptide variant of the G2 domain of nidogen-1 via a linker moiety.

9. The conjugate of claim 8, wherein the linker moiety comprises a protease cleavage site.

10. The conjugate of claim 2, wherein the anticancer agent comprises a microtubule-disrupting agent.

11. The conjugate of claim 10, wherein the microtubule-disrupting agent targets the Vinca alkaloid site of microtubules.

12. The conjugate of claim 10, wherein the microtubule-disrupting agent is a dolastatin.

13. The conjugate of claim 10, wherein the microtubule-disrupting agent is an auristatin.

14. A nanoparticle comprising multiple copies of the conjugate of claim 2.

15. A pharmaceutical composition comprising the conjugate of claim 2.

16. A method of treatment of cancer in a subject in need thereof comprising administering to said subject a therapeutically effective amount of a composition comprising the conjugate of claim 2, wherein the cancer comprises cancer cells that express CXCR4 or overexpress CXCR4.

17. The method of claim 16, wherein the cancer cells that express CXCR4 or overexpress CXCR4 are metastatic stem cells.

18. The method of claim 16, wherein the cancer is a primary tumor or a metastasis.

19. A conjugate comprising, (A) a polypeptide scaffold comprising, from N-terminus to C-terminus, (i) a CXCR4 ligand comprising the sequence RRWCYRKCYKGYCYRKCR (SEQ ID NO: 25), wherein the CXCR4 ligand promotes internalization of the conjugate by cells expressing the CXCR4 receptor on their surface following binding of the CXCR4 ligand to said receptor;

(ii) a polypeptide sequence variant of the G2 domain of nidogen-1 comprising the amino acid sequence set forth in SEQ ID NO:94; and, (iii) a positively charged amino acid-rich region, wherein the positively charged amino acid-rich region is a hexahistidine (SEQ ID NO:73); and, (B) at least one conjugated anticancer agent.

20. The conjugate of claim 19, wherein a linker comprising an amino acid sequence GGSSRSS (SEQ ID NO: 39) is interposed between (i) and (ii), or a positively charged peptide comprising the amino acid sequence RKRKRK (SEQ ID NO: 77) and a linker comprising an amino acid sequence GGSSRSS (SEQ ID NO: 39) are interposed between (i) and (ii).

21. The conjugate of claim 19, wherein a methionine is covalently attached to the N-terminus of the polypeptide scaffold.

22. The conjugate of claim 19, wherein the polypeptide scaffold comprises the polypeptide sequence set forth in SEQ ID NO: 113.

23. The conjugate of claim 19, wherein the at least one conjugated anticancer agent comprises a microtubule-disrupting agent.

24. The conjugate of claim 23, wherein the microtubule-disrupting agent targets the Vinca alkaloid site of microtubules.

25. The conjugate of claim 23, wherein the microtubule-disrupting agent comprises a dolastatin.

26. The conjugate of claim 23, wherein the microtubule-disrupting agent comprises an auristatin.

27. The conjugate of claim 19, wherein the anticancer agent is connected to the polypeptide scaffold via a linker moiety, wherein the linker moiety comprises a protease cleavage site.

28. A polynucleotide encoding the polypeptide scaffold of claim 1.

29. A vector comprising the polynucleotide of claim 28.

30. A host cell comprising the polynucleotide of claim 28.

* * * * *

SEQUENCE LISTING

```
Sequence total quantity: 133
SEQ ID NO: 1            moltype = AA  length = 6
FEATURE                 Location/Qualifiers
source                  1..6
                        mol_type = protein
                        note = Loop region AB
                        organism = synthetic construct
SEQUENCE: 1
GSSQVP                                                                6

SEQ ID NO: 2            moltype = AA  length = 4
FEATURE                 Location/Qualifiers
source                  1..4
                        mol_type = protein
                        note = Loop region BC
                        organism = synthetic construct
SEQUENCE: 2
MNHG                                                                  4

SEQ ID NO: 3            moltype = AA  length = 38
FEATURE                 Location/Qualifiers
source                  1..38
                        mol_type = protein
                        note = Loop region CD
                        organism = synthetic construct
SEQUENCE: 3
PETVGYSLLP LAPVGGIIGW MFAVEQDGFK NGFSITGG                             38

SEQ ID NO: 4            moltype = AA  length = 6
FEATURE                 Location/Qualifiers
source                  1..6
                        mol_type = protein
                        note = Loop region DE
                        organism = synthetic construct
SEQUENCE: 4
VGHPGN                                                                6

SEQ ID NO: 5            moltype = AA  length = 7
FEATURE                 Location/Qualifiers
source                  1..7
                        mol_type = protein
                        note = Loop region EF
                        organism = synthetic construct
SEQUENCE: 5
GIDEHGH                                                               7

SEQ ID NO: 6            moltype = AA  length = 7
FEATURE                 Location/Qualifiers
source                  1..7
                        mol_type = protein
                        note = Loop region FG
                        organism = synthetic construct
SEQUENCE: 6
PQIPFGS                                                               7

SEQ ID NO: 7            moltype = AA  length = 9
FEATURE                 Location/Qualifiers
source                  1..9
                        mol_type = protein
                        note = Loop region HI
                        organism = synthetic construct
SEQUENCE: 7
EPERDGASP                                                             9

SEQ ID NO: 8            moltype = AA  length = 15
FEATURE                 Location/Qualifiers
source                  1..15
                        mol_type = protein
                        note = Loop region IJ
                        organism = synthetic construct
SEQUENCE: 8
FQECVHDDSR PALPS                                                      15

SEQ ID NO: 9            moltype = AA  length = 5
FEATURE                 Location/Qualifiers
source                  1..5
                        mol_type = protein
                        note = Loop region JK
```

```
                        organism = synthetic construct
SEQUENCE: 9
NQEEK                                                              5

SEQ ID NO: 10           moltype = AA  length = 13
FEATURE                 Location/Qualifiers
source                  1..13
                        mol_type = protein
                        note = beta strand A
                        organism = synthetic construct
SEQUENCE: 10
QRVNGKVKGR IFV                                                     13

SEQ ID NO: 11           moltype = AA  length = 13
FEATURE                 Location/Qualifiers
source                  1..13
                        mol_type = protein
                        note = beta strand B
                        organism = synthetic construct
SEQUENCE: 11
IVFENTDLHS YVV                                                     13

SEQ ID NO: 12           moltype = AA  length = 7
FEATURE                 Location/Qualifiers
source                  1..7
                        mol_type = protein
                        note = beta strand C
                        organism = synthetic construct
SEQUENCE: 12
RSYTAIS                                                            7

SEQ ID NO: 13           moltype = AA  length = 10
FEATURE                 Location/Qualifiers
source                  1..10
                        mol_type = protein
                        note = beta strand D
                        organism = synthetic construct
SEQUENCE: 13
EFTRQAEVTF                                                         10

SEQ ID NO: 14           moltype = AA  length = 8
FEATURE                 Location/Qualifiers
source                  1..8
                        mol_type = protein
                        note = beta strand E
                        organism = synthetic construct
SEQUENCE: 14
LVIKQRFS                                                           8

SEQ ID NO: 15           moltype = AA  length = 11
FEATURE                 Location/Qualifiers
source                  1..11
                        mol_type = protein
                        note = beta strand F
                        organism = synthetic construct
SEQUENCE: 15
LTIDTELEGR V                                                       11

SEQ ID NO: 16           moltype = AA  length = 14
FEATURE                 Location/Qualifiers
source                  1..14
                        mol_type = protein
                        note = beta strand G
                        organism = synthetic construct
SEQUENCE: 16
SVHIEPYTEL YHYS                                                    14

SEQ ID NO: 17           moltype = AA  length = 13
FEATURE                 Location/Qualifiers
source                  1..13
                        mol_type = protein
                        note = beta strand H
                        organism = synthetic construct
SEQUENCE: 17
VITSSSTREY TVT                                                     13

SEQ ID NO: 18           moltype = AA  length = 13
FEATURE                 Location/Qualifiers
source                  1..13
```

```
                        mol_type = protein
                        note = beta strand I
                        organism = synthetic construct
SEQUENCE: 18
SRIYTYQWRQ TIT                                                      13

SEQ ID NO: 19           moltype = AA  length = 13
FEATURE                 Location/Qualifiers
source                  1..13
                        mol_type = protein
                        note = beta strand J
                        organism = synthetic construct
SEQUENCE: 19
TQQLSVDSVF VLY                                                      13

SEQ ID NO: 20           moltype = AA  length = 11
FEATURE                 Location/Qualifiers
source                  1..11
                        mol_type = protein
                        note = beta strand K
                        organism = synthetic construct
SEQUENCE: 20
ILRYALSNSI G                                                        11

SEQ ID NO: 21           moltype = AA  length = 6
FEATURE                 Location/Qualifiers
source                  1..6
                        mol_type = protein
                        note = alpha helical region 1
                        organism = synthetic construct
SEQUENCE: 21
TVGYSL                                                              6

SEQ ID NO: 22           moltype = AA  length = 9
FEATURE                 Location/Qualifiers
source                  1..9
                        mol_type = protein
                        note = alpha helical region 2
                        organism = synthetic construct
SEQUENCE: 22
PVGGIIGWM                                                           9

SEQ ID NO: 23           moltype = AA  length = 5
FEATURE                 Location/Qualifiers
source                  1..5
                        mol_type = protein
                        note = Alfa helical region 3
                        organism = synthetic construct
SEQUENCE: 23
GFSIT                                                               5

SEQ ID NO: 24           moltype = AA  length = 4
FEATURE                 Location/Qualifiers
source                  1..4
                        mol_type = protein
                        note = CalphaD loop region
                        organism = synthetic construct
SEQUENCE: 24
TIPE                                                                4

SEQ ID NO: 25           moltype = AA  length = 18
FEATURE                 Location/Qualifiers
source                  1..18
                        mol_type = protein
                        note = T22 peptide
                        organism = synthetic construct
SEQUENCE: 25
RRWCYRKCYK GYCYRKCR                                                 18

SEQ ID NO: 26           moltype = AA  length = 21
FEATURE                 Location/Qualifiers
source                  1..21
                        mol_type = protein
                        note = V1 peptide
                        organism = synthetic construct
SEQUENCE: 26
LGASWHRPDK CCLGYQKRPL P                                             21

SEQ ID NO: 27           moltype = AA  length = 67
```

```
FEATURE                Location/Qualifiers
source                 1..67
                       mol_type = protein
                       note = CXCL12 peptide
                       organism = synthetic construct
SEQUENCE: 27
KPVSLSYRCP CRFFESHVAR ANVKHLKILN TPNCALQIVA RLKNNNRQVC IDPKLKWIQE  60
YLEKALN                                                            67

SEQ ID NO: 28          moltype = AA  length = 68
FEATURE                Location/Qualifiers
source                 1..68
                       mol_type = protein
                       note = vCCL2 peptide
                       organism = synthetic construct
SEQUENCE: 28
LGASWHRPDK CCLGYQKRPL PQVLLSSWYP TSQLCSKPGV IFLTKRGRQV CADKDWVKKL  60
MQQLPVTA                                                           68

SEQ ID NO: 29          moltype = AA  length = 24
FEATURE                Location/Qualifiers
source                 1..24
                       mol_type = protein
                       note = Optimized EPI-X4
                       organism = synthetic construct
SEQUENCE: 29
IVRWSKKVPC VSIVRWSKKV PCVS                                         24

SEQ ID NO: 30          moltype = AA  length = 9
FEATURE                Location/Qualifiers
source                 1..9
                       mol_type = protein
                       note = Polycationic peptide
                       organism = synthetic construct
SEQUENCE: 30
RRRRRRRRR                                                          9

SEQ ID NO: 31          moltype = AA  length = 9
FEATURE                Location/Qualifiers
source                 1..9
                       mol_type = protein
                       note = Polycationic peptide
                       organism = synthetic construct
SEQUENCE: 31
RRRGRGRRR                                                          9

SEQ ID NO: 32          moltype = AA  length = 9
FEATURE                Location/Qualifiers
source                 1..9
                       mol_type = protein
                       note = Polycationic peptide
                       organism = synthetic construct
SEQUENCE: 32
RARGRGRRR                                                          9

SEQ ID NO: 33          moltype = AA  length = 9
FEATURE                Location/Qualifiers
source                 1..9
                       mol_type = protein
                       note = Polycationic peptide
                       organism = synthetic construct
SEQUENCE: 33
RARGRGGGA                                                          9

SEQ ID NO: 34          moltype = AA  length = 13
FEATURE                Location/Qualifiers
source                 1..13
                       mol_type = protein
                       note = A5G27
                       organism = synthetic construct
SEQUENCE: 34
RLVSYNGIIF FLK                                                     13

SEQ ID NO: 35          moltype = AA  length = 69
FEATURE                Location/Qualifiers
source                 1..69
                       mol_type = protein
                       note = FNI/II/V
                       organism = synthetic construct
```

```
SEQUENCE: 35
WQPPRARITG YIIKYEKPGS PPREVVPRPR PGVTEATITG LEPGTEYTIY VIALKNNQKS  60
EPLIGRKKT                                                          69

SEQ ID NO: 36           moltype = AA  length = 18
FEATURE                 Location/Qualifiers
source                  1..18
                        mol_type = protein
                        note = Seq-1-7
                        organism = synthetic construct
SEQUENCE: 36
KYLAYPDSVH IWRKRKRK                                                18

SEQ ID NO: 37           moltype = AA  length = 19
FEATURE                 Location/Qualifiers
source                  1..19
                        mol_type = protein
                        note = Seq-1-8
                        organism = synthetic construct
SEQUENCE: 37
KYLAYPDSVH IWRKRKRKR                                               19

SEQ ID NO: 38           moltype = AA  length = 22
FEATURE                 Location/Qualifiers
source                  1..22
                        mol_type = protein
                        note = Angiopep-2-7 peptide
                        organism = synthetic construct
SEQUENCE: 38
TFFYGGSRGK RNNFKTEEYR KR                                           22

SEQ ID NO: 39           moltype = AA  length = 7
FEATURE                 Location/Qualifiers
source                  1..7
                        mol_type = protein
                        note = Linker
                        organism = synthetic construct
SEQUENCE: 39
GGSSRSS                                                            7

SEQ ID NO: 40           moltype = AA  length = 5
FEATURE                 Location/Qualifiers
source                  1..5
                        mol_type = protein
                        note = Linker
                        organism = synthetic construct
SEQUENCE: 40
GGGNS                                                              5

SEQ ID NO: 41           moltype = AA  length = 14
FEATURE                 Location/Qualifiers
SITE                    3
                        note = X is L-3-(2-naphthyl)alanine
SITE                    8
                        note = X is D-Lysine
SITE                    12
                        note = X is L-Citrulline
source                  1..14
                        mol_type = protein
                        note = T140 peptide
                        organism = synthetic construct
SEQUENCE: 41
RRXCYRKXPY RXCR                                                    14

SEQ ID NO: 42           moltype = AA  length = 14
FEATURE                 Location/Qualifiers
SITE                    3
                        note = X is L-3-(2-naphthyl)alanine
SITE                    6
                        note = X is L-Citrulline
SITE                    8
                        note = X is D-Lysine
SITE                    12
                        note = X is is L-Citrulline
source                  1..14
                        mol_type = protein
                        note = TN14003 peptide
                        organism = synthetic construct
SEQUENCE: 42
```

```
RRXCYXKXPY RXCR                                                    14

SEQ ID NO: 43          moltype = AA  length = 14
FEATURE                Location/Qualifiers
SITE                   3
                       note = X is L-3-(2-naphthyl)alanine
SITE                   8
                       note = X is D-Citrulline
SITE                   12
                       note = X is L-Citrulline
source                 1..14
                       mol_type = protein
                       note = TC14012 peptide
                       organism = synthetic construct
SEQUENCE: 43
RRXCYEKXPY RXCR                                                    14

SEQ ID NO: 44          moltype = AA  length = 14
FEATURE                Location/Qualifiers
SITE                   3
                       note = X is L-3-(2-naphthyl)alanine
SITE                   6
                       note = X is  L-Citrulline
SITE                   8
                       note = X is D-Glutamic acid
SITE                   12
                       note = X is  L-Citrulline
source                 1..14
                       mol_type = protein
                       note = TE14011 peptide
                       organism = synthetic construct
SEQUENCE: 44
RRXCYXKXPY RXCR                                                    14

SEQ ID NO: 45          moltype = AA  length = 14
FEATURE                Location/Qualifiers
SITE                   3
                       note = X is L-3-(2)-naphthyl)alanine
SITE                   6
                       note = X is L-Citrulline
SITE                   8
                       note = X is D-Lysine
SITE                   12
                       note = X is L-Citrulline
source                 1..14
                       mol_type = protein
                       note = TZ14011 peptide
                       organism = synthetic construct
SEQUENCE: 45
RRXCYXKXPY RXCR                                                    14

SEQ ID NO: 46          moltype = AA  length = 20
FEATURE                Location/Qualifiers
source                 1..20
                       mol_type = protein
                       note = GW-H1 peptide
                       organism = synthetic construct
SEQUENCE: 46
GYNYAKKLAN LAKKFANALW                                              20

SEQ ID NO: 47          moltype = AA  length = 31
FEATURE                Location/Qualifiers
source                 1..31
                       mol_type = protein
                       note = Nucleolin binding peptide
                       organism = synthetic construct
SEQUENCE: 47
KDEPQRRSAR LSAKPAPPKP EPKPKKAPAK K                                 31

SEQ ID NO: 48          moltype = AA  length = 39
FEATURE                Location/Qualifiers
source                 1..39
                       mol_type = protein
                       note = Nucleolin-binding peptide
                       organism = synthetic construct
SEQUENCE: 48
KDEPQRRSAR LSAKPAPPKP EPKPKKAPAK KRKRKRKRK                         39

SEQ ID NO: 49          moltype = AA  length = 14
```

```
FEATURE                Location/Qualifiers
source                 1..14
                       mol_type = protein
                       note = Linker region
                       organism = synthetic construct
SEQUENCE: 49
SGGTSGSTSG TGST                                                14

SEQ ID NO: 50          moltype = AA  length = 15
FEATURE                Location/Qualifiers
source                 1..15
                       mol_type = protein
                       note = Linker region
                       organism = synthetic construct
SEQUENCE: 50
AGSSTGSSTG PGSTT                                               15

SEQ ID NO: 51          moltype = AA  length = 7
FEATURE                Location/Qualifiers
source                 1..7
                       mol_type = protein
                       note = Linker region
                       organism = synthetic construct
SEQUENCE: 51
GGSGGAP                                                        7

SEQ ID NO: 52          moltype = AA  length = 8
FEATURE                Location/Qualifiers
source                 1..8
                       mol_type = protein
                       note = Linker region
                       organism = synthetic construct
SEQUENCE: 52
GGGVEGGG                                                       8

SEQ ID NO: 53          moltype = AA  length = 10
FEATURE                Location/Qualifiers
source                 1..10
                       mol_type = protein
                       note = Linker region
                       organism = synthetic construct
SEQUENCE: 53
PKPSTPPGSS                                                     10

SEQ ID NO: 54          moltype = AA  length = 11
FEATURE                Location/Qualifiers
source                 1..11
                       mol_type = protein
                       note = Linker region
                       organism = synthetic construct
SEQUENCE: 54
APAETKAEPM T                                                   11

SEQ ID NO: 55          moltype = AA  length = 5
FEATURE                Location/Qualifiers
source                 1..5
                       mol_type = protein
                       note = Cleavage site
                       organism = synthetic construct
SEQUENCE: 55
AAALE                                                          5

SEQ ID NO: 56          moltype = AA  length = 5
FEATURE                Location/Qualifiers
source                 1..5
                       mol_type = protein
                       note = Cleavage site
                       organism = synthetic construct
SEQUENCE: 56
DDDDK                                                          5

SEQ ID NO: 57          moltype = AA  length = 5
FEATURE                Location/Qualifiers
source                 1..5
                       mol_type = protein
                       note = Cleavage site
                       organism = synthetic construct
SEQUENCE: 57
IEDGR                                                          5
```

```
SEQ ID NO: 58          moltype = AA  length = 6
FEATURE                Location/Qualifiers
source                 1..6
                       mol_type = protein
                       note = Cleavage site
                       organism = synthetic construct
SEQUENCE: 58
LVPRGS                                                    6

SEQ ID NO: 59          moltype = AA  length = 7
FEATURE                Location/Qualifiers
source                 1..7
                       mol_type = protein
                       note = Cleavage site
                       organism = synthetic construct
SEQUENCE: 59
ENLYFQG                                                   7

SEQ ID NO: 60          moltype = AA  length = 8
FEATURE                Location/Qualifiers
source                 1..8
                       mol_type = protein
                       note = Cleavage site
                       organism = synthetic construct
SEQUENCE: 60
LEVLFQGP                                                  8

SEQ ID NO: 61          moltype = AA  length = 270
FEATURE                Location/Qualifiers
source                 1..270
                       mol_type = protein
                       note = T22-NidMut-H6
                       organism = synthetic construct
SEQUENCE: 61
RRWCYRKCYK GYCYRKCRGG SSRSSSPQRV NGKVKGRIFV GSSQVPIVFE NTDLASYVVM  60
NHGNSYTAIS TIPETVGYSL LPLAPVGGII GWMFAVEQDG FKNGFSITGG EFTRQAEVTF  120
VGHPGNLVIK QRFSGIDEHG HLTIDTELEG RVPQIPFGSS VHIEPYTELY HYSTSVITSS  180
STREYTVTEP ERDGASPSRI YTYQWRQTIT FQECVHDDSR PALPSTQQLS VDSVSVLYNQ  240
EEKILAYALS NSIGPVREGS PDAKHHHHHH                                   270

SEQ ID NO: 62          moltype = AA  length = 238
FEATURE                Location/Qualifiers
source                 1..238
                       mol_type = protein
                       note = Nidogen G2 domain
                       organism = synthetic construct
SEQUENCE: 62
SPQRVNGKVK GRIFVGSSQV PIVFENTDLH SYVVMNHGRS YTAISTIPET VGYSLLPLAP  60
VGGIIGWMFA VEQDGFKNGF SITGGEFTRQ AEVTFVGHPG NLVIKQRFSG IDEHGHLTID  120
TELEGRVPQI PFGSSVHIEP YTELYHYSTS VITSSSTREY TVTEPERDGA SPSRIYTYQW  180
RQTITFQECV HDDSRPALPS TQQLSVDSVF VLYNQEEKIL RYALSNSIGP VREGSPDA    238

SEQ ID NO: 63          moltype = AA  length = 236
FEATURE                Location/Qualifiers
source                 1..236
                       mol_type = protein
                       note = Human nidogen G2 domain (truncated)
                       organism = synthetic construct
SEQUENCE: 63
QRVNGKVKGR IFVGSSQVPI VFENTDLHSY VVMNHGRSYT AISTIPETVG YSLLPLAPVG  60
GIIGWMFAVE QDGFKNGFSI TGGEFTRQAE VTFVGHPGNL VIKQRFSGID EHGHLTIDTE  120
LEGRVPQIPF GSSVHIEPYT ELYHYSTSVI TSSSTREYTV TEPERDGASP SRIYTYQWRQ  180
TITFQECVHD DSRPALPSTQ QLSVDSVFVL YNQEEKILRY ALSNSIGPVR EGSPDA      236

SEQ ID NO: 64          moltype = AA  length = 238
FEATURE                Location/Qualifiers
source                 1..238
                       mol_type = protein
                       note = Human nidogen G2 domain with H459A., R468N, F639S
                        and R650A mutations
                       organism = synthetic construct
SEQUENCE: 64
SPQRVNGKVK GRIFVGSSQV PIVFENTDLA SYVVMNHGNS YTAISTIPET VGYSLLPLAP  60
VGGIIGWMFA VEQDGFKNGF SITGGEFTRQ AEVTFVGHPG NLVIKQRFSG IDEHGHLTID  120
TELEGRVPQI PFGSSVHIEP YTELYHYSTS VITSSSTREY TVTEPERDGA SPSRIYTYQW  180
RQTITFQECV HDDSRPALPS TQQLSVDSVS VLYNQEEKIL AYALSNSIGP VREGSPDA    238

SEQ ID NO: 65          moltype = AA  length = 236
```

```
FEATURE                 Location/Qualifiers
source                  1..236
                        mol_type = protein
                        note = Human nidogen G2 domain with H459A., R468N, F639S
                         and R650A mutations (truncated)
                        organism = synthetic construct
SEQUENCE: 65
QRVNGKVKGR IFVGSSQVPI VFENTDLASY VVMNHGNSYT AISTIPETVG YSLLPLAPVG  60
GIIGWMFAVE QDGFKNGFSI TGGEFTRQAE VTFVGHPGNL VIKQRFSGID EHGHLTIDTE  120
LEGRVPQIPF GSSVHIEPYT ELYHYSTSVI TSSSTREYTV TEPERDGASP SRIYTYQWRQ  180
TITFQECVHD DSRPALPSTQ QLSVDSVSVL YNQEEKILAY ALSNSIGPVR EGSPDA      236

SEQ ID NO: 66           moltype = AA  length = 270
FEATURE                 Location/Qualifiers
source                  1..270
                        mol_type = protein
                        note = T22-G2-H6
                        organism = synthetic construct
SEQUENCE: 66
RRWCYRKCYK GYCYRKCRGG SSRSSSPQRV NGKVKGRIFV GSSQVPIVFE NTDLHSYVVM  60
NHGRSYTAIS TIPETVGYSL LPLAPVGGII GWMFAVEQDG FKNGFSITGG EFTRQAEVTF  120
VGHPGNLVIK QRFSGIDEHG HLTIDTELEG RVPQIPFGSS VHIEPYTELY HYSTSVITSS  180
STREYTVTEP ERDGASPSRI YTYQWRQTIT FQECVHDDSR PALPSTQQLS VDSVFVLYNQ  240
EEKILRYALS NSIGPVREGS PDAKHHHHHH                                   270

SEQ ID NO: 67           moltype = AA  length = 210
FEATURE                 Location/Qualifiers
source                  1..210
                        mol_type = protein
                        organism = Homo sapiens
SEQUENCE: 67
MASGQGPGPP RQECGEPALP SASEEQVAQD TEEVFRSYVF YRHQQEQEAE GVAAPADPEM  60
VTLPLQPSST MGQVGRQLAI IGDDINRRYD SEFQTMLQHL QPTAENAYEY FTKIATSLFE  120
SGINWGRVVA LLGFGYRLAL HVYQHGLTGF LGQVTRFVVD FMLHHCIARW IAQRGGWVAA  180
LNLGNGPILN VLVVLGVVLL GQFVVRRFFK                                   210

SEQ ID NO: 68           moltype = AA  length = 15
FEATURE                 Location/Qualifiers
source                  1..15
                        mol_type = protein
                        note = BH3 domain
                        organism = synthetic construct
SEQUENCE: 68
VGRQLAIIGD DINRR                                                   15

SEQ ID NO: 69           moltype = AA  length = 193
FEATURE                 Location/Qualifiers
source                  1..193
                        mol_type = protein
                        organism = Homo sapiens
SEQUENCE: 69
MARARQEGSS PEPVEGLARD GPRPFPLGRL VPSAVSCGLC EPGLAAAPAA PTLLPAAYLC  60
APTAPPAVTA ALGGSRWPGG PRSRPRGPRP DGPQPSLSLA EQHLESPVPS APGALAGGPT  120
QAAPGVRGEE EQWAREIGAQ LRRMADDLNA QYERRRQEEQ QRHRPSPWRV LYNLIMGLLP  180
LPRGHRAPEM EPN                                                     193

SEQ ID NO: 70           moltype = AA  length = 187
FEATURE                 Location/Qualifiers
source                  1..187
                        mol_type = protein
                        organism = Corynebacterium diphtheriae
SEQUENCE: 70
GADDVVDSSK SFVMENFSSY HGTKPGYVDS IQKGIQKPKS GTQGNYDDDW KGFYSTDNKY  60
DAAGYSVDNE NPLSGKAGGV VKVTYPGLTK VLALKVDNAE TIKKELGLSL TEPLMEQVGT  120
EEFIKRFGDG ASRVVLSLPF AEGSSSVEYI NNWEQAKALS VELEINFETR GKRGQDAMYE  180
YMAQACA                                                            187

SEQ ID NO: 71           moltype = AA  length = 209
FEATURE                 Location/Qualifiers
source                  1..209
                        mol_type = protein
                        organism = Pseudomonas aeruginosa
SEQUENCE: 71
GDISFSTRGT QNWTVERLLQ AHRQLEERGY VFVGYHGTFL EAAQSIVFGG VRARSQDLDA  60
IWRGFYIAGD PALAYGYAQD QEPDARGRIR NGALLRVYVP RSSLPGFYRT GLTLAAPEAA  120
GEVERLIGHP LPLRLDAITG PEEEGGRLET ILGWPLAERT VVIPSAIPTD PRNVGGDLDP  180
SSIPDKEQAI SALPDYASQP GKPPREDLK                                    209

SEQ ID NO: 72           moltype = AA  length = 1247
```

```
FEATURE                 Location/Qualifiers
source                  1..1247
                        mol_type = protein
                        organism = Homo sapiens
SEQUENCE: 72
MLASSSRIRA AWTRALLLPL LLAGPVGCLS RQELFPFGPG QGDLELEDGD DFVSPALELS  60
GALRFYDRSD IDAVYVTTNG IIATSEPPAK ESHPGLFPPT FGAVAPFLAD LDTTDGLGKV  120
YYREDLSPSI TQRAAECVHR GFPEISFQPS SAVVVTWESV APYQGPSRDP DQKGKRNTFQ  180
AVLASSDSSS YAIFLYPEDG LQFHTTFSKK ENNQVPAVVA FSQGSVGFLW KSNGAYNIFA  240
NDRESVENLA KSSNSGQQGV WVFEIGSPAT TNGVVPADVI LGTEDGAEYD DEDEDYDLAT  300
TRLGLEDVGT TPFSYKALRR GGADTYSVPS VLSPRRAATE RPLGPPTERT RSFQLAVETF  360
HQQHPQVIDV DEVEETGVVF SYNTDSRQTC ANNRHQCSVH AECRDYATGF CCSCVAGYTG  420
NGRQCVAEGS PQRVNGKVKG RIFVGSSQVP IVFENTDLHS YVVMNHGRSY TAISTIPETV  480
GYSLLPLAPV GGIIGWMFAV EQDGFKNGFS ITGGEFTRQA EVTFVGHPGN LVIKQRFSGI  540
DEHGHLTIDT ELEGRVPQIP FGSSVHIEPY TELYHYSTSV ITSSSTREYT VTEPERDGAS  600
PSRIYTYQWR QTITFQECVH DDSRPALPST QQLSVDSVFV LYNQEEKILR YALSNSIGPV  660
REGSPDALQN PCYIGTHGCD TNAACRPGPR TQFTCECSIG FRGDGRTCYD IDECSEQPSV  720
CGSHTICNNH PGTFRCECVE GYQFSDEGTC VAVVDQRPIN YCETGLHNCD IPQRAQCIYT  780
GGSSYTCSCL PGFSGDGQAC QDVDECQPSR CHPDAFCYNT PGSFTCQCKP GYQGDGFRCV  840
PGEVEKTRCQ HEREHILGAA GATDPQRPIP PGLFVPECDA HGHYAPTQCH GSTGYCWCVD  900
RDGREVEGTR TRPGMTPPCL STVAPPIHQG PAVPTAVIPL PPGTHLLFAQ TGKIERLPLE  960
GNTMRKTEAK AFLHVPAKVI IGLAFDCVDK MVYWTDITEP SIGRASLHGG EPTTIIRQDL  1020
GSPEGIAVDH LGRNIFWTDS NLDRIEVAKL DGTQRRVLFE TDLVNPRGIV TDSVRGNLYW  1080
TDWNRDNPKI ETSYMDGTNR RILVQDDLGL PNGLTFDAFS SQLCWVDAGT NRAECLNPSQ  1140
PSRRKALEGL QYPFAVTSYG KNLYFTDWKM NSVVALDLAI SKETDAFQPH KQTRLYGITT  1200
ALSQCPQGHN YCSVNNGGCT HLCLATPGSR TCRCPDNTLG VDCIEQK               1247

SEQ ID NO: 73           moltype = AA  length = 6
FEATURE                 Location/Qualifiers
source                  1..6
                        mol_type = protein
                        note = Hexahistidine tag
                        organism = synthetic construct
SEQUENCE: 73
HHHHHH                                                            6

SEQ ID NO: 74           moltype = AA  length = 7
FEATURE                 Location/Qualifiers
source                  1..7
                        mol_type = protein
                        note = IL-6 ligand
                        organism = synthetic construct
SEQUENCE: 74
LSLITRL                                                           7

SEQ ID NO: 75           moltype = AA  length = 31
FEATURE                 Location/Qualifiers
source                  1..31
                        mol_type = protein
                        note = IL-6 ligand
                        organism = synthetic construct
SEQUENCE: 75
WQDPHSWNSS FYRLRFELRY RAERSKTFTT W                                31

SEQ ID NO: 76           moltype = AA  length = 8
FEATURE                 Location/Qualifiers
source                  1..8
                        mol_type = protein
                        note = linker region
                        organism = synthetic construct
SEQUENCE: 76
GGSSRSSS                                                          8

SEQ ID NO: 77           moltype = AA  length = 6
FEATURE                 Location/Qualifiers
source                  1..6
                        mol_type = protein
                        note = positively charged peptide region
                        organism = synthetic construct
SEQUENCE: 77
RKRKRK                                                            6

SEQ ID NO: 78           moltype = AA  length = 6
FEATURE                 Location/Qualifiers
source                  1..6
                        mol_type = protein
                        note = positively charged peptide region
                        organism = synthetic construct
SEQUENCE: 78
```

```
RRRRRR                                                                 6

SEQ ID NO: 79          moltype = AA  length = 6
FEATURE                Location/Qualifiers
source                 1..6
                       mol_type = protein
                       note = positively charged peptide region
                       organism = synthetic construct
SEQUENCE: 79
KKKKKK                                                                 6

SEQ ID NO: 80          moltype = AA  length = 6
FEATURE                Location/Qualifiers
source                 1..6
                       mol_type = protein
                       note = Positively charged peptide region
                       organism = synthetic construct
SEQUENCE: 80
HHHHHH                                                                 6

SEQ ID NO: 81          moltype = AA  length = 6
FEATURE                Location/Qualifiers
source                 1..6
                       mol_type = protein
                       note = positively charged peptide region
                       organism = synthetic construct
SEQUENCE: 81
RHRHRH                                                                 6

SEQ ID NO: 82          moltype = AA  length = 8
FEATURE                Location/Qualifiers
source                 1..8
                       mol_type = protein
                       note = positively charged peptide region
                       organism = synthetic construct
SEQUENCE: 82
RKRKRKRK                                                               8

SEQ ID NO: 83          moltype = AA  length = 6
FEATURE                Location/Qualifiers
source                 1..6
                       mol_type = protein
                       note = positively charged peptide region
                       organism = synthetic construct
SEQUENCE: 83
RKRHRK                                                                 6

SEQ ID NO: 84          moltype = AA  length = 6
FEATURE                Location/Qualifiers
source                 1..6
                       mol_type = protein
                       note = positively charged peptide region
                       organism = synthetic construct
SEQUENCE: 84
RKRHRH                                                                 6

SEQ ID NO: 85          moltype = AA  length = 6
FEATURE                Location/Qualifiers
source                 1..6
                       mol_type = protein
                       note = positively charged peptide region
                       organism = synthetic construct
SEQUENCE: 85
RHRHRH                                                                 6

SEQ ID NO: 86          moltype = AA  length = 7
FEATURE                Location/Qualifiers
source                 1..7
                       mol_type = protein
                       note = positively charged peptide region
                       organism = synthetic construct
SEQUENCE: 86
RKRKRKR                                                                7

SEQ ID NO: 87          moltype = AA  length = 238
FEATURE                Location/Qualifiers
source                 1..238
                       mol_type = protein
                       note = NIDOmut3
```

```
                          organism = synthetic construct
SEQUENCE: 87
SPQRVNGKVK GRIFVGSSQV PIVFENTDLA SYVVMNHGNS YTAISTIPET VGYSLLPLAP  60
VGGIIGWMFA VEQDGFKNGF SITGGEFTRQ AEVTFVGHPG NLVIKQRFSG IDEKGNLTID  120
TELEGRVPQI PFGSSVHIEP YTELYHYSTS VITSSSTREY TVTEPERDGA SPSRIYTYQW  180
RQTITFQECV HDDSRPALPS TQQLSVDSVS VLYNQEEKIL AYALSNSIGP VREGSPDA    238

SEQ ID NO: 88             moltype = AA  length = 238
FEATURE                   Location/Qualifiers
source                    1..238
                          mol_type = protein
                          note = NIDOmut3_V45T
                          organism = synthetic construct
SEQUENCE: 88
SPQRVNGKVK GRIFVGSSQT PIVFENTDLA SYVVMNHGNS YTAISTIPET VGYSLLPLAP  60
VGGIIGWMFA VEQDGFKNGF SITGGEFTRQ AEVTFVGHPG NLVIKQRFSG IDEKGNLTID  120
TELEGRVPQI PFGSSVHIEP YTELYHYSTS VITSSSTREY TVTEPERDGA SPSRIYTYQW  180
RQTITFQECV HDDSRPALPS TQQLSVDSVS VLYNQEEKIL AYALSNSIGP VREGSPDA    238

SEQ ID NO: 89             moltype = AA  length = 238
FEATURE                   Location/Qualifiers
source                    1..238
                          mol_type = protein
                          note = NIDOmut3_V121Q
                          organism = synthetic construct
SEQUENCE: 89
SPQRVNGKVK GRIFVGSSQV PIVFENTDLA SYVVMNHGNS YTAISTIPET VGYSLLPLAP  60
VGGIIGWMFA VEQDGFKNGF SITGGEFTRQ AEVTFQGHPG NLVIKQRFSG IDEKGNLTID  120
TELEGRVPQI PFGSSVHIEP YTELYHYSTS VITSSSTREY TVTEPERDGA SPSRIYTYQW  180
RQTITFQECV HDDSRPALPS TQQLSVDSVS VLYNQEEKIL AYALSNSIGP VREGSPDA    238

SEQ ID NO: 90             moltype = AA  length = 238
FEATURE                   Location/Qualifiers
source                    1..238
                          mol_type = protein
                          note = NIDOmut3_F157E
                          organism = synthetic construct
SEQUENCE: 90
SPQRVNGKVK GRIFVGSSQV PIVFENTDLA SYVVMNHGNS YTAISTIPET VGYSLLPLAP  60
VGGIIGWMFA VEQDGFKNGF SITGGEFTRQ AEVTFVGHPG NLVIKQRFSG IDEKGNLTID  120
TELEGRVPQI PEGSSVHIEP YTELYHYSTS VITSSSTREY TVTEPERDGA SPSRIYTYQW  180
RQTITFQECV HDDSRPALPS TQQLSVDSVS VLYNQEEKIL AYALSNSIGP VREGSPDA    238

SEQ ID NO: 91             moltype = AA  length = 238
FEATURE                   Location/Qualifiers
source                    1..238
                          mol_type = protein
                          note = NIDOmut3_V215T
                          organism = synthetic construct
SEQUENCE: 91
SPQRVNGKVK GRIFVGSSQV PIVFENTDLA SYVVMNHGNS YTAISTIPET VGYSLLPLAP  60
VGGIIGWMFA VEQDGFKNGF SITGGEFTRQ AEVTFVGHPG NLVIKQRFSG IDEKGNLTID  120
TELEGRVPQI PFGSSVHIEP YTELYHYSTS VITSSSTREY TVTEPERDGA SPSRIYTYQW  180
RQTITFQECT HDDSRPALPS TQQLSVDSVS VLYNQEEKIL AYALSNSIGP VREGSPDA    238

SEQ ID NO: 92             moltype = AA  length = 238
FEATURE                   Location/Qualifiers
source                    1..238
                          mol_type = protein
                          note = Seq_93
                          organism = synthetic construct
SEQUENCE: 92
SPQRVNGKVK GRIFVGSSQT PIVFENTDLA SYVVMNHGNS YTAISTIPET VGYSLLPLAP  60
VGGIIGWMFA VEQDGFKNGF SITGGEFTRQ AEVTFQGHPG NLVIKQRFSG IDEKGNLTID  120
TELEGRVPQI PEGSSVHIEP YTELYHYSTS VITSSSTREY TVTEPERDGA SPSRIYTYQW  180
RQTITFQECT HDDSRPALPS TQQLSVDSVS VLYNQEEKIL AYALSNSIGP VREGSPDA    238

SEQ ID NO: 93             moltype = AA  length = 238
FEATURE                   Location/Qualifiers
source                    1..238
                          mol_type = protein
                          note = NIDOmut4_T215V
                          organism = synthetic construct
SEQUENCE: 93
SPQRVNGKVK GRIFVGSSQT PIVFENTDLA SYVVMNHGNS YTAISTIPET VGYSLLPLAP  60
VGGIIGWMFA VEQDGFKNGF SITGGEFTRQ AEVTFQGHPG NLVIKQRFSG IDEKGNLTID  120
TELEGRVPQI PEGSSVHIEP YTELYHYSTS VITSSSTREY TVTEPERDGA SPSRIYTYQW  180
RQTITFQECV HDDSRPALPS TQQLSVDSVS VLYNQEEKIL AYALSNSIGP VREGSPDA    238
```

```
SEQ ID NO: 94          moltype = AA  length = 238
FEATURE                Location/Qualifiers
source                 1..238
                       mol_type = protein
                       note = NIDOmut5
                       organism = synthetic construct
SEQUENCE: 94
SPQRVNGKVK GRIFVGSSQT PIVFENTDLA SYVVMNHGNS YTAISTIPET VGYSLLPLAP  60
VGGIIGWMFA VEQDGFKNGF SITGGEFTRQ AEVTFQGHPG NLVIKQRFSG IDEKGNLTID  120
TELEGRVPQI PEGSSVHIEP YTELYHYSTS VITSSSTREY TVTEPERDGA SPSRIYTYQW  180
RQTITFQEST HDDSRPALPS TQQLSVDSVS VLYNQEEKIL AYALSNSIGP VREGSPDA    238

SEQ ID NO: 95          moltype = AA  length = 238
FEATURE                Location/Qualifiers
source                 1..238
                       mol_type = protein
                       note = NIDOmut3_V176T
                       organism = synthetic construct
SEQUENCE: 95
SPQRVNGKVK GRIFVGSSQV PIVFENTDLA SYVVMNHGNS YTAISTIPET VGYSLLPLAP  60
VGGIIGWMFA VEQDGFKNGF SITGGEFTRQ AEVTFVGHPG NLVIKQRFSG IDEKGNLTID  120
TELEGRVPQI PFGSSVHIEP YTELYHYSTS TITSSSTREY TVTEPERDGA SPSRIYTYQW  180
RQTITFQECV HDDSRPALPS TQQLSVDSVS VLYNQEEKIL AYALSNSIGP VREGSPDA    238

SEQ ID NO: 96          moltype = AA  length = 238
FEATURE                Location/Qualifiers
source                 1..238
                       mol_type = protein
                       note = NIDOmut3_I200T
                       organism = synthetic construct
SEQUENCE: 96
SPQRVNGKVK GRIFVGSSQV PIVFENTDLA SYVVMNHGNS YTAISTIPET VGYSLLPLAP  60
VGGIIGWMFA VEQDGFKNGF SITGGEFTRQ AEVTFVGHPG NLVIKQRFSG IDEKGNLTID  120
TELEGRVPQI PFGSSVHIEP YTELYHYSTS VITSSSTREY TVTEPERDGA SPSRTYTYQW  180
RQTITFQECV HDDSRPALPS TQQLSVDSVS VLYNQEEKIL AYALSNSIGP VREGSPDA    238

SEQ ID NO: 97          moltype = AA  length = 238
FEATURE                Location/Qualifiers
source                 1..238
                       mol_type = protein
                       note = NIDOmut3_V236Y
                       organism = synthetic construct
SEQUENCE: 97
SPQRVNGKVK GRIFVGSSQV PIVFENTDLA SYVVMNHGNS YTAISTIPET VGYSLLPLAP  60
VGGIIGWMFA VEQDGFKNGF SITGGEFTRQ AEVTFVGHPG NLVIKQRFSG IDEKGNLTID  120
TELEGRVPQI PFGSSVHIEP YTELYHYSTS VITSSSTREY TVTEPERDGA SPSRIYTYQW  180
RQTITFQECV HDDSRPALPS TQQLSVDSVS YLYNQEEKIL AYALSNSIGP VREGSPDA    238

SEQ ID NO: 98          moltype = AA  length = 238
FEATURE                Location/Qualifiers
source                 1..238
                       mol_type = protein
                       note = NIDOmut3_L237T
                       organism = synthetic construct
SEQUENCE: 98
SPQRVNGKVK GRIFVGSSQV PIVFENTDLA SYVVMNHGNS YTAISTIPET VGYSLLPLAP  60
VGGIIGWMFA VEQDGFKNGF SITGGEFTRQ AEVTFVGHPG NLVIKQRFSG IDEKGNLTID  120
TELEGRVPQI PFGSSVHIEP YTELYHYSTS VITSSSTREY TVTEPERDGA SPSRIYTYQW  180
RQTITFQECV HDDSRPALPS TQQLSVDSVS VTYNQEEKIL AYALSNSIGP VREGSPDA    238

SEQ ID NO: 99          moltype = AA  length = 238
FEATURE                Location/Qualifiers
source                 1..238
                       mol_type = protein
                       note = NIDOmut3_S65I
                       organism = synthetic construct
SEQUENCE: 99
SPQRVNGKVK GRIFVGSSQV PIVFENTDLA SYVVMNHGNI YTAISTIPET VGYSLLPLAP  60
VGGIIGWMFA VEQDGFKNGF SITGGEFTRQ AEVTFVGHPG NLVIKQRFSG IDEKGNLTID  120
TELEGRVPQI PFGSSVHIEP YTELYHYSTS VITSSSTREY TVTEPERDGA SPSRIYTYQW  180
RQTITFQECV HDDSRPALPS TQQLSVDSVS VLYNQEEKIL AYALSNSIGP VREGSPDA    238

SEQ ID NO: 100         moltype = AA  length = 238
FEATURE                Location/Qualifiers
source                 1..238
                       mol_type = protein
                       note = NIDOmut3_R114I
                       organism = synthetic construct
SEQUENCE: 100
```

```
SPQRVNGKVK GRIFVGSSQV PIVFENTDLA SYVVMNHGNS YTAISTIPET VGYSLLPLAP  60
VGGIIGWMFA VEQDGFKNGF SITGGEFTIQ AEVTFVGHPG NLVIKQRFSG IDEKGNLTID  120
TELEGRVPQI PFGSSVHIEP YTELYHYSTS VITSSSTREY TVTEPERDGA SPSRIYTYQW  180
RQTITFQECV HDDSRPALPS TQQLSVDSVS VLYNQEEKIL AYALSNSIGP VREGSPDA    238

SEQ ID NO: 101          moltype = AA  length = 238
FEATURE                 Location/Qualifiers
source                  1..238
                        mol_type = protein
                        note = NIDOmut3_C214S
                        organism = synthetic construct
SEQUENCE: 101
SPQRVNGKVK GRIFVGSSQV PIVFENTDLA SYVVMNHGNS YTAISTIPET VGYSLLPLAP  60
VGGIIGWMFA VEQDGFKNGF SITGGEFTRQ AEVTFVGHPG NLVIKQRFSG IDEKGNLTID  120
TELEGRVPQI PFGSSVHIEP YTELYHYSTS VITSSSTREY TVTEPERDGA SPSRIYTYQW  180
RQTITFQESV HDDSRPALPS TQQLSVDSVS VLYNQEEKIL AYALSNSIGP VREGSPDA    238

SEQ ID NO: 102          moltype = AA  length = 238
FEATURE                 Location/Qualifiers
source                  1..238
                        mol_type = protein
                        note = NIDOmut3_S65I_R114I
                        organism = synthetic construct
SEQUENCE: 102
SPQRVNGKVK GRIFVGSSQV PIVFENTDLA SYVVMNHGNI YTAISTIPET VGYSLLPLAP  60
VGGIIGWMFA VEQDGFKNGF SITGGEFTIQ AEVTFVGHPG NLVIKQRFSG IDEKGNLTID  120
TELEGRVPQI PFGSSVHIEP YTELYHYSTS VITSSSTREY TVTEPERDGA SPSRIYTYQW  180
RQTITFQECV HDDSRPALPS TQQLSVDSVS VLYNQEEKIL AYALSNSIGP VREGSPDA    238

SEQ ID NO: 103          moltype = AA  length = 238
FEATURE                 Location/Qualifiers
source                  1..238
                        mol_type = protein
                        note = NIDOmut5_S65I_R114I
                        organism = synthetic construct
SEQUENCE: 103
SPQRVNGKVK GRIFVGSSQT PIVFENTDLA SYVVMNHGNI YTAISTIPET VGYSLLPLAP  60
VGGIIGWMFA VEQDGFKNGF SITGGEFTIQ AEVTFQGHPG NLVIKQRFSG IDEKGNLTID  120
TELEGRVPQI PEGSSVHIEP YTELYHYSTS VITSSSTREY TVTEPERDGA SPSRIYTYQW  180
RQTITFQEST HDDSRPALPS TQQLSVDSVS VLYNQEEKIL AYALSNSIGP VREGSPDA    238

SEQ ID NO: 104          moltype = AA  length = 238
FEATURE                 Location/Qualifiers
source                  1..238
                        mol_type = protein
                        note = NIDOmut5_S51I
                        organism = synthetic construct
SEQUENCE: 104
SPQRVNGKVK GRIFVGSSQT PIVFENTDLA SYVVMNHGNI YTAISTIPET VGYSLLPLAP  60
VGGIIGWMFA VEQDGFKNGF SITGGEFTRQ AEVTFQGHPG NLVIKQRFSG IDEKGNLTID  120
TELEGRVPQI PEGSSVHIEP YTELYHYSTS VITSSSTREY TVTEPERDGA SPSRIYTYQW  180
RQTITFQEST HDDSRPALPS TQQLSVDSVS VLYNQEEKIL AYALSNSIGP VREGSPDA    238

SEQ ID NO: 105          moltype = AA  length = 238
FEATURE                 Location/Qualifiers
source                  1..238
                        mol_type = protein
                        note = NIDOmut5_R114I
                        organism = synthetic construct
SEQUENCE: 105
SPQRVNGKVK GRIFVGSSQT PIVFENTDLA SYVVMNHGNS YTAISTIPET VGYSLLPLAP  60
VGGIIGWMFA VEQDGFKNGF SITGGEFTIQ AEVTFQGHPG NLVIKQRFSG IDEKGNLTID  120
TELEGRVPQI PEGSSVHIEP YTELYHYSTS VITSSSTREY TVTEPERDGA SPSRIYTYQW  180
RQTITFQEST HDDSRPALPS TQQLSVDSVS VLYNQEEKIL AYALSNSIGP VREGSPDA    238

SEQ ID NO: 106          moltype = AA  length = 270
FEATURE                 Location/Qualifiers
source                  1..270
                        mol_type = protein
                        note = T22-NIDOmut3-H6
                        organism = synthetic construct
SEQUENCE: 106
RRWCYRKCYK GYCYRKCRGG SSRSSSPQRV NGKVKGRIFV GSSQVPIVFE NTDLASYVVM  60
NHGNSYTAIS TIPETVGYSL LPLAPVGGII GWMFAVEQDG FKNGFSITGG EFTRQAEVTF  120
VGHPGNLVIK QRFSGIDEKG NLTIDTELEG RVPQIPFGSS VHIEPYTELY HYSTSVITSS  180
STREYTVTEP ERDGASPSRI YTYQWRQTIT FQECVHDDSR PALPSTQQLS VDSVSVLYNQ  240
EEKILAYALS NSIGPVREGS PDAKHHHHHH                                   270

SEQ ID NO: 107          moltype = AA  length = 270
```

```
FEATURE                Location/Qualifiers
source                 1..270
                       mol_type = protein
                       note = T22-NIDOmut3_V45T-H6
                       organism = synthetic construct
SEQUENCE: 107
RRWCYRKCYK GYCYRKCRGG SSRSSSPQRV NGKVKGRIFV GSSQTPIVFE NTDLASYVVM  60
NHGNSYTAIS TIPETVGYSL LPLAPVGGII GWMFAVEQDG FKNGFSITGG EFTRQAEVTF  120
VGHPGNLVIK QRFSGIDEKG NLTIDTELEG RVPQIPFGSS VHIEPYTELY HYSTSVITSS  180
STREYTVTEP ERDGASPSRI YTYQWRQTIT FQECVHDDSR PALPSTQQLS VDSVSVLYNQ  240
EEKILAYALS NSIGPVREGS PDAKHHHHHH                                  270

SEQ ID NO: 108         moltype = AA  length = 270
FEATURE                Location/Qualifiers
source                 1..270
                       mol_type = protein
                       note = T22-NIDOmut3_V121Q-H6
                       organism = synthetic construct
SEQUENCE: 108
RRWCYRKCYK GYCYRKCRGG SSRSSSPQRV NGKVKGRIFV GSSQVPIVFE NTDLASYVVM  60
NHGNSYTAIS TIPETVGYSL LPLAPVGGII GWMFAVEQDG FKNGFSITGG EFTRQAEVTF  120
QGHPGNLVIK QRFSGIDEKG NLTIDTELEG RVPQIPFGSS VHIEPYTELY HYSTSVITSS  180
STREYTVTEP ERDGASPSRI YTYQWRQTIT FQECVHDDSR PALPSTQQLS VDSVSVLYNQ  240
EEKILAYALS NSIGPVREGS PDAKHHHHHH                                  270

SEQ ID NO: 109         moltype = AA  length = 270
FEATURE                Location/Qualifiers
source                 1..270
                       mol_type = protein
                       note = T22-NIDOmut3_F157E-H6
                       organism = synthetic construct
SEQUENCE: 109
RRWCYRKCYK GYCYRKCRGG SSRSSSPQRV NGKVKGRIFV GSSQVPIVFE NTDLASYVVM  60
NHGNSYTAIS TIPETVGYSL LPLAPVGGII GWMFAVEQDG FKNGFSITGG EFTRQAEVTF  120
VGHPGNLVIK QRFSGIDEKG NLTIDTELEG RVPQIPEGSS VHIEPYTELY HYSTSVITSS  180
STREYTVTEP ERDGASPSRI YTYQWRQTIT FQECVHDDSR PALPSTQQLS VDSVSVLYNQ  240
EEKILAYALS NSIGPVREGS PDAKHHHHHH                                  270

SEQ ID NO: 110         moltype = AA  length = 270
FEATURE                Location/Qualifiers
source                 1..270
                       mol_type = protein
                       note = T22-NIDOmut3_V215T-H6
                       organism = synthetic construct
SEQUENCE: 110
RRWCYRKCYK GYCYRKCRGG SSRSSSPQRV NGKVKGRIFV GSSQVPIVFE NTDLASYVVM  60
NHGNSYTAIS TIPETVGYSL LPLAPVGGII GWMFAVEQDG FKNGFSITGG EFTRQAEVTF  120
VGHPGNLVIK QRFSGIDEKG NLTIDTELEG RVPQIPFGSS VHIEPYTELY HYSTSVITSS  180
STREYTVTEP ERDGASPSRI YTYQWRQTIT FQECTHDDSR PALPSTQQLS VDSVSVLYNQ  240
EEKILAYALS NSIGPVREGS PDAKHHHHHH                                  270

SEQ ID NO: 111         moltype = AA  length = 270
FEATURE                Location/Qualifiers
source                 1..270
                       mol_type = protein
                       note = T22-NIDOmut4-H6
                       organism = synthetic construct
SEQUENCE: 111
RRWCYRKCYK GYCYRKCRGG SSRSSSPQRV NGKVKGRIFV GSSQTPIVFE NTDLASYVVM  60
NHGNSYTAIS TIPETVGYSL LPLAPVGGII GWMFAVEQDG FKNGFSITGG EFTRQAEVTF  120
QGHPGNLVIK QRFSGIDEKG NLTIDTELEG RVPQIPEGSS VHIEPYTELY HYSTSVITSS  180
STREYTVTEP ERDGASPSRI YTYQWRQTIT FQECTHDDSR PALPSTQQLS VDSVSVLYNQ  240
EEKILAYALS NSIGPVREGS PDAKHHHHHH                                  270

SEQ ID NO: 112         moltype = AA  length = 270
FEATURE                Location/Qualifiers
source                 1..270
                       mol_type = protein
                       note = T22-NIDOmut4_T215V-H6
                       organism = synthetic construct
SEQUENCE: 112
RRWCYRKCYK GYCYRKCRGG SSRSSSPQRV NGKVKGRIFV GSSQTPIVFE NTDLASYVVM  60
NHGNSYTAIS TIPETVGYSL LPLAPVGGII GWMFAVEQDG FKNGFSITGG EFTRQAEVTF  120
QGHPGNLVIK QRFSGIDEKG NLTIDTELEG RVPQIPEGSS VHIEPYTELY HYSTSVITSS  180
STREYTVTEP ERDGASPSRI YTYQWRQTIT FQECVHDDSR PALPSTQQLS VDSVSVLYNQ  240
EEKILAYALS NSIGPVREGS PDAKHHHHHH                                  270

SEQ ID NO: 113         moltype = AA  length = 270
FEATURE                Location/Qualifiers
```

```
source                1..270
                      mol_type = protein
                      note = T22-NIDOmut5-H6
                      organism = synthetic construct
SEQUENCE: 113
RRWCYRKCYK GYCYRKCRGG SSRSSSPQRV NGKVKGRIFV GSSQTPIVFE NTDLASYVVM  60
NHGNSYTAIS TIPETVGYSL LPLAPVGGII GWMFAVEQDG FKNGFSITGG EFTRQAEVTF  120
QGHPGNLVIK QRFSGIDEKG NLTIDTELEG RVPQIPEGSS VHIEPYTELY HYSTSVITSS  180
STREYTVTEP ERDGASPSRI YTYQWRQTIT FQESTHDDSR PALPSTQQLS VDSVSVLYNQ  240
EEKILAYALS NSIGPVREGS PDAKHHHHHH                                  270

SEQ ID NO: 114        moltype = AA  length = 270
FEATURE               Location/Qualifiers
source                1..270
                      mol_type = protein
                      note = T22-NIDOmut3_V176T-H6
                      organism = synthetic construct
SEQUENCE: 114
RRWCYRKCYK GYCYRKCRGG SSRSSSPQRV NGKVKGRIFV GSSQVPIVFE NTDLASYVVM  60
NHGNSYTAIS TIPETVGYSL LPLAPVGGII GWMFAVEQDG FKNGFSITGG EFTRQAEVTF  120
VGHPGNLVIK QRFSGIDEKG NLTIDTELEG RVPQIPFGSS VHIEPYTELY HYSTSTITSS  180
STREYTVTEP ERDGASPSRI YTYQWRQTIT FQECVHDDSR PALPSTQQLS VDSVSVLYNQ  240
EEKILAYALS NSIGPVREGS PDAKHHHHHH                                  270

SEQ ID NO: 115        moltype = AA  length = 270
FEATURE               Location/Qualifiers
source                1..270
                      mol_type = protein
                      note = T22-NIDOmut3_I200T-H6
                      organism = synthetic construct
SEQUENCE: 115
RRWCYRKCYK GYCYRKCRGG SSRSSSPQRV NGKVKGRIFV GSSQVPIVFE NTDLASYVVM  60
NHGNSYTAIS TIPETVGYSL LPLAPVGGII GWMFAVEQDG FKNGFSITGG EFTRQAEVTF  120
VGHPGNLVIK QRFSGIDEKG NLTIDTELEG RVPQIPFGSS VHIEPYTELY HYSTSVITSS  180
STREYTVTEP ERDGASPSRT YTYQWRQTIT FQECVHDDSR PALPSTQQLS VDSVSVLYNQ  240
EEKILAYALS NSIGPVREGS PDAKHHHHHH                                  270

SEQ ID NO: 116        moltype = AA  length = 270
FEATURE               Location/Qualifiers
source                1..270
                      mol_type = protein
                      note = T22-NIDOmut3_V236Y-H6
                      organism = synthetic construct
SEQUENCE: 116
RRWCYRKCYK GYCYRKCRGG SSRSSSPQRV NGKVKGRIFV GSSQVPIVFE NTDLASYVVM  60
NHGNSYTAIS TIPETVGYSL LPLAPVGGII GWMFAVEQDG FKNGFSITGG EFTRQAEVTF  120
VGHPGNLVIK QRFSGIDEKG NLTIDTELEG RVPQIPFGSS VHIEPYTELY HYSTSVITSS  180
STREYTVTEP ERDGASPSRI YTYQWRQTIT FQECVHDDSR PALPSTQQLS VDSVSYLYNQ  240
EEKILAYALS NSIGPVREGS PDAKHHHHHH                                  270

SEQ ID NO: 117        moltype = AA  length = 270
FEATURE               Location/Qualifiers
source                1..270
                      mol_type = protein
                      note = T22-NIDOmut3_L237T-H6
                      organism = synthetic construct
SEQUENCE: 117
RRWCYRKCYK GYCYRKCRGG SSRSSSPQRV NGKVKGRIFV GSSQVPIVFE NTDLASYVVM  60
NHGNSYTAIS TIPETVGYSL LPLAPVGGII GWMFAVEQDG FKNGFSITGG EFTRQAEVTF  120
VGHPGNLVIK QRFSGIDEKG NLTIDTELEG RVPQIPFGSS VHIEPYTELY HYSTSVITSS  180
STREYTVTEP ERDGASPSRI YTYQWRQTIT FQECVHDDSR PALPSTQQLS VDSVSVTYNQ  240
EEKILAYALS NSIGPVREGS PDAKHHHHHH                                  270

SEQ ID NO: 118        moltype = AA  length = 270
FEATURE               Location/Qualifiers
source                1..270
                      mol_type = protein
                      note = T22-NIDOmut3_S65I-H6
                      organism = synthetic construct
SEQUENCE: 118
RRWCYRKCYK GYCYRKCRGG SSRSSSPQRV NGKVKGRIFV GSSQVPIVFE NTDLASYVVM  60
NHGNIYTAIS TIPETVGYSL LPLAPVGGII GWMFAVEQDG FKNGFSITGG EFTRQAEVTF  120
VGHPGNLVIK QRFSGIDEKG NLTIDTELEG RVPQIPFGSS VHIEPYTELY HYSTSVITSS  180
STREYTVTEP ERDGASPSRI YTYQWRQTIT FQECVHDDSR PALPSTQQLS VDSVSVLYNQ  240
EEKILAYALS NSIGPVREGS PDAKHHHHHH                                  270

SEQ ID NO: 119        moltype = AA  length = 270
FEATURE               Location/Qualifiers
source                1..270
```

```
                        mol_type = protein
                        note = T22-NIDOmut3_R114I-H6
                        organism = synthetic construct
SEQUENCE: 119
RRWCYRKCYK GYCYRKCRGG SSRSSSPQRV NGKVKGRIFV GSSQVPIVFE NTDLASYVVM  60
NHGNSYTAIS TIPETVGYSL LPLAPVGGII GWMFAVEQDG FKNGFSITGG EFTIQAEVTF  120
VGHPGNLVIK QRFSGIDEKG NLTIDTELEG RVPQIPFGSS VHIEPYTELY HYSTSVITSS  180
STREYTVTEP ERDGASPSRI YTYQWRQTIT FQECVHDDSR PALPSTQQLS VDSVSVLYNQ  240
EEKILAYALS NSIGPVREGS PDAKHHHHHH                                  270

SEQ ID NO: 120          moltype = AA  length = 270
FEATURE                 Location/Qualifiers
source                  1..270
                        mol_type = protein
                        note = T22-NIDOmut3_C214S-H6
                        organism = synthetic construct
SEQUENCE: 120
RRWCYRKCYK GYCYRKCRGG SSRSSSPQRV NGKVKGRIFV GSSQVPIVFE NTDLASYVVM  60
NHGNSYTAIS TIPETVGYSL LPLAPVGGII GWMFAVEQDG FKNGFSITGG EFTRQAEVTF  120
VGHPGNLVIK QRFSGIDEKG NLTIDTELEG RVPQIPFGSS VHIEPYTELY HYSTSVITSS  180
STREYTVTEP ERDGASPSRI YTYQWRQTIT FQESVHDDSR PALPSTQQLS VDSVSVLYNQ  240
EEKILAYALS NSIGPVREGS PDAKHHHHHH                                  270

SEQ ID NO: 121          moltype = AA  length = 270
FEATURE                 Location/Qualifiers
source                  1..270
                        mol_type = protein
                        note = T22-NIDOmut3_S65I_R114I-H6
                        organism = synthetic construct
SEQUENCE: 121
RRWCYRKCYK GYCYRKCRGG SSRSSSPQRV NGKVKGRIFV GSSQVPIVFE NTDLASYVVM  60
NHGNIYTAIS TIPETVGYSL LPLAPVGGII GWMFAVEQDG FKNGFSITGG EFTIQAEVTF  120
VGHPGNLVIK QRFSGIDEKG NLTIDTELEG RVPQIPFGSS VHIEPYTELY HYSTSVITSS  180
STREYTVTEP ERDGASPSRI YTYQWRQTIT FQECVHDDSR PALPSTQQLS VDSVSVLYNQ  240
EEKILAYALS NSIGPVREGS PDAKHHHHHH                                  270

SEQ ID NO: 122          moltype = AA  length = 270
FEATURE                 Location/Qualifiers
source                  1..270
                        mol_type = protein
                        note = T22-NIDOmut5_S51I_R114I
                        organism = synthetic construct
SEQUENCE: 122
RRWCYRKCYK GYCYRKCRGG SSRSSSPQRV NGKVKGRIFV GSSQTPIVFE NTDLASYVVM  60
NHGNIYTAIS TIPETVGYSL LPLAPVGGII GWMFAVEQDG FKNGFSITGG EFTIQAEVTF  120
QGHPGNLVIK QRFSGIDEKG NLTIDTELEG RVPQIPEGSS VHIEPYTELY HYSTSVITSS  180
STREYTVTEP ERDGASPSRI YTYQWRQTIT FQESTHDDSR PALPSTQQLS VDSVSVLYNQ  240
EEKILAYALS NSIGPVREGS PDAKHHHHHH                                  270

SEQ ID NO: 123          moltype = AA  length = 270
FEATURE                 Location/Qualifiers
source                  1..270
                        mol_type = protein
                        note = T22-NIDOmut5_S65I-H6
                        organism = synthetic construct
SEQUENCE: 123
RRWCYRKCYK GYCYRKCRGG SSRSSSPQRV NGKVKGRIFV GSSQTPIVFE NTDLASYVVM  60
NHGNIYTAIS TIPETVGYSL LPLAPVGGII GWMFAVEQDG FKNGFSITGG EFTRQAEVTF  120
QGHPGNLVIK QRFSGIDEKG NLTIDTELEG RVPQIPEGSS VHIEPYTELY HYSTSVITSS  180
STREYTVTEP ERDGASPSRI YTYQWRQTIT FQESTHDDSR PALPSTQQLS VDSVSVLYNQ  240
EEKILAYALS NSIGPVREGS PDAKHHHHHH                                  270

SEQ ID NO: 124          moltype = AA  length = 270
FEATURE                 Location/Qualifiers
source                  1..270
                        mol_type = protein
                        note = T22-NIDOmut5_R114I-H6
                        organism = synthetic construct
SEQUENCE: 124
RRWCYRKCYK GYCYRKCRGG SSRSSSPQRV NGKVKGRIFV GSSQTPIVFE NTDLASYVVM  60
NHGNSYTAIS TIPETVGYSL LPLAPVGGII GWMFAVEQDG FKNGFSITGG EFTIQAEVTF  120
QGHPGNLVIK QRFSGIDEKG NLTIDTELEG RVPQIPEGSS VHIEPYTELY HYSTSVITSS  180
STREYTVTEP ERDGASPSRI YTYQWRQTIT FQESTHDDSR PALPSTQQLS VDSVSVLYNQ  240
EEKILAYALS NSIGPVREGS PDAKHHHHHH                                  270

SEQ ID NO: 125          moltype = AA  length = 360
FEATURE                 Location/Qualifiers
source                  1..360
                        mol_type = protein
```

```
                        note = Human Nidogen G2 domain from Figure 13A
                        organism = synthetic construct
SEQUENCE: 125
HQQHPQVIDV DEVEETGVVF SYNTDSRQTC ANNRHQCSVH AECRDYATGF CCSCVAGYTG  60
NGRQCVAEGS PQRVNGKVKG RIFVGSSQVP IVFENTDLHS YVVMNHGRSY TAISTIPETV  120
GYSLLPLAPV GGIIGWMFAV EQDGFKNGFS ITGGEFTRQA EVTFVGHPGN LVIKQRFSGI  180
DEHGHLTIDT ELEGRVPQIP FGSSVHIEPY TELYHYSTSV ITSSSTREYT VTEPERDGAS  240
PSRIYTYQWR QTITFQECVH DDSRPALPST QQLSVDSVFV LYNQEEKILR YALSNSIGPV  300
REGSPDALQN PCYIGTHGCD TNAACRPGPR TQFTCECSIG FRGDGRTCYD IDECSEQPSV  360

SEQ ID NO: 126          moltype = AA  length = 360
FEATURE                 Location/Qualifiers
source                  1..360
                        mol_type = protein
                        note = Mouse Nidogen G2 domain from Figure 13A
                        organism = synthetic construct
SEQUENCE: 126
PQHHPQVIDV DEVEETGVVF SYNTGSQQTC ANNRHQCSVH AECRDYATGF CCRCVANYTG  60
NGRQCVAEGS PQRVNGKVKG RIFVGSSQVP VVFENTDLHS YVVMNHGRSY TAISTIPETV  120
GYSLLPLAPI GGIIGWMFAV EQDGFKNGFS ITGGEFTRQA EVTFLGHPGK LVLKQQFSGI  180
DEHGHLTIST ELEGRVPQIP YGASVHIEPY TELYHYSSSV ITSSSTREYT VMEPDQDGAA  240
PSHTHIYQWR QTITFQECAH DDARPALPST QQLSVDSVFV LYNKEERILR YALSNSIGPV  300
RDGSPDALQN PCYIGTHGCD SNAACRPGPG TQFTCECSIG FRGDGQTCYD IDECSEQPSR  360

SEQ ID NO: 127          moltype = AA  length = 1247
FEATURE                 Location/Qualifiers
source                  1..1247
                        mol_type = protein
                        note = Human Nidogen (Uniprot P14534)
                        organism = synthetic construct
SEQUENCE: 127
MLASSSRIRA AWTRALLLPL LLAGPVGCLS RQELFPFGPG QGDLELEDGD DFVSPALELS  60
GALRFYDRSD IDAVYVTTNG IIATSEPPAK ESHPGLFPPT FGAVAPFLAD LDTTDGLGKV  120
YYREDLSPSI TQRAAECVHR GFPEISFQPS SAVVVTWESV APYQGPSRDP DQKGKRNTFQ  180
AVLASSDSSS YAIFLYPEDG LQFHTTFSKK ENNQVPAVVA FSQGSVGFLW KSNGAYNIFA  240
NDRESVENLA KSSNSGQQGV WVFEIGSPAT TNGVVPADVI LGTEDGAEYD DEDEDYDLAT  300
TRLGLEDVGT TPFSYKALRR GGADTYSVPS VLSPRRAATE RPLGPPTERT RSFQLAVETF  360
HQQHPQVIDV DEVEETGVVF SYNTDSRQTC ANNRHQCSVH AECRDYATGF CCSCVAGYTG  420
NGRQCVAEGS PQRVNGKVKG RIFVGSSQVP IVFENTDLHS YVVMNHGRSY TAISTIPETV  480
GYSLLPLAPV GGIIGWMFAV EQDGFKNGFS ITGGEFTRQA EVTFVGHPGN LVIKQRFSGI  540
DEHGHLTIDT ELEGRVPQIP FGSSVHIEPY TELYHYSTSV ITSSSTREYT VTEPERDGAS  600
PSRIYTYQWR QTITFQECVH DDSRPALPST QQLSVDSVFV LYNQEEKILR YALSNSIGPV  660
REGSPDALQN PCYIGTHGCD TNAACRPGPR TQFTCECSIG FRGDGRTCYD IDECSEQPSV  720
CGSHTICNNH PGTFRCECVE GYQFSDEGTC VAVVDQRPIN YCETGLHNCD IPQRAQCIYT  780
GGSSYTCSCL PGFSGDGQAC QDVDECQPSR CHPDAFCYNT PGSFTCQCKP GYQGDGFRCV  840
PGEVEKTRCQ HEREHILGAA GATDPQRPIP PGLFVPECDA HGHYAPTQCH GSTGYCWCVD  900
RDGREVEGTR TRPGMTPPCL STVAPPIHQG PAVPTAVIPL PPGTHLLFAQ TGKIERLPLE  960
GNTMRKTEAK AFLHVPAKVI IGLAFDCVDK MVYWTDITEP SIGRASLHGG EPTTIIRQDL  1020
GSPEGIAVDH LGRNIFWTDS NLDRIEVAKL DGTQRRVLFE TDLVNPRGIV TDSVRGNLYW  1080
TDWNRDNPKI ETSYMDGTNR RILVQDDLGL PNGLTFDAFS SQLCWVDAGT NRAECLNPSQ  1140
PSRRKALEGL QYPFAVTSYG KNLYFTDWKM NSVVALDLAI SKETDAFQPH KQTRLYGITT  1200
ALSQCPQGHN YCSVNNGGCT HLCLATPGSR TCRCPDNTLG VDCIEQK                1247

SEQ ID NO: 128          moltype = AA  length = 270
FEATURE                 Location/Qualifiers
source                  1..270
                        mol_type = protein
                        note = T22-NIDOmut2-H6 (Sequence in figure 13B)
                        organism = synthetic construct
SEQUENCE: 128
RRWCYRKCYK GYCYRKCRGG SSRSSSPQRV NGKVKGRIFV GSSQVPIVFE NTDLASYVVM  60
NHGNSYTAIS TIPETVGYSL LPLAPVGGII GWMFAVEQDG FKNGFSITGG EFTRQAEVTF  120
VGHPGNLVIK QRFSGIDEKG NLTIDTELEG RVPQIPFGSS VHIEPYTELY HYSTSVITSS  180
STREYTVTEP ERDGASPSRI YTYQWRQTIT FQECVHDDSR PALPSTQQLS VDSVSVLYNQ  240
EEKILAYALS NSIGPVREGS PDAKHHHHHH                                   270

SEQ ID NO: 129          moltype = AA  length = 279
FEATURE                 Location/Qualifiers
source                  1..279
                        mol_type = protein
                        note = EPI-X4-(RK)-GFP-H6
                        organism = synthetic construct
SEQUENCE: 129
IVRWSKKVPC VSIVRWSKKV PCVSRKRKRK GGSSRSSSKG EELFTGVVPI LVELDGDVNG  60
HKFSVSGEGE GDATYGKLTL KFICTTGKLP VPWPTLVTTL TYGVQCFSRY PDHMKRHDFF  120
KSAMPEGYVQ ERTISFKDDG NYKTRAEVKF EGDTLVNRIE LKGIDFKEDG NILGHKLEYN  180
YNSHNVYITA DKQKNGIKAN FKIRHNIEDG SVQLADHYQQ NTPIGDGPVL LPDNHYLSTQ  240
SALSKDPNEK RDHMVLLEFV TAAGITHGMD ELYHHHHHH                         279
```

-continued

```
SEQ ID NO: 130          moltype = AA  length = 236
FEATURE                 Location/Qualifiers
source                  1..236
                        mol_type = protein
                        note = GFP
                        organism = synthetic construct
SEQUENCE: 130
SKGEELFTGV VPILVELDGD VNGHKFSVSG EGEGDATYGK LTLKFICTTG KLPVPWPTLV  60
TTLTYGVQCF SRYPDHMKRH DFFKSAMPEG YVQERTISFK DDGNYKTRAE VKFEGDTLVN  120
RIELKGIDFK EDGNILGHKL EYNYNSHNVY ITADKQKNGI KANFKIRHNI EDGSVQLADH  180
YQQNTPIGDG PVLLPDNHYL STQSALSKDP NEKRDHMVLL EFVTAAGITH GMDELY      236

SEQ ID NO: 131          moltype = AA  length = 30
FEATURE                 Location/Qualifiers
source                  1..30
                        mol_type = protein
                        note = Optimized EPI-X4 coupled to RKRKRK positively
                         charged peptide region
                        organism = synthetic construct
SEQUENCE: 131
IVRWSKKVPC VSIVRWSKKV PCVSRKRKRK                                   30

SEQ ID NO: 132          moltype = AA  length = 17
FEATURE                 Location/Qualifiers
source                  1..17
                        mol_type = protein
                        note = EPI-X4
                        organism = synthetic construct
SEQUENCE: 132
LLVRYTKKVP QVSTPTL                                                 17

SEQ ID NO: 133          moltype = AA  length = 23
FEATURE                 Location/Qualifiers
source                  1..23
                        mol_type = protein
                        note = EPI-X4 coupled to RKRKRK positively charged peptide
                         region
                        organism = synthetic construct
SEQUENCE: 133
LLVRYTKKVP QVSTPTLRKR KRK                                          23
```